US008232294B2

(12) United States Patent
Xi

(10) Patent No.: US 8,232,294 B2

(45) Date of Patent: Jul. 31, 2012

(54) AMINO ESTER DERIVATIVES, SAILTS THEREOF AND METHODS OF USE

(75) Inventor: Ning Xi, Thousand Oaks, CA (US)

(73) Assignees: Ning Xi, Newbury Park, CA (US); Sunshine Lake Pharma Co., Ltd., Northern Industrial Area, Songshan Lake, Dongguan, Guangdong (CN)

( * ) Notice: Subject to any disclaimer, the term of this patent is extended or adjusted under 35 U.S.C. 154(b) by 358 days.

(21) Appl. No.: 12/728,153

(22) Filed: Mar. 19, 2010

(65) Prior Publication Data

US 2010/0239576 A1 Sep. 23, 2010

Related U.S. Application Data

(60) Provisional application No. 61/162,260, filed on Mar. 21, 2009.

(51) Int. Cl.
*C07D 215/38* (2006.01)
*A61K 31/04* (2006.01)

(52) U.S. Cl. ......................... 514/312; 546/153; 546/159

(58) Field of Classification Search .................. 546/159, 546/163; 514/312

See application file for complete search history.

(56) References Cited

U.S. PATENT DOCUMENTS

| | | | |
|---|---|---|---|
| 614,376 | A | 12/2000 | Kubo et al. |
| 663,048 | A1 | 10/2003 | Crawley |
| 679,782 | A1 | 9/2004 | Kubo et al. |
| 690,020 | A1 | 5/2005 | Salvati et al. |
| 699,517 | A1 | 2/2006 | Autry et al. |
| 707,480 | A1 | 7/2006 | Stokes et al. |
| 708,762 | A1 | 8/2006 | Li |
| 720,850 | A1 | 4/2007 | Lou et al. |
| 7,235,559 | B1 | 6/2007 | Mortlock et al. |
| 726,513 | A1 | 9/2007 | Johnson et al. |
| 742,556 | A1 | 9/2008 | Fujiwara et al. |
| 743,582 | A1 | 10/2008 | Potashman et al. |
| 745,956 | A1 | 12/2008 | Borzilleri et al. |
| 749,510 | A1 | 2/2009 | Miwa et al. |
| 756,055 | A1 | 7/2009 | Shimizu et al. |
| 7,566,784 | B2 | 7/2009 | Borzilleri et al. |
| 757,607 | A1 | 8/2009 | Rice et al. |
| 757,947 | A1 | 8/2009 | Bannen et al. |
| 785,862 | A1 | 12/2010 | Kim et al. |
| 2004/0053908 | A1 | 3/2004 | Funahashi et al. |
| 2005/0245547 | A1 | 11/2005 | Kim et al. |
| 2006/0052396 | A1 | 3/2006 | Berg et al. |
| 2006/0074056 | A1 | 4/2006 | Vaisburg et al. |
| 2006/0183911 | A1 | 8/2006 | Charrier et al. |
| 2006/0241104 | A1 | 10/2006 | Borzilleri et al. |
| 2006/0252777 | A1 | 11/2006 | Kim et al. |
| 2007/0004675 | A1 | 1/2007 | Saavedra et al. |
| 2007/0117802 | A1 | 5/2007 | Borzilleri et al. |
| 2007/0129389 | A1 | 6/2007 | Bilbe |
| 2007/0161651 | A1 | 7/2007 | Ibrahim et al. |
| 2007/0179130 | A1 | 8/2007 | Bannen |
| 2007/0244116 | A1 | 10/2007 | Bannen et al. |
| 2008/0161305 | A1 | 7/2008 | Forsyth et al. |
| 2008/0227811 | A1 | 9/2008 | Chen |
| 2008/0312232 | A1 | 12/2008 | Kim et al. |
| 2009/0034420 | A1 | 2/2009 | Boeckle et al. |
| 2009/0069316 | A1 | 3/2009 | Hong et al. |
| 2009/0264440 | A1 | 10/2009 | Claridge et al. |
| 2009/0306103 | A1 | 12/2009 | Boyer et al. |
| 2011/0118252 | A1 | 5/2011 | Tae-Seongkim et al. |

FOREIGN PATENT DOCUMENTS

| | | |
|---|---|---|
| EP | 1889836 | 2/2008 |
| JP | 2010178651 | 8/2010 |
| WO | WO2004092196 | 10/2004 |
| WO | WO2005121125 | 12/2005 |
| WO | WO2008049855 | 5/2008 |
| WO | WO2008053157 | 5/2008 |
| WO | WO2008102870 | 8/2008 |
| WO | WO2009033084 | 3/2009 |
| WO | WO2009042646 | 4/2009 |
| WO | WO2009049028 | 4/2009 |
| WO | WO2009087381 | 7/2009 |
| WO | WO2009093049 | 7/2009 |
| WO | WO2009094417 | 7/2009 |
| WO | WO2009096435 | 8/2009 |
| WO | WO2009125597 | 10/2009 |
| WO | WO2010011538 | 1/2010 |
| WO | WO2010036831 | 4/2010 |
| WO | WO2010042646 | 4/2010 |
| WO | WO2010042649 | 4/2010 |
| WO | WO2010044543 | 4/2010 |
| WO | WO2010045095 | 4/2010 |
| WO | WO2010051373 | 5/2010 |
| WO | WO2010056960 | 5/2010 |
| WO | WO2010065838 | 6/2010 |
| WO | WO2010144909 | 12/2010 |
| WO | WO2010151710 | 12/2010 |
| WO | WO2011017142 | 2/2011 |
| WO | WO2011017639 | 2/2011 |
| WO | WO2011023081 | 3/2011 |
| WO | WO2011029001 | 3/2011 |
| WO | WO2011050245 | 4/2011 |
| WO | WO2011052923 | 5/2011 |
| WO | WO2011054433 | 5/2011 |
| WO | WO2011060873 | 5/2011 |

OTHER PUBLICATIONS

Teffera, Chem Res Toxicol, vol. 21, pp. 2216-2222, 2008.*

Liu et al., J. Med. Chem., Jun. 14, 2008, vol. 51, No. 13, p. 3688-3691.

Schiering et al., PNAS, Oct. 28, 2003, vol. 100, No. 22, p. 12654-12659.

* cited by examiner

*Primary Examiner* — D M Seaman

(74) *Attorney, Agent, or Firm* — Kam W. Law; Squires Sanders

(57) ABSTRACT

The present invention provides amino ester compounds, salts, and pharmaceutical formulations thereof useful in modulating the protein tyrosine kinase activity, and in modulating inter- and/or intra-cellular signaling. The invention also provides pharmaceutically acceptable compositions comprising such compounds and methods of using the compositions in the treatment of hyperproliferative disorders in mammals, especially humans.

25 Claims, 2 Drawing Sheets

AMINO ESTER DERIVATIVES, SAILTS THEREOF AND METHODS OF USE

CROSS-REFERENCE TO RELATED APPLICATIONS

This application claims the benefit of U.S. provisional application No. 61/162,260, filed Mar. 21, 2009, the content of which is hereby incorporated by reference in its entirety.

FIELD OF THE INVENTION

This invention relates to novel heterocyclic amino ester derivatives, and salts thereof, which are useful in the treatment of hyperproliferative diseases, such as cancers, in mammals. In particular, the invention relates to compounds, and metabilites thereof, which inhibit the protein tyrosine kinase activity, resulting in the inhibition of inter- and/or intra-cellular signaling. This invention also relates to a method of using such compounds in the treatment of hyperproliferative diseases in mammals, especially humans, and to pharmaceutical compositions containing such compounds.

BACKGROUND OF THE INVENTION

Protein kinases are a large family of proteins that play a pivotal role in the regulation of a wide variety of cellular processes, maintaining control over cellular function. Protein tyrosine kinases may be classified as growth factor receptor (e.g. VEGFR, EGFR, PDGFR, FGFR and erbB2) or non-receptor (e.g. c-src and bcr-abl) kinases. Receptor tyrosine kinases (RTKs) play a key role in the regulation of cell proliferation, differentiation, metabolism, migration, and survival. Upon ligand binding, they undergo tyrosine phosphorylation at specific residues in the cytoplasmic tail. This leads to the binding of protein substrates and/or the establishment docking sites for adaptor proteins involved in RTK-mediated signal transduction. When unregulated, receptor tyrosine kinases can contribute to the rise of disease states associated with such aberrant kinase activity.

A partial list of such kinases include abl, AATK, ALK, Akt, axl, bmx, bcr-abl, Blk, Brk, Btk, csk, c-kit, c-Met, c-src, c-fins, CDK1, CDK2, CDK3, CDK4, CDK5, CDK6, CDK7, CDK8, CDK9, CDK10, cRaf1, CSF1R, CSK, DDR1, DDR2, EPHA, EPHB, EGFR, ErbB2, ErbB3, ErbB4, Erk, Fak, fes, FER, FGFR1, FGFR2, FGFR3, FGFR4, FGFR5, Fgr, flt-1, Fps, Frk, Fyn, GSG2, GSK, Hck, ILK, INSRR, IRAK4, ITK, IGF-1R, INS-R, Jak, KSR1, KDR, LMTK2, LMTK3, LTK, Lck, Lyn, MATK, MERTK, MLTK, MST1R, MUSK, NPR1, NTRK, MEK, PLK4, PTK, p38, PDGFR, PIK, PKC, PYK2, RET, ROR1, ROR2, RYK, ros, Ron, SGK493, SRC, SRMS, STYK1, SYK, TEC, TEK, TEX14, TNK1, TNK2, TNNI3K, TXK, TYK2, TYRO3, tie, tie2, TRK, Yes, and Zap70.

Aberrant angiogenesis contributes to some pathological disorders and in particular to tumor growth. VEGF-A (vascular endothelial growth factor A) is a key factor promoting neovascularization (angiogenesis) of tumors. VEGF induces endothelial cell proliferation and migration by signaling through two high affinity receptors, the fms-like tyrosine kinase receptor, flt-1 or VEGFR-1, and the kinase insert domain-containing receptor, KDR or VEGFR-2. The binding of VEGF to VEGFRs stimulates receptor dimerization and activation of the RTK domain. The kinase activity autophosphorylates cytoplasmic receptor tyrosine residues, which then serve as binding sites for molecules involved in the propagation of a signaling cascade.

Disruption of VEGFR signaling is a highly attractive therapeutic target in cancer, as angiogenesis is a prerequisite for all solid tumor growth. A number of drugs inhibiting VEGF signaling, including use of neutralizing antibodies receptor antagonists, small molecule antagonists, have been approved by US Food & Drug Administration (FDA) ("Molecular basis for sunitinib efficacy and future clinical development." *Nature Review Drug Discovery,* 2007, 6, 734; Angiogenesis: "an organizing principle for drug discovery?" *Nature Review Drug Discovery,* 2007, 6, 273).

Hepatocyte growth factor (HGF), also known as scatter factor, is a multifunctional growth factor that promotes cell proliferation, scattering, invasion, survival, and angiogenesis. In order to produce cellular effects, HGF must bind to its receptor, c-Met, a receptor tyrosine kinase. c-Met is overexpressed in a significant percentage of various types of human cancers and is often amplified during the transition between primary tumors and metastasis ("Molecular cancer therapy: can our expectation be MET." *Euro. J. Cancer,* 2008, 44, 641-651). c-Met is also implicated in atherosclerosis and lung fibrosis.

Binding of HGF to c-Met leads to receptor phosphorylation and activation of Ras/mitogen-activated protein kinase (MAPK) signaling pathway, thereby enhancing malignant behaviors of cancer cells. Moreover, stimulation of the HGF/c-Met pathway itself can lead to the induction of VEGF expression, itself contributing directly to angiogenic activity. Because of the dual role of c-Met as an adjuvant, pro-metastatic gene for some tumor types and as a necessary oncogene for others, c-Met is a versatile candidate for targeted cancer therapeutic intervention. ("From Tpr-Met to Met, tumorigenesis and tubes." *Oncogene.* 2007, 26, 1276; "Drug development of MET inhibitors: targeting oncogene addiction and expedience." *Nature Review Drug Discovery,* 2008, 7, 504).

Anti-tumor approaches that target VEGF/VEGFR and HGF/c-Met signaling may circumvent the ability of tumor cells to overcome VEGFR or HGFR inhibition alone and may represent improved cancer therapeutics. Here we describe small molecules that are potent inhibitors of protein tyrosine kinase activity, such as that of, for example, the VEGF receptor KDR and the HGF receptor c-Met, among others.

SUMMARY OF THE INVENTION

Provided herein are new compounds and methods for treating cell proliferative diseases. The compounds or their metabolites disclosed herein may be inhibitors of protein tyrosine kinase activity. In some embodiments, the compounds disclosed herein are multiple function inhibitors, capable of inhibiting, for example, VEGF and HGF receptor signaling. Accordingly, provided herein are new inhibitors of protein tyrosine kinase receptor signaling, such as for example, VEGF receptor signaling and HGF receptor signaling.

Specifically, it has been found that compounds of this invention, and pharmaceutically acceptable compositions thereof, are effective as inhibitors of receptor tyrosine kinases such as c-Met and VEGFR. Accordingly, in one aspect, provides herein is compound having Formula (I) as shown below:

Formula (I)

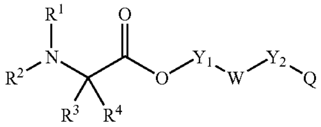

or a recemic mixture, a stereoisomer, a geometric isomer, a tautomer, a solvate, an N-oxide, a metabolite, or a pharmaceutically acceptable salt thereof, wherein each of $R^1$, $R^2$, $R^3$, $R^4$, $Y_1$, $Y_2$, W, and Q is as defined herein.

In some embodiments, each of $R^1$, $R^2$, $R^3$ and $R^4$ is independently H, —C(═O)$R^{11}$, —C(═O)O$R^{11}$, —C(═O)—N$R^{11}R^{11a}$, $R^{11}R^{11a}$N—$O_2$S—, $R^{11}O_2$S—, $R^{11a}R^{11}$N-alkyl, $R^{11}$O-alkyl, aliphatic, haloaliphatic, arylaliphatic, heterocyclyl aliphatic, cycloalkyl aliphatic, aryl, heteroaryl, heterocyclyl, or carbocyclyl, with the proviso that $R^1$ and $R^2$, together with the nitrogen atom they are attached to, optionally form a substituted or unsubstituted 3-8 membered heterocyclic ring; and $R^3$ and $R^4$, together with the carbon atom they are attached to, optionally form a substituted or unsubstituted 3-8 membered carbocyclic or heterocyclic ring;

each of $Y_1$ and $Y_2$ is independently a divalent group derived from aliphatic-C(═O)—, aliphatic-C(═O)O—, aliphatic-C(═O)N$R^{11}$—, —$R^{11}$N—$O_2$S-aliphatic, —$O_2$S—, —$R^{11}$N-aliphatic, —S(═O)-aliphatic, —$R^{11}$N—C(═O)-aliphatic, fused bicyclylalkylene, fused hetero-bicyclyl alkylene, spiro bicyclylalkylene, spiro heterobicyclyl alkylene, arylalkylene, heteroarylalkylene, alkylene; haloalkylene, heterocyclylene, carbocyclylene, heterocyclylalkylene, carbocyclylalkylene, fused bicyclylene, fused heterobicyclylene, spiro bicyclylene, spiro heterobicyclylene, arylene, or heteroarylene;

W is O, N—$R^{11}$ or $(CR^{12}R^{12a})$m; m is selected from 0, 1, 2 or 3;

Q is:

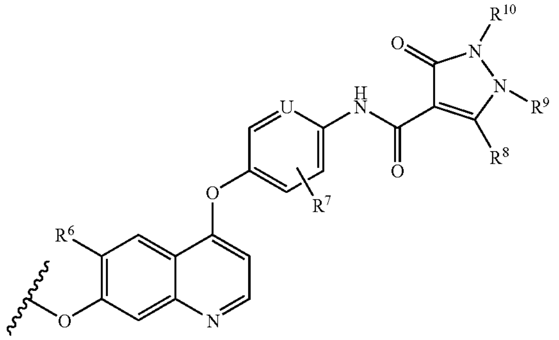

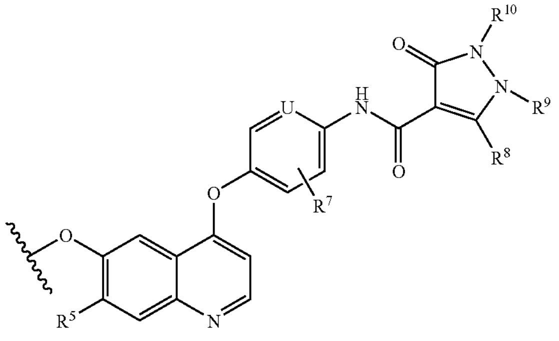

-continued

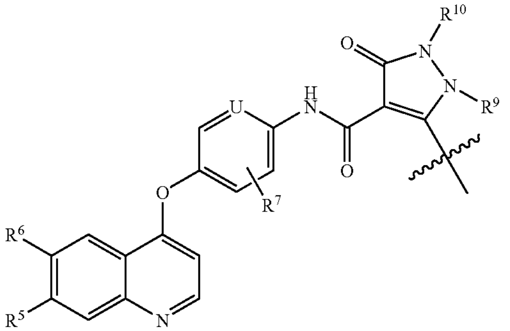

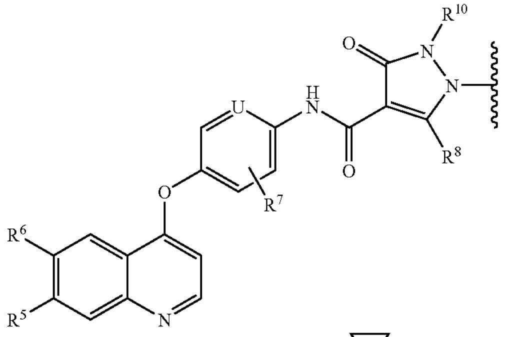

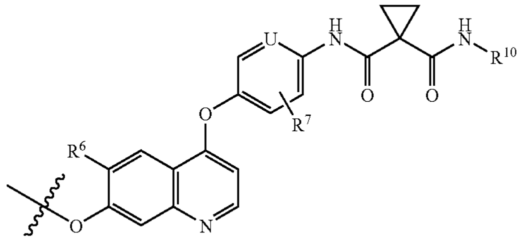

or

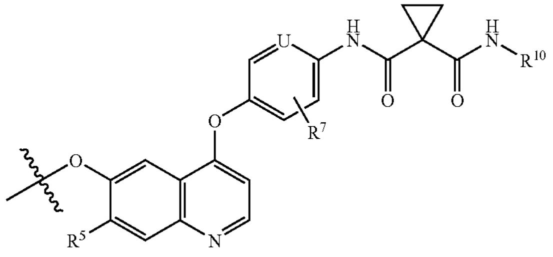

U is $CR^{12}$ or N;

each of $R^5$, $R^6$ is independently H, F, Cl, Br, I, cyano(CN), hydroxyl, $R^{11a}R^{11}$N—, —C(═O)—$R^{11}$, —C(═O)N$R^{11}R^{11a}$, —OC(═O)N$R^{11}R^{11a}$, —OC(═O)O$R^{11}$, —N$R^{11}$C—(═O)N$R^{11}R^{11a}$, —N$R^{11}$C(═O)O$R^{11a}$, —N$R^{11}$C(═O)—$R^{11a}$, $R^{11}R^{11a}$N—$O_2$S—, $R^{11}O_2$S—, $R^{11}O_2$S—$R^{11a}$N—, $R^{11a}R^{11}$N-alkyl, $R^{11}$(S═O)-alkyl, $R^{11}R^{11a}$N—(C═O)-alkyl, $R^{11a}R^{11}$N-alkoxy, $R^{11}$(S═O)-alkoxy, $R^{11}R^{11a}$N—(C═O)-alkoxy, aliphatic, alkoxy, hydroxyalkoxy, amino-alkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxy-alkoxy, arylalkoxy, heterocyclylalkoxy, carbocyclylalkoxy, heterocyclyl(hydroxy-alkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicycloxoalkoxy, fused heterobicycloxoalkoxy, fused bicyclyl aminoalkoxy, fused hetero-bicyclyl aminoalkoxy, spiro bicyclyl, spiro heterobicyclyl, spiro bicyclyl aliphatic, spiro heterobicyclyl aliphatic, spiro bicycloxy, spiro hetero-bicycloxy, spiro bicycloxo-alkoxy, spiro heterobicy-cloxoalkoxy, spiro bicyclylaminoalkoxy, spiro heterobicy-clyl-aminoalkoxy, aryl, heteroaryl, arylaliphatic or heteroarylaliphatic;

$R^7$ is one or more substituents independently selected at each occurrence from H, F, Cl, Br, I, —CN, hydroxyl, $R^{11a}R^{11}N$—, aliphatic, alkoxy, haloalkyl, hetero-cyclyl, heterocyclylalkyl, cycloalkyl, cycloalkylalkyl, cycloalkylalkoxy, and heterocyclylalkoxy;

each of $R^8$, $R^9$ and $R^{10}$ is independently H, —C(═O)$R^{11}$, —C(═O)O$R^{11}$, —C(═O)—N$R^{11}R^{11a}$, $R^{11}R^{11a}N$—$O_2S$—, $R^{11}O_2S$—, $R^{11a}R^{11}$N-alkyl, $R^{11}$(S═O)-alkyl, $R^{11}R^{11a}$N(C═O)-alkyl, aliphatic, hydroxyalkyl, hydroxy-substituted aminoalkyl, haloalkyl, amino-substituted haloalkyl, alkylamino haloalkyl, hydroxy-substituted haloalkyl, alkoxyalkyl, arylalkyl, heterocyclylalkyl, carbocyclylalkyl, heterocyclyl-hydroxyalkyl, carbocyclyl-hydroxyalkyl, aryl-hydroxyalkyl, aryloxyalkyl, heterocyclyloxyalkyl, carbocyclyloxy-alkyl, heterocyclylyl, cycloalkylyl, (heterocyclo)hydroxy-alkyl, azidoalkyl, fused bicyclyl, fused heterobicyclyl, fused bicyclyl aliphatic, fused heterobicyclyl aliphatic, fused bicycloxoalkyl, fused heterobicycloxoalkyl, fused bicyclyl aminoalkyl, fused heterobicyclyl aminoalkyl, spiro bicyclyl, spiro heterobicyclyl, spiro bicyclyl aliphatic, spiro heterobicyclyl aliphatic, spiro bicycloxoalkyl, spiro hetero-bicycloxoalkyl, spiro bicyclylaminoalkyl, spiro heterobicyclylaminoalkyl, aryl, heteroaryl, arylaliphatic or heteroarylaliphatic;

each of $R^{11}$ and $R^{11a}$ is independently H, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryl, heteroaryl, heterocyclyl, or carbocyclyl, with the proviso that where $R^{11}$ and $R^{11a}$ are bonded to the same nitrogen atom, $R^{11}$ and $R^{11a}$ together with the nitrogen atom they are attached to, optionally form a substituted or unsubstituted 3-8 membered ring (including a spiro ring or a fused bicyclic ring); and each of $R^{12}$ and $R^{12a}$ is independently H, F, Cl, Br, I, cyano (CN), hydroxyl, —N$R^{11a}R^{11}$, —OC(═O)$R^{11}$, —C(═O)O$R^{11}$, —C(═O)N$R^{11}R^{11a}$, —OC(═O)N$R^{11}R^{11a}$, —OC(═O)O$R^{11}$, —C(═O)N$R^{11}R^{11a}$, —N$R^{11}$C(═O)O$R^{11a}$, —N$R^{11}$—C(═O)—$R^{11a}$, $R^{11}R^{11a}N$—$O_2S$—, $R^{11}O_2S$—, $R^{11}O_2S$—N($R^{11a}$)—, alkoxy, cycloalkoxy, heterocycloalkoxy, aliphatic, haloaliphatic, hydroxyaliphatic, aminoaliphatic, alkoxyaliphatic, alkylaminoaliphatic, alkylthioaliphatic, arylaliphatic, heterocyclyl-aliphatic, cycloalkylaliphatic, aryl, heteroaryl, heterocyclyl, or carbocyclyl, with the proviso that where $R^{12}$ and $R^{12a}$ are bonded to the same carbon atom, $R^{12}$ and $R^{12a}$, together with the carbon atom they are attached to, optionally form a substituted or unsubstituted 3-8 membered carbocyclic or heterocyclic ring.

In certain embodiments, the pharmaceutically acceptable salt is a salt with hydrochloric acid, hydrobromic acid, sulfuric acid, nitric acid, phosphoric acid, acetic acid, maleic acid, succinic acid, mandelic acid, fumaric acid, malonic acid, malic acid, 2-hydroxypropanic acid, pyruvic acid, oxalic acid, glycolic acid, salicylic acid, glucuronic acid, galacturonic acid, citric acid, tartaric acid, aspartic acid, glutamic acid, benzoic acid, cinnamic acid, p-toluenesulfonic acid, benzenesulfonic acid, mthanesulfonic acid, ethanesulfonic acid, trifluoromthanesulfonic acid and a combination thereof.

In some embodiments, the α-amino acetyl group defined by $R^1$, $R^2$, $R^3$ and $R^4$ of Formula (I) is derived from a naturally occurring and commercially available α-amino acid or an optically isomer thereof.

In another embodiment, the natural and commercially available α-amino acid is isoleucine, leucine, lysine, methionine, phenylalanine, threonine, tryptophan, valine, alanine, asparagine, aspartate, glutamate, glutamine, proline, serine, para-tyrosine, arginine, histidine, cysteine, glycine, sarcosine, N,N-dimethyl glycine, homoserine, norvaline, norleucine, ornithine, homocysteine, homophenylalanine, phenylglycine, ortho-tyrosine, meta-tyrosine or hydroxyproline.

In another embodiment, the natural α-amino acid is isoleucine, leucine, lysine, methionine, phenylalanine, threonine, tryptophan, valine, alanine, asparagine, aspartate, glutamate, glutamine, proline, serine, tyrosine, arginine, or histidine, each of which has a S-configuration at the α-position.

In another embodiment, the natural and commercially available α-amino acid is the cysteine having a R-configuration at its α-position.

In another embodiment, the natural and commercially available α-amino acid is glycine, sarcosine or N,N-dimethyl glycine, each of which is a non-chiral compound.

In some embodiments, each of $Y_1$ and $Y_2$ is independently a divalent group derived from $C_{1-6}$aliphatic-C(═O)—, $C_{1-6}$aliphatic-C(═O)O—, $C_{1-6}$aliphatic-C(═O)N$R^{11}$—, —$R^{11}$N—$O_2SC_{1-6}$aliphatic, —$O_2S$—$C_{1-6}$aliphatic, —$R^{11}NC_{1-6}$aliphatic, —S(═O)$C_{1-6}$ aliphatic, —$R^{11}$N—C(═O)—$C_{1-6}$aliphatic, fused $C_{6-10}$bicyclyl $C_{1-6}$alkylene, fused $C_{5-9}$hetero-bicyclyl $C_{1-6}$ alkylene, spiro $C_{7-11}$bicyclyl $C_{1-6}$ alkylene, spiro $C_{6-10}$heterobicyclyl $C_{1-6}$ alkylene, $C_{1-6}$haloalkylene, $C_{2-8}$heterocyclylene, $C_{3-8}$carbocyclylene, $C_{2-8}$heterocyclyl $C_{1-6}$ alkylene, $C_{3-8}$carbocyclyl $C_{1-6}$alkylene, fused $C_{6-10}$bicyclylene, fused $C_{5-9}$heterobicyclyl-ene, spiro $C_{7-11}$bicyclylene, or spiro $C_{6-10}$heterobicyclylene;

W is O, N—$R^{11}$ or ($CR^{12}R^{12a}$)m; m is selected from 0, 1 and 2;

Q is:

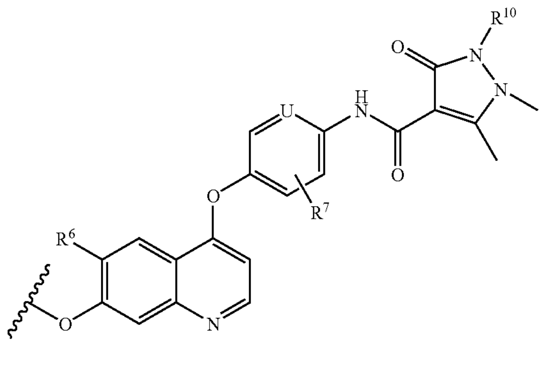

-continued

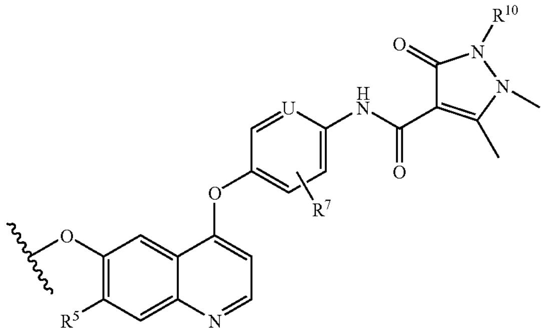

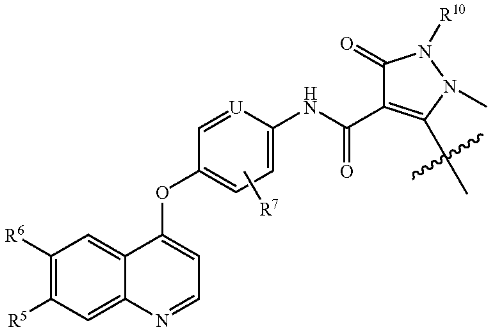

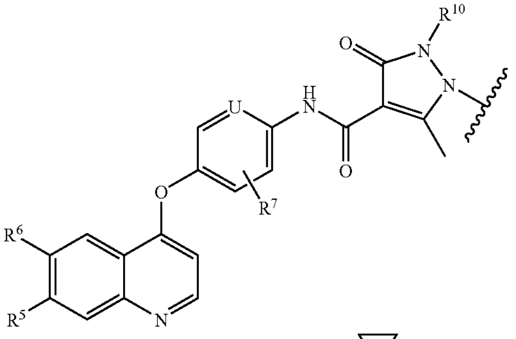

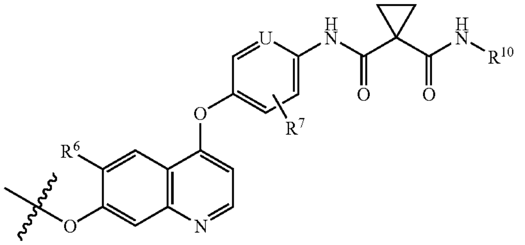

or

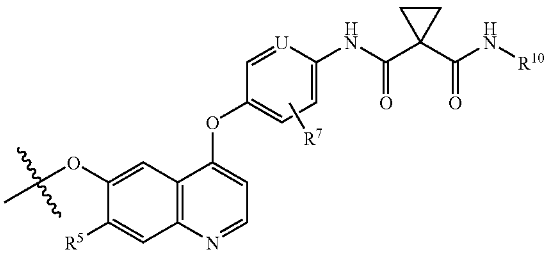

U is CH or N;

Each of $R^5$ and $R^6$ is independently H or methoxy;

$R^7$ is H or F;

$R^{10}$ is phenyl or fluorophenyl;

Each of $R^{11}$ and $R^{11a}$ is independently H, $C_{1-3}$alkyl, $C_{1-3}$haloalkyl, $C_{1-3}$ hydroxy-alkyl, $C_{1-3}$aminoalkyl, $C_{1-3}$alkoxy $C_{1-3}$alkyl, $C_{1-3}$alkylamino $C_{1-3}$alkyl, $C_{6-10}$aryl $C_{1-3}$alkyl, $C_{5-9}$heterocyclyl $C_{1-3}$alkyl, $C_{3-6}$cycloalkyl $C_{1-3}$alkyl, $C_{6-10}$aryl, $C_{5-9}$heteroaryl, $C_{2-5}$ hetero-cyclyl, or $C_{3-6}$carbocyclyl, with the proviso that where $R^{11}$ and $R^{11a}$ are bonded to the same nitrogen atom, $R^{11}$ and $R^{11a}$, together with the nitrogen atom they are attached to, optionally form a substituted or unsubstituted 3-8 membered ring (including spiro and fused bicyclic ring); and Each of $R^{12}$ and $R^{12a}$ is independently H, halo (F, Cl, Br and I), hydroxyl, —$NR^{11a}R^{11}$, —OC(═O)$R^{11}$, —C(═O)$R^{11}$, —C(═O)O$R^{11}$, —C(═O)N$R^{11}R^{11a}$, —OC(═O)N$R^{11}R^{11a}$, —OC(═O)R, C(═O)O$R^{11}$, —N$R^{11}$C(═O)N$R^{11}R^{11a}$, —N$R^{11}$C(═O)O$R^{11a}$, —N$R^{11}$C(═O)—$R^{11a}$, $R^{11}R^{11a}$N—$O_2$S—, $R^{11}O_2$S—, $R^{11}R^{11a}O_2$SN—, —CN, hydroxyl, $C_{1-6}$alkoxy, $C_{3-6}$cycloalkoxy, $C_{2-5}$ hetero-cyclo $C_{1-6}$alkoxy, $C_{1-6}$aliphatic, $C_{1-6}$haloaliphatic, hydroxy $C_{1-6}$aliphatic, amino $C_{1-6}$ aliphatic, $C_{1-6}$alkoxy $C_{1-6}$aliphatic, $C_{1-6}$alkylamino $C_{1-6}$aliphatic, $C_{1-6}$alkylthio $C_{1-6}$ aliphatic, $C_{6-10}$aryl $C_{1-6}$aliphatic, $C_{1-9}$ heteroaryl $C_{1-6}$aliphatic, $C_{2-5}$ heterocyclyl $C_{1-6}$ aliphatic, $C_{3-6}$cycloalkyl $C_{1-6}$aliphatic, $C_{6-10}$aryl, $C_{1-9}$heteroaryl, $C_{2-5}$heterocyclyl, or $C_{3-6}$ carbocyclyl, with the proviso that where $R^{12}$ and $R^{12a}$ are bonded to the same carbon atom, $R^{12}$ and $R^{12a}$, together with the carbon atom they are attached to, optionally form a substituted or unsubstituted 3-8 membered carbocyclic or heterocyclic ring.

In some embodiments, Q is:

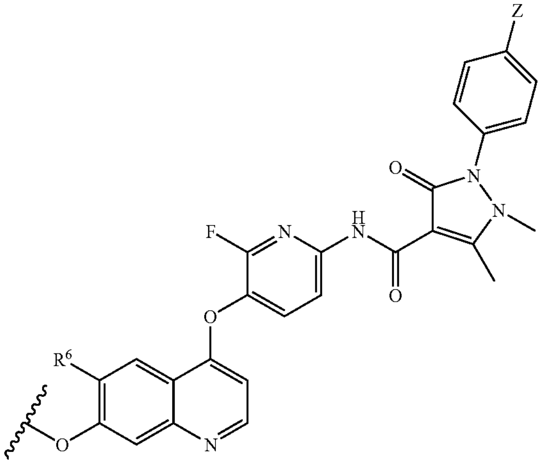

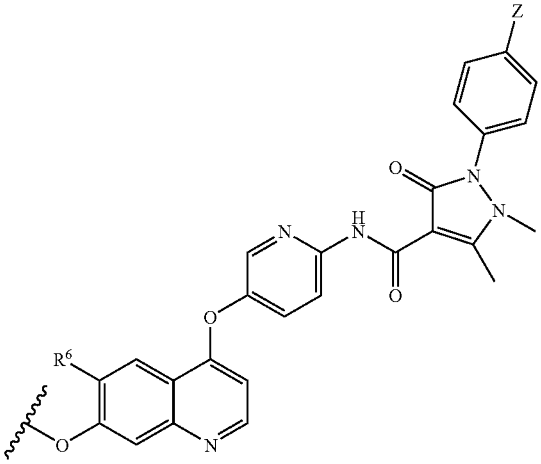

-continued
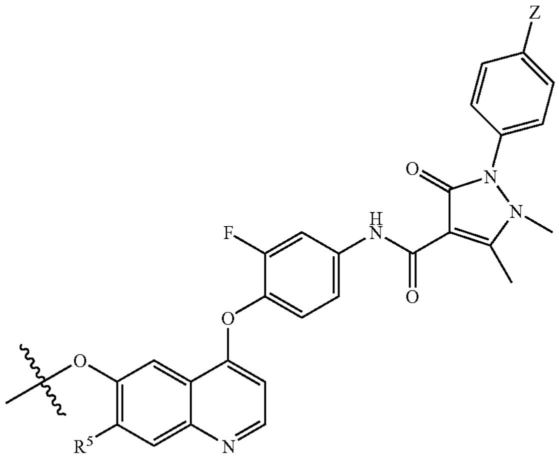
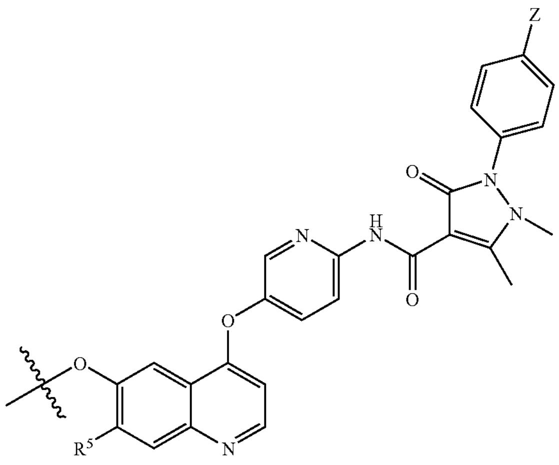
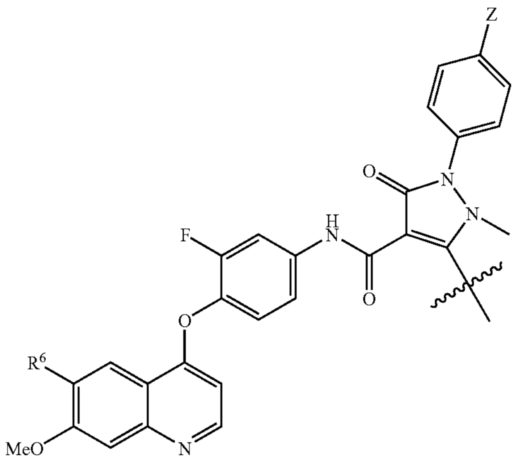
-continued
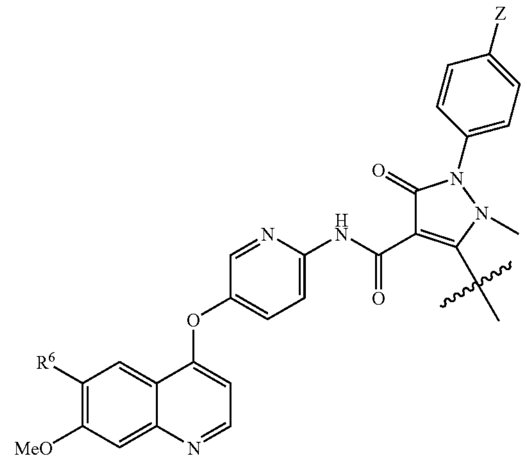
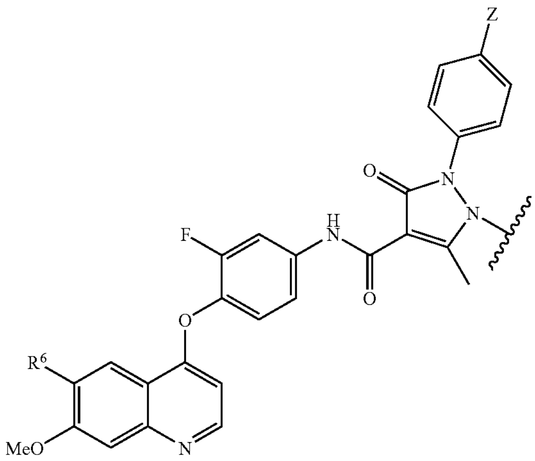
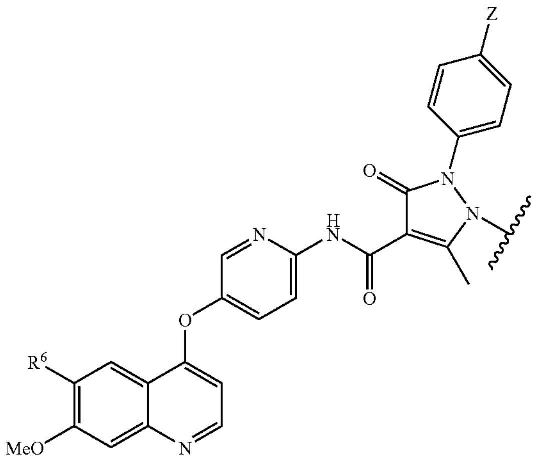
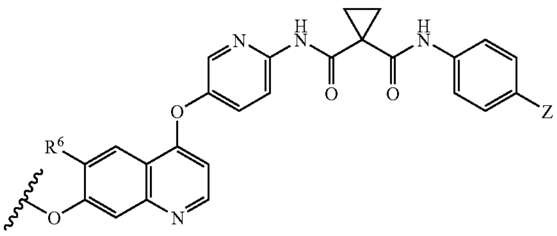

-continued
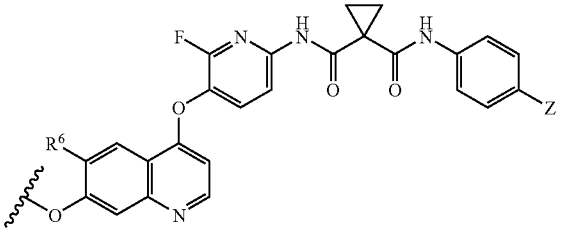
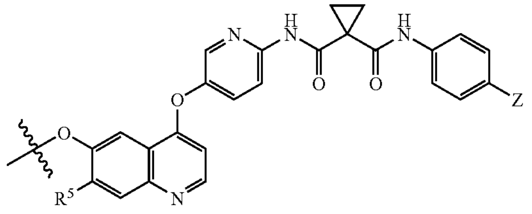
or
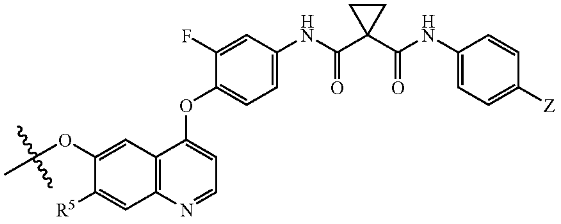
each of $R^5$ and $R^6$ is independently H or OMe; Z is H or F.
In some embodiments, the structure defined by $Y_1$, $Y_2$, W and Q is:
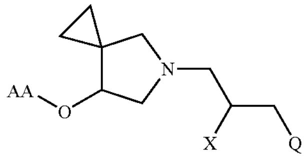
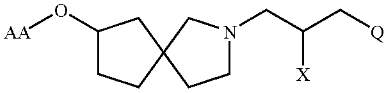
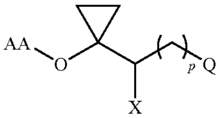
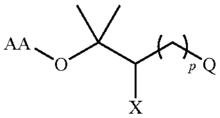
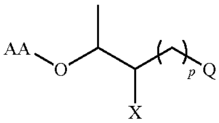
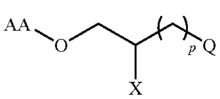
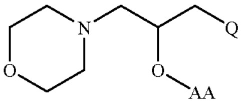
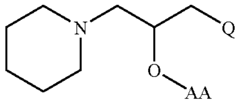
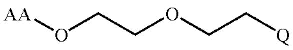
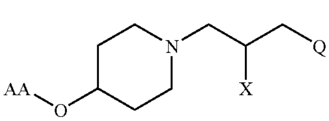
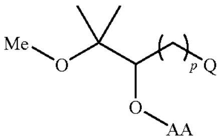
-continued
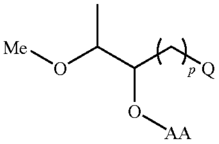
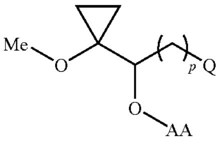
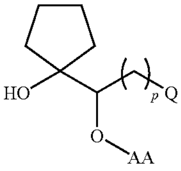
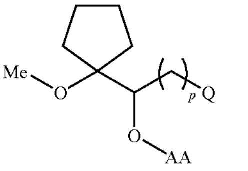
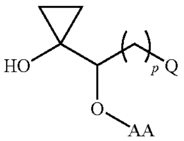
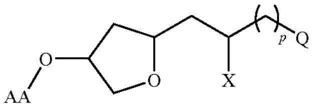
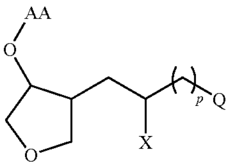
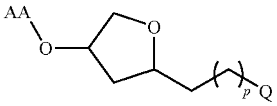
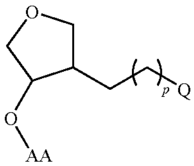
or
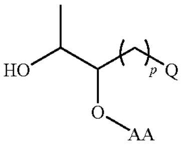
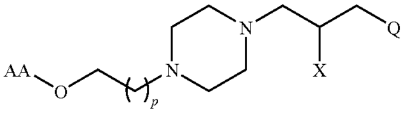
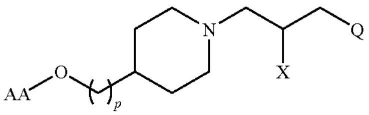
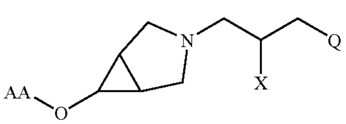
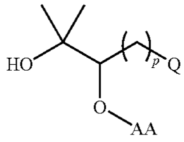
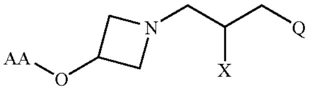
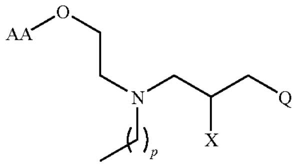
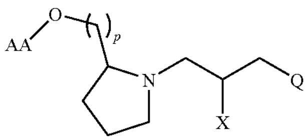
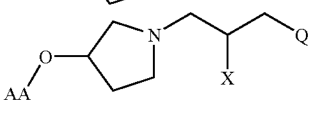
wherein AA is an amino acetyl moiety defined by $R^1$, $R^2$, $R^3$ and $R^4$; X is H or OH; p is 0, 1, 2 or 3.

In some embodiments, non-limiting examples of compounds disclosed herein, and their pharmaceutically acceptable salts and solvates thereof, are shown in the following:
TABLE 1
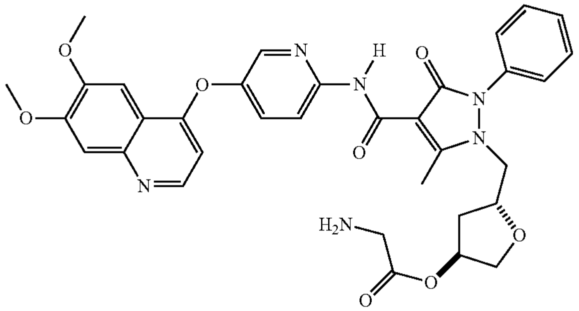
(1)
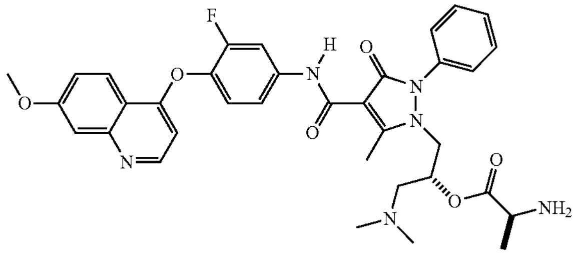
(2)
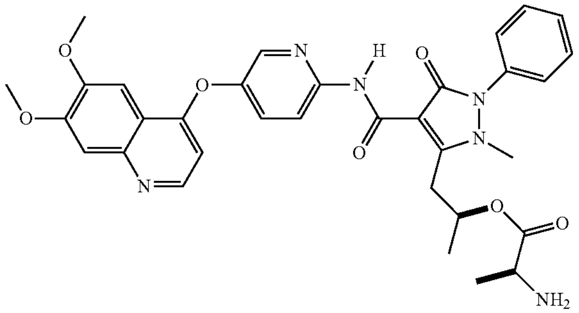
(3)
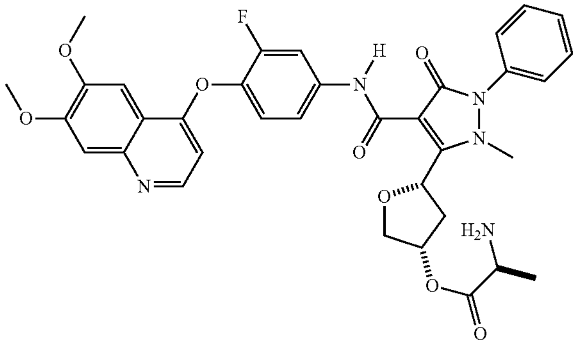
(4)
TABLE 1-continued
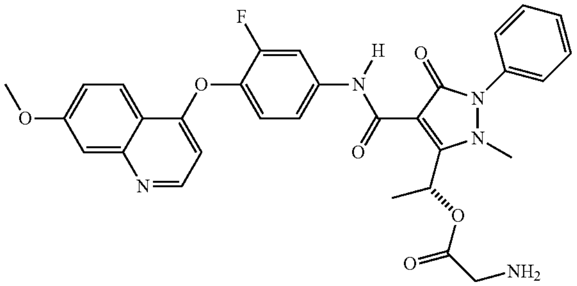
(5)
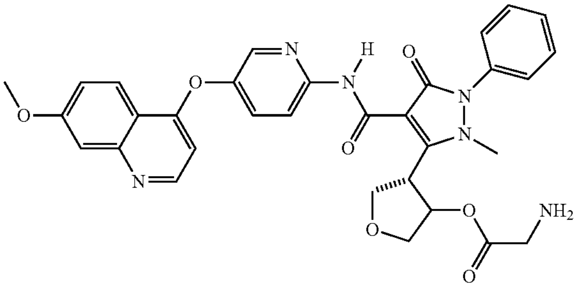
(6)
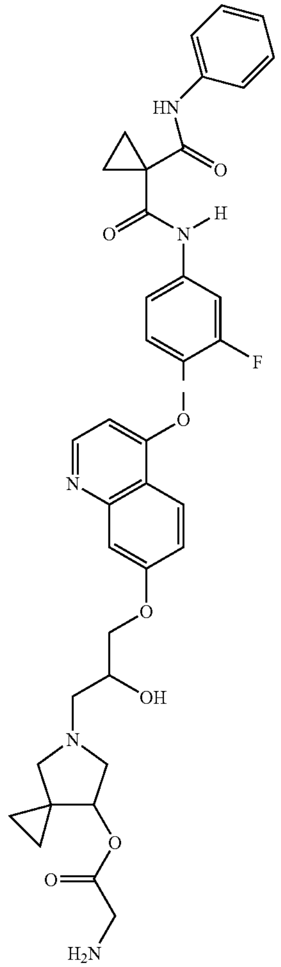
(7)

TABLE 1-continued
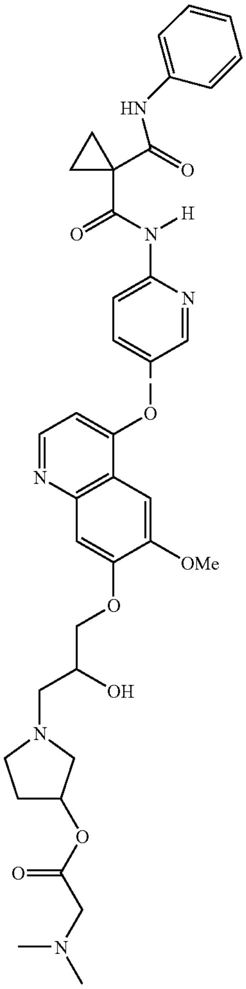
(8)
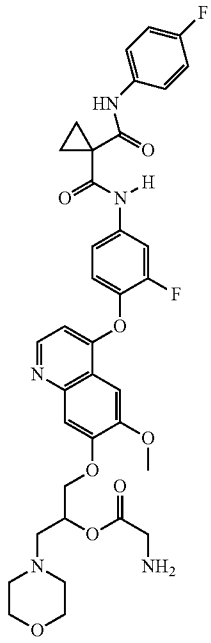
(9)
TABLE 1-continued
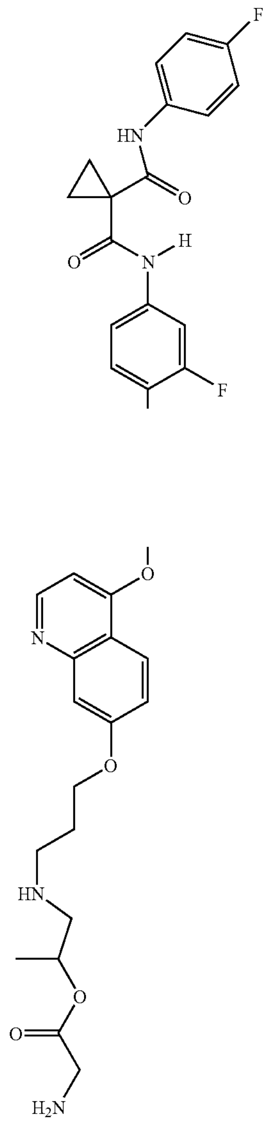
(10)
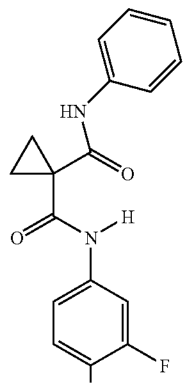

TABLE 1-continued
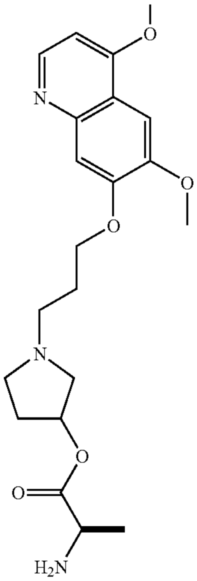
(11)
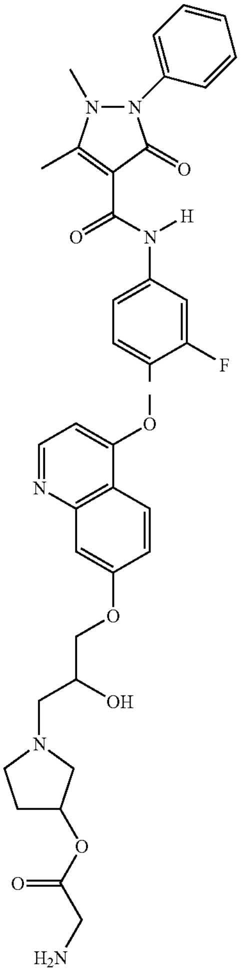
(12)
TABLE 1-continued
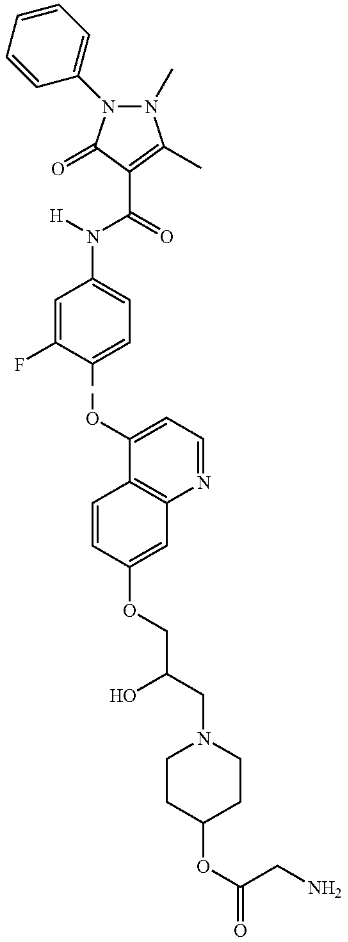
(13)
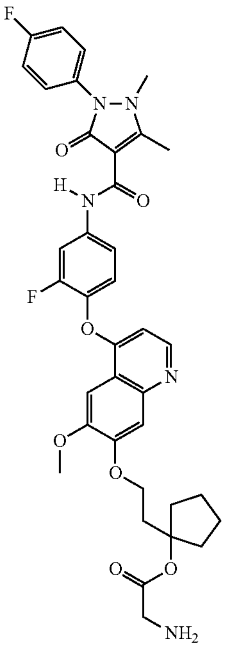
(14)

TABLE 1-continued
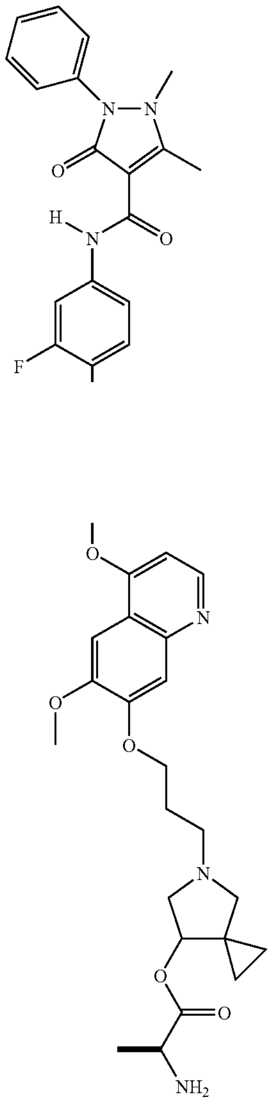
(15)
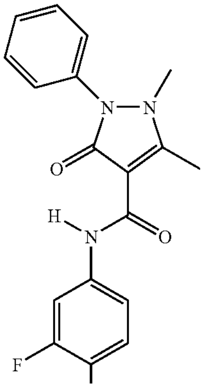
TABLE 1-continued
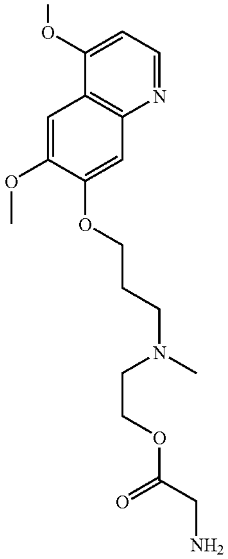
(16)
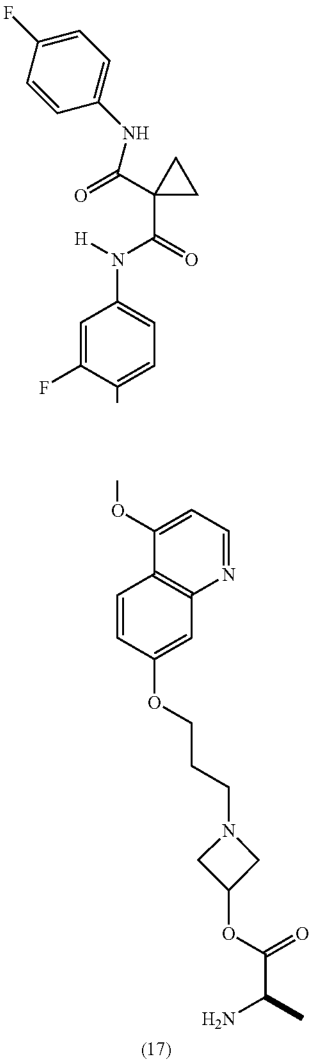
(17)

TABLE 1-continued
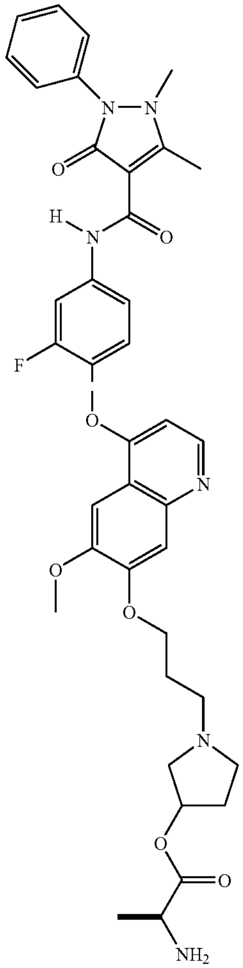
(18)
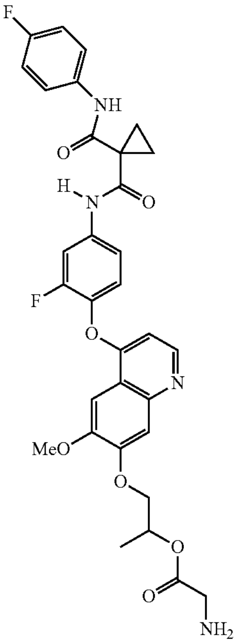
(19)
TABLE 1-continued
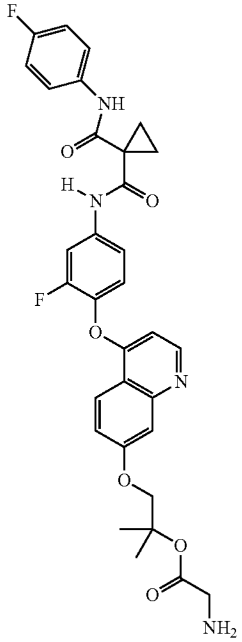
(20)
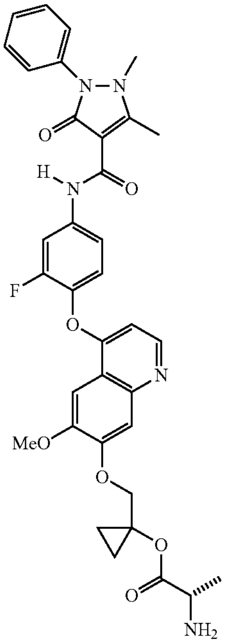
(21)

TABLE 1-continued

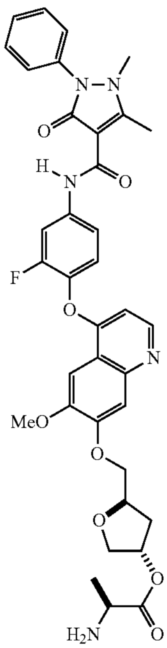

(22)

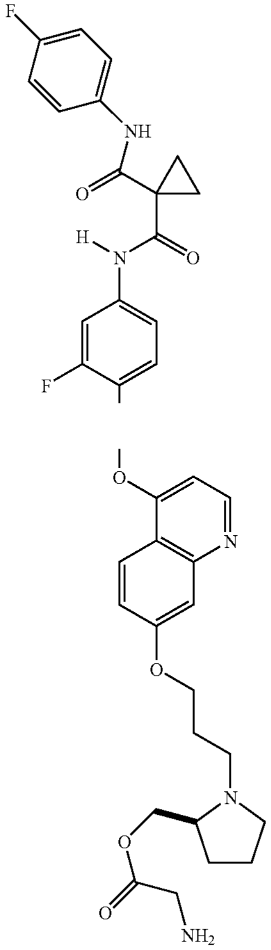

(23)

TABLE 1-continued

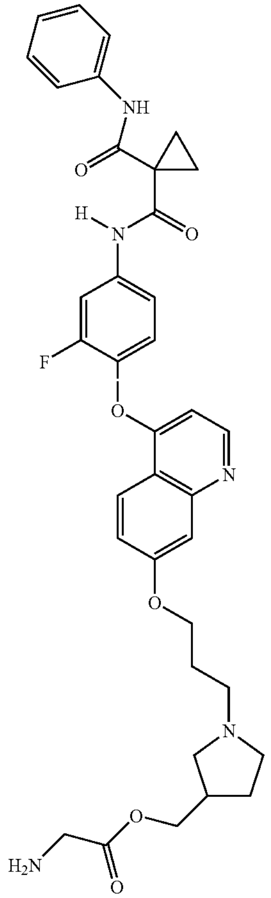

(24)

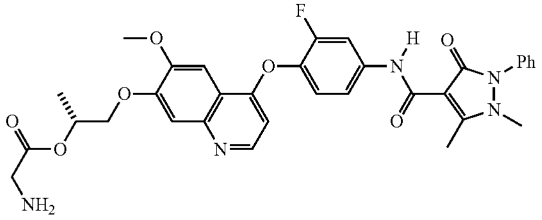

and (25)

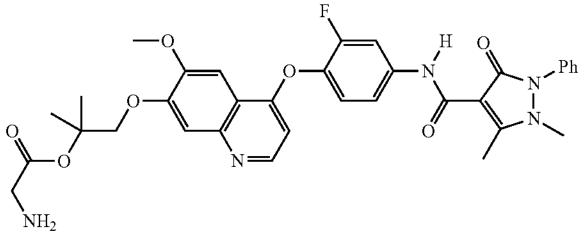

(26)

In another aspect, provided herein are pharmaceutical compositions comprising a compound disclosed herein, or a stereoisomer, geometric isomer, tautomer, solvate, metabolite, pharmaceutically acceptable salt or prodrug thereof, and an optional pharmaceutically acceptable carrier, excipient, diluent, adjuvant, vehicle or a combination thereof. In certain embodiments, the compound is an inhibitor of protein tyrosine kinase. In other embodiments, the compound is an inhibitor of VEGF receptor signaling, HGF receptor signaling and/or IGF receptor signaling.

In some embodiments, the pharmaceutical composition disclosed herein further comprises an additional therapeutic agent. In other embodiments, the therapeutic agent is a chemotherapeutic agent, an anti-proliferative agent, an agent for treating atherosclerosis, an agent for treating lung fibrosis, and combinations thereof.

In certain embodiments, the therapeutic agent is adriamycin, rapamycin, temsirolimus, everolimus, ixabepilone, gemcitabine, cyclophosphamide, dexamethasone, etoposide, fluorouracil, imatinib mesylate, dasatinib, nilotinib, erlotinib, lapatinib, iressa, sorafenib, sunitinib, pazopanib, an interferon, carboplatin, topotecan, taxol, vinblastine, vincristine, temozolomide, tositumomab (Bexxar), trabedectin, bevacizumab (Avastin), trastuzumab (Herceptin), cetuximab (Erbitux), panitumumab (Vectibix) or a combination thereof.

In another aspect, provided herein are methods for preventing, managing, treating or lessening the severity of a proliferative disorder in a patient infected with the proliferative disorder, which comprises administrating a pharmaceutically effective amount of a compound disclosed herein, or the pharmaceutical composition disclosed herein to the patient.

In another aspect, provided herein is use of the compound disclosed herein, or the pharmaceutical composition disclosed herein in the manufacture of a medicament for preventing, managing, treating or lessening the severity of a proliferative disorder in a patient.

In some embodiments, the proliferative disorder is metastatic cancer. In other embodiments, the proliferative disorder is colon cancer, gastric adenocarcinoma, bladder cancer, breast cancer, kidney cancer, liver cancer, lung cancer, thyroid cancer, cancer of the head and neck, prostate cancer, pancreatic cancer, cancer of the CNS, glioblastoma, or a myeloproliferative disorder. In further embodiments, the proliferative disorder is atherosclerosis or lung fibrosis.

In another aspect, provided herein is a method of inhibiting or modulating protein kinase activity in a biological sample comprising contacting a biological sample with the compound disclosed herein, or the pharmaceutical composition disclosed herein.

In some embodiments, the protein kinases are receptor tyrosine kinases. In other embodiments, the receptor tyrosine kinases are KDR and/or c-Met.

In another aspect, provided herein is a method of inhibiting protein tyrosine kinase, the method comprises contacting the kinase with the compound disclosed herein, or with the composition disclosed herein. In other embodiments, provided herein is a method of inhibiting VEGF receptor signaling and/or HGF receptor signaling, the method comprises contacting the receptor with the compound disclosed herein, or with the pharmaceutical composition disclosed herein. In some embodiments, inhibition of receptor protein kinase activity, such as VEGF and/or HGF receptor signaling, can be in a cell or a multicellular organism. If in a multicellular organism, the method disclosed herein may comprise administering to the organism the compound disclosed herein, or the pharmaceutical composition disclosed herein. In some embodiments, the organism is a mammal; in other embodiments, the organism is a human. In still other embodiments, the method further comprises contacting the kinase with an additional therapeutic agent.

In another aspect, provided herein is a method of inhibiting proliferative activity of a cell, wherein the method comprises contacting the cell with an effective proliferative inhibiting amount of the compound disclosed herein or the pharmaceutical composition disclosed herein. In some embodiments, the method further comprises contacting the cell with an additional therapeutic agent.

In another aspect, provided herein is a method of treating a cell proliferative disease in a patient, wherein the method comprises administering to the patient in need of such treatment an effective therapeutic amount of the compound disclosed herein or the pharmaceutical composition disclose herein. In other embodiments, the method further comprises administering an additional therapeutic agent.

In another aspect, provided herein is a method of inhibiting tumor growth in a patient, the method comprises administering to the patient in need thereof an effective therapeutic amount of a compound disclosed herein or a composition thereof. In other embodiments, the method further comprises administering an additional therapeutic agent.

In another aspect, provided herein include methods of preparing, methods of separating, and methods of purifying compounds of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Figure 1:
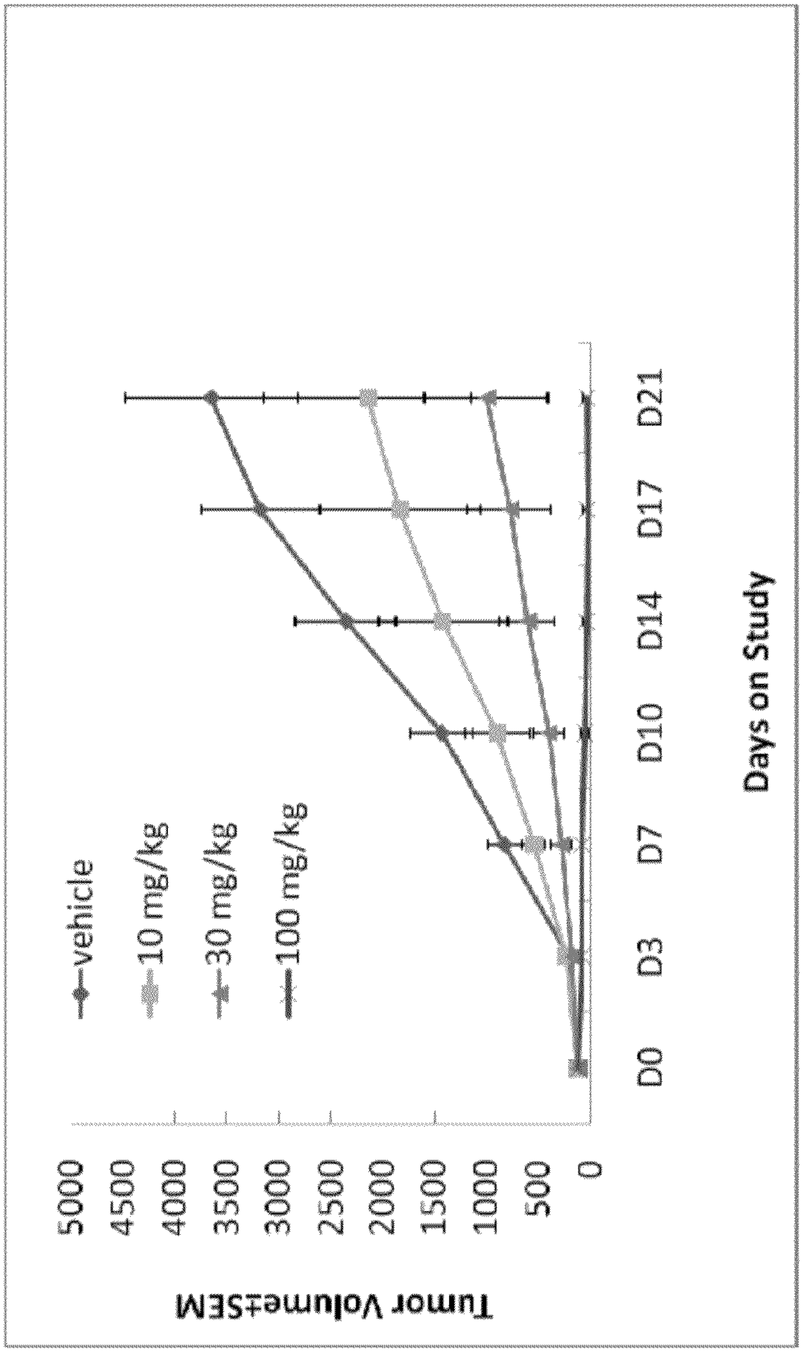
FIG. 1 depicts U87MG Tumor Growth Inhibition with Example 53.
Figure 2:
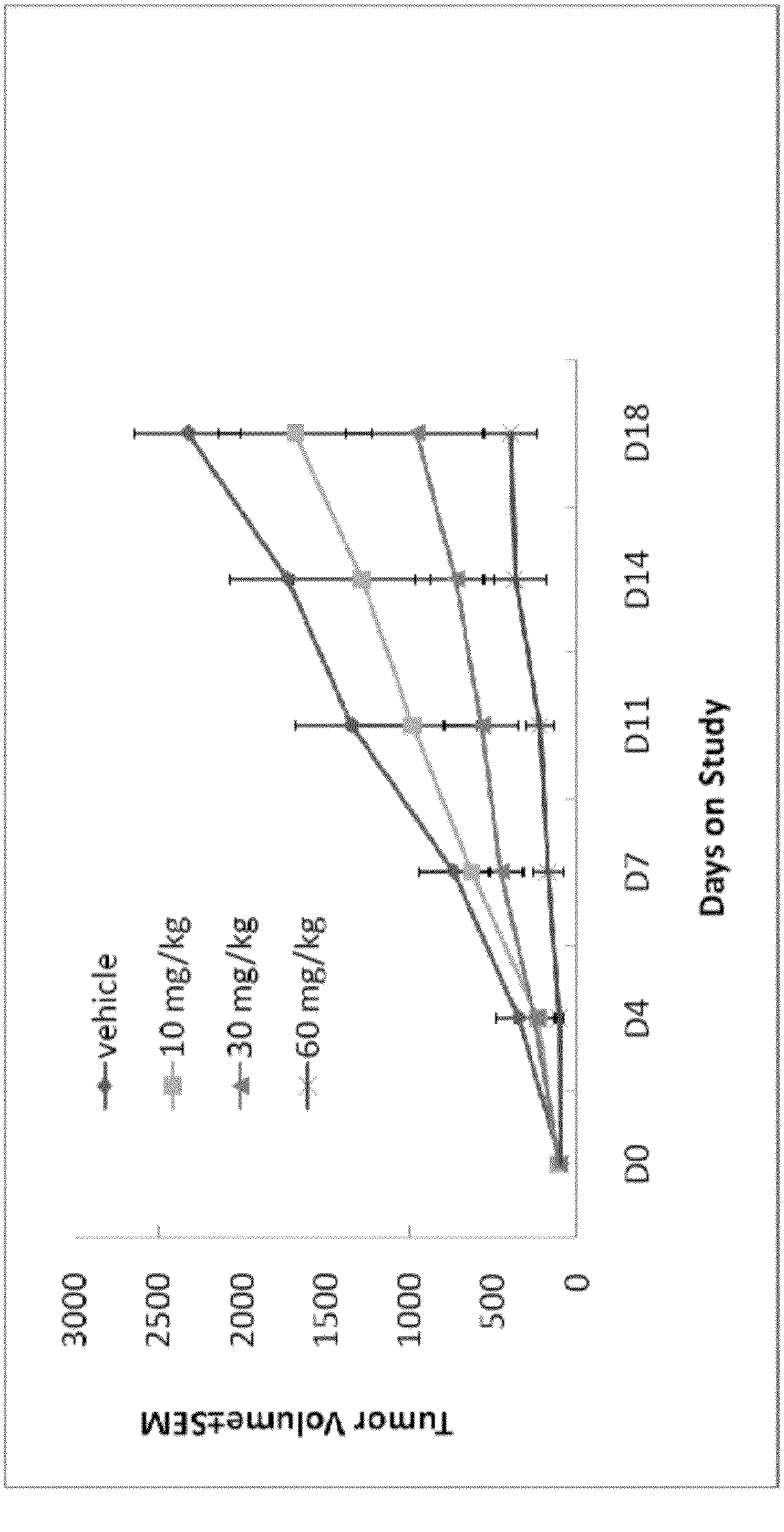
FIG. 2 depicts MKN45 Tumor Growth Inhibition with Example 72.

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and the *Handbook of Chemistry and Physics,* $75^{th}$ Ed. 1994. Additionally, general principles of organic chemistry are described in "*Organic Chemistry*", Thomas Sorrell, University Science Books, Sausalito: 1999, and "*March's Advanced Organic Chemistry*" by Michael B. Smith and Jerry March, John Wiley & Sons, New York: 2007, the entire contents of which are hereby incorporated by reference.

As described herein, compounds may optionally be substituted with one or more substituents, such as are illustrated generally above, or as exemplified by particular classes, subclasses, and species disclosed herein. It will be appreciated that the phrase "optionally substituted" is used interchangeably with the phrase "substituted or unsubstituted". In general, the term "substituted" whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

The term "aliphatic" or "aliphatic group" as used herein, refers to a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkylene, alkenyl, or alkynyl groups.

The term "alkyl" as used herein refers to a saturated linear or branched-chain monovalent hydrocarbon radical of one to twenty carbon atoms, wherein the alkyl radical may be optionally substituted independently with one or more substituents described below. Further examples of aliphatic groups include, but are not limited to, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$, 1-heptyl, 1-octyl, and the like. The terms "alkyl" and the prefix "alk-" as used herein, are inclusive of both straight chain and branched saturated carbon chain.

The term "alkylene", as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkenyl" refers to linear or branched-chain monovalent hydrocarbon radical of two to twelve carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl ($-CH=CH_2$), allyl ($-CH_2CH=CH_2$), and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl ($-C\equiv CH$), propynyl (propargyl, $-CH_2C\equiv CH$), and the like.

The term "cycloaliphatic" (or "carbocycle", "carbocyclyl", "carbocyclic ring" and "cycloalkyl") refers to a monovalent or multivalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Suitable cycloaliphatic groups include, but are not limited to, cycloalkyl, cycloalkenyl, and cycloalkynyl. Further examples of cycloaliphatic groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "carbocyclylene", as used herein, represents a saturated divalent hydrocarbon ring having 3 to 12 carbon atoms as a monocyclic ring or 7 to 12 carbon atoms as a bicyclic ring by the removal of two hydrogen atoms, and is exemplified by cyclopropylene, cyclobutylene, cyclopentylene, 1-cyclopent-1-enylene, 1-cyclopent-2-enylene, and the like.

The term "heterocycle", "heterocyclyl", "heterocycloaliphatic", or "heterocyclic" as used interchangeably herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. One or more ring atoms are optionally substituted independently with one or more substituents described below. In some embodiments, the "heterocycle", "heterocyclyl", "heterocycloaliphatic" or "heterocyclic" group is a monocycle having 3 to 7 ring members (e.g., 1 to 6 carbon atoms and 1 to 3 heteroatoms selected from N, O, P or S, wherein the S or P is optionally substituted with one or more oxo to provide the group SO or $SO_2$, PO or $PO_2$, with the proviso that when the ring is a 3-membered ring, there is only one heteroatom) or a bicycle having 7 to 10 ring members (e.g., 4 to 9 carbon atoms and 1 to 3 heteroatoms selected from N, O, P or S, wherein the S or P is optionally substituted with one or more oxo to provide the group SO or $SO_2$, PO or $PO_2$).

The heterocyclyl may be a carbon radical or heteroatom radical. "Heterocyclyl" also includes radicals where heterocycle radicals are fused with a saturated, partially unsaturated ring, or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 1,2,3,4-tetrahydroisoquinolinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Some non-limiting examples of a heterocyclic ring include 1,1-dioxo-thiomorpholinyl and heterocyclic group wherein 2 carbon atoms on the ring are substituted with oxo (=O) moieties are pyrimidindionyl. The heterocyclic groups herein are optionally substituted independently with one or more substituents described herein.

The term "heterocyclylene", as used herein, represents a monocyclic, bicyclic, or tricyclic ring system in which one or more ring members are an independently selected heteroatom and that is completely saturated or that contains one or more units of unsaturation, but which is not aromatic, that has two points of attachment to the rest of the molecule.

The term "heterocyclylalkyl" refers to heterocyclic-substituted alkyl radical. The term "heterocyclylalkoxy" refers to hetercyclic-substituted alkoxy radical wherein oxygen atom serves as the attaching point to the rest of the molecule. The term "heterocyclylalkylamino" refers to heterocyclic-substituted alkylamino radical wherein nitrogen atom serves as the attaching point to the rest of the molecule. The term "heterocyclyloxy" refers to heterocyclic-substituted oxygen radical wherein oxygen atom serves as the attaching point to the rest of the molecule. The terms "heterocyclylamino" refers to heterocyclic-substituted nitrogen radical wherein nitrogen atom serves as the attaching point to the rest of the molecule. The term "heterocyclylalkylene", as used herein, refers to a heterocyclylalkyl moiety as described herein, but has two points of attachment to the rest of the molecule.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to F, Cl, Br or I.

The term "unsaturated" as used herein, refers to that a moiety has one or more units of unsaturation.

The term "alkoxy" as used herein, refers to an alkyl group, as previously defined, attached to the principal carbon chain through an oxygen ("alkoxy") atom.

The terms "haloalkyl", "haloalkenyl" or "haloalkoxy" refers to alkyl, alkenyl, or alkoxy, as the case may be, substituted with one or more halogen atoms.

The term "haloalkylene", as used herein, represents a haloalkyl moiety as described herein, but has two points of attachment to the rest of the molecule.

The term "aryl" used alone or as part of a larger moiety as in "aralkyl", "aralkoxy" or "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Some non-limiting examples of aryl rings include phenyl, naphthyl, and anthracene.

The term "arylene", as used herein, represents an aryl system as described herein, but has two points of attachment to the rest of the molecule.

The term "heteroaryl" used alone or as part of a larger moiety as in "heteroaralkyl" or "heteroarylalkoxy" refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic".

The term "heteroarylene", as used herein, represents a heteroaryl system as described herein, but has two points of attachment to the rest of the molecule.

Some non-limiting examples of suitable heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), or isoquinolinyl (e.g., 1-isoquinolinyl, 3-isoquinolinyl, or 4-isoquinolinyl).

The term "sulfonyl", whether used alone or linked to other terms such as alkylsulfonyl, refers to respectively divalent radicals $—SO_2—$. The term "alkylsulfonyl", refers to a sulfonyl radical substituted with an alkyl radical, forming a alkylsulfonyl ($—SO_2CH_3$).

The terms "sulfamyl", "aminosulfonyl" and "sulfonamidyl" refer to a sulfonyl radical substituted with an amine radical, forming a sulfonamide ($—SO_2NH_2$).

The term "carboxy" or "carboxyl", whether used alone or with other terms, such as "carboxyalkyl", refers to $—CO_2H$. The term "carbonyl", whether used alone or with other terms, such as "aminocarbonyl" or "carbonyloxy", refers to $—(C{=}O)—$.

The term "alkylthio" refers to radicals containing a linear or branched alkyl radical, of one to ten carbon atoms, attached to a divalent sulfur atom. In other embodiments alkylthio radicals are lower alkylthio radicals having one to three carbon atoms. Some non-limiting examples of "alkylthio" include methylthio ($CH_3S—$).

The term "haloalkylthio" refers to radicals containing a haloalkyl radical, of one to ten carbon atoms, attached to a divalent sulfur atom. In other embodiments, haloalkylthio radicals are lower haloalkylthio radicals having one to three carbon atoms. Some non-limiting examples of "haloalkylthio" include trifluoromethylthio.

The term "alkylamino" refers to "N-alkylamino" and "N,N-dialkylamino" where amino groups are independently substituted with one alkyl radical or with two alkyl radicals, respectively. In other embodiments, alkylamino radicals are "lower alkylamino" radicals having one or two alkyl radicals of one to six carbon atoms, attached to a nitrogen atom. In still other embodiments, alkylamino radicals are lower alkylamino radicals having one to three carbon atoms. Some non-limiting examples of suitable alkylamino radicals include mono or dialkylamino such as N-methylamino, N-ethylamino, N,N-dimethylamino, N,N-diethylamino, and the like.

The term "arylamino" refers to amino groups, which have been substituted with one or two aryl radicals, Some non-limiting examples of arylamino include N-phenylamino. In some embodiments, the arylamino radicals include substituted on the aryl ring portion of the radical.

The term "heteroarylamino" refers to amino groups, which have been substituted with one or two heteroaryl radicals, Some non-limiting examples of heteroarylamino include N-thienylamino. In other embodiments, the "heteroarylamino" radicals include substituted on the heteroaryl ring portion of the radical.

The term "aminoalkyl" refers to linear or branched alkyl radicals having one to about ten carbon atoms any one of which includes substituted with one or more amino radicals. In some embodiments, aminoalkyl radicals are "lower aminoalkyl" radicals having one to six carbon atoms and one or more amino radicals. Some non-limiting examples of such radicals include aminomethyl, aminoethyl, aminopropyl, aminobutyl or aminohexyl.

The term "alkylaminoalkyl" refers to alkyl radicals substituted with alkylamino radicals. In some embodiments, alkylaminoalkyl radicals are "lower alkylaminoalkyl" radicals having alkyl radicals of one to six carbon atoms. In other embodiments, alkylaminoalkyl radicals are lower alkylaminoalkyl radicals having alkyl radicals of one to three carbon atoms. Some non-limiting examples of suitable alkylaminoalkyl radicals include mono or dialkyl substituted, such as N-methylaminomethyl, N,N-dimethyl-aminoethyl, N,N-diethylaminomethyl, and the like.

The term "alkylaminoalkoxy" refers to alkoxy radicals substituted with alkylamino radicals. Some non-limiting examples of suitable alkylaminoalkoxy radicals include mono or dialkyl substituted, such as N-methylaminoethoxy, N,N-dimethylaminoethoxy, N,N-diethylaminoethoxy, and the like.

The term "alkylaminoalkoxyalkoxy" refers to alkoxy radicals substituted with alkylaminoalkoxy radicals. Some non-limiting examples of suitable alkylaminoalkoxyalkoxy radicals include mono or dialkyl substituted, such as N-methylaminomethoxyethoxy, N-methylaminoethoxyethoxy, N,N-dimethylaminoethoxyethoxy, N,N-diethylaminomethoxymethoxy, and the like.

The term "carboxyalkyl" refers to linear or branched alkyl radicals having one to about ten carbon atoms any one of which maybe substituted with one or more carboxy radicals. Some non-limiting examples of such radicals include carboxymethyl, carboxypropyl, and the like.

The term "aryloxy" refers to optionally substituted aryl radicals, as defined above, attached to an oxygen atom. Some non-limiting examples of such radicals include phenoxy.

The term "heteroaryloxy" refers to optionally substituted heteroaryl radicals, as defined above, attached to an oxygen atom.

The term "heteroarylalkoxy" refers to oxy-containing heteroarylalkyl radicals attached through an oxygen atom to other radicals.

The term "cycloalkylalkyl" refers to cycloalkyl-substituted alkyl radicals. Some non-limiting examples of such radicals include cyclohexylmethyl. The cycloalkyl in the radicals may be additionally substituted with halo, alkyl, alkoxy or hydroxy.

The terms "fused bicyclic", "fused cyclic", "fused bicyclyl" and "fused cyclyl" refer to saturated bridged ring system, which refers to a bicyclic ring system that is not aromatic. Such a system may contain isolated or conjugated unsaturation, but not aromatic or heteroaromatic rings in its core structure (but may have aromatic substitution thereon). The fused bicyclyl may be a carbon radical or heteroatom radical. Each cyclic ring in a fused bicyclyl can be either a carbocyclic or a heterocyclic. Fused bicyclyl having 6 to 12 atoms can be arranged, for example, as a bicyclo[3,5], [4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Some non-limiting examples of fused bicyclic ring system include hexahydro-furo[3,2-b]furan, 2,3,3a,4,7,7a-hexahydro-1H-indene, 7-azabicyclo[2.2.1]heptane, and 1,2,3,4,4a,5,8,8a-octahydro-naphthalene.

The term "fused bicyclylene", as used herein, represents a fused bicyclic system as described herein, but has two points of attachment to the rest of the molecule.

The terms "spirocyclyl", "spirocyclic", "spiro bicyclyl" or "spiro bicyclic" refer to a ring originating from a particular annular carbon of another ring. For example, as depicted below, a saturated bridged ring system (ring B and B') is termed as "fused bicyclic", whereas ring A and ring B share an atom between the two saturated ring system, which terms as a "spirocyclyl" or "spiro bicyclyl". Each cyclic ring in a spirocyclyl can be either a carbocyclic or a heteroalicyclic.

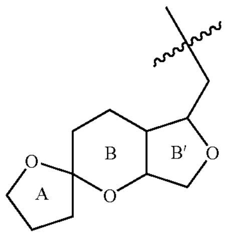

The term "spiro bicyclylene", as used herein, represents a spiro bicyclic system as described herein, but has two points of attachment to the rest of the molecule.

As described herein, a bond drawn from a substituent to the center of one ring within a ring system (as shown below) represents substitution of the substituent at any substitutable position on the rings to which it is attached. For example, Figure a represents possible substitution in any of the positions on the B ring shown in Figure b.

Figure a

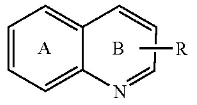

Figure b

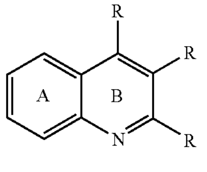

As described herein, a dot line drawn together with a bond within a ring system (as shown in Figure c) represents either a double bond or a single bond. For example, structure in Figure c represents any structures selected from Figure d.

Figure c

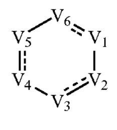

-continued

Figure d

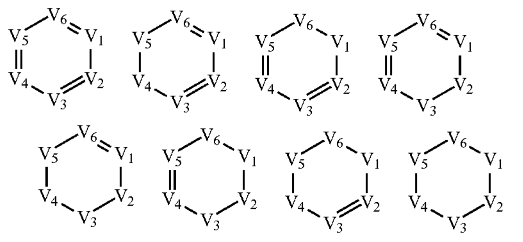

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

The term "prodrug" as used herein, represents a compound that is transformed in vivo into a compound that possesses desired biological activities. Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, J. Rautio et al, Prodrugs: Design and Clinical Applications, *Nature Review Drug Discovery,* 2008, 7, 255-270, and S. J. Hecker et al, Prodrugs of Phosphates and Phosphonates, *Journal of Medicinal Chemistry,* 2008, 51, 2328-2345, each of which is incorporated herein by reference.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons.

A "pharmaceutically acceptable salt" as used herein, refers to organic or inorganic salts of a compound disclosed herein. Pharmaceutically acceptable salts are well known in the art. For example, S. M. Berge et al., describe pharmaceutically acceptable salts in detail in *J. Pharmaceutical Sciences,* 66: 1-19, 1977, which is incorporated herein by reference. Examples of pharmaceutically acceptable, nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, oxalic acid, maleic acid, malic acid, 2-hydroxy propanic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, methanesulfonate, 2-naphthalenesulfonate, nicotinate, nitrate, oleate, palmitate, pamoate, pectinate, persulfate, 3-phenylpropionate, phosphate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "Pg" or "PG" refers to a substituent that is commonly employed to block or protect a particular functionality while reacting other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (Boc), benzyloxycarbonyl (Cbz) and 9-fluorenylmethylenoxycarbonyl (Fmoc). Similarly, a "hydroxy-protecting group" refers to a substituent of a hydroxy group that blocks or protects the hydroxy functionality. Some non-limiting examples of suitable hydroxy-protecting groups include acetyl and silyl. A "carboxy-protecting group" refers to a substituent of the carboxy group that blocks or protects the carboxy functionality. Some non-limiting examples of common carboxy-protecting groups include $-CH_2CH_2SO_2Ph$, cyanoethyl, 2-(trimethylsilyl)ethyl, 2-(trimethylsilyl)ethoxy methyl, 2-(p-toluenesulfonyl)ethyl, 2-(p-nitrophenylsulfonyl)ethyl, 2-(diphenyl phosphino)-ethyl, nitroethyl, and the like. For a general description of protecting groups and their use, see T. W. Greene, *Protective Groups in Organic Synthesis*, John Wiley & Sons, New York, 1991; and P. J. Kocienski, *Protecting Groups*, Thieme, Stuttgart, 2005.

Description of Compounds of the Invention

Disclosed herein are heterocyclic compounds, and pharmaceutical formulations thereof, that are potentially useful in the treatment of diseases, conditions and/or disorders modulated by protein kinases, especially VEGFR, c-Met receptor. In one aspect, provided herein include compounds of Formula (I):

(I)

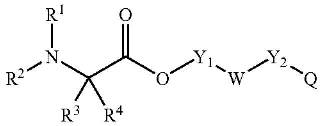

or a recemic mixture, a diastereoisomer, an enantiomer, a geometric isomer, a tautomer, an N-oxide, a hydrate, a solvate, a metabolite, or a pharmaceutically acceptable salt thereof, wherein each of $R^1$, $R^2$, $R^3$, $R^4$, $Y_1$, $Y_2$, W and Q is as defined herein.

In some embodiments of the compound of Formula (I), each of $R^1$, $R^2$, $R^3$ and $R^4$ is independently H, $-C(=O)R^{11}$, $-C(=O)OR^{11}$, $-C(=O)-NR^{11}R^{11a}$, $R^{11}R^{11a}N-O_2S-$, $R^{11}O_2S-$, $R^{11a}R^{11}N$-alkyl, $R^{11}O$-alkyl, aliphatic, haloaliphatic, arylaliphatic, heterocyclyl aliphatic, cycloalkyl aliphatic, aryl, heteroaryl, heterocyclyl, or carbocyclyl, with the proviso that $R^1$ and $R^2$, together with the nitrogen atom they are attached to, optionally form a substituted or unsubstituted 3-8 membered heterocyclic ring; and $R^3$ and $R^4$, together with the carbon atom they are attached to, optionally form a substituted or unsubstituted 3-8 membered carbocyclic or heterocyclic ring;

each of $Y_1$ and $Y_2$ is independently a divalent group derived from aliphatic-$C(=O)-$, aliphatic-$C(=O)O-$, aliphatic-$C(=O)NR^{11}-$, $R^{11}N-O_2S$-aliphatic, $-O_2S-$, $-R^{11}N$-aliphatic, $-S(=O)$-aliphatic, $-R^{11}N-C(=O)$-aliphatic, fused bicyclylalkylene, fused hetero-bicyclyl alkylene, spiro bicyclylalkylene, spiro heterobicyclyl alkylene, arylalkylene, heteroarylalkylene, alkylene; haloalkylene, heterocyclylene, carbocyclylene, heterocyclylalkylene, carbocyclylalkylene, fused bicyclylene, fused heterobicyclylene, spiro bicyclylene, spiro heterobicyclylene, arylene, or heteroarylene;

W is O, $N-R^{11}$, or $(CR^{12}R^{12a})m$; m is 0, 1, 2 or 3;

Q is:

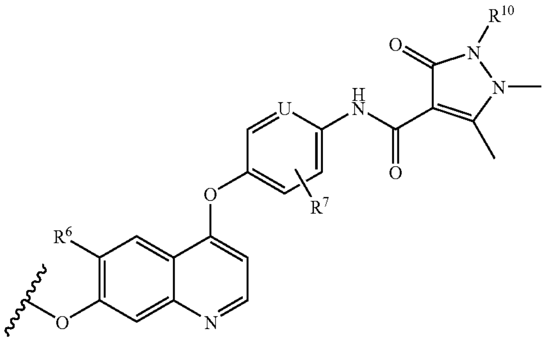

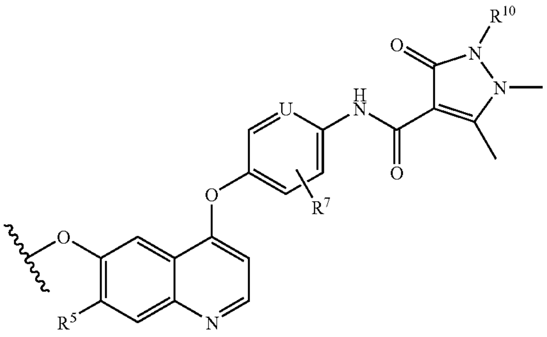

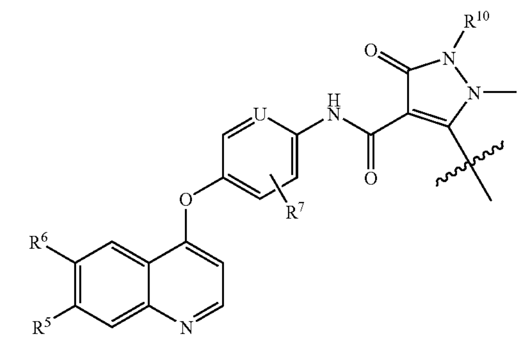

-continued

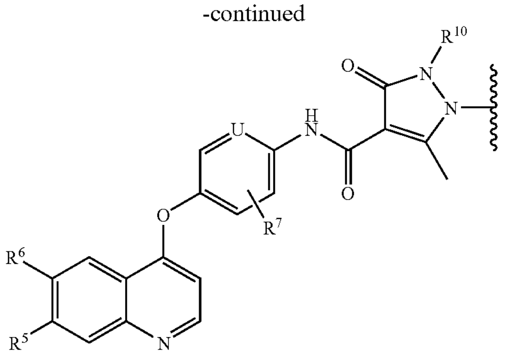

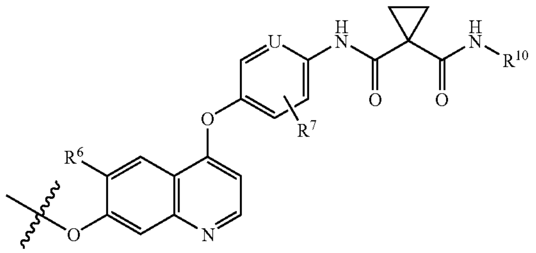

or

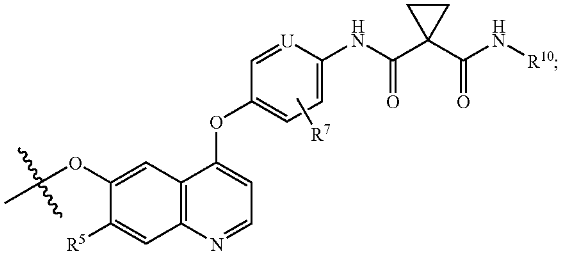

;

U is $CR^{12}$ or N;

each of $R^5$, $R^6$ is independently H, halo, cyano(CN), hydroxyl, $R^{11a}R^{11}N$—, —C(=O)—$R^{11}$, —C(=O)—$OR^{11}$, —C(=O)$NR^{11}R^{11a}$, —OC(=O)$NR^{11}R^{11a}$, —OC(=O)$OR^{11}$, —$NR^{11}C$(=O)$NR^{11}R^{11a}$, $NR^{11}C$(=O)$OR^{11a}$, $NR^{11}C(R^{11a}$, $R^{11}R^{11a}N$—$O_2S$—, $R^{11}O_2S$—, $R^{11}O_2SR^{11a}N$—, $R^{11}$N-alkyl, $R^{11}$(S=O)-alkyl, $R^{11}R^{11a}N$—(C=O)-alkyl, $R^{11}R^{11}$N-alkoxy, $R^{11}$(S=O)-alkoxy, $R^{11}R^{11a}N$—(C=O)-alkoxy, optionally substituted aliphatic, alkoxy, hydroxyalkoxy, aminoalkoxy, hydroxy-substituted aminoalkoxy, haloalkoxy, amino-substituted haloalkoxy, alkylamino haloalkoxy, hydroxy-substituted haloalkoxy, alkylaminoalkoxy, alkoxyalkoxy, arylalkoxy, heterocyclylalkoxy, carbocyclylalkoxy, heterocyclyl(hydroxyalkoxy), carbocyclyl(hydroxyalkoxy), aryl(hydroxyalkoxy), aryloxyalkoxy, aryloxy, heterocyclyloxyalkoxy, carbo-cyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicycloxo-alkoxy, fused heterobicycloxoalkoxy, fused bicyclyl aminoalkoxy, fused hetero-bicyclyl aminoalkoxy, spiro bicyclyl, spiro heterobicyclyl, spiro bicyclyl aliphatic, spiro heterobicyclyl aliphatic, spiro bicycloxy, spiro heterobicycloxy, spiro bicycloxo-alkoxy, spiro heterobicycloxoalkoxy, spiro bicyclylaminoalkoxy, spiro heterobicyclylaminoalkoxy, aryl, heteroaryl, arylaliphatic or heteroarylaliphatic;

$R^7$ is one or more substituents independently selected at each occurrence from H, F, Cl, Br, I, —CN, hydroxyl, $R^{11a}R^{11}N$—, aliphatic, alkoxy, haloalkyl, hetero-cyclyl, heterocyclylalkyl, cycloalkyl, cycloalkylalkyl, cycloalkylalkoxy, and heterocyclylalkoxy;

each of $R^8$, $R^9$ and $R^{10}$ is independently H, —C(=O)$R^{11}$, —C(=O)$OR^{11}$, —C(=O)—$NR^{11}R^{11a}$, $R^{11}R^{11a}N$—$O^2S$—, $R^{11}O_2S$—, $R^{11a}R^{11}$N-alkyl, $R^{11}$(S=O)-alkyl, $R^{11}R^{11a}N$—(C=O)-alkyl, optionally substituted aliphatic, hydroxyalkyl, hydroxy-substituted aminoalkyl, haloalkyl, amino-substituted haloalkyl, alkylamino haloalkyl, hydroxy-substituted haloalkyl, alkoxyalkyl, arylalkyl, heterocyclylalkyl, carbocyclylalkyl, heterocyclyl-hydroxyalkyl, carbocyclyl-hydroxyalkyl, aryl-hydroxyalkyl, aryloxyalkyl, hetero-cyclyloxyalkyl, carbocyclyloxyalkyl, heterocyclylyl, cycloalkylyl, (heterocyclo)-hydroxyalkyl, azidoalkyl, fused bicyclyl, fused heterobicyclyl, fused bicyclyl aliphatic, fused heterobicyclyl aliphatic, fused bicycloxoalkyl, fused heterobicycloxoalkyl, fused bicyclyl aminoalkyl, fused heterobicyclyl aminoalkyl, spiro bicyclyl, spiro heterobicyclyl, spiro bicyclyl aliphatic, spiro heterobicyclyl aliphatic, spiro bicycloxoalkyl, spiro hetero-bicycloxoalkyl, spiro bicyclylaminoalkyl, spiro heterobicyclylaminoalkyl, aryl, heteroaryl, arylaliphatic or heteroarylaliphatic;

each of $R^{11}$ and $R^{11a}$ is independently H, aliphatic, haloaliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryl, heteroaryl, heterocyclyl, or carbocyclyl, with the proviso that where $R^{11}$ and $R^{11a}$ are bonded to the same nitrogen atom, $R^{11}$ and $R^{11a}$, together with the nitrogen atom they are attached to, optionally form a substituted or unsubstituted 3-8 membered ring (including a spiro ring or a fused bicyclic ring); and each of $R^{12}$ and $R^{12a}$ is independently H, F, Cl, Br. I, cyano (CN), hydroxyl, —$NR^{11a}R^{11}$, —OC(=O)$R^{11}$, —C(=O)$R^{11}$, —C(=O)$OR^{11}$, —C(=O)$NR^{11}R^{11a}$, —OC(=O)$NR^{11}R^{11a}$, —OC(=O)$OR^{11}$, —$NR^{11}C$(=O)$NR^{11}R^{11a}$, —$NR^{11}C$(=O)$OR^{11a}$, —$NR^{11}$—C(=O)—$R^{11a}$, $R^{11}R^{11a}N$—$O_2S$—, $R^{11}O_2S$—, $R^{11}O_2S$—N($R^{11a}$)—, alkoxy, cycloalkoxy, heterocycloalkoxy, aliphatic, halo-aliphatic, hydroxyaliphatic, aminoaliphatic, alkoxyaliphatic, alkylaminoaliphatic, alkylthioaliphatic, arylaliphatic, heterocyclylaliphatic, cycloalkylaliphatic, aryl, heteroaryl, heterocyclyl, or carbocyclyl, with the proviso that where $R^{12}$ and $R^{12a}$ are bonded to the same carbon atom, $R^{12}$ and $R^{12a}$, together with the carbon atom they are attached to, optionally form a substituted or unsubstituted 3-8 membered carbocyclic or heterocyclic ring.

In another embodiment, each of $R^1$, $R^2$, $R^3$ and $R^4$ is independently H, —C(=O)$R^{11}$, —C(=O)$OR^{11}$, —C(=O)$NR^{11}R^{11a}$, $R^{11}R^{11a}N$—$O_2S$—, $R^{11}O_2S$—, $R^{11a}R^{11}N$—$C_{1-6}$ alkyl, $R^{11}O$—$C_{1-6}$alkyl, optionally substituted $C_{1-6}$aliphatic, $C_{1-6}$haloaliphatic, $C_{6-10}$aryl $C_{1-6}$aliphatic, $C_{2-6}$ heterocyclyl $C_{1-6}$ aliphatic, $C_{3-6}$cycloalkyl $C_{1-6}$aliphatic, $C_{6-10}$aryl, $C_{1-9}$heteroaryl, $C_{2-6}$ heterocyclyl, or $C_{3-6}$ carbocyclyl, with the proviso that $R^1$ and $R^2$, together with the nitrogen atom they are attached to, may optionally form a substituted or unsubstituted 3-8 membered heterocyclic ring; and $R^3$ and $R^4$, together with the carbon atom they are attached to, may optionally form a substituted or unsubstituted 3-8 membered carbocyclic or heterocyclic ring;

each of $Y_1$ and $Y_2$ is independently a divalent group derived from $C_{1-6}$aliphatic-C(=O)—, $C_{1-6}$aliphatic-C(=O)O—, $C_{1-6}$aliphatic-C(=O)$NR^{11}$—, —$R^{11}N$—$O_2S$—$C_{1-6}$-aliphatic, —$O_2S$—$C_{1-6}$aliphatic, —$R^{11}NC_{1-6}$aliphatic, —S(=O)$C_{1-6}$ aliphatic, —$R^{11}N$—C(=O)—$C_{1-6}$-aliphatic, fused $C_{6-10}$bicyclyl $C_{1-6}$alkylene, fused $C_{5-9}$ hetero-bicyclyl $C_{1-6}$ alkylene, spiro $C_{7-11}$bicyclyl $C_{1-6}$ alkylene, spiro $C_{6-10}$heterobicyclyl $C_{1-6}$ alkylene, $C_{1-6}$haloalkylene, $C_{2-8}$-heterocyclyl $C_{1-6}$ alkylene, $C_{3-8}$carbocyclyl $C_{1-6}$ alkylene, $C_{2-8}$-heterocyclylene, $C_{3-8}$carbocyclylene, fused $C_{6-10}$bicyclyl-ene, fused $C_{5-9}$heterobicyclylene, spiro $C_{7-11}$bicyclylene, or spiro $C_{6-10}$heterobicyclylene;

W is O, N—$R^{11}$, or $(CR^{12}R^{12a})m$; m is 0, 1 or 2;

Q is:

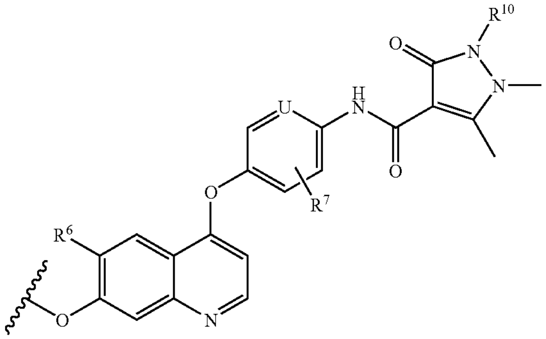

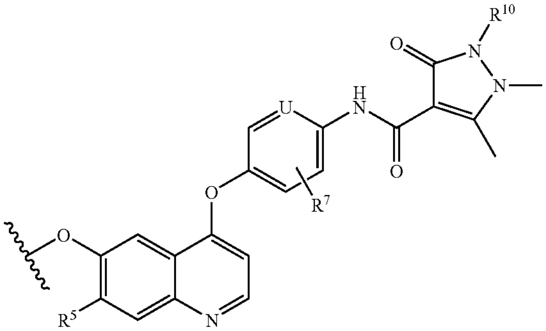

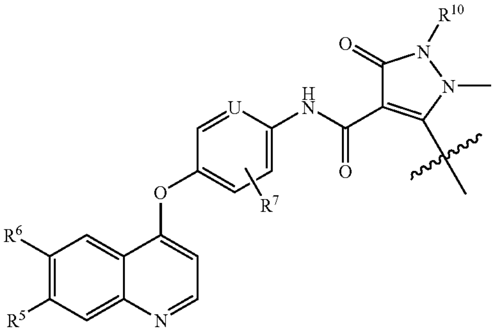

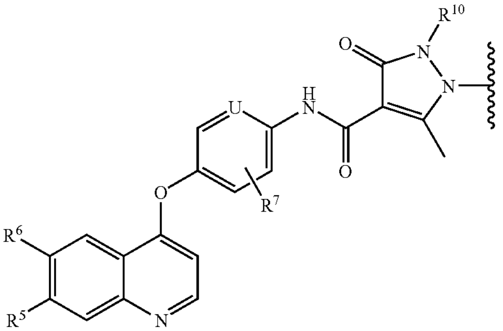

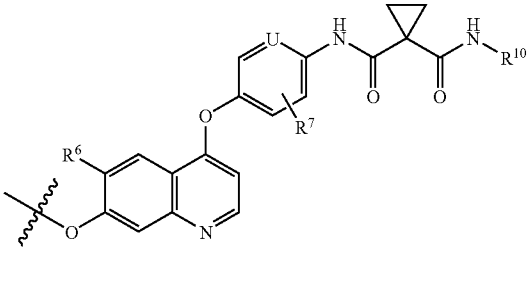

or

-continued

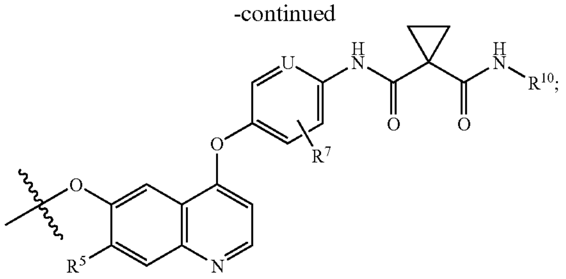

U is $CR^{12}$ or N;

each of $R^5$, $R^6$ is independently H, halo, cyano(CN), $R^{11a}R^{11}N$—$C_{1-6}$alkoxy, $R^{11}$(S═O)—$C_{1-6}$alkoxy, $R^{11}R^{11a}N$—(C═O)—$C_{1-6}$alkoxy, optionally substituted $C_{1-6}$aliphatic, optionally substituted $C_{1-6}$alkoxy, hydroxy $C_{2-6}$alkoxy, hydroxy-substituted amino $C_{2-6}$ alkoxy, $C_{1-6}$haloalkoxy, amino-substituted $C_{2-6}$haloalkoxy, $C_{1-6}$alkylamino $C_{2-6}$ haloalkoxy, hydroxy-substituted $C_{2-6}$haloalkoxy, $C_{1-6}$alkoxy $C_{1-6}$alkoxy, $C_{6-10}$aryl $C_{1-6}$ alkoxy, $C_{2-5}$heterocyclyl $C_{1-6}$alkoxy, $C_{3-6}$carbocyclyl $C_{1-6}$alkoxy, $C_{2-5}$heterocyclyl(hydroxy $C_{2-6}$alkoxy), $C_{3-6}$carbocyclyl(hydroxy $C_{2-6}$alkoxy), $C_{6-10}$aryl(hydroxy $C_{2-6}$ alkoxy), $C_{6-10}$aryloxy $C_{1-6}$alkoxy, $C_{6-10}$aryloxy, $C_{2-5}$ heterocyclyloxy $C_{1-6}$alkoxy, $C_{3-6}$ carbocyclyloxy $C_{1-6}$alkoxy, $C_{2-5}$heterocyclyloxy, $C_{3-6}$cycloalkyloxy, ($C_{2-5}$ heterocyclo)hydroxy $C_{1-6}$alkoxy, azido $C_{2-6}$alkoxy, fused $C_{6-10}$bicyclyl, fused $C_{5-9}$ heterobicyclyl, fused $C_{6-10}$bicyclyl $C_{1-6}$aliphatic, fused $C_{5-9}$heterobicyclyl $C_{1-6}$aliphatic, fused $C_{6-10}$ bicycloxy, fused $C_{5-9}$heterobicycloxy, fused $C_{6-10}$bicycloxo $C_{1-6}$alkoxy, fused $C_{5-9}$ heterobicycloxo $C_{1-6}$ alkoxy, fused $C_{6-10}$bicyclyl amino $C_{1-6}$alkoxy, fused $C_{5-9}$ heterobicyclyl amino $C_{1-6}$alkoxy, spiro $C_{7-11}$bicyclyl, spiro $C_{6-10}$heterobicyclyl, spiro $C_{7-11}$bicyclyl $C_{1-6}$aliphatic, spiro $C_{6-10}$ heterobicyclyl $C_{1-6}$aliphatic, spiro $C_{7-11}$ bicycloxy, spiro $C_{6-10}$heterobicycloxy, spiro $C_{7-11}$bicycloxo $C_{1-6}$ alkoxy, spiro $C_{6-10}$ heterobicycloxo $C_{1-6}$alkoxy, spiro $C_{7-11}$bicyclylamino $C_{1-6}$alkoxy, spiro $C_{6-10}$ heterobi-cyclylamino $C_{1-6}$alkoxy, $C_{6-10}$aryl, $C_{1-9}$heteroaryl, $C_{6-10}$ aryl $C_{1-6}$ aliphatic or $C_{1-9}$ hetero-aryl $C_{1-6}$aliphatic;

$R^7$ is one or more substituents independently selected at each occurrence from H, F, Cl, Br, I, —CN, hydroxyl, $R^{11a}R^{11}N$—, $C_{1-6}$ aliphatic, $C_{1-6}$alkoxy, $C_{1-6}$ haloalkyl, $C_{2-5}$ heterocyclyl, $C_{2-5}$heterocyclyl $C_{1-6}$alkyl, $C_{3-6}$cycloalkyl, $C_{3-6}$ cycloalkyl $C_{1-6}$alkyl, $C_{3-6}$ cycloalkyl $C_{1-6}$alkoxy, and $C_{2-5}$heterocyclyl $C_{1-6}$alkoxy;

each of $R^8$, $R^9$ and $R^{10}$ is independently H, —C(═O)$R^{11}$, —C(═O)—O$R^{11}$, —C(═O)N$R^{11}R^{11a}$, $R^{11a}R^{11}N$—$C_{1-6}$ alkyl, $R^{11}O$—$C_{1-6}$alkyl, $R^{11}$(S═O)—$C_{1-6}$ alkyl, $R^{11}R^{11a}N$—(C═O)—$C_{1-6}$alkyl, optionally substituted $C_{1-6}$aliphatic, $C_{6-10}$aryl $C_{1-6}$ alkyl, $C_{1-9}$ heteroaryl $C_{1-6}$alkyl, $C_{2-5}$heterocyclyl $C_{1-6}$alkyl, $C_{3-6}$carbocyclyl $C_{1-6}$alkyl, $C_{6-10}$aryloxy $C_{1-6}$alkyl, $C_{1-9}$ heteroaryloxy $C_{1-6}$alkyl, $C_{2-5}$heterocyclyloxy $C_{1-6}$alkyl, $C_{3-6}$ carbocyclyloxy $C_{1-6}$alkyl, $C_{2-5}$ heterocyclylyl, $C_{3-6}$cycloalkyl, azido $C_{1-6}$alkyl, fused $C_{6-10}$bicyclyl, fused $C_{5-9}$-hetero-bicyclyl, fused $C_{6-10}$bicyclyl $C_{1-6}$aliphatic, fused $C_{5-9}$ heterobicyclyl $C_{1-6}$aliphatic, fused $C_{6-10}$bicycloxo $C_{1-6}$alkyl, fused $C_{5-9}$heterobicycloxo $C_{1-6}$alkyl, fused $C_{6-10}$bicyclyl amino $C_{1-6}$alkyl, fused $C_{5-9}$heterobicyclyl amino $C_{1-6}$ alkyl, spiro $C_{7-11}$bicyclyl, spiro $C_{6-10}$-hetero-bicyclyl, spiro $C_{7-11}$bicyclyl $C_{1-6}$aliphatic, spiro $C_{6-10}$heterobicyclyl $C_{1-6}$aliphatic, spiro $C_{7-11}$bicycloxo $C_{1-6}$alkyl, spiro $C_{6-10}$ heterobicycloxo $C_{1-6}$alkyl, spiro $C_{7-11}$ bicyclylamino $C_{1-6}$alkyl, spiro $C_{6-10}$ heterobi-cyclylamino $C_{1-6}$alkyl, $C_{6-10}$aryl, or $C_{1-9}$ heteroaryl;

each of $R^{11}$ and $R^{11a}$ is independently H, $C_{1-6}$aliphatic, $C_{1-6}$haloaliphatic, $C_{1-6}$ hydroxyaliphatic, $C_{1-6}$aminoaliphatic, $C_{1-6}$alkoxy $C_{1-6}$aliphatic, $C_{1-6}$alkylamino $C_{1-6}$ aliphatic, $C_{1-6}$alkylthio $C_{1-6}$aliphatic, $C_{6-10}$ aryl $C_{1-6}$aliphatic, $C_{5-9}$heterocyclyl $C_{1-6}$ aliphatic, $C_{3-6}$cycloalkyl $C_{1-6}$aliphatic, $C_{6-10}$aryl, $C_{1-9}$heteroaryl, $C_{2-5}$heterocyclyl, or $C_{3-6}$ carbocyclyl, with the proviso where $R^{11}$ and $R^{11a}$ are bonded to the same nitrogen atom, $R^{11}$ and $R^{11a}$, together with the nitrogen atom they are attached to, optionally form a substituted or unsubstituted 3-8 membered heterocyclic ring, a fused $C_{5-9}$heterobicyclic ring or a spiro $C_{6-10}$heterobicyclic ring;

each of $R^{12}$ and $R^{12a}$ is independently H, F, Cl, Br, I), —CN, hydroxyl, —$NR^{11a}R^{11}$, —OC(═O)$R^{11}$, —C(═O)$R^{11}$, —C(═O)O$R^{11}$, —C(═O)$NR^{11}R^{11a}$, —OC(═O)—$NR^{11}R^{11a}$, —OC(═O)O$R^{11}$, —$NR^{11}$C(═O)$NR^{11}R^{11a}$, —$NR^{11}$C(═O)O$R^{11a}$, —$NR^{11}$C(═O)—$R^{11a}$, $R^{11}O_2S$—, $R^{11}R^{11a}NO_2S$—, $R^{11}O_2S$—N($R^{11a}$)—, $C_{1-6}$alkoxy, $C_{3-6}$ cycloalkoxy, $C_{2-5}$ hetero-cyclo $C_{1-6}$ alkoxy, $C_{1-6}$aliphatic, $C_{1-6}$haloaliphatic, hydroxy $C_{1-6}$ aliphatic, amino $C_{1-6}$ aliphatic, $C_{1-6}$ alkoxy$C_{1-6}$ aliphatic, $C_{1-6}$alkylamino $C_{1-6}$aliphatic, $C_{1-6}$alkylthio $C_{1-6}$ aliphatic, $C_{6-10}$ aryl $C_{1-6}$ aliphatic, $C_{2-5}$heterocyclyl $C_{1-6}$aliphatic, $C_{3-6}$ cycloalkyl $C_{1-6}$ aliphatic, $C_{6-10}$aryl, $C_{1-9}$ heteroaryl, $C_{2-5}$ heterocyclyl, or $C_{3-6}$ carbocyclyl, with the proviso where $R^{12}$ and $R^{12a}$ are bonded to the same carbon atom, $R^{12}$ and $R^{12a}$, together with the carbon atom they are attached to, may optionally form a substituted or unsubstituted 3-8 membered carbocyclic or heterocyclic ring;

In another embodiment, the amino acetyl group defined by $R^1$, $R^2$, $R^3$ and $R^4$ in formula (I) is selected from naturally occurring and commercially available α-amino acids and their optically isomers thereof. Typical natural and commercially available α-amino acids are isoleucine, leucine, lysine, methionine, phenyl-alanine, threonine, tryptophan, valine, alanine, asparagine, aspartate, glutamate, proline, glutamine, serine, tyrosine, arginine, histidine, cysteine, glycine, sarcosine, N,N-dimethyl glycine, homoserine, norvaline, norleucine, ornithine, homocysteine, homo-phenylalanine, phenylglycine, ortho-tyrosine, meta-tyrosine, hydroxyproline. Preferably, the chiral centers in these α-amino acids are the same as they are found in nature. Thus, isoleucine, leucine, lysine, methionine, phenylalanine, threonine, tryptophan, valine, alanine, asparagine, aspartate, glutamate, glutamine, proline, serine, tyrosine, arginine, histidine have S-configurations at their α-position; and cysteine has a R-configuration at its α-position. Glycine, sarcine and N,N-dimethyl glycine are non-chiral molecules;

each of $Y_1$ and $Y_2$ is independently $C_{1-6}$ aliphatic-C(═O)—, $C_{1-6}$ aliphatic-C(═O)O—, $C_{1-6}$ aliphatic-C(═O)$NR^{11}$—, —$R^{11}N$—$O_2S$—$C_{1-6}$aliphatic, —$O_2S$—$C_{1-6}$ aliphatic, —$R^{11}N$—$C_{1-6}$ aliphatic, —(S═O)—$C_{1-6}$aliphatic, —$R^{11}N$—(C═O)—$C_{1-6}$aliphatic, $C_{1-6}$ haloalkylene, $C_{2-8}$-heterocyclylene, $C_{3-8}$ carbocyclylene, $C_{2-8}$-heterocyclyl $C_{1-6}$ alkylene, $C_{3-8}$ carbocyclyl $C_{1-6}$ alkylene, fused $C_{6-10}$ bicyclylene, fused $C_{5-9}$ heterobicyclylene, fused $C_{6-10}$bicyclyl$C_{1-6}$ alkylene, fused $C_{5-9}$ heterobicyclyl $C_{1-6}$ alkylene, spiro $C_{7-11}$ bicyclylene, spiro $C_{6-10}$ heterobicyclylene, spiro $C_{7-11}$ bicyclyl $C_{1-6}$ alkylene, or spiro $C_{6-10}$ heterobicyclyl $C_{1-6}$ alkylene;

W is O, N—$R^{11}$, or ($CR^{12}R^{12a}$)m; m is 0, 1 and 2;

Q is:

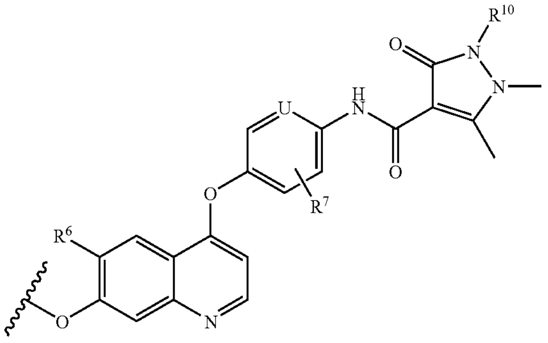

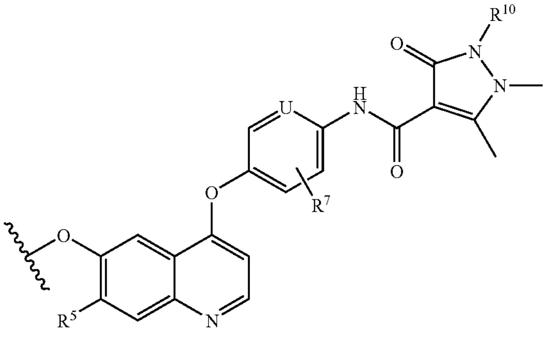

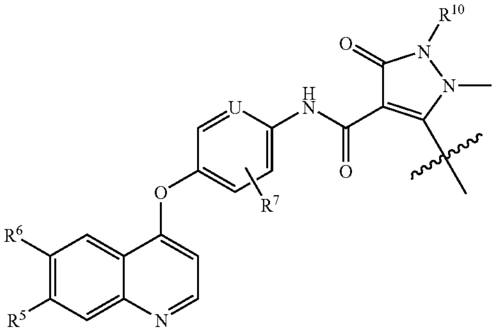

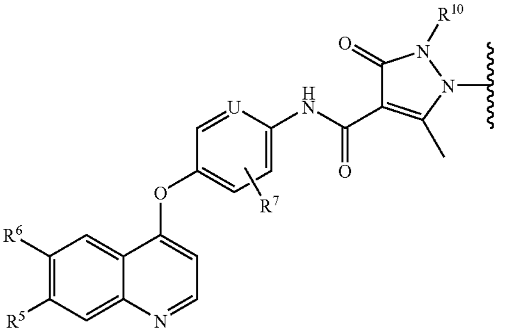

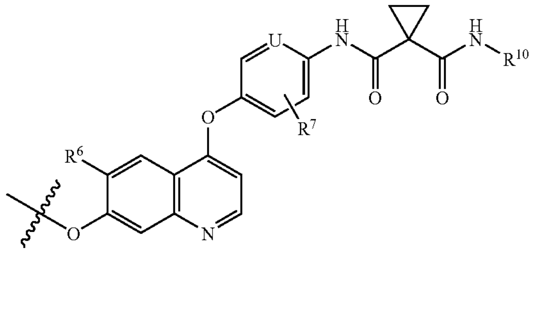

or

-continued
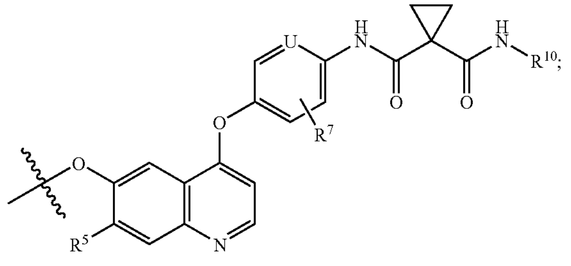
U is CH or N;
each of $R^5$ and $R^6$ is independently H or methoxy;
$R^7$ is H or F;
$R^{10}$ is phenyl or fluorophenyl.
In some embodiments, Q is:
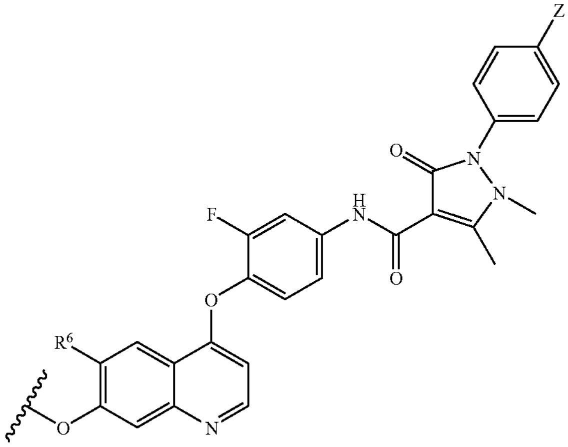
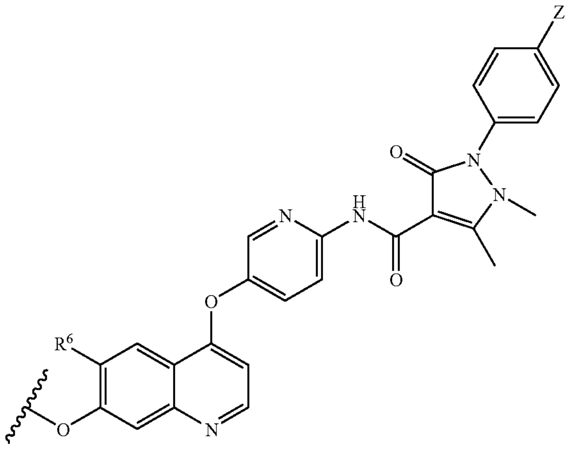
-continued
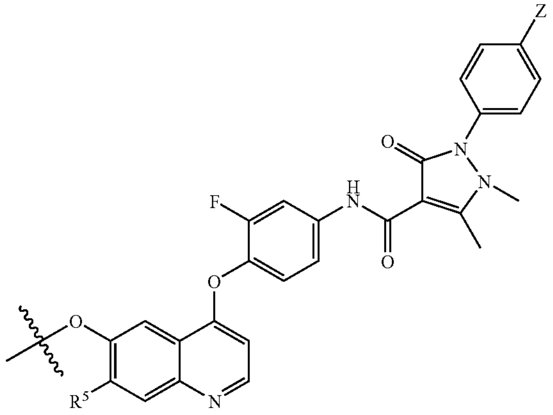
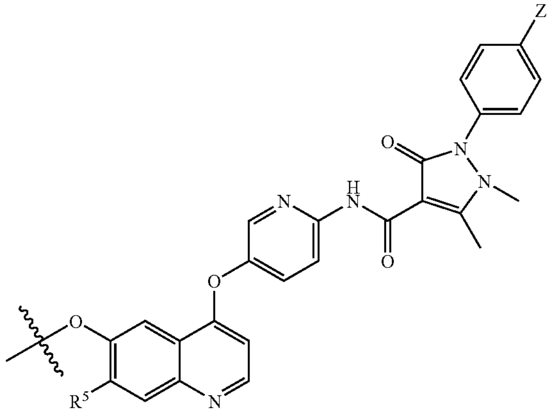
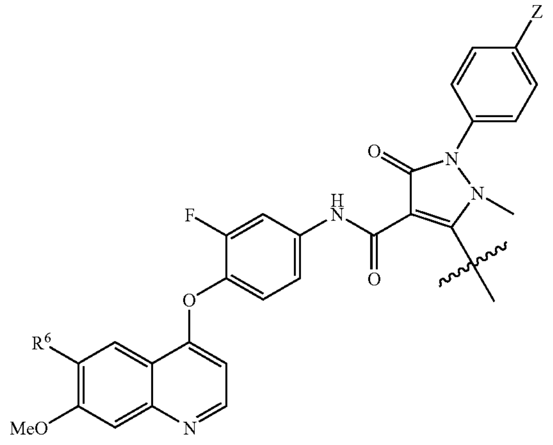
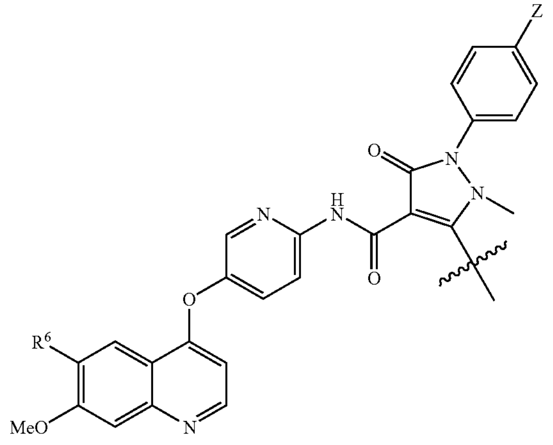

-continued
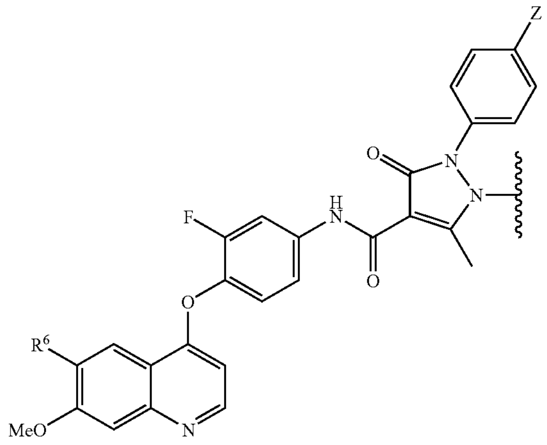
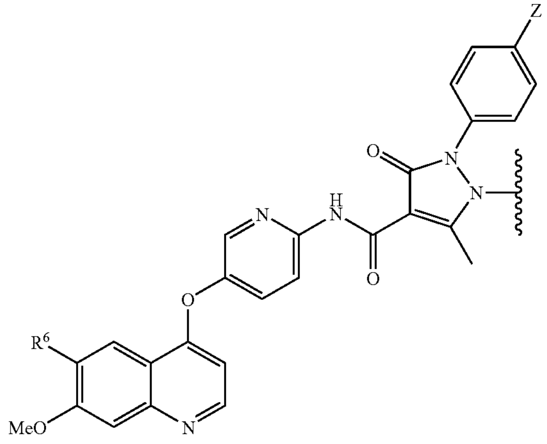
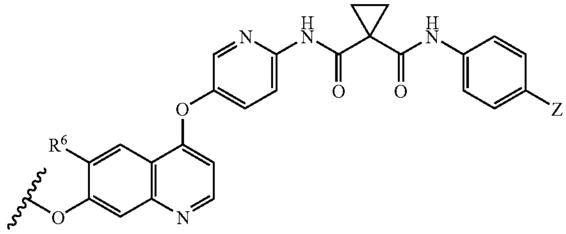
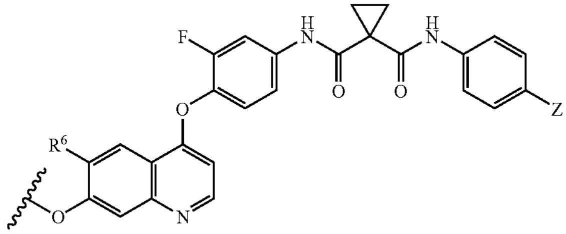
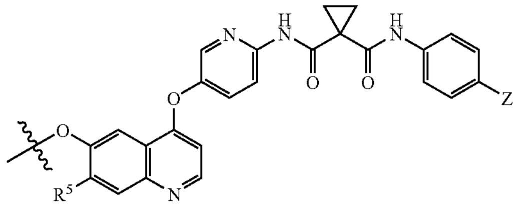
or
-continued
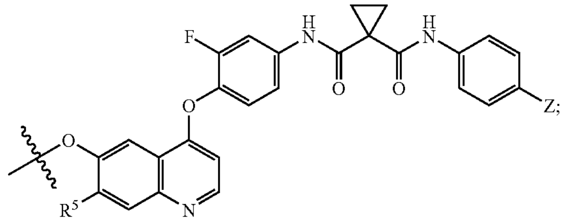
each of $R^5$ and $R^6$ is independently H or OMe; Z is H or F.
In some embodiments, each structure defined by $Y_1$, $Y_2$, W and Q is one of the following structures:
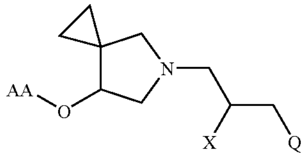
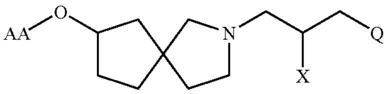
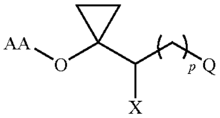
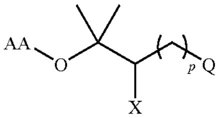
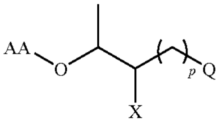
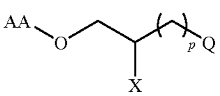
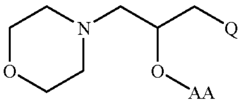
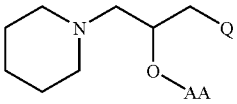
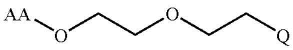
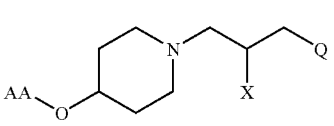
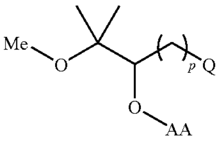
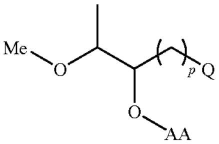
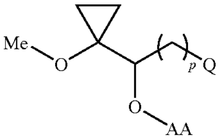
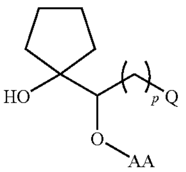
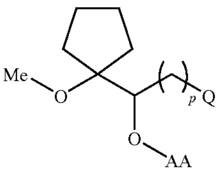
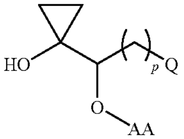
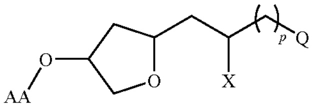

-continued
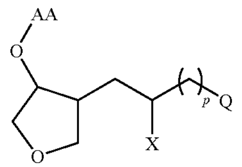
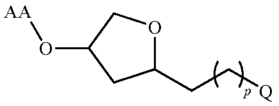
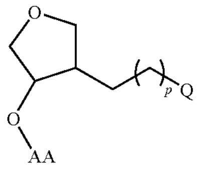
or
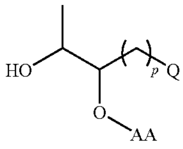
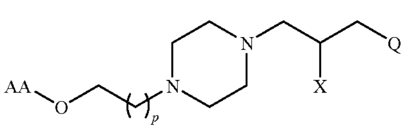
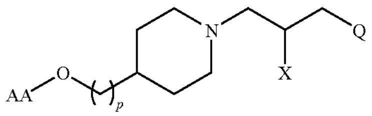
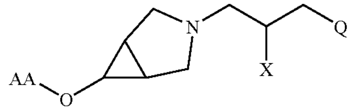
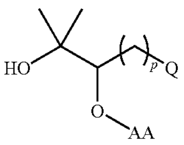
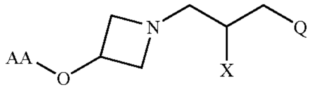
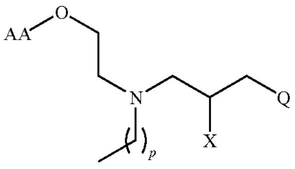
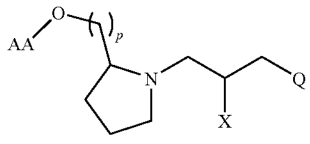
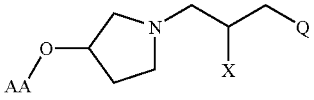
AA is an amino acetyl moiety defined by $R^1$, $R^2$, $R^3$ and $R^4$; X is H or OH; p is 0, 1, 2, or 3.
Some non-limiting examples of the compounds disclosed herein, and their pharmaceutically acceptable salts and solvates thereof, are shown in the following:
TABLE 1
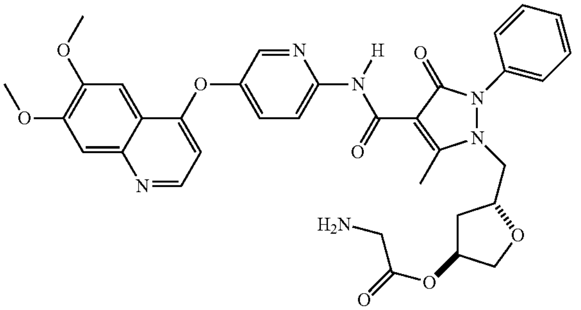
(1)
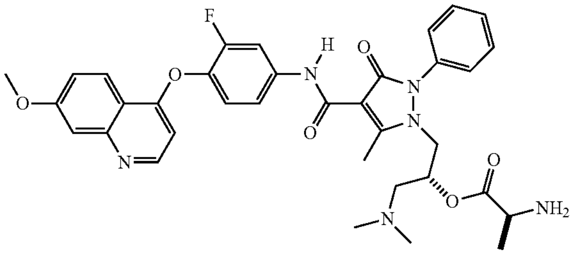
(2)
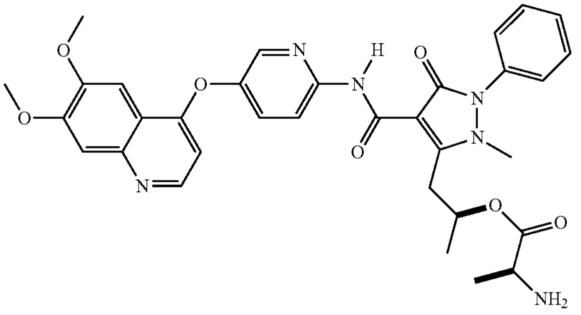
(3)
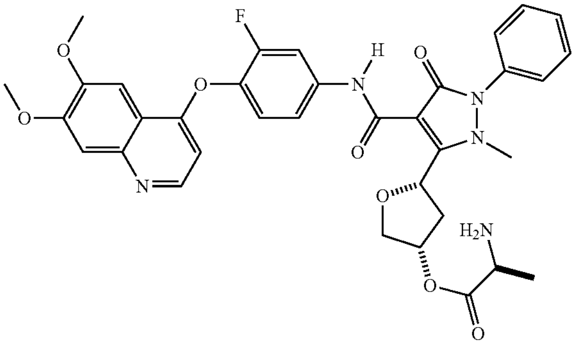
(4)
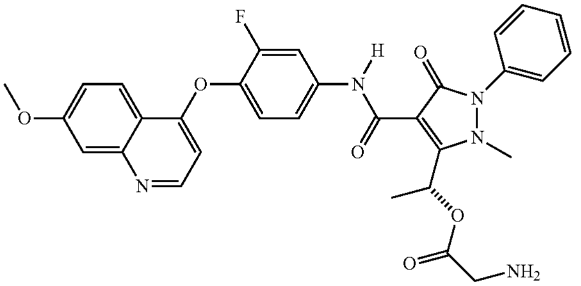
(5)

TABLE 1-continued
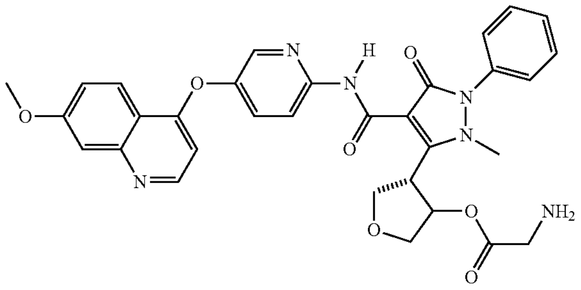
(6)
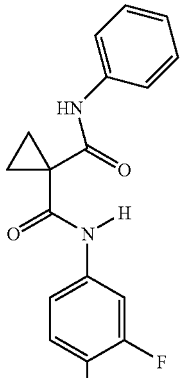
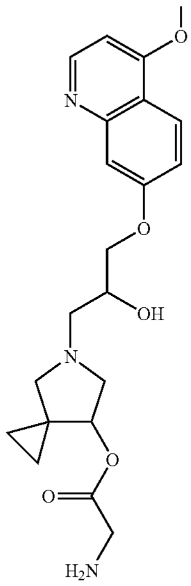
(7)
TABLE 1-continued
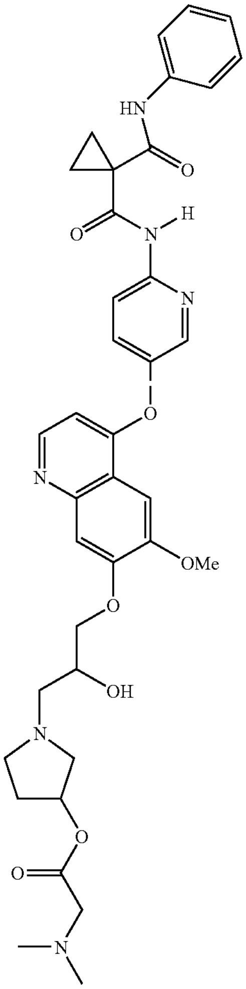
(8)
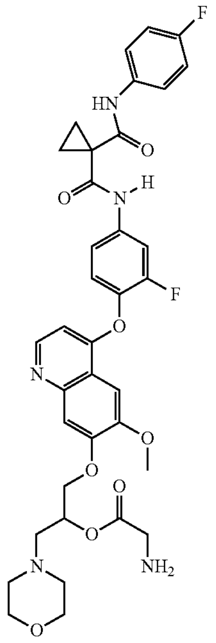
(9)

TABLE 1-continued
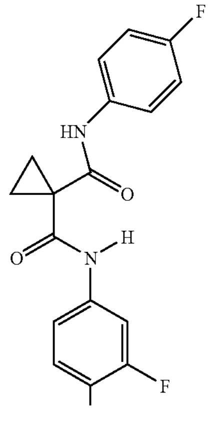
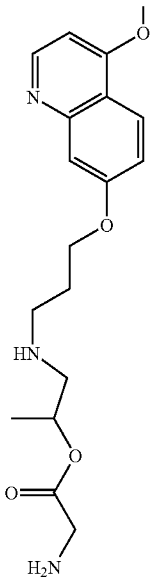
(10)
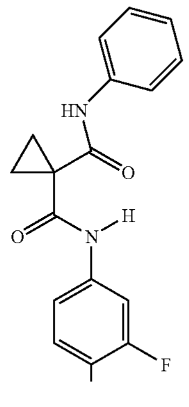
TABLE 1-continued
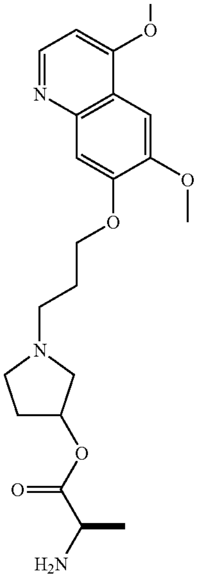
(11)
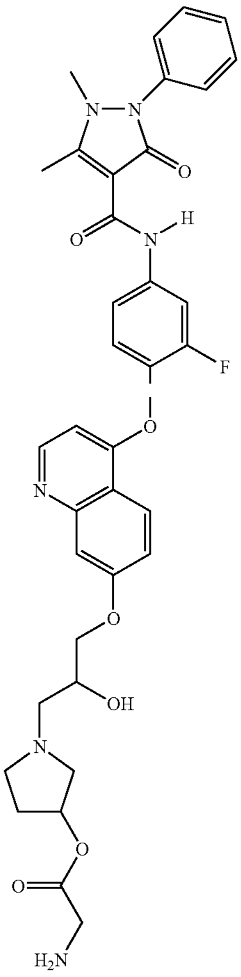
(12)

TABLE 1-continued
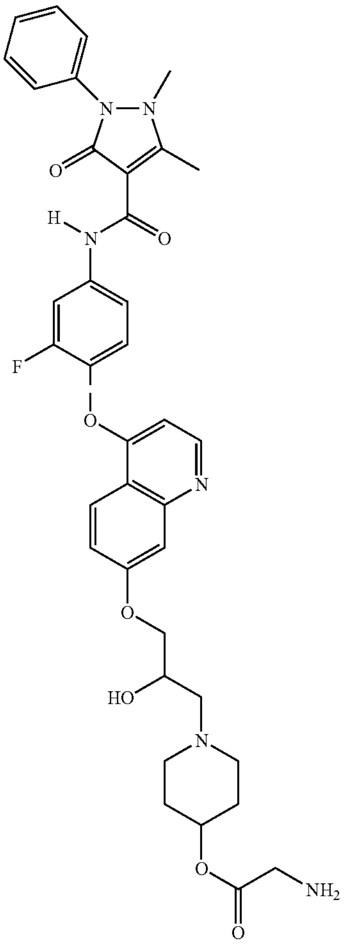
(13)
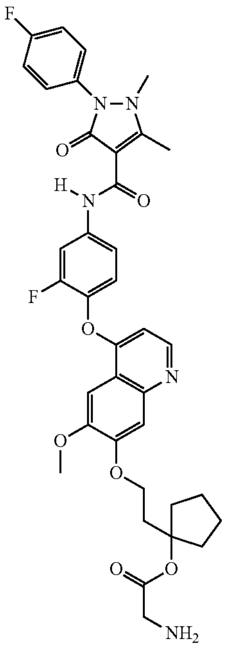
(14)
TABLE 1-continued
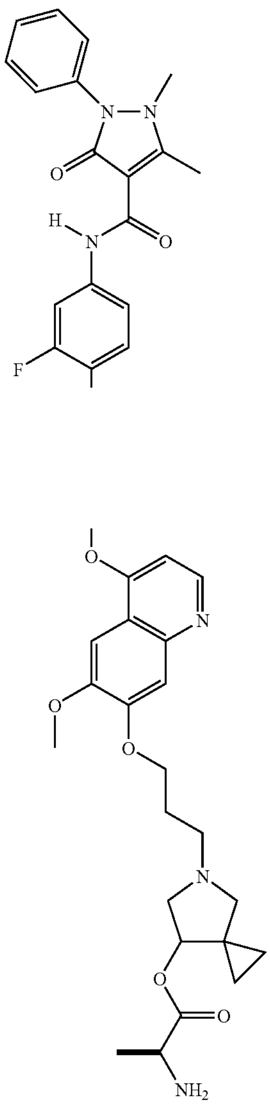
(15)
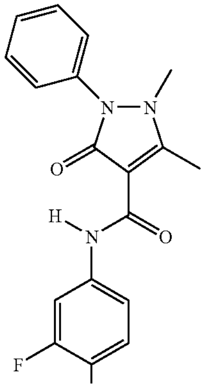

TABLE 1-continued
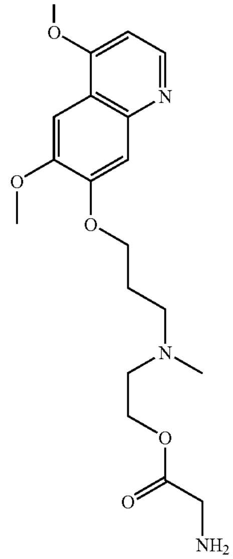
(16)
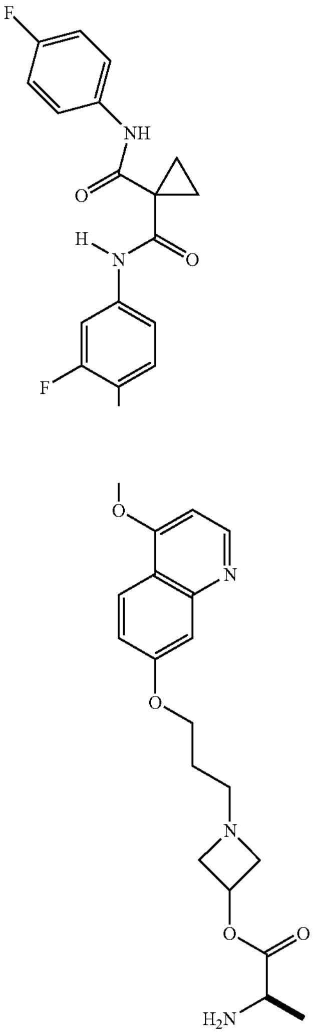
(17)
TABLE 1-continued
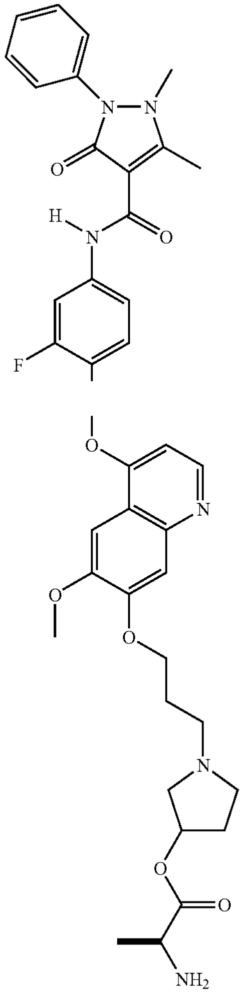
(18)
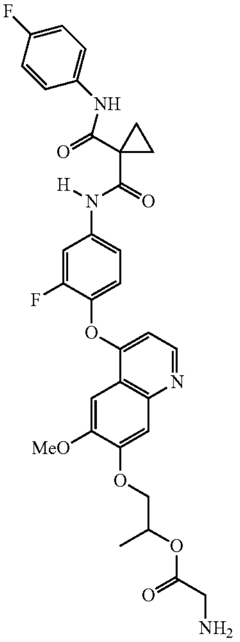
(19)

TABLE 1-continued
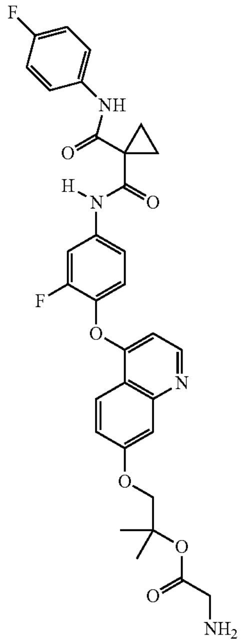
(20)
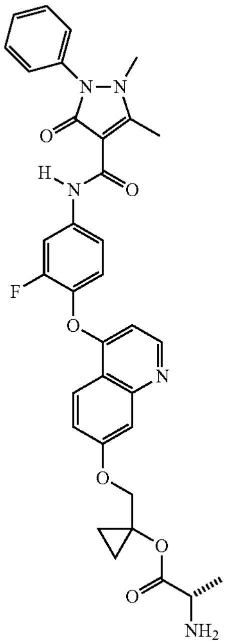
(21)
TABLE 1-continued
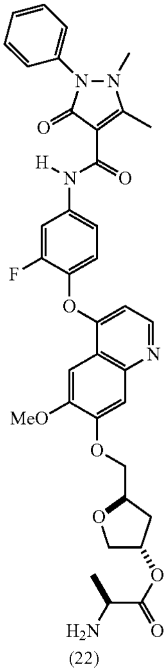
(22)
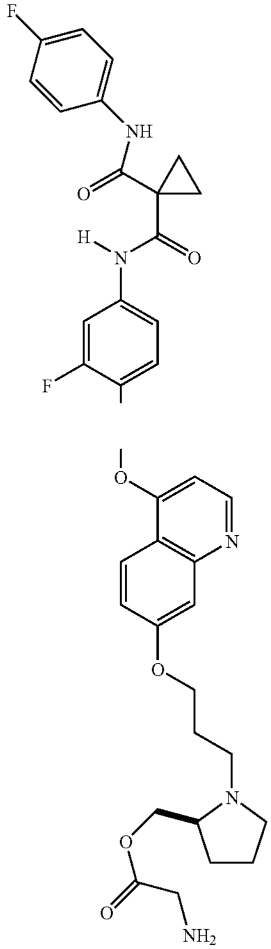
(23)

TABLE 1-continued

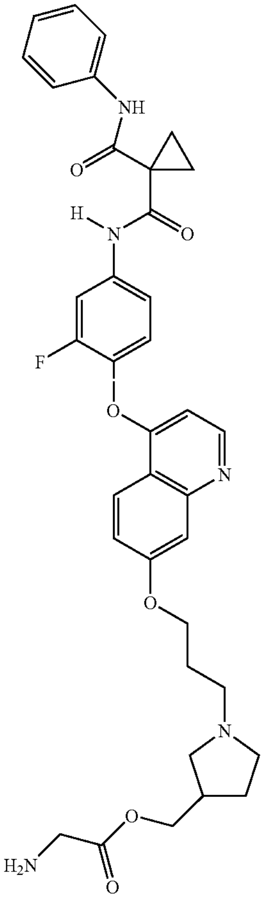

(24)

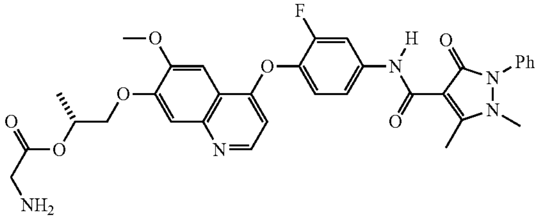

and (25)

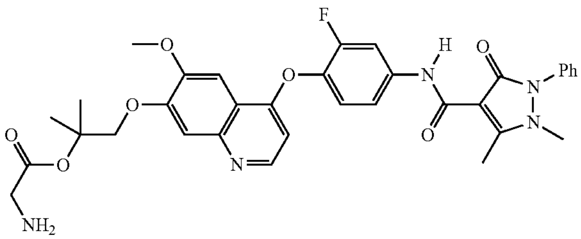

(26)

Provided herein includes the use of the compound disclosed herein, or the pharmaceutically acceptable salt thereof, in the manufacture of a medicament for the treatment either acutely or chronically of an angiogenesis mediated disease state, including those described herein. The compounds disclosed herein are useful in the manufacture of an anti-cancer medicament. The compounds disclosed herein are also useful in the manufacture of a medicament to attenuate, prevent, manage or treat disorders through inhibition of VEGFR and c-Met. Also provided herein is the pharmaceutical composition comprising a therapeutically effective amount of the compound of Formula (I) in association with at least one pharmaceutically acceptable carrier, adjuvant or diluent.

Also provided herein is a method of treating angiogenesis related disorders in a subject having or susceptible to such disorder, the method comprising treating the subject with a therapeutically effective amount of the compound of Formula (I).

Unless otherwise stated, all stereoisomers, geometric isomers, tautomers, solvates, metabolites, salts, and pharmaceutically acceptable prodrugs of the compounds disclosed herein are within the scope of the invention.

In certain embodiments, the salt is a pharmaceutically acceptable salt. The phrase “pharmaceutically acceptable” refers to that the substance or composition must be compatible chemically and/or toxicologically, with the other ingredients comprising a formulation, and/or the mammal being treated therewith.

The compounds disclosed herein also include salts of such compounds which are not necessarily pharmaceutically acceptable salts, and which may be useful as intermediates for preparing and/or purifying compounds of Formula (I) for separating enantiomers of compounds of Formula (I).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as malic acid, 2-hydroxy propanic acid, citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or alkaline earth metal hydroxide, and the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum, lithium, and the like.

Composition, Formulations and Administration of Compounds of the Invention

According to another aspect, the invention features pharmaceutical compositions that include a compound of Formula (I), a compound listed herein, or a compound named in Examples 1-79, and a pharmaceutically acceptable carrier, adjuvant, or vehicle. The amount of the compound in the compositions disclosed herein is such that is effective to detectably inhibit a protein kinase in a biological sample or in a patient.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The compositions disclosed herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. In some embodiments, the compositions are administered orally, intraperitoneally or intravenously. Sterile injectable forms of the compositions disclosed herein include aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that include water, Ringer's solution and isotonic sodium chloride solution. In addition, sterile, fixed oils are conventionally employed as a solvent or suspending medium.

For this purpose, any bland fixed oil includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions disclosed herein include orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions disclosed herein include administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The pharmaceutically acceptable compositions disclosed herein also include administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used. For topical applications, the pharmaceutically acceptable compositions may be formulated in a suitable ointment containing the active component suspended or dissolved in one or more carriers. Carriers for topical administration of the compounds disclosed herein include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, In other embodiments, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions disclosed herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Some non-limiting examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds disclosed herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as, for example, carboxymethyl-cellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain pacifying agents and can also be of a composition that they release the active ingredient(s) only, or in other embodiments, in a certain part of the intestinal tract, optionally, in a delayed manner. Some non-limiting examples of embedding compositions that can be used include polymeric substances and waxes.

Dosage forms for topical or transdermal administration of a compound disclosed herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, contemplated herein is the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds disclosed herein are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds disclosed herein that may be combined with the carrier materials to produce a composition in a single dosage form will vary depending upon the host treated, the particular mode of administration. In other embodiments, the compositions should be formulated so that a dosage of between 0.01-300 mg/kg body weight/day of the inhibitor can be administered to a patient receiving these compositions.

Compounds disclosed herein can be administered as the sole pharmaceutical agent or in combination with one or more other additional therapeutic (pharmaceutical) agents where the combination causes no unacceptable adverse effects. This may be of particular relevance for the treatment of hyper-proliferative diseases such as cancer. In this instance, the compound disclosed herein can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" refers to include chemotherapeutic agents and other anti-proliferative agents.

For example, chemotherapeutic agents or other antiproliferative agents may be combined with the compounds disclosed herein to treat proliferative disease or cancer. Examples of chemotherapeutic agents or other antiproliferative agents include HDAC inhibitors including, but are not limited to, SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. No 6,268,137, U.S. Pat. No. 5,578,716, U.S. Pat. No. 5,919,772, U.S. Pat. No. 6,054,439, U.S. Pat. No. 6,184,211, U.S. Pat. No. 6,020,318, U.S. Pat. No. 6,066,625, U.S. Pat. No. 6,506,735, U.S. Pat. No. 6,221,849, U.S. Pat. No. 6,953,783, U.S. Pat. No. 11,393,380.

In another embodiment disclosed herein, for example, chemotherapeutic agents or other anti-proliferative agents may be combined with the compounds disclosed herein to treat proliferative diseases and cancer. Examples of known chemotherapeutic agents include, but are not limited to, for example, other therapies or anticancer agents that may be used in combination with the inventive anticancer agents disclosed herein and include surgery, radiotherapy (in but a few examples, gamma-radiation, neutron beam radiotherapy, electron beam radiotherapy, proton therapy, brachytherapy, and systemic radioactive isotopes, to name a few), endocrine therapy, taxanes (taxol, taxotere etc), platinum derivatives, biologic response modifiers (interferons, interleukins, and tumor necrosis factor (TNF), TRAIL receptor targeting, agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate, Pemetrexed etc), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), Cell cycle inhibitors (KSP mitotic kinesin inhibitors, CENP-E and CDK inhibitors), enzymes (Asparaginase), and hormones (Tamoxifen, Leuprolide, Flutamide, and Megestrol), Gleevec™, adriamycin, dexamethasone, and cyclophosphamide. Antiangiogenic agents (Avastin and others). Kinase inhibitors (imatinib, sunitinib, sorafenib, tasigna, dasatinib, lapatinib, cetuximab (Erbitux), trastuzumab (Herceptin), erlotinib, gefitinib, pazopanib and others). Agents inhibiting or activating cancer pathways such as the mTOR, HIF (hypoxia induced factor) pathways and others. For a more comprehensive discussion of updated cancer therapies see, http://www.nci.nih.gov/, a list of the FDA approved oncology drugs at http://www.fda.gov/cder/cancer/druglist-rame.htm, and The Merck Manual, Eighteenth Ed. 2006, the entire contents of which are hereby incorporated by reference.

In another embodiment, the compounds disclosed herein can be combined with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, or vindesine.

Other cytotoxic drugs suitable for use with the compounds disclosed herein include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, or vinorelbine.

Other cytotoxic anti-cancer agents suitable for use in combination with the compounds disclosed herein also include newly discovered cytotoxic principles, some examples of cytotoxic principles include, but are not limited to, oxaliplatin, gemcitabine, capecitabine, epothilone and its natural or synthetic derivatives, temozolomide (Quinn et al., *J. Clin. Oncology,* 2003, 21(4), 646-651), tositumomab (Bexxar), trabedectin (Vidal et al., *Proceedings of the American Society for Clinical Oncology,* 2004, 23, abstract, 3181), and the inhibitors of the kinesin spindle protein Eg5 (Wood et al., *Curr. Opin. Pharmacol.* 2001, 1, 370-377).

In another embodiment, the compounds disclosed herein can be combined with other signal transduction inhibitors. Of particular interest are signal transduction inhibitors which target the EGFR family, such as EGFR, HER-2, and HER-4 (Raymond et al., *Drugs,* 2000, 60 (Suppl.1), 15-23; Harari et al., *Oncogene,* 2000, 19 (53), 6102-6114), and their respective ligands. Examples of such agents include, by no way of limitation, antibody therapies such as Herceptin (trastuzumab), Erbitux (cetuximab), Vectibix (panitumumab), and pertuzumab. Examples of such therapies also include, by no way of limitation, small-molecule kinase inhibitors such as Iressa (Gefitinib), Tarceva (Erlotinib), Tykerb (Lapatinib), Canertinib (CI1033), AEE788.

In another embodiment, the compounds disclosed herein can be combined with other signal transduction inhibitors targeting receptor kinases of the split-kinase domain families (VEGFR, FGFR, PDGFR, flt-3, c-kit, c-fins, and the like), and their respective ligands. These agents include, by no way of limitation, antibodies such as Avastin (bevacizumab). These agents also include, by no way of limitation, small-molecule inhibitors such as Gleevec (Imanitib), Sprycel (Dasatinib), Tasigna (Nilotinib), Nexavar (Sorafenib), Raf265 (CHIR-265), Pazopanib, Recentin (Cediranib), Zactima (Vandetanib), Vatalanib (PTK787), Telatinib (BAY-579352), BMS-690514 (de LaMotte Rouge, Cancer Res. 2007, 67, 6253), Brivanib (BMS582664), BMS540215, Axitinib (AG-013736). Motesanib (AMG706), Sunitinib, Vandetanib, Tivozanib (KRN-951), Dovitinib (TKI-258/CHIR-258), Tandutinib.

In another embodiment, the compounds disclosed herein can be combined with inhibitors of histone deacetylase. Examples of such agents include, by no way of limitation, suberoylanilide hydroxamic acid (SAHA), LAQ-824 (Ottmann et al., *Proceedings of the American Society for Clinical Oncology,* 2004, 23, abstract, 3024), LBH-589 (Beck et al., *Proceedings of the American Society for Clinical Oncology,* 2004, 23, abstract, 3025), MS-275 (Ryan et al., *Proceedings of the American Association of Cancer Research,* 2004, 45, abstract, 2452), FR-901228 (Piekarz et al., *Proceedings of the American Society for Clinical Oncology,* 2004, 23, abstract, 3028) and MGCD0103 (U.S. Pat. No. 6,897,220).

In another embodiment, the compounds disclosed herein can be combined with other anti-cancer agents such as proteasome inhibitors, and m-TOR inhibitors. These include, by no way of limitation, bortezomib, and sirolimus (rapamycin), everolimus, temsirolimus. The compounds disclosed herein can be combined with other anti-cancer agents such as topoisomerase inhibitors, including but not limited to camptothecin.

Those additional agents may be administered separately from the compound-containing composition, as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another that would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions disclosed herein will be no more than the amount that would normally be administered in a composition comprising that therapeutic agent as the only active agent. In other embodiment, the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound disclosed herein may act synergistically.

Uses of the Compounds and Compositions of the Invention

The invention features pharmaceutical compositions that include a compound of Formula (I) or a compound listed herein, and a pharmaceutically acceptable carrier, adjuvant, or vehicle. The amount of compound in the compositions disclosed herein is such that is effective to detectably inhibit a protein kinase, such as VEGFR/KDR, and/or c-Met inhibitory activity. The compounds disclosed herein are useful in therapy as antineoplasia agents or to minimize deleterious effects of VEGF and/or HGF.

Compounds disclosed herein would be useful for, but not limited to, the prevention or treatment of proliferative diseases, conditions, or disorders in a patient by administering to the patient a compound or a composition disclosed herein in an effective amount. Such diseases, conditions, or disorders include cancer, particularly metastatic cancer, atherosclerosis, and lung fibrosis.

Compounds disclosed herein would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds disclosed herein are also useful in the treatment of diabetic conditions such as diabetic retinopathy and microangiopathy. The compounds disclosed herein are also useful in the reduction of blood flow in a tumor in a subject. The compounds disclosed herein are also useful in the reduction of metastasis of a tumor in a subject.

Besides being useful for human treatment, these compounds are also useful for veterinary treatment of companion animals, exotic animals and farm animals, including mammals, rodents, and the like. In other embodiments, animals include horses, dogs, and cats. As used herein, the compounds disclosed herein include the pharmaceutically acceptable derivatives thereof.

Where the plural form is used for compounds, salts, and the like, this is taken to refer to also a single compound, salt, and the like.

The treatment method that includes administering a compound or composition disclosed herein can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition disclosed herein as a single dosage form or separately from the compound or composition as part of a multiple dosage form. The additional therapeutic agent may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

The invention also features a method of inhibiting the growth of a cell that expresses VEGFR, or c-Met, that includes contacting the cell with a compound or composition disclosed herein, thereby causing inhibition of growth of the cell. Examples of a cell whose growth can be inhibited include: a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

Provided herein a method of inhibiting VEGFR, and/or c-Met kinase activity in a biological sample that includes contacting the biological sample with a compound or composition disclosed herein. The term "biological sample" as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly VEGFR or c-Met kinase activity, in a biological sample is useful for a variety of purposes known to one of skill in the art. Examples of such purposes include, but are not limited to, blood transfusion, organ-transplantation, biological specimen storage, and biological assays.

In certain embodiments disclosed herein, an "effective amount" or "effective dose" of the compound or pharmaceutically acceptable composition is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds disclosed herein or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound disclosed herein.

Suitable coatings and the general preparation of coated implantable devices are described in U.S. Pat. Nos. 6,099,562, 5,886,026, and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics into the composition. Implantable devices coated with a compound disclosed herein are another embodiment disclosed herein. The compounds may also be coated on implantable medical devices, such as beads, or co-formulated with a polymer or other molecule, to provide a "drug depot" thus permitting the drug to be released over a longer time period than administration of an aqueous solution of the drug.

General Synthetic Procedures

Generally, the compounds disclosed herein may be prepared by methods described herein, wherein the substituents are as defined for formulas (I), (IV) or (V), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers: Aldrich Chemical Company, Arco Chemical Company and Alfa Chemical Company, and were used without further purification unless otherwise indicated. Common solvents were purchased from commercial suppliers: Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMA and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz spectrometer at ambient temperature. $^1$H NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis, An ESI source was used on the LC-MS spectrometer.

Low-resolution mass spectral (MS) data were also determined on an Agilent 6120 series LC-MS spectrometer equipped with G1311A Quaternary pump, a G1316A TCC (Temperature Control of Column, maintained at 30° C.), a G1329A autosampler and a G1315D DAD detector were used in the analysis, An ESI source was used on the LC-MS spectrometer.

Both LC-MS spectrometers were equipped with an Agilent Zorbax SB-C18, 2.1×30 mm, 5 nm column. Inject volumn was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient condition is shown in Table 2:

TABLE 2

| Time (min) | A (Acetonitrile, 0.1% HCOOH) | B (water, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were also assessed by Agilent 1100 Series high performance liquid chromatography (HPLC) with UV detection at 210 nm and 254 nm (Zorbax SB-C18, 2.1×30 mm, 4 micorn, 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:

HOAc acetic acid
MeCN, $CH_3CN$ acetonitrile
$NH_3$ ammonia
$NH_4Cl$ ammonium chloride
HBTU O-benzotriazol-1-yl-N,N,N',N'-tetramethyluronium hexafluorophosphate
HATU O-(7-azabenzotriazol-1-yl)-N,N,N',N'-tetramethyluronium hexafluorophosphate
PyBop benzotriazol-1-yl-oxy-tripyrrolidino-phosphonium hexafluorophosphate
$Pd_2(dba)_3$ bis(dibenzylideneacetone) palladium
BINAP 2,2'-bis(diphenylphosphino)-1,1'-binaphthyl
TEAC bis(tetra-ethylammonium)carbonate
$BBr_3$ boron tribromide
BSA bovine serum albumin
$Br_2$ bromine
BOC, Boc tert-butyloxycarbonyl
$Cs_2CO_3$ cesium carbonate
$CHCl_3$ chloroform
$CDCl_3$ chloroform deuterated
Cu copper
CuI copper(I) iodide
$Et_2O$ diethyl ether
DBU 1,8-diazabicyclo[5,4,0]undec-7-ene
DIBAL diisobutylaluminum hydride
DIAD diisopropyl azodicarboxylate
DIEA diisopropylethylamine
DEAD dimethyl azodicarboxylate
DMF dimethylformamide
DMAP 4-dimethylaminopyridine
DMSO dimethylsulfoxide
EDC, EDCI 1-(3-dimethylaminopropyl)-3-ethylcarbodiimide hydrochloride
dppa diphenylphosphoryl azide
EtOAc ethyl acetate
HBr hydrobromic acid
HCl hydrochloric acid
HOAt HOAT 1-hydroxy-7-Azabenzotriazole
HOBt 1-hydroxybenzotriazole hydrate
$H_2$ hydrogen
$H_2O_2$ hydrogen peroxide
Fe iron
LiHMDS lithium bis(trimethylsilyl)-amide
LDA lithium diisopropylamide
MCPBA meta-chloroperbenzoic acid
$MgSO_4$ magnesium sulfate
MeOH, $CH_3OH$ methanol
MeI methyl iodide
$CH_2Cl_2$, DCM methylene chloride
NMP N-methylpyrrolidinone
mL, ml milliliter
$N_2$ nitrogen
Pd/C palladium on carbon
$Pd(OAc)_2$ palladium acetate
$Pd(OH)_2$ palladium hydroxide
$Pd(PPh_3)_4$ palladium tetrakis triphenylphosphine
$Pd(dppf)Cl_2$ 1,1-bis(diphenylphosphino)ferrocene palladium chloride
PE petroleum ether (60-90° C.)

PBS phosphate buffered saline $POCl_3$ phosphorous oxychloride $K_2CO_3$ potassium carbonate KOH potassium hydroxide RT, rt, room temperature Rt retention time $NaHCO_3$ sodium bicarbonate $NaBH_4$ sodium borohydride $NaBH_3CN$ sodium cyanoborohydride NaOtBu sodium tert-butoxide NaOH sodium hydroxide $NaClO_2$ sodium chlorite NaCl sodium chloride $NaH_2PO_4$ sodium dihydric phosphate NaH sodium hydride NaI sodium iodide $Na_2SO_4$ sodium sulfate TBTU O-benzotriazol-1-yl-N,N,N',N'-tetramethyluronium tetrafluoroborate THF tetrahydrofuran $Et_3N$, TEA triethylamine TFA trifluoroacetic acid $P(t\text{-}bu)_3$ tri(tert-butyl)phosphine NBS N-bromosuccinimide TBAI Tetrabutylammonium iodide $H_2O$ water Scheme 1

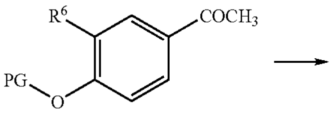

1

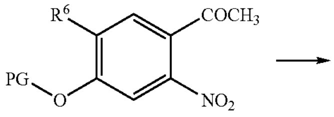

2

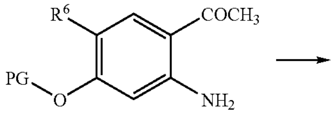

3

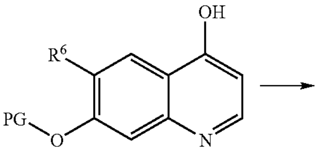

4

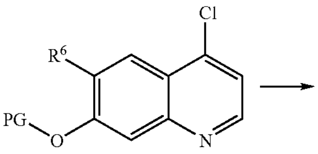

5

-continued

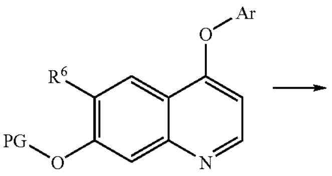

6

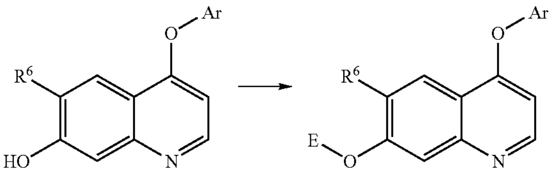

7 8

Kinase inhibitor 8 disclosed herein can be prepared by the process illustrated in Scheme 1. Substituted aryl 1 is nitrated to give compound 2 by a suitable nitration reagent such as $HNO_3$ at appropriate temperature such as 0° C. The $NO_2$ group is then reduced by a reducing reagent such as Fe or Zn powder, or under hydrogenation condition in the presence of Pd catalyst such as Pd/C. Aniline 3 is condensed with a formate (for example, ethyl formate) under basic condition to give substituted quinoline 4. The hydroxy group in compound 4 is converted to Cl using a chlorinating agent such as $POCl_3$ or $SOCl_2$ under heating conditions to afford quinoline chloride 5. Coupling of 5 with appropriate aryl derivatives (with a free OH group) yields substituted diaryl ethers 6 (for references, see Kubo, K., et al, *J. Med Chem.,* 2005, 48, 1359; Harmange, J.-C., et al, *J. Med Chem.,* 2008, 51, 1649.). The protecting group PG is removed to provide compound 7, which is condensed with E-L (L=a suitable leaving group such as OMs, Cl, Br or I, E is a moiety as defined by $R^1$-$R^4$, $Y_1$, $Y_2$ and W or its precursor) to afford kinase inhibitor 8.

Scheme 2

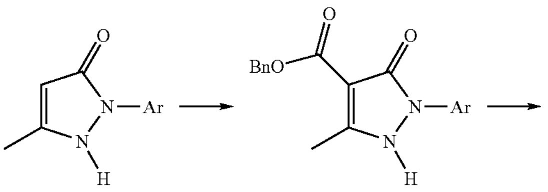

9

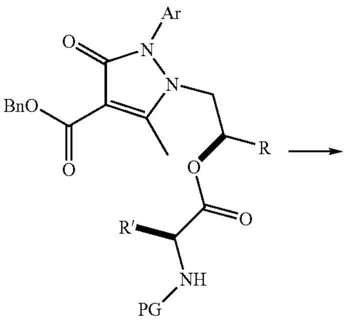

10

-continued

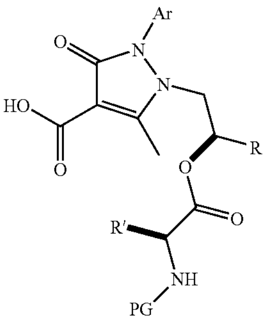

11

Substituted pyrazolone derivatives 11 can be synthesized through the procedure depicted in Scheme 2. 5-Methyl-2-aryl-1,2-dihydropyrazol-3-one is first acylated with alkyl chloroformate to afford 9 under basic conditions (such as $Ca(OH)_2$ in dioxane or 2-MeTHF under heating conditions). The free nitrogen on the pyrazolone ring 9 can then be alkylated with chiral oxiranes in the presence of Lewis acid such as $Mg(ClO_4)_2$, $Ca(SO_3CF_3)_2$, etc. to afford intermediate alcohol, which is coupled with appropriate protected amino acid (such as Boc- or Cbz-protected α-aminoacid) with the help of condensing agent such as EDCI/DMAP to give intermediate 10. Hydrogenation of 10 under catalyst Pd/C gives acids 11 after treating 11 with an acid (ref: Liu, L. et al, *J. Med Chem.* 2008, 51, 3688).

Scheme 3

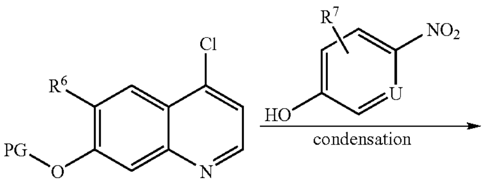

12

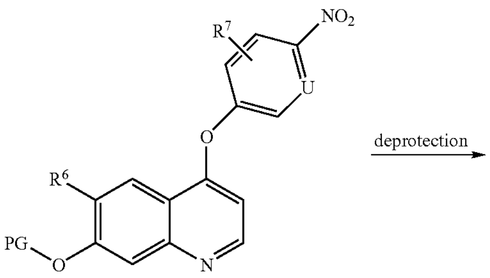

13

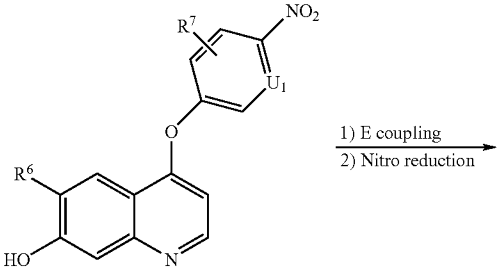

14

-continued

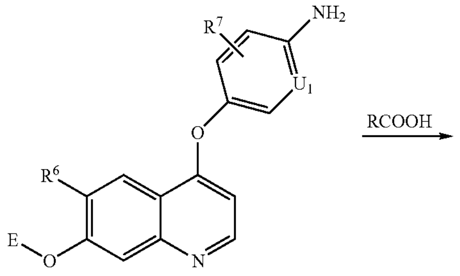

15

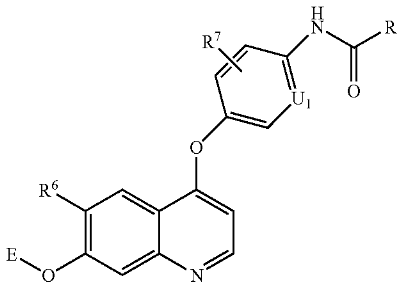

16

Substituted kinase inhibitor 16 disclosed herein can be prepared using a process as demonstrated in Scheme 3. Condensation of 12 under heating conditions with a nitro-aryl derivative gives compound 13. Deprotection to remove the protecting group PG leads to compound 14. Attachment of E group through a coupling process followed by the reduction of nitro group affords compound 15. Coupling of aniline 15 with an acid in the presence of coupling reagent such as EDCI or HATU furnishes desired kinase inhibitor 16 (R represents pyrazolone or 1-(arylcarbamoyl)cyclopropanyl group).

Scheme 4

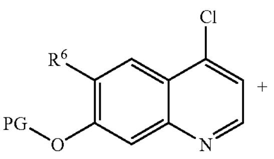

17

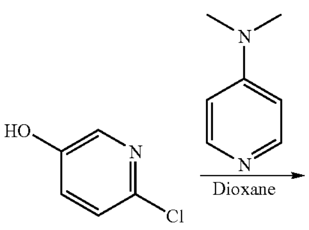

18

-continued

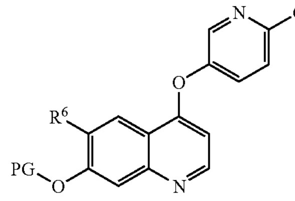

19

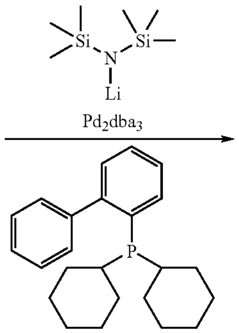

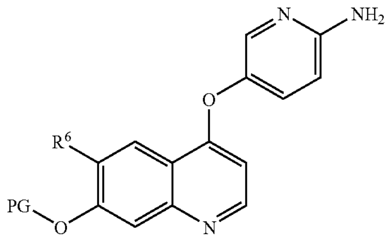

20

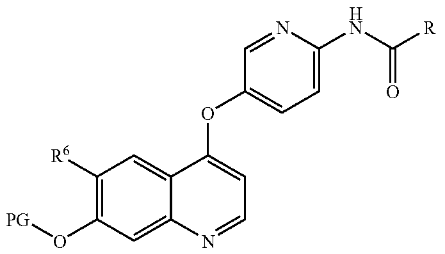

21

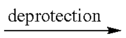

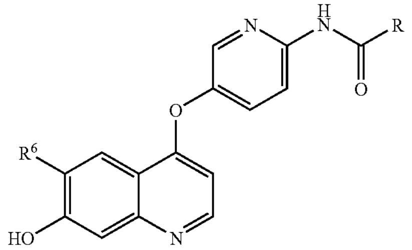

22

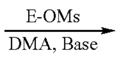

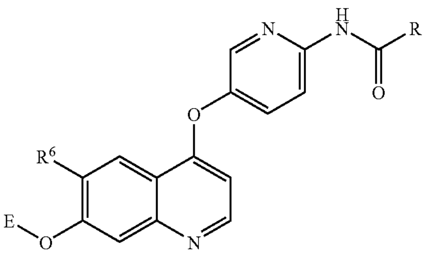

23

Alternatively, kinase inhibitors disclosed herein can be obtained through the process as described in Scheme 4. Thus, compound 20 is prepared through Pd catalyzed amination of 2-chloropyridine derivative 19. Coupling of aniline 20 with an acid followed by the removal of protecting group PG gives compound 22 (ref: Liu, L. et al, *J. Med Chem.* 2008, 51, 3688.). An appropriate group containing free hydroxy (OH) moiety is appended to the quinoline portion to yield compound 23. In a special case, PG can be a methyl group in compound 7, providing compound 21 as the desired kinase inhibitor.

Scheme 5

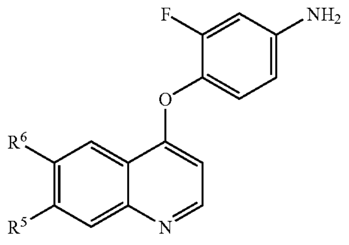

24

+

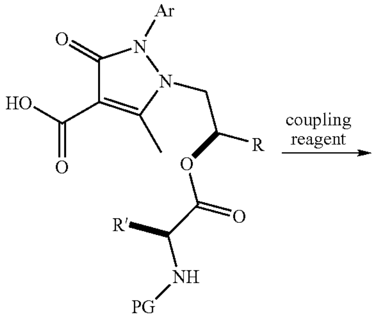

11

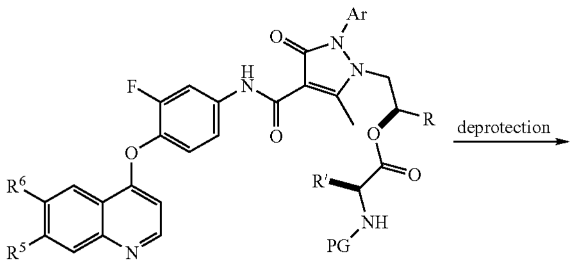

25

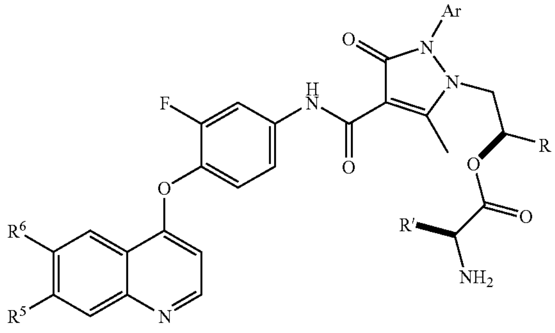

26

Alternatively, kinase inhibitors 26 disclosed herein can be obtained through the process as described in Scheme 5. Amine derivatives 24 first coupled with acids 11 to afford protected α-amino acid derivatives 25. The protecting group PG (such as Boc or Cbz) can then be removed under standard conditions to furnish kinase inhibitors 26 disclosed herein, preferably in a pharmaceutically acceptable salt form.

Scheme 6

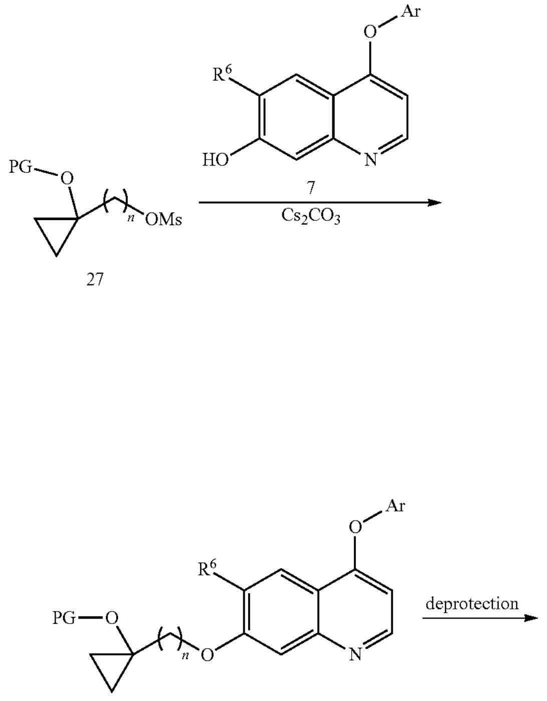

7

27

28

-continued

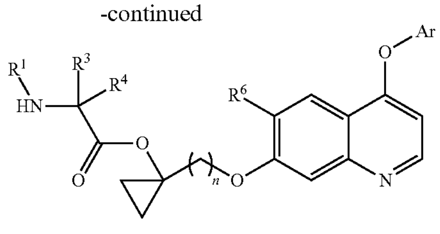

32

$n = 1, 2, 3, 4, 5.$

Alternatively, kinase inhibitors 32 disclosed herein can be obtained through the process as described in Scheme 6. Free hydroxy group in 7 is coupled with compound 27 under basic conditions to afford compound 28. The protecting group PG (such as acetate, benzoate or protected aminoacid) can then be removed under standard conditions to furnish alcohol 29. Coupling of 29 with protected α-aminoacid 30 with the aid of condensing agents such as EDCI/DAMP afforded compound 31. The protecting group PG (such as Boc or Cbz) can then be removed under standard conditions to furnish kinase inhibitors 32 disclosed herein, preferably in a pharmaceutically acceptable salt form.

EXAMPLES

Example 1

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate fumarate

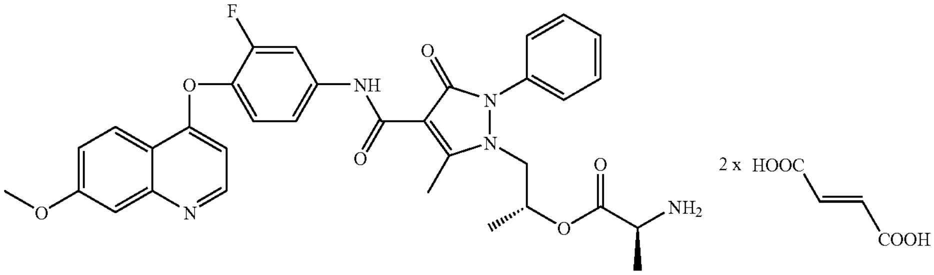

-continued

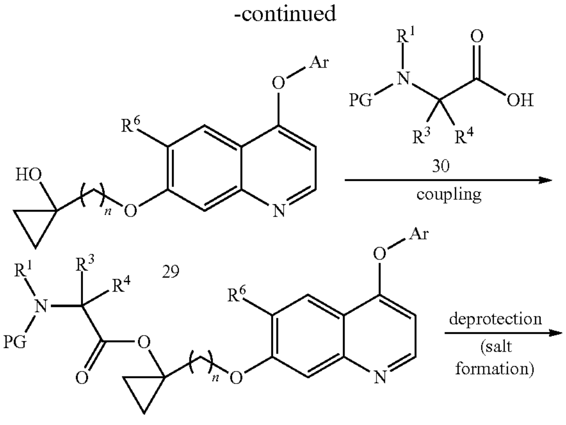

29

30

32

Step 1) (S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl) 2-(benzyloxycarbonyl-amino)propanoate To a mixture of (R)—N-(3-fluoro-4-(7-methoxyquinolin-4-yloxy)phenyl-1-(2-hydr-oxypropyl)-5-methyl-3-oxo-2-phenyl-2,3-dihydro-1H-pyrazole-4-carboxamide (2.0 g, 3.68 mmol), (S)—N-Cbz-alanine (1.647 g, 7.36 mmol, Shanghai Hanhong Chemical CO., LTD.) and DMAP (0.90 g, 7.36 mmol, Aladdin) in $CH_2Cl_2$ (30 mL) was added EDC solid (2.116 g, 11.04 mmol, Aladdin) in portions at 0° C. After stirring at 0° C. for 2 hrs, the reaction mixture was warmed up to room temperature and continued to stir at rt for 20 hrs. The mixture was diluted with 180 mL of $CH_2Cl_2$. The resulted mixture was washed with 30 mL of 0.1 N HCl, followed by 50 mL of saturated $NaHCO_3$ solution. The aqueous phase was extracted with EtOAc (50 mL×3), and the combined organic phases were dried over $Na_2SO_4$, filtered and concentrated in vacuo. The residue was purified by a silica gel column chromatography (EtOAc) to give the desired compound as a pale yellow solid (2.1 g, 73.1%).

MS (ESI, pos. ion) m/z: 748 (M+1);

$^1$H NMR (400 MHz, $CDCl_3$): δ 1.21 (d, J=5.4 Hz, 3H), 1.39 (d, J=6.6 Hz, 3H), 3.0 (s, 3H), 3.75 (d, J=3.2 Hz, 1H), 3.78 (s, 3H), 4.05 (m, 1H), 4.23 (t, 1H), 4.95 (s, 1H), 5.09 (dd, J=12.4 Hz, J=37.2 Hz, 2H), 5.22 (d, J=7.2 Hz, 1H), 6.40 (dd, J=0.8 Hz, J=6.0 Hz, 1H), 7.16 (t, 1H), 7.22 (dd, J=2.8 Hz, J=12 Hz, 1H), 7.27 (t, 2H), 7.35 (m, 5H), 7.41 (m, 1H), 7.47 (m, 1H), 7.55 (m, 2H), 7.90 (dd, J=2.0 Hz, J=14.4 Hz, 1H), 8.28 (d, J=9.2 Hz, 1H), 8.66 (d, J=5.2 Hz, 1H), 10.81 (s, 1H).

Step 2) (S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl) 2-aminopropanoat To a solution of (S)—((R)-1-(4-(3-fluoro-4-(7-methoxyquinolin-4-yloxy)phenyl carbamoyl)-5-methyl-3-oxo-2-phenyl-2,3-dihydropyrazol-1-yl)propan-2-yl)2-(benzyloxycarbonyl-amino)propanoate (74.7 mg, 0.1 mmol) in a mixture of EtOAc (15 mL) and MeOH (10 mL) was added catalytic amount Pd/C (10%, ~55% w/w water content, 20 mg) under $N_2$ atmosphere. The suspension was degassed under vacuum and then purged with $H_2$. The reaction mixture was stirred at rt for 20 minutes under $H_2$ balloon. The mixture was filtered and the residue was washed with MeOH (5 mL×3). The filtrate used for the next step immediately.

MS (ESI, pos. ion) m/z: 614.1 (M+1).

Step 3) (S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl) 2-aminopropanoate fumarate To a solution of (S)—((R)-1-(4-(3-fluoro-4-(7-methoxyquinolin-4-yloxy)phenyl carbamoyl)-5-methyl-3-oxo-2-phenyl-2,3-dihydropyrazol-1-yl)propan-2-yl)2-amino propanoate (61.3 mg, 0.1 mmol) in EtOAc (15 mL)/MeOH (10 mL) was added fumaric acid (23.2 mg, 0.2 mmol, Shantou Xilong chemical factory). After stirring for 40 min, the reaction mixture was concentrated in vacuo, and the residue was crystallized in MeOH (2 mL)/EtOAc (10 mL) (v/v=1:5). The solid was collected by filtration, washed with EtOAc (5 mL×3) and dried under vacuum to give the title compound as a white solid (68.2 mg, 81%).

MS (ESI, pos. ion) m/z: 614.1 (M+1); LC-MS Rt: 3.418 min;

$^1$H NMR (400 MHz, $d_6$-DMSO): δ 1.06 (d, J=6.4 Hz, 3H), 1.23 (d, J=2.0 Hz, 3H), 2.79 (s, 3H), 3.59 (dd, J=7.2 Hz, J=14.4 Hz, 1H), 3.94 (s, 3H), 3.98 (dd, J=3.2 Hz, J=16 Hz, 1H), 4.27 (dd, J=9.2 Hz, J=16 Hz, 1H), 4.83 (m, 1H), 6.47 (d, J=5.2 Hz, 1H), 6.60 (s, 4H), 7.31 (dd, J=2.4 Hz, J=9.2 Hz, 1H), 7.36 (dd, J=2.0 Hz, J=8.8 Hz, 1H), 7.43 (m, 4H), 7.53 (m, 1H), 7.62 (t, 2H), 7.98 (dd, J=2.4 Hz, J=12.8 Hz, 1H), 8.23 (d, J=9.2 Hz, 1H), 8.62 (d, J=5.2 Hz, 1H), 10.87 (s, 1H).

Example 2

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate benzoate

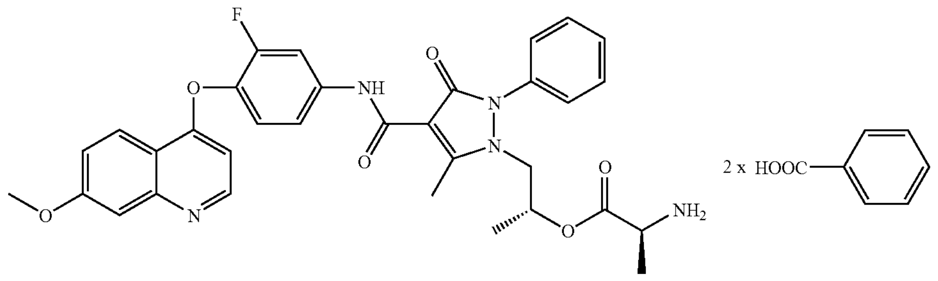

The title compound was prepared according to the procedure described in Example 1 Step 3 by using (S)—((R)-1-(4-(3-fluoro-4-(7-methoxyquinolin-4-yloxy)phenyl carbamoyl)-5-methyl-3-oxo-2-phenyl-2,3-dihydropyrazol-1-yl) propan-2-yl)2-amino-propanoate (61.3 mg, 0.1 mmol) and benzoic acid (24.4 mg, 0.2 mmol, Tianjin Chemical Reagent Factory). The title compound was obtained as a pale yellow solid (64 mg, 74.7%.

MS (ESI, pos. ion) m/z: 614.1 (M+1); LC-MS Rt: 3.422 min;

$^1$H NMR (400 MHz, $d_6$-DMSO): δ 1.28 (d, J=4.0 Hz, 3H), 1.32 (d, J=6.8 Hz, 3H), 2.87 (s, 3H), 3.61 (m, 1H), 3.79 (dd, J=3.6 Hz, J=19.2 Hz, 1H), 3.99 (s, 3H), 4.09 (m, 1H), 4.97 (m, 2H), 5.28 (s, 2H), 6.46 (d, J=5.6 Hz, 1H), 7.17 (t, 1H), 7.28 (m, 3H), 7.38 (d, J=7.6 Hz, 1H), 7.46 (m, 3H), 7.57 (m, 3H), 7.91 (dd, J=2.0 Hz, J=14.4 Hz, 1H), 8.10 (d, J=7.6 Hz, 3H), 8.28 (d, J=9.2 Hz, 1H), 8.67 (d, J=5.2 Hz, 1H), 10.78 (s, 1H).

Example 3

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate methanesulfonate

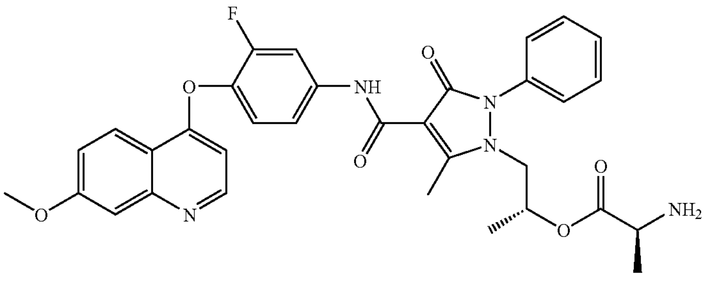

2 x $CH_3SO_3H$

The title compound was prepared according to the procedure described in Example 1 Step 3 by using (S)—((R)-1-(4-(3-fluoro-4-(7-methoxyquinolin-4-yloxy)phenyl carbamoyl)-5-methyl-3-oxo-2-phenyl-2,3-dihydropyrazol-1-yl) propan-2-yl)2-amino-propanoate (61.3 mg, 0.1 mmol) and methanesulfonic acid (19.3 mg, 0.2 mmol, Shanghai Rich-Joint Chemical Reagents CO., Ltd). The title compound was obtained as a pale yellow solid (61.2 mg, 76%).

MS (ESI, pos. ion) m/z: 614.1 (M+1); LC-MS Rt: 3.47 min;

Example 4

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate 4-methylbenzenesulfonate

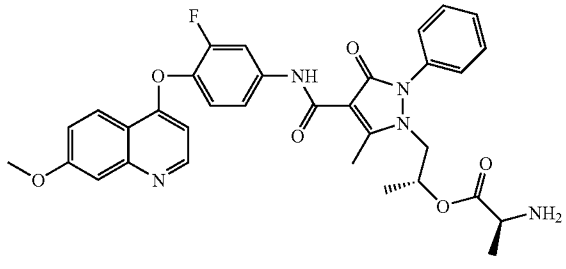

2 x 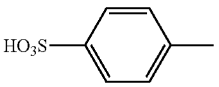

To a solution of (S)—((R)-1-(4-(3-fluoro-4-(7-methoxyquinolin-4-yloxy)phenyl carbamoyl)-5-methyl-3-oxo-2-phenyl-2,3-dihydropyrazol-1-yl)propan-2-yl)2-aminopropanoate (61.3 mg, 0.1 mmol) in EtOAc (15 mL)/MeOH (10 mL) was added p-toluene sulfonic acid (38 mg, 0.2 mmol, Shanghai chemical reagent factory). After stirring for 40 min, the mixture was concentrated in vacuo, and the resulted oil was washed with a mixture of MeOH (2 mL)/EtOAc (10 mL) followed by EtOAc (5 mL×3) to give the title compound as yellow oil (59.6 mg, 60%).

MS (ESI, pos. ion) m/z: 614.1 (M+1); LC-MS Rt: 3.59 min.

Example 5

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate oxalic acid

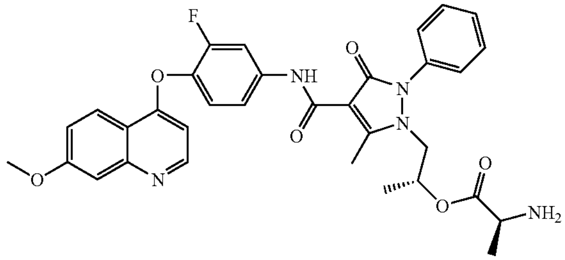

HOOC—COOH

The title compound was prepared according to the procedure described in Example 1 Step 3 by using (S)—((R)-1-(4-(3-fluoro-4-(7-methoxyquinolin-4-yloxy)phenyl carbamoyl)-5-methyl-3-oxo-2-phenyl-2,3-dihydropyrazol-1-yl) propan-2-yl)2-amino-propanoate (61.3 mg, 0.1 mmol) and oxalic acid dihydrate (25.2 mg, 0.2 mmol, Tianjin Chemical Factory). The title compound was obtained as a white solid (66.3 mg, 94.0%).

MS (ESI, pos. ion) m/z: 614.1 (M+1); LC-MS Rt: 3.53 min;

$^1$H NMR (400 MHz, $d_6$-DMSO): δ 1.07 (d, J=8.4 Hz, 3H), 1.34 (d, J=7.2 Hz, 3H), 2.79 (s, 3H), 3.89 (dd, J=6.8 Hz, J=14 Hz, 1H), 3.94 (s, 3H), 4.03 (dd, J=7.2 Hz, J=14 Hz, 1H), 4.30 (dd, J=9.2 Hz, J=16 Hz, 1H), 4.87 (m, 1H), 6.47 (d, J=4.8 Hz, 1H), 7.32 (dd, J=2.8 Hz, J=9.2 Hz, 1H), 7.36 (dd, J=1.6 Hz, J=8.8 Hz, 1H), 7.44 (m, 4H), 7.54 (t, 1H), 7.62 (t, 2H), 7.98 (dd, J=2.4 Hz, J=13.2 Hz, 1H), 8.23 (d, J=9.2 Hz, 1H), 8.63 (d, J=5.2 Hz, 1H), 10.87 (s, 1H).

Example 6

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate(2S,3S)-2,3-dihydroxysuccinate

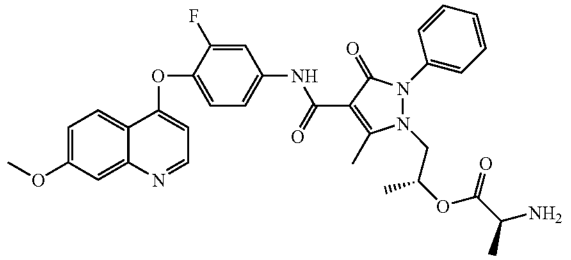

2.5 x

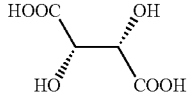

The title compound was prepared according to the procedure described in Example 1 Step 3 by using (S)—((R)-1-(4-(3-fluoro-4-(7-methoxyquinolin-4-yloxy)phenyl carbamoyl)-5-methyl-3-oxo-2-phenyl-2,3-dihydropyrazol-1-yl) propan-2-yl)2-amino-propanoate (61.3 mg, 0.1 mmol) and L-tartaric acid (30.0 mg, 0.2 mmol). The title compound was obtained as a white solid (70.5 mg, 89.2%).

MS (ESI, pos. ion) m/z: 614.1 (M+1); LC-MS Rt: 3.60 min;

$^1$H NMR (400 MHz, $d_6$-DMSO): δ 1.08 (d, J=6.4 Hz, 3H), 1.29 (d, J=6.8 Hz, 3H), 1.99 (s, 1H), 2.79 (s, 3H), 3.77 (dd, J=7.2 Hz, J=12.8 Hz, 1H), 3.94 (s, 3H), 4.0 (dd, J=2.8 Hz, J=15.2 Hz, 1H), 4.18 (s, 5H), 4.29 (dd, J=9.6 Hz, J=16.8 Hz, 1H), 4.86 (m, 1H), 6.47 (d, J=5.2 Hz, 1H), 7.31 (dd, J=2.4 Hz, J=8.8 Hz, 1H), 7.36 (dd, J=2.0 Hz, J=8.8 Hz, 1H), 7.44 (m, 4H), 7.54 (t, 1H), 7.62 (t, 2H), 7.99 (dd, J=2.4 Hz, J=13.2 Hz, 1H), 8.23 (d, J=9.2 Hz, 1H), 8.63 (d, J=5.2 Hz, 1H), 10.88 (s, 1H).

Example 7

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate hydrochloride

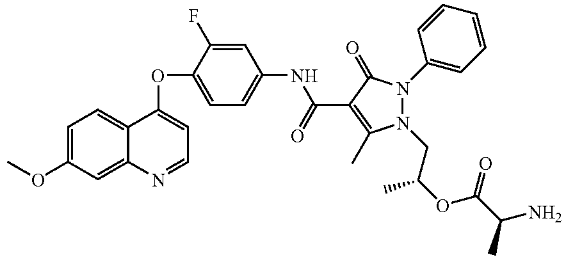

2 x HCl

The title compound was prepared according to the procedure described in Example 1 Step 3 by using (S)—((R)-1-(4-(3-fluoro-4-(7-methoxyquinolin-4-yloxy)phenyl-carbamoyl)-5-methyl-3-oxo-2-phenyl-2,3-dihydropyrazol-1-yl) propan-2-yl)2-amino-propanoate (61.3 mg, 0.1 mmol) and a saturated HCl solution in EtOAc (3 mL). The title compound was obtained as a pale yellow solid (57.1 mg, 83%).

MS (ESI, pos. ion) m/z: 614.1 (M+1); LC-MS Rt: 3.61 min;

$^1$H NMR (400 MHz, $d_6$-DMSO): δ1.07 (d, J=6.4 Hz, 3H), 1.34 (d, J=7.2 Hz, 3H), 2.78 (s, 3H), 3.88 (dd, J=6.8 Hz, J=12.4 Hz, 1H), 4.0 (s, 3H), 4.04 (d, J=3.6 Hz, 1H), 4.29 (dd, J=8.8 Hz, J=16 Hz, 1H), 4.85 (m, 1H), 6.87 (d, J=4.8 Hz, 1H), 7.42 (m, 2H), 7.54 (m, 2H), 7.61 (m, 3H), 8.04 (dd, J=2.4 Hz, J=12.8 Hz, 1H), 8.44 (m, 3H), 8.9 (d, J=6.0 Hz, 1H), 10.93 (s, 1H).

Example 8

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate 2-hydroxypropane-1,2,3-tricarboxylate

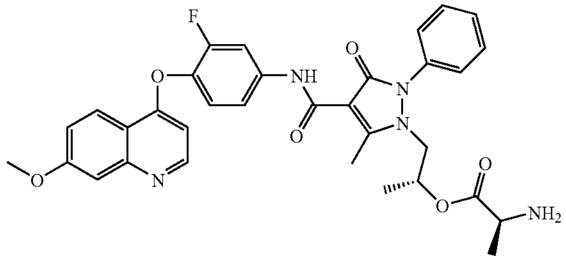

2 x

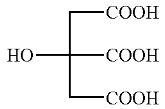

The title compound was prepared according to the procedure described in Example 1 Step 3 by using (S)—((R)-1-(4-(3-fluoro-4-(7-methoxyquinolin-4-yloxy)phenyl-carbamoyl)-5-methyl-3-oxo-2-phenyl-2,3-dihydropyrazol-1-yl) propan-2-yl)2-amino-propanoate (61.3 mg, 0.1 mmol) and citric acid (38.4 mg, 0.2 mmol, Tianjin Chemical Factory). The title compound was obtained as a white solid (78.7 mg,79%)

MS (ESI, pos. ion) m/z: 614.1 (M+1); LC-MS Rt: 3.61 min.

Example 9

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate sulfate

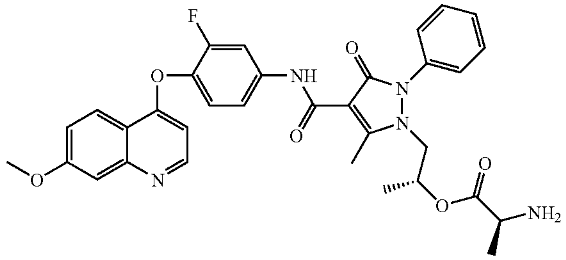

$H_2SO_4$

.

The title compound was prepared according to the procedure described in Example 1 Step 3 by using (S)—((R)-1-(4-(3-fluoro-4-(7-methoxyquinolin-4-yloxy)phenyl-carbamoyl)-5-methyl-3-oxo-2-phenyl-2,3-dihydropyrazol-1-yl)propan-2-yl)2-amino-propanoate (61.3 mg, 0.1 mmol) and sulfuric acid (19.6 mg, 0.2 mmol). The title compound was obtained as a white solid (63.4 mg, 89.2%).

MS (ESI, pos. ion) m/z: 614.1 (M+1); LC-MS Rt: 3.59 min.

Example 10

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate succinate

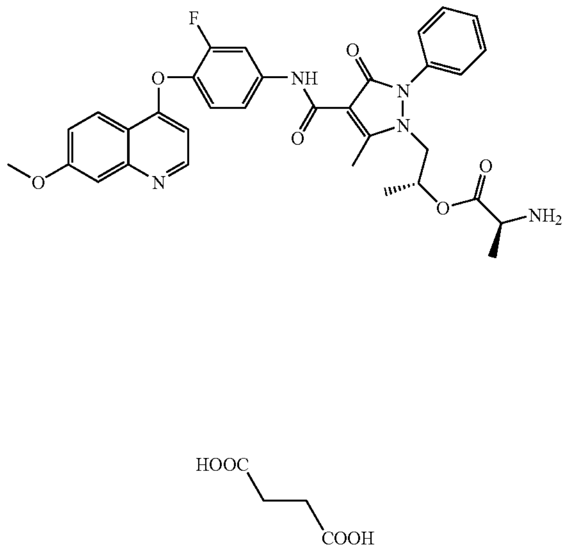

The title compound was prepared according to the procedure described in Example 1 Step 3 by using (S)—((R)-1-(4-(3-fluoro-4-(7-methoxyquinolin-4-yloxy)phenyl-carbamoyl)-5-methyl-3-oxo-2-phenyl-2,3-dihydropyrazol-1-yl)propan-2-yl)2-amino-propanoate (61.3 mg, 0.1 mmol) and succinic acid (23.6 mg, 0.2 mmol, Shantou Xilong chemical factory). The title compound was obtained as a white solid (68.5 mg, 93.7%).

MS (ESI, pos. ion) m/z: 614.1 (M+1); LC-MS Rt: 3.418 min;

$^1$H NMR (400 MHz, $d_6$-DMSO): δ 1.06 (d, J=6.4 Hz, 3H), 1.23 (d, J=2.0 Hz, 3H), 2.79 (s, 3H), 3.59 (dd, J=7.2 Hz, J=14.4 Hz, 1H), 3.94 (s, 3H), 3.98 (dd, J=3.2 Hz, J=16 Hz, 1H), 4.27 (dd, J=9.2 Hz, J=16 Hz, 1H), 4.83 (m, 1H), 6.47 (d, J=5.2 Hz, 1H), 6.60 (s, 4H), 7.31 (dd, J=2.4 Hz, J=9.2 Hz, 1H), 7.36 (dd, J=2.0 Hz, J=8.8 Hz, 1H), 7.43 (m, 4H), 7.53 (m, 1H), 7.62 (t, 2H), 7.98 (dd, J=2.4 Hz, J=12.8 Hz, 1H), 8.23 (d, J=9.2 Hz, 1H), 8.62 (d, J=5.2 Hz, 1H), 10.87 (s, 1H).

Example 11

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate maleate

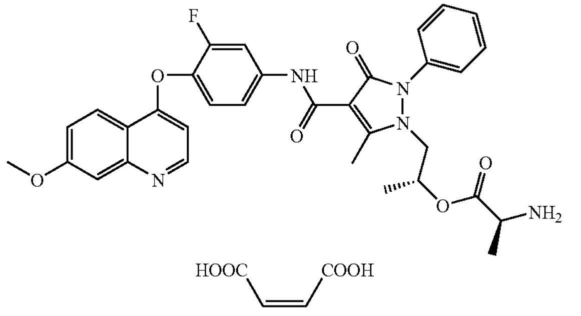

To a solution of (S)—((R)-1-(4-(3-fluoro-4-(7-methoxyquinolin-4-yloxy)phenyl carbamoyl)-5-methyl-3-oxo-2-phenyl-2,3-dihydropyrazol-1-yl)propan-2-yl)2-amino-propanoate (61.3 mg, 0.1 mmol) in EtOAc (15 mL)/MeOH (10 mL) was added maleic acid (23.2 mg, 0.2 mmol, Shantou Xilong chemical factory). After stirring for 40 min, the mixture was concentrated in vacuo, and the resulted oil was washed with a mixture of MeOH (2 mL)/EtOAc (10 mL) followed by EtOAc (5 mL×3) to give the title compound as yellow oil (62.6 mg, 85.6%).

MS (ESI, pos. ion) m/z: 614.1 (M+1); LC-MS Rt: 3.428 min.

Example 12

(S)—((R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate phosphoric acid

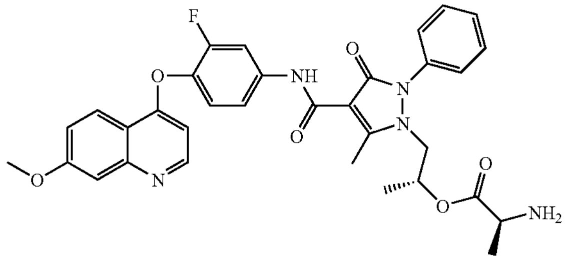

$H_3PO_4$

To a solution of (S)—((R)-1-(4-(3-fluoro-4-(7-methoxyquinolin-4-yloxy)phenyl carbamoyl)-5-methyl-3-oxo-2-phenyl-2,3-dihydropyrazol-1-yl)propan-2-yl)2-amino-propanoate (61.3 mg, 0.1 mmol) in EtOAc (15 mL)/MeOH (10 mL) was added phosphoric acid (19.6 mg, 0.2 mmol). After stirring for 40 min, the mixture was concentrated in vacuo, and the resulted oil was washed with a mixture of MeOH (2 mL)/EtOAc (10 mL) followed by EtOAc (5 mL×3) to give the title compound as yellow oil (67.2 mg, 91.9%).

MS (ESI, pos. ion) m/z: 614.1 (M+1); LC-MS Rt: 3.47 min.

Example 13

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate fumarate

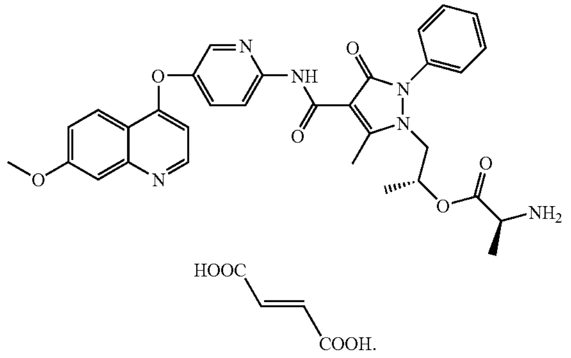

Step 1) (S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-(benzyloxycarbonyl-amino)propanoate To a mixture of (R)-1-(2-hydroxypropyl)-N-(6-(7-methoxyquinolin-4-yloxy)pyridin-3-yl)-5-methyl-3-oxo-2-phenyl-2,3-dihydro-1H-pyrazole-4-carboxamide (1.93 g, 3.68 mmol), (S)—N-Cbz-alanine (1.647 g, 7.36 mmol, Shanghai Hanhong Chemical CO., LTD.) and DMAP (0.90 g, 7.36 mmol, Aladdin) in 30 mL of $CH_2Cl_2$ at 0° C. was added EDC solid (2.116 g, 11.04 mmol, Aladdin) in portions. The mixture was continued to stir at 0° C. for 2 hrs, and then the mixture was warmed up to room temperature, and continued to stir at rt for 20 hrs. The mixture was diluted with 180 mL of $CH_2Cl_2$ and the resulted solution was washed with 30 mL of 0.1 N HCl, followed by 30 mL of saturated $NaHCO_3$. The aqueous phase was extracted with EtOAc (50 mL×3), and the combined organic phases were dried over $Na_2SO_4$, filtered and concentrated in vacuo. The residue was purified by a silica gel column chromatography (EtOAc) to give the desired compound as a pale yellow solid (2.0 g, 74.1%).

MS (ESI, pos. ion) m/z: 731.3 (M+1);

$^1$H NMR (400 MHz, $CDCl_3$): δ 1.09 (d, J=6.4 Hz, 3H), 1.33 (d, J=8.0 Hz, 3H), 2.82 (s, 3H), 3.79 (dd, J=4.0 Hz, J=15.6 Hz, 1H), 3.98 (s, 3H), 4.01 (dd, J=3.2 Hz, J=8.8 Hz, 1H), 4.13 (dd, J=6.8 Hz, J=14.0 Hz, 1H), 4.24 (m, 1H), 4.96 (dd, J=3.6 Hz, J=6.0 Hz, 1H), 5.06 (s, 2H), 5.18 (d, J=7.2 Hz, 1H), 6.35 (d, J=5.2 Hz, 1H), 7.23 (dd, J=2.4 Hz, J=9.2 Hz, 1H), 7.31-7.50 (m, 8H), 7.55 (t, 2H), 8.22 (t, 2H), 8.39 (d, J=9.2 Hz, 1H), 8.55 (d, J=5.2 Hz, 1H), 11.20 (s, 1H).

Step 2) (S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate To a solution of compound (S)—((R)-1-(4-(6-(7-methoxyquinolin-4-yloxy)pyridin-3-ylcarbamoyl))-5-methyl-3-oxo-2-phenyl-2,3-dihydropyrazol-1-yl)propan-2-yl)2-(benzyloxycarbonyl-amino)propanoate (73 mg, 0.1 mmol) in a mixture of EtOAc (15 mL) and MeOH (10 mL) was added catalytic amount of Pd/C (10%, ~55% w/w water content, 18 mg) under $N_2$ atmosphere. The suspension was degassed in vacuum and purged with $H_2$. The reaction mixture was stirred at rt for 20 min under $H_2$ balloon. The mixture was filtered and the solid was washed with MeOH (5 mL×3). The filtrate was used for the next step immediately.

MS (ESI, pos. ion) m/z: 614.1 (M+1).

Step 3) (S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate fumarate To a solution of (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-aminopropanoate (59.6 mg, 0.1 mmol) in a mixture of EtOAc (15 mL)/MeOH (10 mL) was added fumaric acid (23.2 mg, 0.2 mmol, Shantou Xilong chemical factory). After stirring for 40 min, the reaction mixture was concentrated in vacuo, and the residue was crystallized in a mixture solution of MeOH (2 mL)/EtOAc (10 mL) (v/v=1:5). The solid was collected by filtration, washed with EtOAc (5 mL×3) and dried under vacuum overnight to afford the title compound as a white solid (65 mg, 91.2%).

MS (ESI, pos. ion) m/z: 597.1 (M+1); LC-MS Rt: 3.013 min;

$^1$H NMR (400 MHz, $d^6$-DMSO): δ 1.05 (d, J=6.4 Hz, 3H), 1.18 (d, J=6.8 Hz, 3H), 2.81 (s, 3H), 3.49 (dd, J=6.8 Hz, J=14 Hz, 1H), 3.94 (s, 3H), 3.98 (dd, J=2.8 Hz, J=14.4 Hz, 1H), 4.27 (dd, J=9.2 Hz, J=16 Hz, 1H), 4.82 (m, 1H), 6.53 (d, J=5.2 Hz, 1H), 6.58 (s, 2H), 7.31 (dd, J=2.4 Hz, J=9.2 Hz, 1H), 7.43 (m, 3H), 7.54 (m, 1H), 7.82 (t, 2H), 7.82 (dd, J=2.8 Hz, J=9.2 Hz, 1H), 8.22 (d, J=9.2 Hz, 1H), 8.34 (t, 1H), 8.37 (s, 1H), 8.63 (d, J=5.2 Hz, 1H), 11.19 (s, 1H).

Example 14

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate benzoate

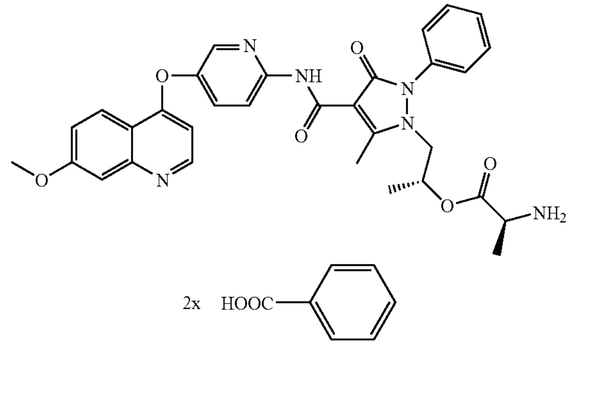

The title compound was prepared according to the procedure described in Example 13 Step 3 by using (S)—((R)-1-(4-(6-(7-methoxyquinolin-4-yloxy)pyridin-3-yl-carbamoyl)-5-methyl-3-oxo-2-phenyl-2,3-dihydropyrazol-1-yl)

propan-2-yl)2-amino-propanoate (59.6 mg, 0.1 mmol) and benzoic acid (24.4 mg, 0.2 mmol). The title compound was obtained as a pale yellow solid (61.2 mg, 85%).

MS (ESI, pos. ion) m/z: 597.1 (M+1); LC-MS Rt: 3.077 min.

Example 15

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate methanesulfonate

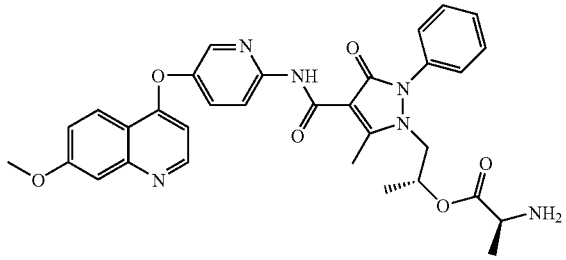

2 x $CH_3SO_3H$

The title compound was prepared according to the procedure described in Example 11 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl) 2-aminopropanoate (59.6 mg, 0.1 mmol) and methanesulfonic acid (19.3 mg, 0.2 mmol, Shanghai Rich-Joint Chemical Reagents CO.). The title compound was obtained as yellow oil (66.5 mg, 84%).

MS (ESI, pos. ion) m/z: 597.1 (M+1); LC-MS Rt: 3.130 min.

Example 16

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate 4-methylbenzenesulfonate

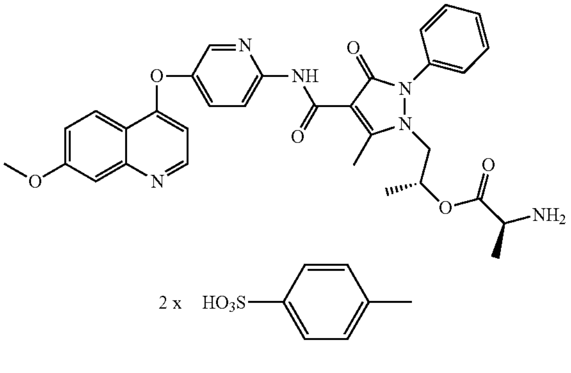

The title compound was prepared according to the procedure described in Example 13 Step 3 by using (S)—((R)-1-(4-(6-(7-methoxyquinolin-4-yloxy)pyridin-3-yl-carbamoyl)-5-methyl-3-oxo-2-phenyl-2,3-dihydropyrazol-1-yl) propan-2-yl)2-amino-propanoate (59.6 mg, 0.1 mmol) and p-toluene sulfonic acid (38 mg, 0.2 mmol, Shanghai Chemical Reagent Factory). The title compound was obtained as a pale yellow solid (71 mg, 72%).

MS (ESI, pos. ion) m/z: 597.1 (M+1); LC-MS Rt: 3.181 min.

Example 17

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate oxalate

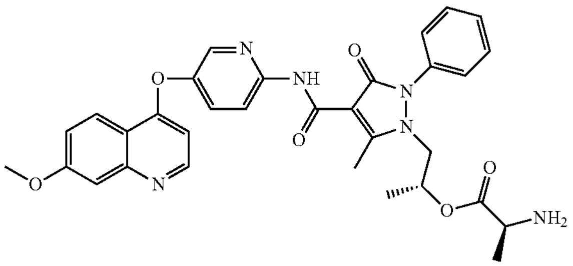

HOOC—COOH

The title compound was prepared according to the procedure described in Example 13 Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-amino-propanoate (59.6 mg, 0.1 mmol) and oxalic acid dihydrate (25.2 mg, 0.2 mmol, Tianjin Chemical Factory). The title compound was obtained as a white solid (65 mg, 95%).

MS (ESI, pos. ion) m/z: 597.1 (M+1); LC-MS Rt: 3.121 min;

$^1H$ NMR (400 MHz, $d_6$-DMSO): δ 1.08 (d, J=6.4 Hz, 3H), 1.33 (d, J=7.2 Hz, 3H), 2.81 (s, 3H), 3.92 (dd, J=7.2 Hz, J=14.8 Hz, 1H), 3.94 (s, 3H), 4.02 (dd, J=3.2 Hz, J=16 Hz, 1H), 4.28 (dd, J=2.4 Hz, J=8.8 Hz, 1H), 4.85 (m, 1H), 6.51 (d, J=5.2 Hz, 1H), 7.31 (dd, J=6.0 Hz, J=8.8 Hz, 1H), 7.43 (d, J=2.8 Hz, 2H), 7.45 (m, 1H), 7.55 (t, 1H), 7.63 (t, 2H), 7.83 (dd, J=3.2 Hz, J=9.2 Hz, 1H), 8.22 (d, J=9.2 Hz, 1H), 8.35 (t, 2H), 8.63 (d, J=5.2 Hz, 1H), 11.19 (s, 1H).

Example 18

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate (2S,3S)-2,3-dihydroxysuccinate

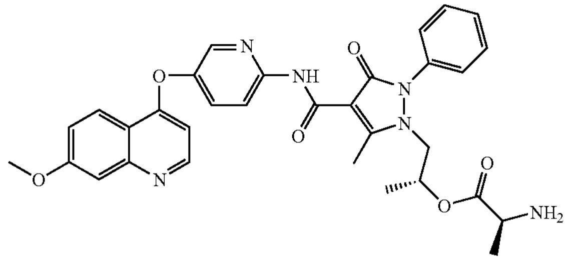

-continued 2 x 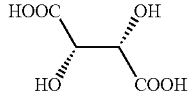

The title compound was prepared according to the procedure described in Example 13 Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-aminopropanoate (59.6 mg, 0.1 mmol) and tartaric acid (30.0 mg, 0.2 mmol). The title compound was obtained as a white solid (71.2 mg, 79%).

MS (ESI, pos. ion) m/z: 597.1 (M+1); LC-MS Rt: 3.045 min;

$^1$H NMR (400 MHz, $d_6$-DMSO): δ 1.07 (d, J=6.4 Hz, 3H), 1.28 (d, J=7.2 Hz, 3H), 2.81 (s, 3H), 3.77 (m, 1H), 3.94 (s, 3H), 4.0 (dd, J=2.8 Hz, J=15.6 Hz, 1H), 4.16 (s, 4H), 4.29 (dd, J=8.8 Hz, J=16 Hz, 1H), 4.85 (m, 1H), 6.52 (d, J=5.2 Hz, 1H), 7.31 (dd, J=2.4 Hz, J=9.2 Hz, 1H), 7.44 (m, 3H), 7.54 (t, 1H), 7.63 (t, 2H), 7.83 (dd, J=3.2 Hz, J=9.2 Hz, 1H), 8.22 (d, J=8.8 Hz, 1H), 8.34 (d, J=3.6 Hz, 2H), 8.63 (d, J=5.2 Hz, 1H), 11.19 (s, 1H).

Example 19

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate hydrochloride

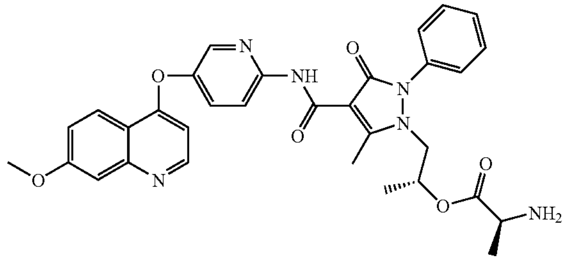

2x HCl

The title compound was prepared according to the procedure described in Example 13, Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-aminopropanoate (59.6 mg, 0.1 mmol) and a saturated solution of HCl/EtOAc (3 mL). The title compound was obtained as a pale yellow solid (55.6 mg, 79%).

MS (ESI, pos. ion) m/z: 597.1 (M+1); LC-MS Rt: 3.076 min;

$^1$H NMR (400 MHz, $d_6$-DMSO): δ 1.08 (d, J=6.4 Hz, 3H), 1.36 (d, J=7.2 Hz, 3H), 2.81 (s, 3H), 3.88 (dd, J=7.6 Hz, J=14.4 Hz, 1H), 4.03 (s, 3H), 4.07 (d, J=12 Hz, 1H), 4.31 (dd, J=9.2 Hz, J=16.4 Hz, 1H), 4.85 (m, 1H), 7.04 (dd, J=6.4 Hz, J=8.8 Hz, 1H), 7.44 (t, 2H), 7.56 (m, 1H), 7.63 (m, 3H), 7.74 (d, J=2.4 Hz, 1H), 7.98 (dd, J=2.8 Hz, J=9.2 Hz, 1H), 8.44 (d, J=8.8 Hz, 1H), 8.47 (d, J=2.8 Hz, 1H), 8.51 (dd, J=2.8 Hz, J=9.6 Hz, 1H), 8.98 (dd, J=3.2 Hz, J=6.8 Hz, 1H), 11.37 (s, 1H).

Example 20

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate 2-hydroxypropane-,2,3-tricarboxylate

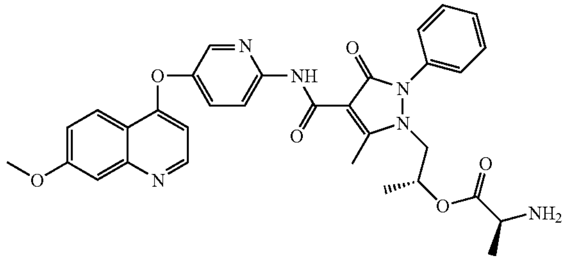

2x 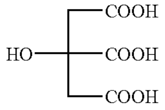

The title compound was prepared according to the procedure described in Example 13 Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-aminopropanoate (59.6 mg, 0.1 mmol) and citric acid (38.4 mg, 0.2 mmol, Tianjin Chemical Factory). The title compound was obtained as a white solid (75.4 mg, 77%).

MS (ESI, pos. ion) m/z: 597.1 (M+1); LC-MS Rt: 3.018 min;

$^1$H NMR (400 MHz, $d_6$-DMSO): δ 1.08 (d, J=6.4 Hz, 3H), 1.33 (d, J=7.2 Hz, 3H), 1.99 (s, 1H), 2.60 (dd, J=15.2 Hz, J=36.8 Hz, 8H), 2.81 (s, 3H), 3.88 (dd, J=7.2 Hz, J=14.4 Hz, 1H), 3.94 (s, 3H), 4.02 (m, 1H), 4.31 (dd, J=9.2 Hz, J=16 Hz, 1H), 4.86 (m, 1H), 6.51 (d, J=5.2 Hz, 1H), 7.31 (dd, J=2.8 Hz, J=9.2 Hz, 1H), 7.43 (t, 3H), 7.55 (t, 1H), 7.63 (t, 2H), 7.83 (d, J=2.8 Hz, J=8.8 Hz, 1H), 8.22 (d, J=9.2 Hz, 1H), 8.34 (d, J=3.2 Hz, 1H), 8.37 (s, 1H), 8.63 (d, J=5.2 Hz, 1H), 11.19 (s, 1H).

Example 21

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate sulfate

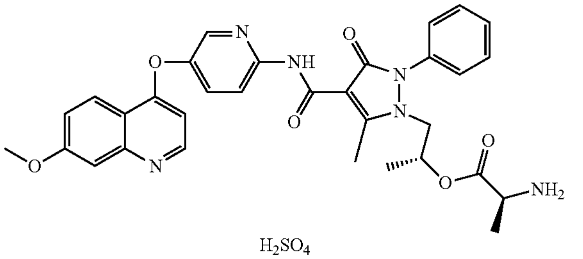

$H_2SO_4$

The title compound was prepared according to the procedure described in Example 13 Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-aminopropanoate (59.6 mg, 0.1 mmol) and sulfuric acid (19.6 mg, 0.2 mmol). The title compound was obtained as a white solid (56.5 mg, 78.5%).

MS (ESI, pos. ion) m/z: 597.1 (M+1); LC-MS Rt: 3.057 min;

$^1$H NMR (400 MHz, $d_6$-DMSO): δ 1.07 (d, J=6.4 Hz, 3H), 1.26 (d, J=7.2 Hz, 3H), 2.80 (s, 3H), 3.71 (dd, J=6.4 Hz, J=14.0 Hz, 1H), 3.94 (s, 3H), 3.99 (d, J=16 Hz, 1H), 4.29 (dd, J=9.2 Hz, J=16 Hz, 1H), 4.84 (m, 1H), 6.52 (d, J=5.2 Hz, 1H), 7.31 (dd, J=2.4 Hz, J=9.2 Hz, 1H), 7.44 (d, J=7.6 Hz, 3H), 7.54 (t, 1H), 7.62 (t, 2H), 7.82 (dd, J=2.8 Hz, J=9.2 Hz, 1H), 8.22 (d, J=8.8 Hz, 1H), 8.34 (t, 2H), 8.37 (s, 1H), 8.63 (d, J=5.2 Hz, 1H), 11.19 (s, 1H).

Example 22

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate succinate

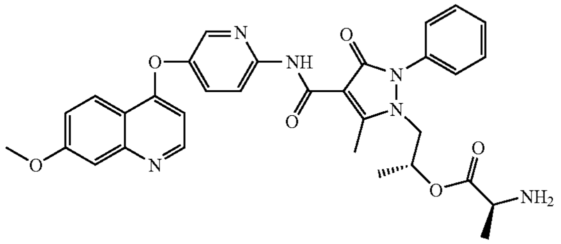

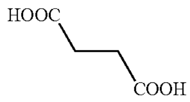

The title compound was prepared according to the procedure described in Example 13 Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-amino-propanoate (59.6 mg, 0.1 mmol) and succinic acid (23.6 mg, 0.2 mmol, Shantou Xilong chemical factory). The title compound was obtained as a white solid (55 mg, 78%).

MS (ESI, pos. ion) m/z: 597.1 (M+1); LC-MS Rt: 3.021 min.

Example 23

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate maleate

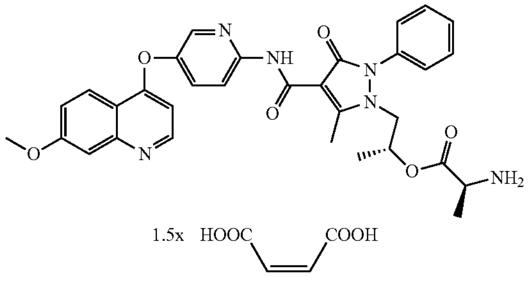

The title compound was prepared according to the procedure described in Example 13 Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-amino-propanoate (59.6 mg, 0.1 mmol) and maleic acid (23.2 mg, 0.2 mmol, Shantou Xilong chemical factory). The title compound was obtained as a white solid (67.8 mg, 88%).

MS (ESI, pos. ion) m/z: 597.1 (M+1); LC-MS Rt: 3.011 min;

$^1$H NMR (400 MHz, $d_6$-DMSO): δ 1.09 (d, J=6.4 Hz, 3H), 1.34 (d, J=7.2 Hz, 3H), 2.81 (s, 3H), 3.91 (d, J=6.8 Hz, 1H), 3.92 (s, 3H), 4.02 (dd, J=2.8 Hz, J=16 Hz, 1H), 4.30 (dd, J=9.2 Hz, J=16.4 Hz, 1H), 4.86 (m, 1H), 6.15 (s, 3H), 7.33 (dd, J=2.4 Hz, J=9.2 Hz, 1H), 7.44 (t, 3H), 7.55 (t, 1H), 7.63 (t, 2H), 7.84 (dd, J=2.8 Hz, J=8.8 Hz, 1H), 8.24 (d, J=9.2 Hz, 1H), 8.36 (t, 2H), 8.66 (d, J=5.6 Hz, 1H), 11.20 (s, 1H).

Example 24

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate phosphoric acid

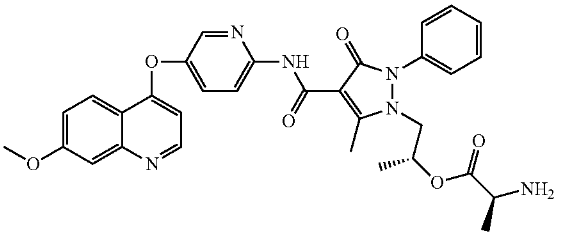

$H_3PO_4$

The title compound was prepared according to the procedure described in Example 13, Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-aminopropanoate (59.6 mg, 0.1 mmol) and phosphoric acid (19.6 mg, 0.2 mmol). The title compound was obtained as yellow oil (60.2 mg, 84.5%).

MS (ESI, pos. ion) m/z: 597.1 (M+1); LC-MS Rt: 3.013 min.

Example 25

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate acetate

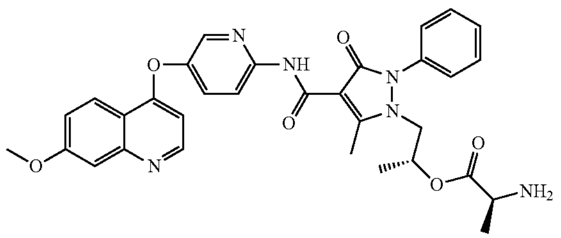

2x $CH_3COOH$

The title compound was prepared according to the procedure described in Example 13 Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-aminopropanoate (59.6 mg, 0.1 mmol) and acetic acid (12.2 mg, 0.2 mmol). The title compound was obtained as a pale yellow solid (58.5 mg, 81%).

MS (ESI, pos. ion) m/z: 597.1 (M+1); LC-MS Rt: 3.078 min;

$^1$H NMR (400 MHz, d$^6$-DMSO): δ 1.06 (d, J=6.4 Hz, 3H), 1.22 (s, 3H), 1.29 (d, J=7.2 Hz, 3H), 2.79 (s, 3H), 3.82 (dd, J=6.8 Hz, J=14.0 Hz, 1H), 3.93 (s, 3H), 3.99 (dd, J=3.2 Hz, J=16.0 Hz, 1H), 4.28 (dd, J=9.2 Hz, J=16.0 Hz, 1H), 4.83 (m, 1H), 6.51 (dd, J=5.2 Hz, J=7.6 Hz, 1H), 7.29 (dd, J=2.4 Hz, J=9.2 Hz, 1H), 7.42 (m, 3H), 7.53 (m, 1H), 7.64 (m, 3H), 7.81 (dd, J=3.2 Hz, J=9.2 Hz, 1H), 8.21 (dd, J=2.8 Hz, J=9.2 Hz, 1H), 8.35 (dd, J=3.2 Hz, J=9.2 Hz, 1H), 8.61 (dd, J=2.0 Hz, J=5.6 Hz, 1H), 11.18 (s, 1H).

Example 26

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate ethanesulfonate

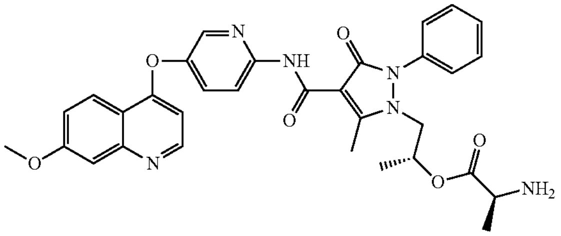

2x $C_2H_5SO_3H$

The title compound was prepared according to the procedure described in Example 13 Step 3 by using (S)—((R)-1-(4-(6-(7-methoxyquinolin-4-yloxy)pyridin-3-ylcarbamoyl)-5-methyl-3-oxo-2-phenyl-2,3-dihydropyrazol-1-yl)propan-2-yl)2-aminopropanoate (59.6 mg, 0.1 mmol) and ethanesulfonic acid (22.1 mg, 0.2 mmol, Shanghai RichJoint Chemical Reagents CO., Ltd). The title compound was obtained as yellow oil (57.6 mg, 80.8%).

MS (ESI, pos. ion) m/z: 597.1 (M+1); LC-MS Rt: 3.123 min.

Example 27

(S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate fumarate

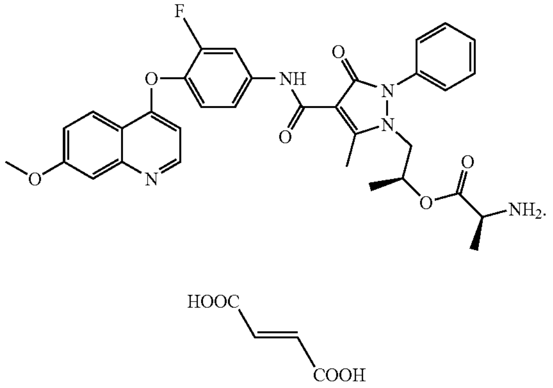

Step 1) (S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-(benzyloxycarbonyl-amino)propanoate To a solution of (S)—N-(3-fluoro-4-(7-methoxyquinolin-4-yloxy)phenyl-1-(2-hydroxypropyl)-5-methyl-3-oxo-2-phenyl-2,3-dihydro-1H-pyrazole-4-carboxamide (2.0 g, 3.68 mmol), (S)—N-Cbz-alanine (1.647 g, 7.36 mmol, Shanghai Hanhong Chemical CO., LTD.) and DMAP (0.90 g, 7.36 mmol, Aladdin) in 30 mL of $CH_2Cl_2$ at 0° C. was added EDC solid (2.116 g, 11.04 mmol, Aladdin) in portions. The mixture was continued to stir at 0° C. for 2 hrs, and then the reaction mixture was warmed up to room temperature, and stirred at rt for 20 hrs. The mixture was diluted with 180 mL $CH_2Cl_2$, and the result solution was washed with 0.1 N HCl (10 mL×3), followed by 50 mL saturated $NaHCO_3$. The aqueous phase was extracted with EtOAc (50 mL×3), the combined organic phases were dried over $Na_2SO_4$, filtered and concentrated in vacuo. The residue was purified by a silica gel column chromatography (EtOAc) to give the desired compound as a pale yellow solid (2.1 g, 73%).

MS (ESI, pos. ion) m/z: 748 (M+1);

$^1$H NMR (400 MHz, $CDCl_3$): δ 1.21 (d, J=5.4 Hz, 3H), 1.39 (d, J=6.6 Hz, 3H), 3.0 (s, 3H), 3.75 (d, J=3.2 Hz, 1H), 3.78 (s, 3H), 4.05 (m, 1H), 4.23 (t, 1H), 4.95 (s, 1H), 5.09 (dd, J=12.4 Hz, J=37.2 Hz, 2H), 5.22 (d, J=7.2 Hz, 1H), 6.40 (dd, J=0.8 Hz, J=6.0 Hz, 1H), 7.16 (t, 1H), 7.22 (dd, J=2.8 Hz, J=12 Hz, 1H), 7.27 (t, 2H), 7.35 (m, 5H), 7.41 (m, 1H), 7.47 (m, 1H), 7.55 (m, 2H), 7.90 (dd, J=2.0 Hz, J=14.4 Hz, 1H), 8.28 (d, J=9.2 Hz, 1H), 8.66 (d, J=5.2 Hz, 1H), 10.81 (s, 1H).

Step 2) (S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate To a solution of (S)—((S)-1-(4-(3-fluoro-4-(7-methoxyquinolin-4-yloxy)phenyl-carbamoyl)-5-methyl-3-oxo-2-phenyl-2,3-dihydropyrazol-1-yl)propan-2-yl)2-(benzyloxycarbonylamino)propanoate (74.7 mg, 0.1 mmol) in EtOAc (15 mL)/MeOH (10 mL) was added catalytic amount of Pd/C (10%, ~55% w/w water content, 20 mg) under $N_2$ atmosphere. The suspension was degassed in vacuo and purged with $H_2$. The reaction mixture was stirred at rt for 20 min under $H_2$ balloon. Then the mixture was filtered and the solid was washed with MeOH (5 mL×3). The filtrate was used for the next step immediately.

MS (ESI, pos. ion) m/z: 614.1 (M+1).

Step 3) (S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate fumarate The title compound was prepared according to the procedure described in Example 13 Step 3 by using (2S)—(S)-1-(4-(4-(7-methoxyquinolin-4-yloxy)-3-fluorophenyl-carbamoyl)-2,3-dihydro-5-methyl-3-oxo-2-phenylpyrazol-1-yl)propan-2-yl2-aminopropanoate (61.3 mg, 0.1 mmol) and fumaric acid (23.2 mg, 0.2 mmol, Shantou Xilong chemical factory). The title compound was obtained as a pale yellow solid (68.5 mg, 94.0%).

MS (ESI, pos. ion) m/z: 614.1 (M+1); LC-MS Rt: 3.418 min;

$^1$H NMR (400 MHz, $d_6$-DMSO): δ 1.04 (d, J=5.6 Hz, 3H), 1.09 (d, J=6.8 Hz, 3H), 2.77 (s, 3H), 3.93 (s, 5H), 4.27 (m, 1H), 4.81 (s, 1H), 6.47 (d, J=5.6 Hz, 1H), 6.55 (s, 2H), 7.32 (dd, J=9.2 Hz, J=28.8 Hz, 2H), 7.40 (m, 4H), 7.51 (t, 1H), 7.59 (t, 1H), 7.95 (d, J=13.6 Hz, 2H), 8.21 (d, J=8.8 Hz, 1H), 8.59 (d, J=5.2 Hz, 1H), 10.84 (s, 1H).

Example 28

(S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate benzoate

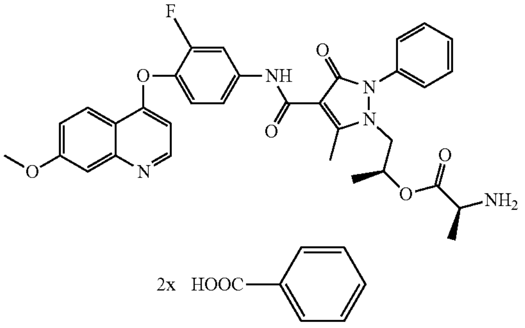

The title compound was prepared according to the procedure described in Example 13 Step 3 by using (2S)—(S)-1-(4-(4-(7-methoxyquinolin-4-yloxy)-3-fluoro-phenylcarbamoyl)-2,3-dihydro-5-methyl-3-oxo-2-phenylpyrazol-1-yl)propan-2-yl2-aminopropanoate (61.3 mg, 0.1 mmol) and benzoic acid (48.8 mg, 0.4 mmol, Shantou Xilong Chemical Factory). The title compound was obtained as a pale yellow solid (64.1 mg, 75%).

MS (ESI, pos. ion) m/z: 614.1 (M+1); LC-MS Rt: 3.422 min;

$^1$H NMR (400 MHz, $d_6$-DMSO): δ 1.28 (d, J=4.0 Hz, 3H), 1.32 (d, J=6.8 Hz, 3H), 2.87 (s, 3H), 3.61 (m, 1H), 3.79 (dd, J=3.6 Hz, J=19.2 Hz, 1H), 3.99 (s, 3H), 4.09 (m, 1H), 4.97 (m, 2H), 5.28 (s, 2H), 6.46 (d, J=5.6 Hz, 1H), 7.17 (t, 1H), 7.28 (m, 3H), 7.38 (d, J=7.6 Hz, 1H), 7.46 (m, 3H), 7.57 (m, 3H), 7.91 (dd, J=2.0 Hz, J=14.4 Hz, 1H), 8.10 (d, J=7.6 Hz, 3H), 8.28 (d, J=9.2 Hz, 1H), 8.67 (d, J=5.2 Hz, 1H), 10.78 (s, 1H).

Example 29

(S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate methanesulfonate

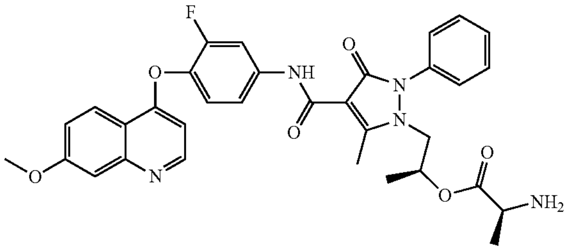

2x $CH_3SO_3H$

The title compound was prepared according to the procedure described in Example 13 Step 3 by using (2S)—(S)-1-(4-(4-(7-methoxyquinolin-4-yloxy)-3-fluorophenyl-carbamoyl)-2,3-dihydro-5-methyl-3-oxo-2-phenylpyrazol-1-yl)propan-2-yl2-aminopr-opanoate (61.3 mg, 0.1 mmol) and methanesulfonic acid (19.3 mg, 0.2 mmol, Shanghai Rich-Joint Chemical Reagents CO., Ltd). The title compound was obtained as a yellow solid (58.2 mg, 72%).

MS (ESI, pos. ion) m/z: 614.1 (M+1); LC-MS Rt: 3.47 min.

Example 30

(S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate 4-methylbenzenesulfonate

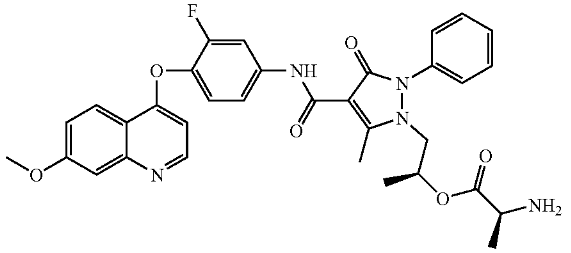

-continued

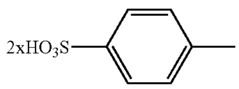

The title compound was prepared according to the procedure described in Example 13 Step 3 by using (2S)—(S)-1-(4-(4-(7-methoxyquinolin-4-yloxy)-3-fluoro-phenylcarbamoyl)-2,3-dihydro-5-methyl-3-oxo-2-phenylpyrazol-1-yl)propan-2-yl-2-aminopropanoate (61.3 mg, 0.1 mmol) and p-toluene sulfonic acid (38 mg, 0.2 mmol). The title compound was obtained as a yellow solid (70.8 mg, 71.5%).

MS (ESI, pos. ion) m/z: 614.1 (M+1); LC-MS Rt: 3.59 min;

$^1$H NMR (400 MHz, $CDCl_3$): δ 1.04 (d, J=6 Hz, 3H), 1.37 (d, J=6.8 Hz, 3H), 2.34 (s, 3H), 2.78 (s, 3H), 3.76-3.86 (m, 2H), 3.92-3.96 (m, 1H), 4.02 (s, 3H), 4.09-4.15 (m, 1H), 4.89-4.98 (m, 1H), 6.66 (d, J=5.2 Hz, 1H), 7.13-7.23 (m, 4H), 7.34-7.57 (m, 6H), 7.75 (d, J=7.6 Hz, 4H), 7.92 (dd, J=19.6 Hz, J=2 Hz, 1H), 8.35 (d, J=9.2 Hz, 1H), 8.73 (d, J=5.6 Hz, 1H), 10.84 (s, 1H).

Example 31

(S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate sulfate

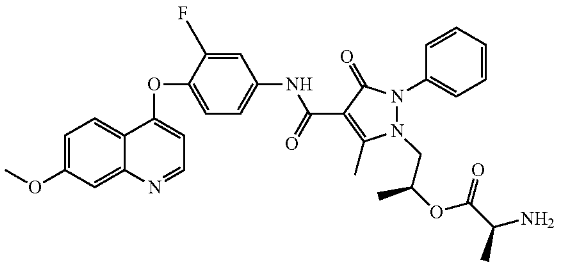

$H_2SO_4$

The title compound was prepared according to the procedure described in Example 13 Step 3 by using (2S)—(S)-1-(4-(4-(7-methoxyquinolin-4-yloxy)-3-fluorophenyl-carbamoyl)-2,3-dihydro-5-methyl-3-oxo-2-phenylpyrazol-1-yl)propan-2-yl 2-aminopropanoate (61.3 mg, 0.1 mmol) and $H_2SO_4$ (1 mL, 0.1 mol/L, Shantou Xilong Chemical Factory). The title compound was obtained as a yellow solid (61.5 mg, 86.5%).

MS (ESI, pos. ion) m/z: 614.1 (M+1); LC-MS Rt: 3.53 min.

Example 32

(S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate maleate

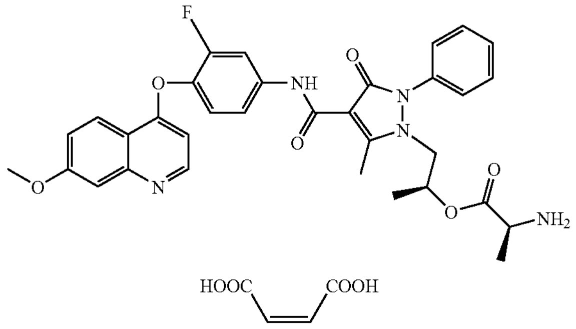

The title compound was prepared according to the procedure described in Example 13 Step 3 by using (2S)—(S)-1-(4-(4-(7-methoxyquinolin-4-yloxy)-3-fluoro-phenyl-carbamoyl)-2,3-dihydro-5-methyl-3-oxo-2-phenylpyrazol-1-yl)propan-2-yl-2-aminopropanoate (61.3 mg, 0.1 mmol) and maleic acid (23.3 mg, 0.2 mmol, Shanghai San'aisi Reagent Co., Ltd). The title compound was obtained as a yellow solid (68.7 mg, 94.2%).

MS (ESI, pos. ion) m/z: 614.1 (M+1); LC-MS Rt: 3.60 min;

$^1$H NMR (400 MHz, $CDCl_3$): δ 1.13 (d, J=7.6 Hz, 3H), 1.39 (d, J=6.8 Hz, 3H), 2.87 (s, 3H), 3.74-3.85 (m, 3H), 3.92-3.96 (m, 1H), 4.04 (s, 3H), 4.09-4.15 (m, 1H), 4.96-5.05 (m, 1H), 6.31 (s, 2H), 6.66 (d, J=5.2 Hz, 1H), 7.18-7.22 (m, 1H), 7.31-7.41 (m, 4H), 7.50-7.52 (m, 1H), 7.56-7.66 (m, 3H), 7.96 (dd, J=20.4 Hz, J=2 Hz, 1H), 8.36 (d, J=9.6 Hz, 1H), 8.72 (d, J=8.4 Hz, 1H), 10.86 (s, 1H).

Example 33

(S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-aminoacetate hydrochloride

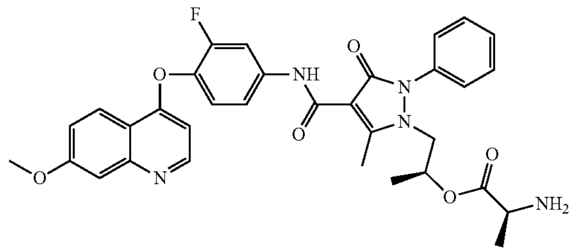

2x HCl

Step 1) (S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(tert-butoxycarbonylamino)acetate To a mixture of (S)—N-(3-fluoro-4-(7-methoxyquinolin-4-yloxy)phenyl)-1-(2-hydroxylpropyl)-5-methyl-3-oxo-2-phenyl-2,3-dihydro-1H-pyrazole-4-carboxamide (1.0 g, 1.84 mmol), N-Boc-glycine (0.644 g, 3.68 mmol, ABCR) and DMAP (0.45 g, 3.68 mmol, Aladdin) in 12 mL of $CH_2Cl_2$ at 0° C. was added EDC solid (1.0582 g, 5.52 mmol, Aladdin) in portions. After stirring at 0° C. for 2 hrs, the reaction mixture was warmed up to room temperature and continued to stir overnight. The reaction mixture was diluted with $CH_2Cl_2$ (100 mL), and the result solution was washed with 0.1 N HCl (10 mL×2), followed by saturated $NaHCO_3$ (10 mL×2) and water (20 mL), the aqueous phase was extracted with EtOAc (15 mL×3). The combined organic phases were dried over $Na_2SO_4$, filtered and concentrated in vacuo. The residue was purified by a silica gel column chromatography (EtOAc:hexane=2:1) to give the desired compound as a yellow solid (1.46 g, 70.1%).

MS (ESI, pos. ion) m/z: 700.2 (M+1); LC-MS Rt: 4.536 min;

$^1$H NMR (400 MHz, $CDCl_3$): δ 1.14 (d, J=6.4 Hz, 3H), 1.45 (s, 9H), 2.85 (s, 3H), 3.68-3.72 (m, 1H), 3.78-3.82 (m, 1H), 3.81-3.88 (m, 1H), 3.97 (s, 3H), 4.00-4.07 (m, 1H), 4.91-5.03 (m, 2H), 6.41 (d, J=5.2 Hz, 1H), 7.15-7.24 (m, 2H), 7.26-7.29 (m, 1H), 7.37-7.41 (m, 3H), 7.42-7.51 (m, 1H), 7.56-7.60 (m, 2H), 7.89 (dd, J=13.2 Hz, J=2.4 Hz, 1H), 8.27 (d, J=5.2 Hz, 1H), 8.58 (d, J=5.6 Hz, 1H), 10.81 (s, 1H).

Step 2) (S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-aminoacetate hydrochloride To a solution of compound (S)-1-(4-(4-(7-methoxyquinolin-4-yloxy)-3-fluoro-phenyl carbamoyl)-2,3-dihydro-5-methyl-3-oxo-2-phenylpyrazol-1-yl)propan-2-yl-(tert-butyloxycarbonylamino)acetate (200 mg, 0.286 mmol) in EtOAc (10 mL) was added a saturated solution of HCl/EtOAc (10 mL) under nitrogen. After stirring at room temperature for 30 hrs, the reaction mixture was filtered and the residue was washed with EtOAc (10 mL×2). The crude product was recrystallized in a mixture solution of MeOH (2 mL)/EtOAc (10 mL) (v/v=1:5), the mixture was filtered, and the solid was washed with EtOAc (5 mL×3). The title compound was obtained as a yellow solid (135.7 mg, 71%).

MS (ESI, pos. ion) m/z: 600.2 (M+1); LC-MS Rt: 3.533 min;

$^1$H NMR (400 MHz, $d_6$-DMSO): δ1.09 (d, J=6.4 Hz, 3H), 2.78 (s, 3H), 3.50-3.56 (m, 1H), 3.77-3.82 (m, 1H), 3.99-4.04 (m, 5H), 4.26-4.32 (m, 1H), 4.87-4.92 (m, 1H), 6.90 (d, J=5.6 Hz, 1H), 7.41-7.44 (m, 3H), 7.53-7.66 (m, 6H), 8.06 (dd, J=13.2 Hz, J=2.4 Hz, 1H), 8.31 (s, 3H), 8.46 (d, J=9.6 Hz, 1H), 8.93 (d, J=6.4 Hz, 1H), 10.94 (s, 1H).

Example 34

(S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-aminoacetate maleate

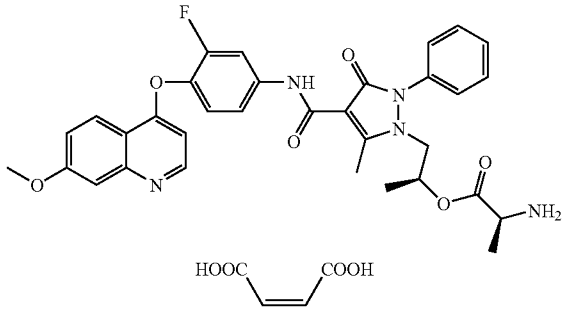

To a solution of compound (S)-1-(4-(4-(7-methoxyquinolin-4-yloxy)-3-fluoro-phenylcarbamoyl)-2,3-dihydro-5-methyl-3-oxo-2-phenylpyrazol-1-yl)propan-2-yl-(tertbutyloxycarbonylamino)acetate (110.3 mg, 0.18 mmol) in 6 mL of MeOH was added a solution of maleic acid (46 mg, 0.4 mmol). After stirring for 30 min, the reaction mixture was filtered and the filtrate was concentrated in vacuo. The resulted residue was recrystallized in of MeOH (2 mL)/EtOAc (10 mL)(v/v=1:5). The solid was collected by filtration, washed with EtOAc (5 mL×3) and dried under vacuum overnight. The title compound was obtained as a yellow solid (124.6 mg, 87%).

MS (ESI, pos. ion) m/z: 600.1 (M+1); LC-MS Rt: 3.47 min;

$^1$H NMR (400 MHz, $d_6$-DMSO): δ 1.07 (d, J=6 Hz, 3H), 2.76 (s, 3H), 3.32-3.76 (m, 3H), 3.92 (s, 3H), 3.97-4.02 (m, 1H), 4.22-4.31 (m, 1H), 4.86-492 (m, 1H), 6.01 (s, 2H), 6.46 (d, J=5.2 Hz, 1H), 6.95 (d, J=5.2 Hz, 1H), 7.28-7.35 (m, 2H), 7.39-7.44 (m, 3H), 7.49-7.54 (m, 1H), 7.58-7.62 (m, 2H), 7.96 (dd, J=13.2 Hz, J=2.4 Hz, 1H), 8.21 (d, J=9.2 Hz, 1H), 8.61 (d, J=5.2 Hz, 1H), 10.86 (s, 1H).

Example 35

(S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino)acetate maleate

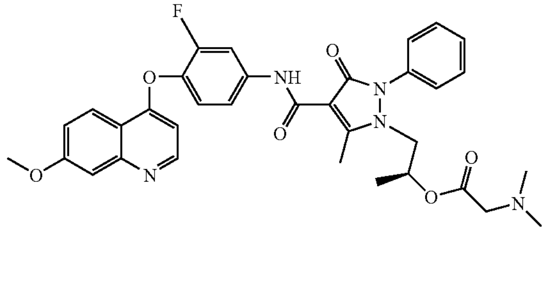

-continued

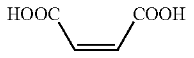

Step 1) (S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino)acetate To a mixture of (S)—N-(3-fluoro-4-(7-methoxyquinolin-4-yloxy)-phenyl-1-(2-hydro-xylpropyl)-5-methyl-3-oxo-2-phenyl-2,3-dihydro-1H-pyrazole-4-carboxamide (0.54 g, 1 mmol), N,N-dimethylglycine (0.206 g, 2 mmol, Alfa) and DMAP (0.244 g, 2 mmol, Aladdin) in 15 mL of $CH_2Cl_2$ at 0° C. was added EDC solid (0.575 g, 3 mmol, Aladdin) in portions. The mixture was continued to stir at 0° C. for 2 hrs, then the reaction mixture was warmed up to room temperature and stirred at rt for 20 hrs. The reaction mixture was diluted with 100 mL of $CH_2Cl_2$ and washed with 0.1 N HCl (10 mL×2), followed by saturated $NaHCO_3$ (20 mL×2) and water (20 mL×8), and the aqueous phase was extracted with EtOAc(15 mL×2). The combined organic phases were dried over $Na_2SO_4$ and concentrated in vacuo. The residue was purified by a silica gel column chromatography (EtOAc) to afford the title compound as a yellow solid (0.387 g, 61.6%).

MS (ESI, pos. ion) m/z: 628.1 (M+1);

$^1$H NMR (400 MHz, $CDCl_3$): δ 1.09 (d, J=6.4 Hz, 3H), 2.67 (s, 6H), 2.84 (s, 3H), 2.98-3.12 (m, 2H), 3.73-3.78 (m, 1H), 3.94 (s, 3H), 3.99-4.03 (m, 1H), 4.94-5.05 (m, 1H), 6.40 (d, J=5.2 Hz, 1H), 7.13-7.22 (m, 3H), 7.36-7.40 (m, 3H), 7.45-7.57 (m, 3H), 7.89 (dd, J=12.4 Hz, J=2.0 Hz, 1H), 8.25 (d, J=9.2 Hz, 1H), 8.57 (d, J=5.2 Hz, 1H), 10.82 (s, 1H).

Step 2) (S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino)acetate maleate To a solution of (S)-1-(4-(4-(7-methoxyquinolin-4-yloxy)-3-fluorophenyl carbamoyl)-2,3-dihydro-5-methyl-3-oxo-2-phenylpyrazol-1-yl)propan-2-yl 2-(dimethylamino)acetate (110.3 mg, 0.176 mmol) in 6 mL of MeOH was added malcic acid (20.4 mg, 0.176 mmol, Shanghai Sanaisi Reagent Co., Ltd). After stirring at room temperature for 0.5 hrs, the mixture was concentrated in vacuo, and the residue was crystallized in a mixture solution of MeOH (2 mL)/EtOAc (10 mL)(v/v=1:5). The solid was collected by filtration, was washed with EtOAc (5 mL×3) and drived under vacuum overnight. The title compound was obtained as a yellow solid (112.3 mg, 86%).

MS (ESI, pos. ion) m/z: 628.1 (M+1); LC-MS Rt: 3.50 min;

$^1$H NMR (400 MHz, $CDCl_3$): δ 1.10 (d, J=6.4 Hz, 3H), 2.52 (s, 6H), 2.79 (s, 3H), 3.19-3.23 (m, 2H), 3.69-3.78 (m, 1H), 3.95 (s, 3H), 3.98-4.04 (m, 1H), 4.89-5.02 (m, 1H), 6.08 (s, 2H), 6.49 (d, J=5.2 Hz, 1H), 7.31-7.38 (m, 2H), 7.43-7.46 (m, 4H), 7.50-7.57 (m, 1H), 7.61-7.65 (m, 2H), 7.98 (dd, J=13.2 Hz, J=2.4 Hz, 1H), 8.24 (d, J=9.2 Hz, 1H), 8.64 (d, J=5.2 Hz, 1H), 10.87 (s, 1H).

Example 36

(S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino)acetate benzoate

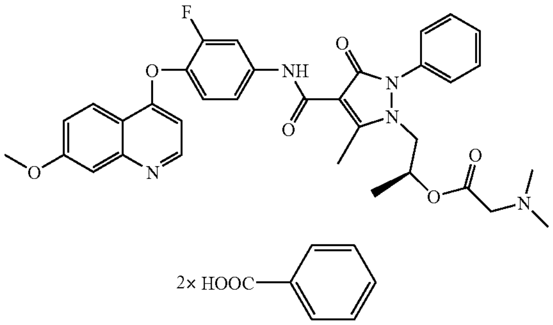

The title compound was prepared according to the procedure described in Example 35 step 2 by using the compound of (S)-1-(4-(4-(7-methoxyquinolin-4-yloxy)-3-fluoro-phenylcarbamoyl)-2,3-dihydro-5-methyl-3-oxo-2-phenylpyrazol-1-yl)propan-2-yl 2-(dimet-hylamino)acetate (63 mg, 0.2 mmol) and benzoic acid (24.4 mg, 0.2 mmol, Tianjin Chemical Reagent Factory). The title compound was abtained as a white solid (67.4 mg, 77%).

MS (ESI, pos. ion) m/z: 628.1 (M+1); LC-MS Rt: 3.49 min;

$^1$H NMR (400 MHz, $CDCl_3$): δ1.10 (d, J=6.4 Hz, 3H), 2.41 (s, 6H), 2.84 (s, 3H), 3.08-3.13 (m, 2H), 3.34 (d, J=16.8 Hz, 1H), 3.65-3.79 (m, 1H), 3.98 (s, 3H), 4.0-4.04 (m, 1H), 5.01-5.06 (m, 1H), 6.49 (d, J=5.6 Hz, 1H), 7.17-7.20 (m, 1H), 7.25-7.32 (m, 3H), 7.38-7.50 (m, 6H), 7.51-7.58 (m, 4H), 7.62 (d, J=2.4 Hz, 1H), 7.94 (dd, J=9.2 Hz, J=2.4 Hz, 1H), 8.11 (d, J=8 Hz, 4H), 8.42 (d, J=6.8 Hz, 1H), 8.71 (d, J=5.6 Hz, 1H), 10.80 (s, 1H).

Example 37

(S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino)acetate 4-methylbenzenesulfonate

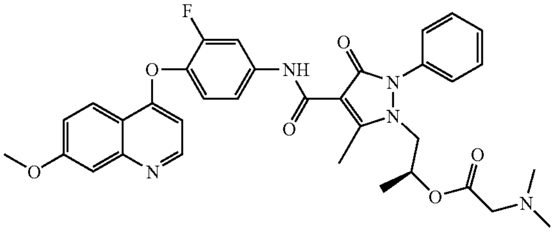

-continued

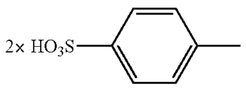

The title compound was prepared according to the procedure described in Example 35 step 2 by using the compound of (S)-1-(4-(4-(7-methoxyquinolin-4-yloxy)-3-fluoro-phenylcarbamoyl)-2,3-dihydro-5-methyl-3-oxo-2-phenylpyrazol-1-yl)propan-2-yl 2-(dimethylamino)acetate (62.9 mg, 0.1 mmol) and p-toluene sulphonic acid (34.6 mg, 0.2 mmol, Shanghai chemical reagent factory). The desired compound was abtained as a yellow solid (56.1 mg, 57%).

MS (ESI, pos. ion) m/z: 628.1 (M+1); LC-MS Rt: 3.42 min;

$^1$H NMR (400 MHz, $CDCl_3$): δ 1.16 (d, J=6.4 Hz, 3H), 2.38 (s, 3H), 2.51 (s, 6H), 2.88 (s, 3H), 3.23 (d, J=16.8 Hz, 1H), 3.34-3.51 (m, 1H), 3.84 (dd, J=15.2 Hz, J=3.6 Hz, 1H), 4.05 (s, 3H), 4.06-4.12 (m, 1H), 5.06-5.09 (m, 1H), 6.66 (d, J=6 Hz, 1H), 7.20-7.28 (m, 3H), 7.33-7.42 (m, 5H), 7.46-7.62 (m, 3H), 7.86-7.88 (m, 3H), 8.0 (dd, J=12.4 Hz, J=2 Hz, 1H), 8.38 (d, J=9.2 Hz, 1H), 8.74 (d, J=6 Hz, 1H), 10.95 (s, 1H).

Example 38

(S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino)acetate methanesulfonate

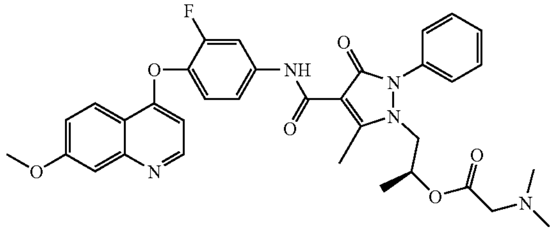

2× $CH_3SO_3H$

The title compound was prepared according to the procedure described in Example 35 step 2 by using the compound of (S)-1-(4-(4-(7-methoxyquinolin-4-yloxy)-3-fluoro-phenylcarbamoyl)-2,3-dihydro-5-methyl-3-oxo-2-phenylpyrazol-1-yl)propan-2-yl 2-(dimet-hylamino)acetate (63.1 mg, 0.1 mmol) and methanesulfonic acid (15.5 mg, 0.16 mmol, Shanghai RichJoint Chemical Reagents CO., Ltd). The title compound was obtained as a yellow solid (60.3 mg, 73%).

MS (ESI, pos. ion) m/z: 628.0 (M+1); LC-MS Rt: 3.28 min;

$^1$H NMR (400 MHz, $CDCl_3$): δ 1.13 (d, J=7.6 Hz, 3H), 2.79 (s, 6H), 2.83 (s, 3H), 2.88 (s, 6H), 3.78 (d, J=17.2 Hz, 1H), 3.87 (dd, J=15.6 Hz, J=3.6 Hz, 1H), 3.98-4.02 (m, 1H), 4.05 (s, 3H), 4.07-4.19 (m, 2H), 5.06-5.09 (m, 1H), 6.78 (d, J=6 Hz, 1H), 7.17-7.22 (m, 1H), 7.28-7.30 (m, 1H), 7.36-7.41 (m, 3H), 7.42-7.58 (m, 3H), 7.86 (d, J=2.4 Hz, 1H), 7.94 (dd, J=12.4 Hz, J=2 Hz, 1H), 8.37 (d, J=9.2 Hz, 1H), 8.78 (d, J=6.4 Hz, 1H), 10.89 (s, 1H).

Example 39

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate maleate

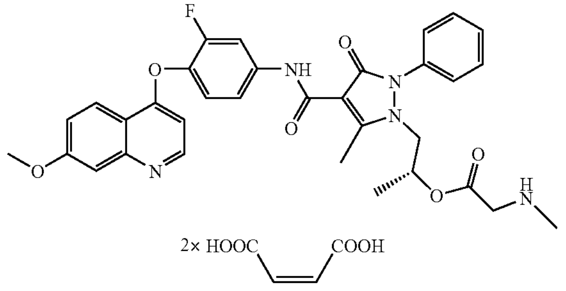

Step 1) (R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-((benzyloxy-carbonyl)(methyl)-amino)acetate To a mixture of (R)—N-(3-fluoro-4-(7-methoxyquinolin-4-yloxy)-phenyl-1-(2-hydroxypropyl)-5-methyl-3-oxo-2-phenyl-2,3-dihydro-1H-pyrazole-4-carboxamide (2.0 g, 3.68 mmol), N-Cbz-sarcosine (1.643 g, 7.36 mmol) and DMAP (0.9 g, 7.36 mmol, Aladdin) in 15 mL of $CH_2Cl_2$ was added EDC solid (1.06 g, 5.52 mmol, Aladdin) in portions at 0° C. After stirring at 0° C. for 2 hrs, the reaction mixture was warmed up to room temperature, and continued to stir at rt overnight. The mixture was diluted with 100 mL of $CH_2Cl_2$ and the resulted solution was washed with 0.1 N HCl (10 mL×2), followed by saturated $NaHCO_3$ solution (20 mL×2) and water (20 mL). The aqueous phase was extracted with EtOAc (50 mL×3), and the combined organic phases were dried over $Na_2SO_4$, filtered and concentrated in vacuo. The residue was purified by a silica gel column chromatography (EtOAc/hexane=2/1) to give the desired compound as a pale yellow solid (2.31 g, 84%).

MS (ESI, pos. ion) m/z: 748.2 (M+1); LC-MS Rt: 4.56 min;

$^1$H NMR (400 MHz, $CDCl_3$): δ 1.10 (d, J=6.0 Hz, 3H), 2.80 (d, J=11.2 Hz, 3H), 2.92 (s, 3H), 3.69-3.82 (m, 2H), 3.96 (s, 3H), 4.0-4.12 (m, 2H), 4.95-5.08 (m, 3H), 6.52-6.56 (m, 1H), 7.13-7.17 (m, 1H), 7.26-7.46 (m, 10H), 7.53-7.55 (m, 3H), 7.89-7.95 (m, 1H), 8.21-8.31 (m, 1H), 8.58-8.63 (m, 1H), 10.87 (s, 1H).

Step 2) (R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate To a solution of (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl-2-(N-benzyloxy-carbo-nyl-N-methylamino)acetate (1.404 g, 1.876 mmol) in a mixture of EtOAc (100 mL) and MeOH (100 mL) was added catalytic amount of Pd/C (10%, ~55% w/w water content, 100 mg) under $N_2$ atmosphere. The suspension was degassed under vacuum and then purged with $H_2$. The reaction mixture was stirred at rt for 1 h under $H_2$ balloon. The mixture was filtered and the residue was washed with MeOH (50 mL×3). The filtrate used for the next step immediately.

MS (ESI, pos. ion) m/z: 614.1 (M+1); LC-MS Rt: 3.47 min.

Step 3) (R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate maleate To a solution (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl 2-(methylamino)acetate (82.3 mg, 0.134 mmol) in a mixture of EtOAc (10 mL) and MeOH (10 mL) was added maleic acid (31.1 mg, 0.268 mmol, Shanghai San'aisi Reagent Co., Ltd). After stirring for 40 min, the reaction mixture was concentrated in vacuo. The residue was recrystallized in a mixture of MeOH (2 mL)/EtOAc (10 mL). The solid was collected by filtration, washed with EtOAc (5 mL×3) and dried under vacuum overnight. The title compound was obtained as a yellow solid (60.2 mg, 53%).

MS (ESI, pos. ion) m/z: 614.1 (M+1); LC-MS Rt: 3.518 min;

$^1$H NMR (400 MHz, $d_6$-DMSO): δ 1.16 (d, J=5.6 Hz, 3H), 2.55 (s, 3H), 2.76 (s, 3H), 3.34-3.39 (m, 1H), 3.76-3.80 (m, 1H), 3.95 (s, 3H), 3.99-4.04 (m, 2H), 4.91-5.0 (m, 1H), 6.20 (s, 4H), 6.58 (d, J=5.6 Hz, 1H), 7.35-7.39 (m, 2H), 7.41-7.46 (m, 4H), 7.53-7.59 (m, 1H), 7.59-7.63 (m, 2H), 7.98 (dd, J=13.2 Hz, J=2.8 Hz, 1H), 8.28 (d, J=9.2 Hz, 1H), 8.70 (d, J=5.6 Hz, 1H), 10.88 (s, 1H).

Example 40

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate fumarate

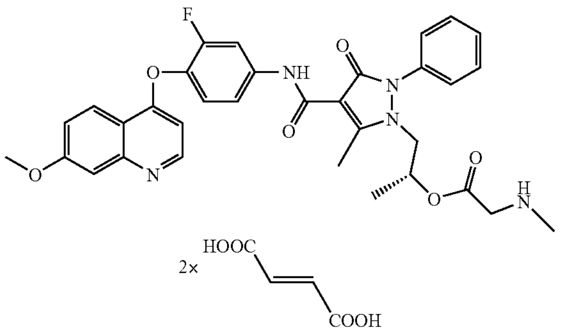

The title compound was prepared according to the procedure described in Example 39 step 3 by using (R)-1-(4-(4-(7-methoxyquinolin-4-yloxy)-3-fluorophenyl-carbamoyl)-2,3-dihydro-5-methyl-3-oxo-2-phenylpyrazol-1-yl)propan-2-yl 2-(methyl-amino)acetate (82.3 mg, 0.134 mmol) and fumaric acid (31.1 mg, 0.268 mmol, Shantou Xilong Chemical Factory). The title compound was abtained as a yellow solid (76.3 mg, 67%).

MS (ESI, pos. ion) m/z: 614.1 (M+1); LC-MS Rt: 3.509 min;

$^1$H NMR (400 MHz, $d_6$-DMSO): δ 1.05 (d, J=6.0 Hz, 3H), 2.25 (s, 3H), 2.78 (s, 3H), 3.15-3.42 (m, 2H), 3.94-3.97 (m, 4H), 4.22-4.28 (m, 1H), 4.88-4.91 (m, 1H), 6.48 (d, J=5.2 Hz, 1H), 6.56 (s, 4H), 7.29-7.37 (m, 2H), 7.41-7.46 (m, 4H), 7.50-7.54 (m, 1H), 7.60-7.64 (m, 2H), 7.97 (dd, J=12.8 Hz, 2.4 Hz, 1H), 8.23 (d, J=7.2 Hz, 1H), 8.62 (d, J=5.2 Hz, 1H), 10.87 (s, 1H).

Example 41

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate hydrochloride

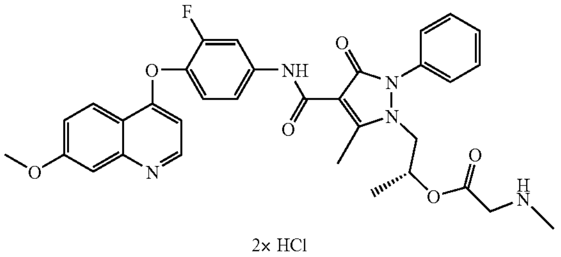

The title compound was prepared according to the procedure described in Example 39 step 3 by using (R)-1-(4-(4-(7-methoxyquinolin-4-yloxy)-3-fluorophenyl-carbamoyl)-2,3-dihydro-5-methyl-3-oxo-2-phenylpyrazol-1-yl)propan-2-yl 2-(methyl-amino)acetate (82.3 mg, 0.134 mmol) and a saturated solution of HCl/EtOAc (3 mL). The title compound was abtained as a yellow solid (64.5 mg, 70%).

MS (ESI, pos. ion) m/z: 614.1 (M+1); LC-MS Rt: 3.754 min;

$^1$H NMR (400 MHz, $d_6$-DMSO): δ 1.09 (d, J=6.0 Hz, 3H), 2.53 (s, 3H), 2.79 (s, 3H), 3.87-3.97 (m, 1H), 4.0-4.07 (m, 4H), 4.26-4.32 (m, 1H), 4.90-4.94 (m, 1H), 6.95 (d, J=6.4 Hz, 1H), 7.42-7.45 (m, 3H), 7.55-7.65 (m, 5H), 7.73-7.77 (m, 1H), 8.07 (dd, J=15.6 Hz, 2.4 Hz, 1H), 8.49 (d, J=9.2 Hz, 1H), 8.97 (d, J=6.4 Hz, 1H), 10.95 (s, 1H).

Example 42

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate sulfate

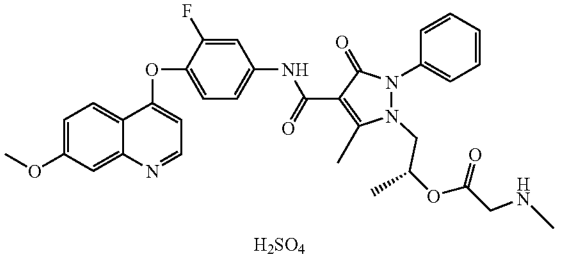

The title compound was prepared according to the procedure described in Example 39 step 3 by using (R)-1-(4-(4-(7- methoxyquinolin-4-yloxy)-3-fluorophenyl-carbamoyl)-2,3-dihydro-5-methyl-3-oxo-2-phenylpyrazol-1-yl)propan-2-yl 2-(methyl-amino)acetate (82.3 mg, 0.134 mmol) and a solution of 0.5 mL of 2N $H_2SO_4$. The title compound was abtained as a yellow solid (77.3 mg, 81%).

MS (ESI, pos. ion) m/z: 614.1 (M+1); LC-MS Rt: 3.452 min;

$^1$H NMR (400 MHz, $d_6$-DMSO): δ 1.10 (d, J=6.4 Hz, 3H), 2.57 (s, 3H), 2.78 (s, 3H), 3.75-3.82 (m, 1H), 3.97-4.07 (m, 5H), 4.26-4.32 (m, 1H), 4.90-4.95 (m, 1H), 6.82 (d, J=6.0 Hz, 1H), 7.40-7.45 (m, 3H), 7.50-7.57 (m, 4H), 7.61-7.65 (m, 2H), 8.04 (dd, J=12.8 Hz, 1.6 Hz, 1H), 8.41 (d, J=8.8 Hz, 1H), 8.87 (d, J=6.0 Hz, 1H), 10.94 (s, 1H).

Example 43

(R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl 2-(methylamino) acetate phosphoric acid

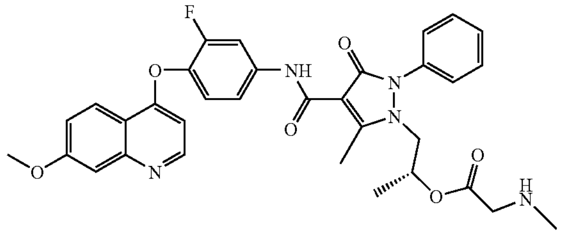

$H_3PO_4$

The title compound was prepared according to the procedure described in Example 39 step 3 by using (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl 2-(methylamino)acetate (82.3 mg, 0.134 mmol) and a solution of 0.4 mL of 2N $H_3PO_4$. The title compound was abtained as yellow oil (82.3 mg, 86%).

MS (ESI, pos. ion) m/z: 614.1 (M+1); LC-MS Rt: 3.424 min.

Example 44

(R)-1-(4-(3-fluoro-4-(7-methoxyquinolin-4-yloxy) phenylcarbamoyl)-5-methyl-3-oxo-2-phenyl-2,3-dihydropyrazol-1-yl)propan-2-yl 2-(methylamino) acetate methanesulfonate

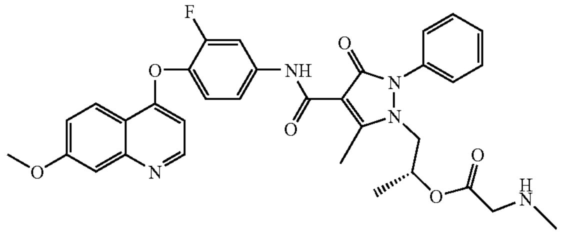

2× $CH_3SO_3H$

The title compound was prepared according to the procedure described in Example 39 step 3 by using (R)-1-(4-(4-(7-methoxyquinolin-4-yloxy)-3-fluorophenylcarbam-oyl)-2,3-dihydro-5-methyl-3-oxo-2-phenylpyrazol-1-yl)propan-2-yl 2-(methylamino)acetate (82.3 mg, 0.134 mmol) and methanesulfonic acid (25.7 mg, 0.268 mmol, Shanghai RichJoint Chemical Reagents CO., Ltd). The title compound was abtained as a yellow solid (63.8 mg, 59%).

MS (ESI, pos. ion) m/z: 614.1 (M+1); LC-MS Rt: 3.453 min;

$^1$H NMR (400 MHz, $d_6$-DMSO): δ 1.10 (d, J=6.0 Hz, 3H), 2.35 (s, 3H), 2.57 (s, 3H), 2.79 (s, 3H), 3.78-3.84 (m, 1H), 3.96-4.07 (m, 5H), 4.26-4.33 (m, 1H), 4.91-4.95 (m, 1H), 7.02 (d, J=6.4 Hz, 1H), 7.44-7.46 (m, 3H), 7.53-7.65 (m, 6H), 8.07 (dd, J=12.8 Hz, 2.4 Hz, 1H), 8.52 (d, J=9.2 Hz, 1H), 9.02 (d, J=6.4 Hz, 1H), 10.97 (s, 1H).

Example 45

(R)-1-(4-(3-fluoro-4-(7-methoxyquinolin-4-yloxy) phenylcarbamoyl)-5-methyl-3-oxo-2-phenyl-2,3-dihydropyrazol-1-yl)propan-2-yl 2-(methylamino) acetate ethanesulfonate

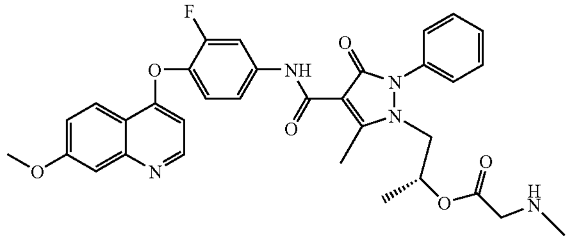

2× $C_2H_5SO_3H$

The title compound was prepared according to the procedure described in Example 39 step 3 by using (R)-1-(4-(4-(7-methoxyquinolin-4-yloxy)-3-fluorophenylcarbam-oyl)-2,3-dihydro-5-methyl-3-oxo-2-phenylpyrazol-1-yl)propan-2-yl 2-(methylamino)acetate (82.3 mg, 0.134 mmol) and ethanesulfonic acid (29.5 mg, 0.268 mmol, Alfa Aesar). The title compound was abtained as a yellow solid (72.8 mg, 65%).

MS (ESI, pos. ion) m/z: 614.1 (M+1); LC-MS Rt: 3.456 min;

$^1$H NMR (400 MHz, $d_6$-DMSO): δ 1.03 (d, J=6.8 Hz, 3H), 1.05-1.09 (m, 3H), 2.63-2.67 (m, 2H), 2.78 (s, 3H), 3.62-3.66 (m, 1H), 3.82-3.86 (m, 1H), 3.94 (s, 3H), 4.0-4.08 (m, 1H), 4.24-4.30 (m, 1H), 4.88-4.96 (m, 1H), 6.47 (d, J=5.6 Hz, 1H), 7.30-7.36 (m, 2H), 7.42-7.46 (m, 4H), 7.52-7.56 (m, 1H), 7.60-7.64 (m, 2H), 7.97 (dd, J=13.2 Hz, J=2.4 Hz, 1H), 8.22 (d, J=9.2 Hz, 1H), 8.62 (d, J=5.2 Hz, 1H), 10.92 (s, 1H).

Example 46

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate benzoate

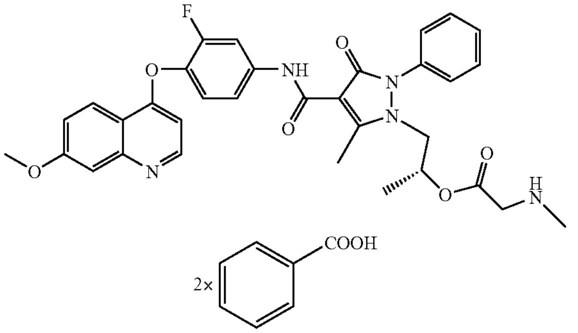

The title compound was prepared according to the procedure described in Example 39 step 3 by using (R)-1-(4-(4-(7-methoxyquinolin-4-yloxy)-3-fluorophenylcarbam-oyl)-2,3-dihydro-5-methyl-3-oxo-2-phenylpyrazol-1-yl)propan-2-yl 2-(methylamino)acetate (82.3 mg, 0.134 mmol) and benzoic acid (32.7 mg, 0.268 mmol, Tianjin Chemical Reagent Factory). The title compound was abtained as a yellow solid (71.3 mg, 62%).

MS (ESI, pos. ion) m/z: 614.1 (M+1); LC-MS Rt: 3.523 min.

Example 47

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate 4-methylbenzenesulfonate

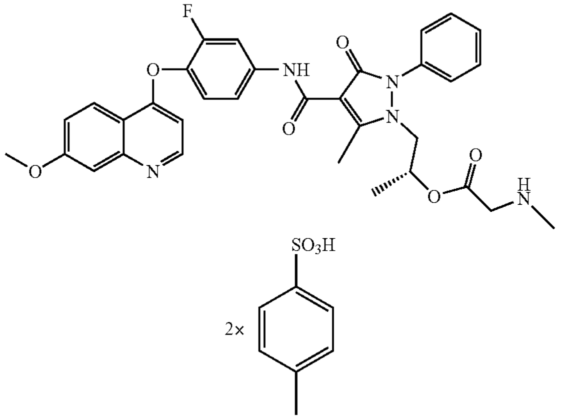

The title compound was prepared according to the procedure described in Example 39 step 3 by using (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl 2-(methylamino)acetate (82.3 mg, 0.134 mmol) and p-toluene sulphonic acid (50.2 mg, 0.268 mmol, Shanghai chemical reagent factory). The title compound was abtained as a yellow solid (88.5 mg, 67%).

MS (ESI, pos. ion) m/z: 614.1 (M+1); LC-MS Rt: 3.376 min;

$^1H$ NMR (400 MHz, $d_6$-DMSO): δ 1.09 (d, J=6.4 Hz, 3H), 2.28 (s, 3H), 2.78 (s, 3H), 3.78-3.83 (m, 1H), 3.97-4.06 (m, 5H), 4.25-4.32 (m, 1H), 4.90-4.96 (m, 1H), 7.0 (d, J=5.2 Hz, 1H), 7.10-7.12 (m, 3H), 7.43-7.49 (m, 6H), 7.53-7.64 (m, 5H), 8.07 (dd, J=13.2 Hz, J=2.4 Hz, 1H), 8.51 (d, J=5.2 Hz, 1H), 9.0 (d, J=6.4 Hz, 1H), 10.96 (s, 1H).

Example 48

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate acetate

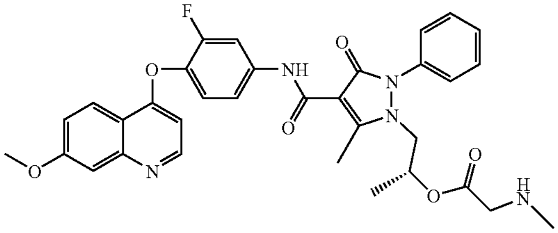

$2\times CH_3COOH$

The title compound was prepared according to the procedure described in Example 39 step 3 by using (R)-1-(4-(4-(7-methoxyquinolin-4-yloxy)-3-fluorophenyl-carbamoyl)-2,3-dihydro-5-methyl-3-oxo-2-phenylpyrazol-1-yl)propan-2-yl 2-(methyl-amino)acetate (82.3 mg, 0.134 mmol) and acetic acid (31.6 mg, 0.268 mmol). The title compound was abtained as a white solid (77.5 mg, 68%).

MS (ESI, pos. ion) m/z: 614.1 (M+1); LC-MS Rt: 3.532 min.

Example 49

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate (2R,3R)-2,3-dihydroxysuccinate

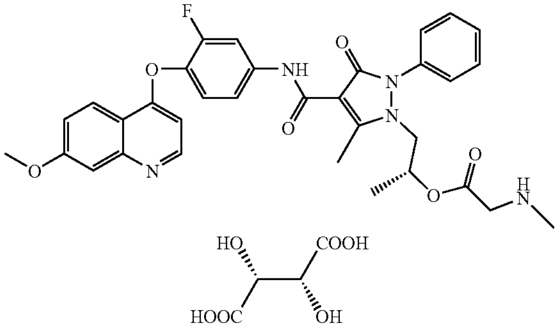

The title compound was prepared according to the procedure described in Example 39 step 3 by using (R)-1-(4-(4-(7-methoxyquinolin-4-yloxy)-3-fluorophenylcarbamoyl)-2,3-dihydro-5-methyl-3-oxo-2-phenylpyrazol-1-yl)prop an-2-yl 2-(methylamino)acetate (82.3 mg, 0.134 mmol) and L-tartaric acid (40.2 mg, 0.268 mmol). The title compound was abtained as a white solid (90.1 mg, 88%).

MS (ESI, pos. ion) m/z: 614.1 (M+1); LC-MS Rt: 3.489 min;

$^1$H NMR (400 MHz, $d_6$-DMSO): δ 1.07 (d, J=6.4 Hz, 3H), 2.36 (s, 3H), 2.77 (s, 3H), 3.62-3.66 (m, 1H), 3.82-3.86 (m, 1H), 3.94 (s, 2H), 4.05 (s, 3H), 4.0-4.04 (m, 3H), 4.20-4.29 (m, 1H), 4.89-4.92 (m, 1H), 6.47 (d, J=5.2 Hz, 1H), 7.30-7.36 (m, 2H), 7.42-7.46 (m, 4H), 7.51-7.55 (m, 1H), 7.60-7.64 (m, 2H), 7.97 (dd, J=13.2 Hz, J=2.4 Hz, 1H), 8.23 (d, J=9.2 Hz, 1H), 8.62 (d, J=5.2 Hz, 1H), 10.87 (s, 1H).

Example 50

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate oxalate

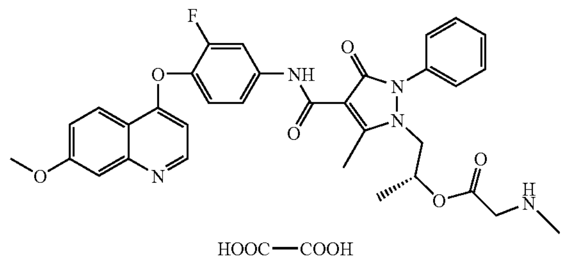

The title compound was prepared according to the procedure described in Example 39 step 3 by using (R)-1-(4-(4-(7-methoxyquinolin-4-yloxy)-3-fluorophenyl-carbamoyl)-2,3-dihydro-5-methyl-3-oxo-2-phenylpyrazol-1-yl)propan-2-yl 2-(methyl-amino)acetate (82.3 mg, 0.134 mmol) and oxalic acid (33.8 mg, 0.268 mmol, Shantou Xilong Chemical Factory). The title compound was abtained as a yellow solid (79.2 mg, 80%).

MS (ESI, pos. ion) m/z: 614.1 (M+1); LC-MS Rt: 3.417 min.

Example 51

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate 2-hydroxypropane-1,2,3-tricarboxylate

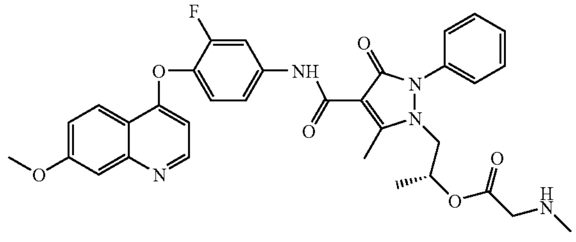

-continued

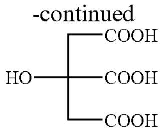

The title compound was prepared according to the procedure described in Example 39 step 3 by using (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl 2-(methylamino)acetate (82.3 mg, 0.134 mmol) and citric acid (51.5 mg, 0.268 mmol, Tianjin Chemical Factory). The title compound was abtained as a pale yellow solid (90.6 mg, 84%).

MS (ESI, pos. ion) m/z: 614.1 (M+1); LC-MS Rt: 3.426 min.

Example 52

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(methylamino)acetate succinate

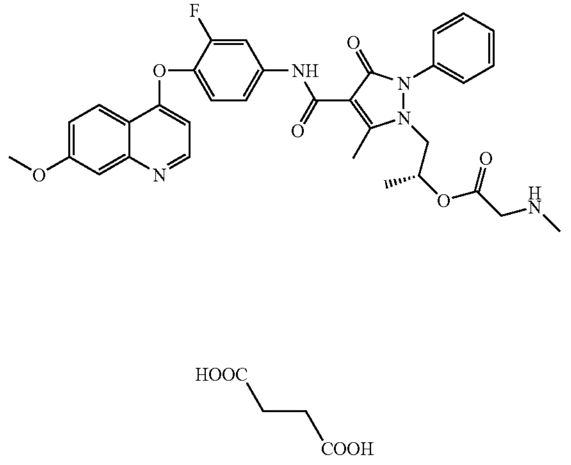

The title compound was prepared according to the procedure described in Example 39 step 3 by using (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl-2-(methylamino)acetate (82.3 mg, 0.134 mmol) and succinic acid (31.6 mg, 0.268 mmol, Guangdong Chemical Reagent Engineering-technological Research and Development Center). The title compound was abtained as a pale yellow solid (70.5 mg, 72%).

MS (ESI, pos. ion) m/z: 614.1 (M+1); LC-MS Rt: 3.506 min;

$^1$H NMR (400 MHz, $d_6$-DMSO): δ 1.06 (d, J=6.4 Hz, 3H), 2.41 (s, 4H), 2.78 (s, 3H), 3.36-3.40 (m, 1H), 3.90-3.97 (m, 4H), 4.0-4.06 (m, 1H), 4.22-4.28 (m, 1H), 4.85-4.90 (m, 1H), 6.48 (d, J=5.2 Hz, 1H), 7.30-7.36 (m, 2H), 7.40-7.44 (m, 4H), 7.49-7.53 (m, 1H), 7.58-7.63 (m, 2H), 7.97 (dd, J=13.2 Hz, J=2.4 Hz, 1H), 8.23 (d, J=9.2 Hz, 1H), 8.62 (d, J=14.8 Hz, 1H), 10.87 (s, 1H).

Example 53

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-minoacetate hydrochloride

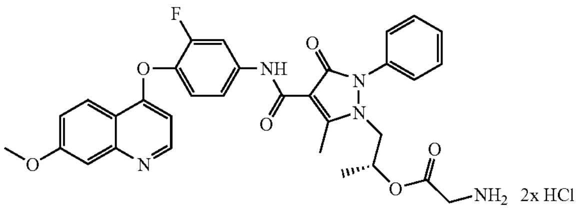

Step 1) (R)-benzyl 1-(2-(2-(tert-butoxycarbonylamino)acetoxy)propyl)-5-methyl-3-oxo-2-phenyl-2,3-dihydro-1H-pyrazole-4-carboxylate To a solution of (R)-benzyl 1-(2-hydroxypropyl)-5-methyl-3-oxo-2-phenyl-2,3-dihydro-1H-pyrazole-4-carboxylate (500 mg, 1.36 mmol), Boc-glycine (263 mg, 1.50 mmol), DMAP (17 mg, 0.136 mmol) in dry $CH_2Cl_2$ (5 mL) was added EDCI (417 mg, 2.18 mmol). The mixture reaction was stirred for 3 h at rt. TLC analysis showed that the starting material was consumed completely. The organic layer was then washed with water (3 mL×2), aqueous $NaH_2PO_4$ (3 mL×2, 2N) and water (3 mL×2). The organic phase was dried over anhydrous $Na_2SO_4$, filtrated and concentrated in vacuo to afford the title compound as a thick oil (750 mg).

MS (ESI, pos. ion) m/z: 524.1 (M+1);

$^1$H NMR (400 MHz, $CDCl_3$): δ 1.10 (d, J=6.4 Hz, 3H), 1.44 (s, 9H), 2.68 (s, 3H), 3.59 (dd, J=18.4, 5.2 Hz, 1H), 3.73 (dd, J=16.0, 4.0 Hz, 1H), 3.88 (dd, J=18.4, 6.8 Hz, 1H), 3.96 (dd, J=15.6, 9.2 Hz, 1H), 4.85~5.05 (m, 2H), 5.25 (dd, J=22.4, 12.8 Hz, 2H), 7.23~7.57 (m, 10H);

$^{13}$C NMR (100 MHz, $CDCl_3$): δ 13.0, 17.8, 28.5, 29.9, 42.5, 50.0, 65.9, 68.5, 80.4, 99.4, 126.1, 127.8, 128.0, 128.6, 128.7, 129.9, 134.1, 136.5, 155.8, 159.2, 163.3, 163.7, 169.4.

Step 2) (R)-1-(2-(2-(tert-butoxycarbonylamino)acetoxy)propyl)-5-methyl-3-oxo-2-phenyl-2,3-dihydro-1H-pyrazole-4-carboxylic acid A mixture of (R)-benzyl 1-(2-(2-(tert-butoxycarbonylamino)acetoxy)propyl)-5-methyl-3-oxo-2-phenyl-2,3-dihydro-1H-pyrazole-4-carboxylate (485 mg, 0.926 mmol) and 10% Pd/C (60 mg) in methanol (8 mL) was stirred for 3 h at rt. TLC analysis showed that the starting material was consumed completely. The catalyst was removed by filtration and the reaction mixture was concentrated in vacuo. The residue was purified by a silica gel column chromatography (100% EtOAc) to afford the title compound as a yellow solid (172 mg, 43% yield).

MS (ESI, pos. ion) m/z: 434.1 (M+1); $^1$H NMR (400 MHz, $CDCl_3$): δ 1.13 (d, J=6.4 Hz, 3H), 1.46 (s, 9H), 2.77 (s, 3H), 3.66 (dd, J=18.4, 5.2 Hz, 1H), 3.83 (dd, J=15.6, 3.6 Hz, 1H), 4.04 (dd, J=15.6, 8.8 Hz, 1H), 4.09~5.05 (m, 2H), 7.37 (d, J=7.6 Hz, 2H), 7.46~7.62 (m, 3H);

$^{13}$C NMR (100 MHz, $CDCl_3$): δ 12.4, 17.7, 28.5, 42.6, 49.7, 68.3, 77.4, 80.5, 97.9, 127.0, 130.0, 130.4, 132.4, 156.2, 163.4, 165.9, 169.5.

Step 3) (R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(tert-butoxycarbonylamino)acetate To a solution of 3-fluoro-4-(7-methoxyquinolin-4-yloxy)benzenamine (399 mg, 1.38 mmol), (R)-1-(2-(2-(tert-butoxycarbonylamino)acetoxy)propyl)-5-methyl-3-oxo-2-phenyl-2,3-dihydro-1H-pyrazole-4-carboxylic acid (500 mg, 1.15 mmol) in dry $CH_2Cl_2$ (5 mL) was added EDCI (264 mg, 1.38 mmol) and HOAT (32 mg, 0.23 mmol). The mixture reaction was refluxed for 3 h. The reaction mixture was then concentrated in vacuo and the residue was purified by a silica gel column chromatography (100% EtOAc) to give the title compound as a white solid (610 mg, 76%).

MS (ESI, pos. ion) m/z: 700.2 (M+1); LC-MS Rt: 4.502 min;

$^1$H NMR (400 MHz, $CDCl_3$): δ 1.15 (d, J=6.4 Hz, 3H), 1.44 (s, 9H), 2.86 (s, 3H), 3.67-3.73 (m, 1H), 3.79-3.83 (m, 1H), 3.86-3.92 (m, 1H), 3.98 (s, 3H), 4.02-4.07 (m, 1H), 4.96-5.05 (m, 2H), 6.43 (d, =5.6 Hz, 1H), 7.16-7.25 (m, 2H), 7.26-7.30 (m, 1H), 7.37-7.40 (m, 3H), 7.42-7.52 (m, 1H), 7.57-7.61 (m, 2H), 7.93 (dd, J=12.4 Hz, J=2.4 Hz, 1H), 8.28 (d, J=7.2 Hz, 1H), 8.60 (d, J=5.6 Hz, 1H), 10.82 (s, 1H).

Step 4) (R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-aminoacetate hydrochloride To a solution of compound (R)-1-(4-(4-(7-methoxyquinolin-4-yloxy)-3-fluoro-phenylcarbamoyl)-2,3-dihydro-5-methyl-3-oxo-2-phenylpyrazol-1-yl)propan-2-yl-(tert-butyloxycarbonylamino)acetate (200 mg, 0.286 mmol) in EtOAc (10 mL) was added a saturated solution of HCl/EtOAc (10 mL) under nitrogen. After stirring at rt for 30 hrs, the reaction mixture was filtered and the residue was washed with EtOAc (10 mL×2). The crude product was recrystallized in a mixture solution of MeOH (2 mL)/EtOAc (10 mL) (v/v=1:5), the mixture was filtered, and the solid was washed with EtOAc (5 mL×3). The title compound was obtained as a pale yellow solid (135.7 mg, 71%).

MS (ESI, pos. ion) m/z: 600.2 (M+1); LC-MS Rt: 3.532 min;

$^1$H NMR (400 MHz, $d_6$-DMSO): δ1.06 (d, J=6.4 Hz, 3H), 2.76 (s, 3H), 3.60 (dd, J=16.4 Hz, J=96 Hz 2H), 3.98-4.03 (m, 5H), 4.25-4.31 (m, 1H), 4.84-4.88 (m, 1H), 6.93 (d, J=6.4 Hz, 1H), 7.37-7.43 (m, 3H), 7.49-7.61 (m, 5H), 7.81 (d, J=2.4 Hz, 1H), 8.02 (dd, J=2.0 Hz, J=13.2 Hz, 1H), 8.44 (d, J=9.2 Hz, 1H), 8.61 (s, 3H), 8.95 (d, J=6.4 Hz, 1H), 10.91 (s, 1H).

Example 54

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino) acetate hydrochloride

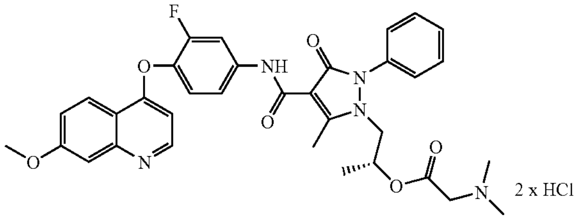

Step 1) (R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino)acetate To a mixture of (R)—N-(3-fluoro-4-(7-methoxyquinolin-4-yloxy)-phenyl-1-(2-hydrox-ylpropyl)-5-methyl-3-oxo-2-phenyl-2,3-dihydro-1H-pyrazole-4-carboxamide (1.08 g, 2.0 mmol), N,N-dimethylglycine (0.516 g, 5 mmol Alfa Aesar), HATU (1.902 g. 5 mmol) and DMAP (62.5 mg, 0.5 mmol, Aladdin) was added TEA (1.012 g, 10 mmol) in DMF (12.5 mL) under nitrogen atmosphere at 0° C. The reaction was stirred at 0° C. for 2 hrs, and then warmed up to room temperature and continued to stir overnight. The reaction was diluted with 100 mL of $CH_2Cl_2$. The resulted solution was washed with 0.1 N HCl (10 mL×2), saturated $NaHCO_3$ (20 mL×2) and followed by water (20 mL). The organic phase was dried over $Na_2SO_4$ and concentrated in vacuo. The residue was purified by a silica gel column chromatography (EtOAc/MeOH=2/1) to give the title compound as a yellow solid (1.1367 g, 84%).

MS (ESI, pos. ion) m/z: 628.1 (M+1); LC-MS Rt: 3.232 min;

$^1$H NMR (400 MHz, $CDCl_3$): δ 1.12 (d, J=6.4 Hz, 3H), 2.11 (s, 3H), 2.32 (s, 6H), 2.98-3.25 (m, 2H), 3.78-3.83 (m, 1H), 3.99 (s, 3H), 4.01-4.08 (m, 1H), 5.03-5.07 (m, 1H), 6.43-6.45 (m, 1H), 7.17-7.21 (m, 1H), 7.30-7.31 (m, 2H), 7.39-7.45 (m, 4H), 7.57-7.62 (m, 2H), 7.90-7.95 (m, 1H), 8.28 (d, J=9.2 Hz, 1H), 8.61 (d, J=5.2 Hz, 1H), 10.87 (s, 1H).

Step 2) (R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino)acetate hydrochloride To a solution of (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl 2-(dimethylamino) acetate (100 mg, 0.16 mmol) in a mixture of MeOH (10 mL)/EtOAc (15 mL) was added a saturated solution of HCl in EtOAc (5 mL). After stirring for 40 minutes, the resulted mixture was concentrated in vacuo. The residue was recrystallized in a mixture of MeOH (2 mL)/EtOAc (8 mL). The solid was collected by filtration, washed with EtOAc (5 mL×3) and dried under vacuum overnight. The title compound was obtained as a yellow solid (90.1 mg, 80%).

MS (ESI, pos. ion) m/z: 628.1 (M+1); LC-MS Rt: 3.295 min;

$^1$H NMR (400 MHz, $CD_3OD$): δ 1.12 (d, J=6.8 Hz, 3H), 1.97 (s, 3H), 2.87 (s, 6H), 3.24-3.26 (m, 2H), 3.52-3.58 (m, 1H), 3.98 (s, 3H), 4.17-4.22 (m, 1H), 5.03-5.07 (m, 1H), 6.43-6.45 (m, 1H), 7.17-7.21 (m, 1H), 7.30-7.39 (m, 2H), 7.41-7.46 (m, 4H), 7.57-7.63 (m, 2H), 8.00-8.03 (m, 1H), 8.51 (d, J=9.2 Hz, 1H), 8.80 (d, J=5.2 Hz, 1H), 10.88 (s, 1H).

Example 55

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino) acetate sulfate

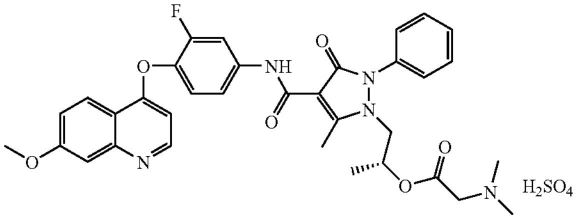

The title compound was prepared according to the procedure described in Example 54 step 2 by using (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl 2-(dimethylamino)acetate (100 mg, 0.16 mmol) and 0.8 mL of 2N $H_2SO_4$. The title compound was obtained as a yellow solid (81.5 mg, 70%).

MS (ESI, pos. ion) m/z: 628.1 (M+1); LC-MS Rt: 3.291 min;

$^1$H NMR (400 MHz, $CD_3OD$): δ 1.09 (d, J=6 Hz, 3H), 1.97 (s, 3H), 2.81 (s, 6H), 3.24-3.26 (m, 2H), 3.65-3.73 (m, 1H), 3.99 (s, 3H), 4.11-4.15 (m, 1H), 5.01-5.05 (m, 1H), 6.77-6.79 (m, 1H), 7.28-7.34 (m, 1H), 7.41-7.44 (m, 2H), 7.49-7.53 (m, 4H), 7.56-7.60 (m, 2H), 7.92-7.95 (m, 1H), 8.38 (d, J=9.6 Hz, 1H), 8.72 (d, J=4.8 Hz, 1H), 10.88 (s, 1H).

Example 56

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino) acetate fumarate

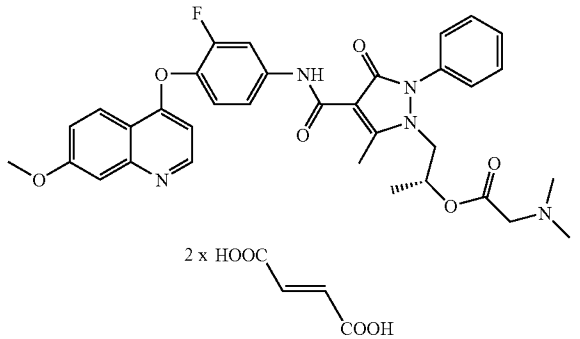

The title compound was prepared according to the procedure described in Example 54 step 2 by using (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl 2-(dimethylamino)acetate (100 mg, 0.16 mmol) and fumaric acid (55.44 mg, 0.48 mmol, Shantou Xilong Chemical Factory). The title compound was obtained as a yellow solid (78.7 mg, 66%).

MS (ESI, pos. ion) m/z: 628.1 (M+1); LC-MS Rt: 3.251 min;

$^1$H NMR (400 MHz, $CD_3OD$): δ 1.11 (d, J=6 Hz, 3H), 1.97 (s, 3H), 2.81 (s, 6H), 3.25-3.29 (m, 2H), 3.63-3.68 (m, 1H), 4.04 (s, 3H), 4.16-4.21 (m, 1H), 5.01-5.07 (m, 1H), 6.74-6.94 (m, 1H), 7.43-7.59 (m, 9H), 7.99-8.02 (m, 1H), 8.52 (d, J=8 Hz, 1H), 8.79 (d, J=4.8 Hz, 1H), 10.88 (s, 1H).

Example 57

(R)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl 2-(dimethylamino)acetate acetate

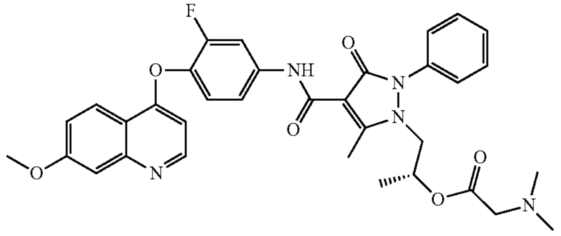

2 x $CH_3COOH$

The title compound was prepared according to the procedure described in Example 54 step 2 by using (R)-1-(4-(4-(7-methoxyquinolin-4-yloxy)-3-fluorophenylcarbamoyl)-2,3-dihydro-5-methyl-3-oxo-2-phenylpyrazol-1-yl)propan-2-yl 2-(dimethylamino)acetate (100 mg, 0.16 mmol) and acetic acid (28.7 mg, 0.48 mmol, Shantou Xilong Chemical Factory). The title compound was obtained as a yellow solid (83.4 mg, 70%).

MS (ESI, pos. ion) m/z: 628.1 (M+1); LC-MS Rt: 3.339 min;

$^1$H NMR (400 MHz, $CD_3OD$): δ 1.07 (d, J=6.4 Hz, 3H), 1.92 (s, 3H), 2.84 (s, 6H), 3.22-3.30 (m, 2H), 3.53-3.59 (m, 1H), 3.93 (s, 3H), 4.20-4.26 (m, 1H), 5.03-5.05 (m, 1H), 6.74-6.94 (m, 1H), 7.29-7.32 (m, 1H), 7.42-7.46 (m, 2H), 7.51-7.55 (m, 4H), 7.58-7.62 (m, 2H), 7.89-7.92 (m, 1H), 8.26 (d, J=9.2 Hz, 1H), 8.50 (d, J=5.2 Hz, 1H), 10.88 (s, 1H).

Example 58

(R)-1-(4-(3-fluoro-4-(7-methoxyquinolin-4-yloxy)phenylcarbamoyl)-5-methyl-3-oxo-2-phenyl-2,3-dihydropyazol-1-yl)propan-2-yl 2-(dimethylamino)acetate oxalate

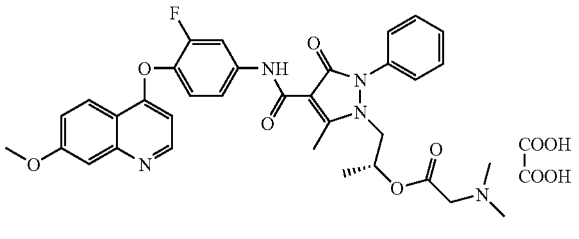

The title compound was prepared according to the procedure described in Example 54 step 2 by using (R)-1-(4-(4-(7-methoxyquinolin-4-yloxy)-3-fluorophenyl-carbamoyl)-2,3-dihydro-5-methyl-3-oxo-2-phenylpyrazol-1-yl)propan-2-yl 2-(dimethyl-amino)acetate (100 mg, 0.16 mmol) and oxalic acid dihydrate (60.3 mg, 0.48 mmol). The title compound was obtained as a yellow solid (98.5 mg, 84%).

MS (ESI, pos. ion) m/z: 628.1 (M+1); LC-MS Rt: 2.009 min;

$^1$H NMR (400 MHz, $CD_3OD$): δ 1.06 (d, J=5.6 Hz, 3H), 1.15 (s, 3H), 1.94 (s, 6H), 2.89-2.91 (m, 2H), 3.70-3.76 (m, 1H), 3.98 (s, 3H), 4.15-4.19 (m, 1H), 5.04-5.09 (m, 1H), 6.91-6.94 (m, 1H), 7.35-7.38 (m, 1H), 7.41-7.45 (m, 2H), 7.52-7.55 (m, 4H), 7.58-7.62 (m, 2H), 7.98-8.02 (m, 1H), 8.50 (d, J=9.2 Hz, 1H), 8.78 (d, J=5.2 Hz, 1H), 10.87 (s, 1H).

Example 59

(R)-1-(4-(5-(7-methoxyquinolin-4-yloxy)pyridin-2-ylcarbamoyl)-5-methyl-3-oxo-2-phenyl-2,3-dihydro-pyrazol-1-yl)propan-2-yl 2-(methylamino)acetate maleate

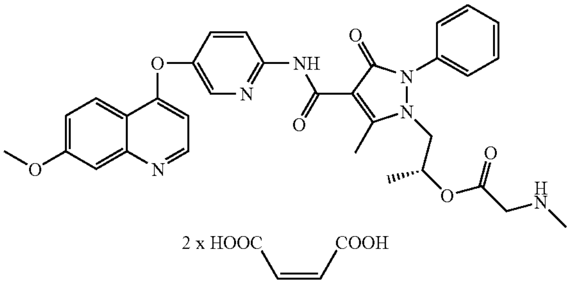

Step 1) (R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-((benzyloxy-carbonyl)-(methyl)amino)acetate To a mixture of (R)-1-(2-hydroxypropyl)-N-(5-(7-methoxyquinolin-4-yloxy)pyridin-2-yl)-5-methyl-3-oxo-2-phenyl-2,3-dihydro-1H-pyrazole-4-carboxamide (2.0 g, 3.81 mmol), N-Cbz-sarcosine (1.7 g, 7.62 mmol) and DMAP (0.93 g, 7.62 mmol, Aladdin) in 15 mL of $CH_2Cl_2$ at 0° C. was added EDC solid (2.19 g, 11.43 mmol, Aladdin) in portions. After stirring at 0° C. for 2 hrs, the mixture was allowed to heat to 40° C. and stirred overnight. The reaction was diluted with 100 mL of $CH_2Cl_2$. The resulted solution was washed with 0.1 N HCl (10 mL×2), saturated $NaHCO_3$ (20 mL×2) and followed by water (20 mL). The organic phase was dried over $Na_2SO_4$ and concentrated in vacuo. The residue was purified by a silica gel column chromatography (EtOAc/MeOH=4/1) to give the title compound as a yellow solid (2.15 g, 77.3%).

MS (ESI, pos. ion) m/z: 731.28 (M+1); LC-MS Rt: 4.199 min;

$^1$H NMR (400 MHz, $CDCl_3$): δ 1.13 (d, J=6.4 Hz, 3H), 1.29 (s, 3H), 2.86 (d, J=6.4 Hz, 2H), 2.94 (s, 3H), 3.97 (s, 3H), 3.99 (s, 2H), 4.16-4.21 (m, 1H), 5.12 (s, 2H), 6.39-6.42 (m, 1H), 7.22-7.25 (m, 1H), 7.29-7.58 (m, 13H), 8.22-8.25 (m, 1H), 8.33-8.37 (m, 1H), 8.57-8.61 (m, 1H), 11.20 (s, 1H).

Step 2) (R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-(methylamino)acetate To a solution of (R)-1-(4-(5-(7-methoxyquinolin-4-yloxy)pyridin-2-ylcarbamoyl)-2,3-dihydro-5-methyl-3-oxo-2-phenylpyrazol-1-yl)propan-2-yl 2-(N-benzyloxycarbonyl-N-methylamino)acetate (1.0 g, 1.4 mmol) in MeOH (100 mL) was added catalytic amount wet Pd/C (10%, ~55% w/w water content, 10 mg) under $N_2$ atmosphere. The suspension was degassed under vacuum and then purged with $H_2$. The reaction mixture was stirred at rt for 20 minutes under $H_2$ balloon. The mixture was filtered and the residue was washed with MeOH (35 mL×3). The filtrate used for the next step immediately.

MS (ESI, pos. ion) m/z: 597.24 (M+1); LC-MS Rt: 3.201 min;

Step 3) (R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-(methylamino)acetate maleate To a solution of (R)-1-(4-(5-(7-methoxyquinolin-4-yloxy)pyridin-2-ylcarbamoyl)-2,3-dihydro-5-methyl-3-oxo-2-phenylpyrazol-1-yl)propan-2-yl 2-(methylamino)acetate (80 mg, 0.134 mmol) in MeOH (10 mL) was added maleic acid (46.74 mg, 0.40 mmol, Shanghai San'aisi Reagent Co., Ltd). After stirring for 40 min, the reaction mixture was concentrated in vacuo. The resulted residue was recrystallized in a mixture of MeOH (4 mL)/EtOAc (8 mL). The solid was collected by filtration, washed with EtOAc (5 mL×3) and dried under vacuum overnight. The title compound was obtained as a yellow solid (68.8 mg, 67%).

MS (ESI, pos. ion) m/z: 597.24 (M+1); LC-MS Rt: 3.221 min;

$^1$H NMR (400 MHz, $CD_3OD$): δ 1.14 (d, J=6.4 Hz, 3H), 1.25 (s, 3H), 2.17-2.20 (m, 1H), 2.78-2.83 (m, 3H), 2.89-2.95 (m, 2H), 3.85-3.93 (m, 2H), 4.06-4.10 (m, 3H), 5.10-5.12 (m, 1H), 6.29-6.35 (m, 2H), 6.98-7.00 (m, 1H), 7.35-7.56 (m, 8H), 7.71-7.72 (m, 1H), 8.21-8.30 (m, 2H), 8.77-8.78 (m, 1H), 11.15 (s, 1H).

Example 60

(R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-(methylamino)acetate hydrochloride

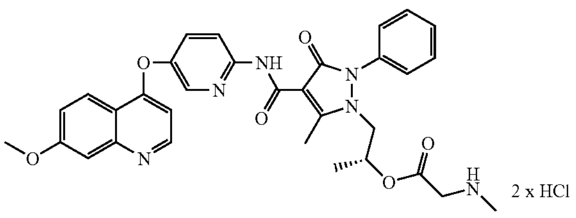

The title compound was prepared according to the procedure described in Example 59 Step 3 by using (R)-1-(4-(5-(7-methoxyquinolin-4-yloxy)pyridin-2-ylcarbamoyl)-2,3-dihydro-5-methyl-3-oxo-2-phenylpyrazol-1-yl)propan-2-yl 2-(methylamino)acetate (100 mg, 0.168 mmol) and a saturated solution of HCl in EtOAc (10 mL). The desired compound was obtained as a yellow solid (80.7 mg, 72%).

MS (ESI, pos. ion) m/z: 597.24 (M+1); LC-MS Rt: 3.262 min;

$^1$H NMR (400 MHz, $CD_3OD$): δ 1.33 (d, J=4.8 Hz, 3H), 1.45 (s, 3H), 2.17-2.25 (m, 1H), 2.96-3.02 (m, 3H), 3.03-3.12 (m, 2H), 3.62-3.68 (m, 2H), 4.19-4.29 (m, 3H), 5.20-5.26 (m, 1H), 6.92-7.30 (m, 1H), 7.60-7.81 (m, 8H), 8.04-8.12 (m, 1H), 8.35-8.73 (m, 2H), 9.00-9.04 (m, 1H), 11.15 (s, 1H).

Example 61

(R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-(methylamino)acetate oxalate

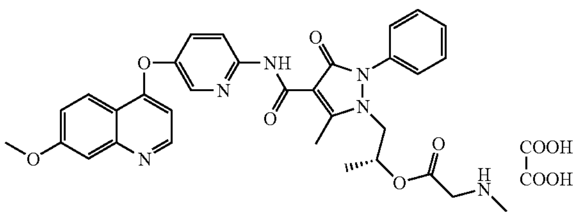

The title compound was prepared according to the procedure described in Example 59 Step 3 by using (R)-1-(4-(5-(7-methoxyquinolin-4-yloxy)pyridin-2-yl-carbamoyl)-2,3-dihydro-5-methyl-3-oxo-2-phenylpyrazol-1-yl)propan-2-yl 2-(methylamino)acetate (100 mg, 0.168 mmol) and oxalic acid dihydrate (63.5 mg, 0.50 mmol). The title compound was obtained as a yellow solid (71.5 mg, 62%).

MS (ESI, pos. ion) m/z: 597.24 (M+1); LC-MS Rt: 3.227 min;

$^1$H NMR (400 MHz, $CD_3OD$): δ 1.23 (d, J=6 Hz, 3H), 1.41 (s, 3H), 2.06-2.15 (m, 1H), 2.79-2.83 (m, 3H), 2.90-3.00 (m, 2H), 3.88-3.98 (m, 2H), 4.07-4.15 (m, 3H), 5.10-5.22 (m, 1H), 6.98-7.07 (m, 1H), 7.54-7.71 (m, 8H), 7.90-7.91 (m, 1H), 8.41-8.61 (m, 2H), 8.80-8.90 (m, 1H), 11.15 (s, 1H).

Example 62

(R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-(methylamino)acetate fumarate

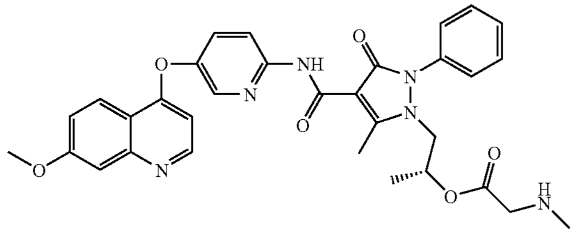

-continued

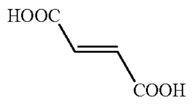

The title compound was prepared according to the procedure described in Example 59 Step 3 by using (R)-1-(4-(5-(7-methoxyquinolin-4-yloxy)pyridin-2-ylcarbamoyl)-2,3-dihydro-5-methyl-3-oxo-2-phenylpyrazol-1-yl)propan-2-yl 2-(methylamino)acetate (100 mg, 0.168 mmol) and fumaric acid (58.4 mg, 0.50 mmol, Shantou Xilong Chemical Factory). The title compound was obtained as a yellow solid (94.1 mg, 79%).

MS (ESI, pos. ion) m/z: 597.24 (M+1); LC-MS Rt: 3.211 min;

$^1$H NMR (400 MHz, $CD_3OD$): δ 1.16 (d, J=5.2 Hz, 3H), 1.28 (s, 3H), 2.02-2.06 (m, 1H), 2.70-2.76 (m, 3H), 2.86-2.93 (m, 2H), 3.84-3.89 (m, 2H), 4.05-4.08 (m, 3H), 4.64-4.65 (m, 1H), 6.94-6.98 (m, 1H), 7.48-7.67 (m, 8H), 7.84-7.87 (m, 1H), 8.35-8.54 (m, 2H), 8.77-8.78 (m, 1H), 11.15 (s, 1H).

Example 63

(R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-(methylamino)acetate acetate

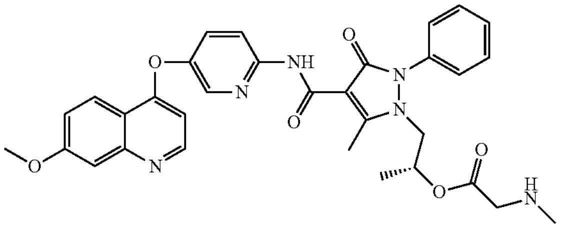

2 x $CH_3COOH$

The title compound was prepared according to the procedure described in Example 59 Step 3 by using acetic acid (30.21 mg, 0.50 mmol, Shantou Xilong Chemical Factory) and (R)-1-(4-(5-(7-methoxyquinolin-4-yloxy)pyridin-2-ylcarbamoyl)-2,3-dihydro-5-methyl-3-oxo-2-phenylpyrazol-1-yl)propan-2-yl 2-(methylamino)acetate (100 mg, 0.168 mmol). The title compound was obtained as a yellow solid (81.4 mg, 73.7%).

MS (ESI, pos. ion) m/z: 597.24 (M+1); LC-MS Rt: 3.103 min;

$^1$H NMR (400 MHz, $CD_3OD$): δ 1.11 (d, J=4 Hz, 3H), 1.23 (s, 3H), 2.31-2.35 (m, 1H), 2.67-2.78 (m, 3H), 2.84-2.87 (m, 2H), 3.92-3.99 (m, 2H), 4.05-4.30 (m, 3H), 5.02-5.04 (m, 1H), 7.01-7.02 (m, 1H), 7.43-7.61 (m, 8H), 7.96-7.99 (m, 1H), 8.33-8.53 (m, 2H), 8.80-8.81 (m, 1H), 11.15 (s, 1H).

Example 64

(R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-(methylamino)acetate 4-methylbenzenesulfonate

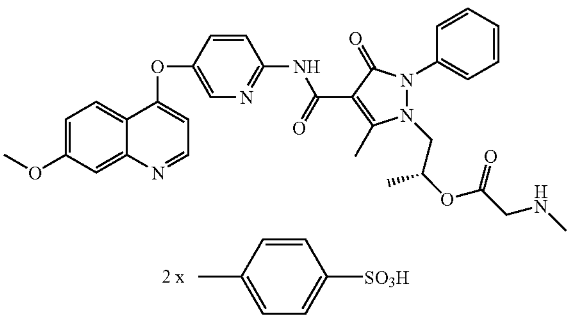

The title compound was prepared according to the procedure described in Example 59 Step 3 by using p-toluene sulphonic acid (76.6 mg, 0.40 mmol, Shanghai chemical reagent procurement and supply of five joint chemical factory) and (R)-1-(4-(5-(7-methoxyquinolin-4-yloxy)pyridin-2-ylcarbamoyl)-2,3-dihydro-5-meth-yl-3-oxo-2-phenylpyrazol-1-yl)propan-2-yl 2-(methylamino)acetate (100 mg, 0.168 mmol). The title compound was obtained as a yellow solid (86.8 mg, 66.4%).

MS (ESI, pos. ion) m/z: 597.24 (M+1); LC-MS Rt: 3.070 min;

$^1$H NMR (400 MHz, $CD_3OD$): δ 0.89 (d, J=4.4 Hz, 3H), 1.23 (s, 3H), 2.20-2.36 (m, 4H), 2.52-2.68 (m, 3H), 2.78-2.92 (m, 2H), 3.47-3.89 (m, 2H), 3.98-4.13 (m, 3H), 5.10-5.30 (m, 1H), 6.98-7.05 (m, 1H), 7.20-7.65 (m, 12H), 8.11-8.19 (m, 1H), 8.51-8.65 (m, 2H), 8.90-8.99 (m, 1H), 11.15 (s, 1H).

Example 65

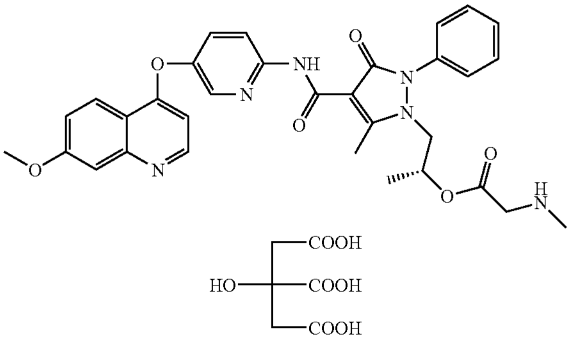

(R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-(methylamino)acetate 2-hydroxypropane-1,2,3-tricarboxylate The title compound was prepared according to the procedure described in Example 59 Step 3 by using citric acid (51.5 mg, 0.268 mmol, Tianjin Chemical Factory) and (R)-1-(4-(5-(7-methoxyquinolin-4-yloxy)pyridin-2-ylcarbamoyl)-2,3-dihydro-5-mety-1-3-oxo-2-phenylpyrazol-1-yl)propan-2-yl 2-(methylamino)acetate (100 mg, 0.168 mmol). The title compound was obtained as a yellow solid (112.4 mg, 85%).

MS (ESI, pos. ion) m/z: 597.24 (M+1); LC-MS Rt: 3.146 min.

Example 66

(S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-amino-3-methylbutanoate hydrochloride

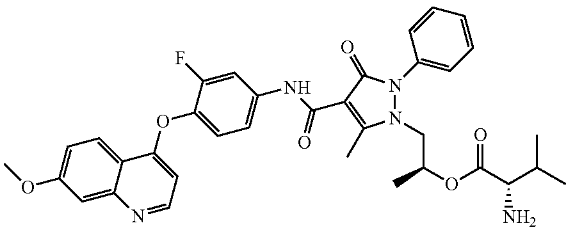

2 x HCl

The title compound was prepared similarly according to the procedure described in Example 59.

MS(ESI, pos. ion) m/z: 642.2 (M+1), LC-MS Rt: 3.419 min;

$^1$H NMR (400 MHz, $D_2O$): δ 0.74-0.75 (d, J=6.8 Hz, 3H), 0.91-0.98 (m, 4H), 1.10-1.12 (d, J=6 Hz, 3H), 2.75 (s, 3H), 3.99 (s, 3H), 4.04-4.05 (d, J=3.6 Hz, 2H), 4.83-4.85 (m, 1H), 6.91-6.92 (d, J=6.8 Hz, 1H), 7.32-7.38 (m, 5H), 7.46-7.49 (m, 1H), 7.58-7.69 (m, 4H), 8.43-8.45 (d, J=9.2 Hz, 1H), 8.62-8.64 (d, J=6.8 Hz, 1H).

Example 67

(S)—((S)-1-(4-(3-fluoro-4-(7-methoxyquinolin-4-yloxy)phenylcarbamoyl)-5-methyl-3-oxo-2-phenyl-2,3-dihydropyrazol-1-yl)propan-2-yl)2-aminopropanoate hydrochloride

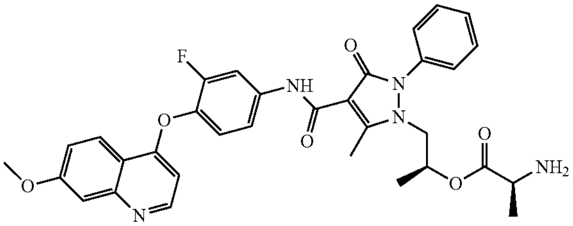

2 x HCl

The title compound was prepared similarly according to the procedure described in Example 59.

MS (ESI, pos. ion) m/z: 614.1 (M+1), LC-MS Rt: 3.357 min;

$^1$H NMR (400 MHz, $D_2O$): δ 1.25-1.26 (d, J=6 Hz, 3H), 1.48-1.50 (d, J=4.4 Hz, 3H), 2.91 (s, 3H), 4.16 (s, 3H), 4.20-4.28 (m, 1H), 4.49-4.55 (m, 1H), 5.11-5.13 (m, 1H), 7.08-

7.10 (d, J=6.8 Hz, 1H), 7.48-7.66 (m, 5H), 7.75-7.86 (m, 5H), 8.61-8.63 (d, J=9.2 Hz, 1H), 8.79-8.80 (d, J=6.8 Hz, 1H).

Example 68

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-amino-3-methylbutanoate hydrochloride

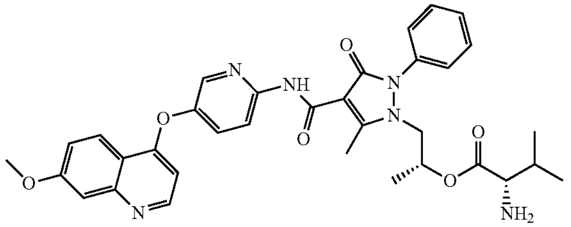

2 x HCl

The title compound was prepared similarly according to the procedure described in Example 59.

MS (ESI, pos. ion) m/z: 625.2 (M+1), LC-MS Rt: 3.275 min;

$^1$H NMR (400 MHz, $CD_3OD$): δ 1.02-1.11 (m, 7H), 1.19-1.20 (d, J=6.4 Hz, 3H), 1.31 (s, 1H), 2.26-2.32 (m, 1H), 2.65 (s, 1H), 2.89 (s, 3H), 3.84-3.89 (m, 1H), 4.11 (s, 3H), 4.36-4.42 (m, 1H), 5.08-5.11 (m, 1H), 6.99-7.01 (d, J=6.4 Hz, 1H), 7.47-7.517 (m, 3H), 7.58-7.69 (m, 4H), 7.88-7.89 (m, 1H), 8.49-8.52 (m, 1H), 8.57-8.59 (m, J=9.6 Hz, 1H), 8.83-8.84 (d, J=6.4 Hz, 1H).

Example 69

(S)—((R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl)2-aminopropanoate hydrochloride

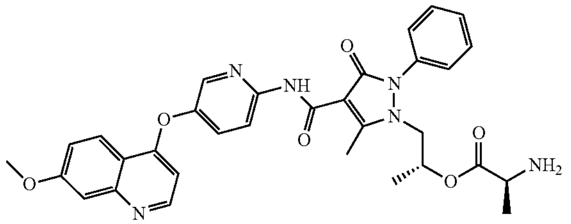

2 x HCl

The title compound was prepared similarly according to the procedure described in Example 59.

MS(ESI, pos. ion) m/z: 597.1 (M+1), LC-MS Rt: 3.136 min;

$^1$H NMR (400 MHz, $CD_3OD$): δ 1.17-1.18 (d, J=6.4 Hz, 3H), 1.54-1.54 (d, J=3.2 Hz, 3H), 1.29-1.34 (m, 2H), 2.88 (s, 3H), 3.96-4.01 (m, 1H), 4.33-4.40 (m, 1H), 5.05-5.10 (m, 1H), 6.99-7.10 (d, J=6.8 Hz, 1H), 7.46-7.49 (m, 3H), 7.57-7.68 (m, 4H), 7.84-7.89 (m, 1H), 8.38 (s, 1H), 8.57-8.59 (d, J=9.6 Hz, 1H), 8.82-8.84 (d, J=6.8 Hz, 1H).

Example 70

1-(2-(4-(4-(1,5-dimethyl-3-oxo-2-phenyl-2,3-dihydro-1H-pyrazole-4-carboxamido)-2-fluorophenoxy)quinolin-7-yloxy)ethyl)cyclopropyl 2-aminoacetate hydrochloride

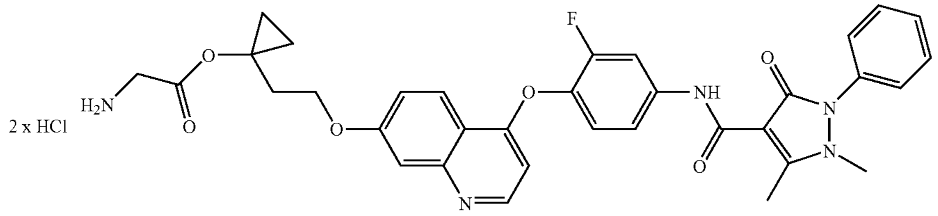

Step 1) benzyl 3-hydroxypropanoat

To a solution of 3-hydroxypropanoic acid (7.2 g, 80.1 mmol, TCI, TOKYO KASEI) in 250 mL of methanol was added KOH (4.49 g, 80.1 mmol) at 0° C., the mixture continued to stir until KOH was dissolved. The methanol was evaporated and the residue was dissolved in 300 ml anhydrous THF. BnBr was added to the solution (13.85 g, 80.1 mmol, Aldrich) via a syringe at 0° C. The reaction mixture was refluxing at 80° C. for two days. The reaction was quenched with water (30 mL) and extracted with EtOAc (30 mL×5). The combined organic phases were dried over $Na_2SO_4$ and concentrated in vacuo. The residue was chromatographed on a silica gel column (PE: EtOAc=6:1) to give the desired compound as yellow oil (2.02 mg, 27.1%).

Step 2) benzyl 3-(tetrahydro-2H-pyran-2-yloxy)propanoate

To a mixture of benzyl 3-hydroxypropanoate (2.041 g, 11.34 mmol) and DHP (1.428 g, 17.01 mmol, Alfa) in 30 mL of dichloromethane was added PPTS (0.283 g, 1.13 mmol, Aldrich) slowly. After stirring at 40° C. for 3 days, the reaction mixture was concentrated in vacuo, and the residue was purified by a silica gel column chromatography (PE: EtOAc=20:1) to afford the title compound as pale yellow oil (2.64 g, 88.3%).

Step 3) 1-(2-(tetrahydro-2H-pyran-2-yloxy)ethyl)cyclopropanol

To a solution of benzyl 3-(tetrahydro-2H-pyran-2-yloxy)propanoate (1.1 g, 4.17 mmol) in 14.2 mL of THF was added $Ti(Oi\text{-}Pr)_4$(0.252 mL, 0.834 mmol, 0.955 g/L, Aldrich) via a syringe under nitrogen at rt. The reaction mixture was then cooled to 18° C. over 30 min. EtMgBr (3.54 mL, 10.4 mmol, 3M ether solution, Aldrich) was added via a syringe pump over 2 hrs. The reaction was quenched with saturated $NH_4Cl$ solution (50 mL) when benzyl 3-(tetrahydro-2H-pyran-2-yloxy)propanoate reacted completely (monitored by TLC). The mixture was filtered and the filtrate was extracted with ethyl acetate (30 mL×3). The combined organic phases were dried over $Na_2SO_4$ and concentrated in vacuo. The residue was purified by a silica gel column chromatography (PE: EtOAc=10:1) to give the desired compound as yellow oil (507 mg, 65%).

$^1H$ NMR (400 MHz, $CDCl_3$): δ 0.46 (m, 2H), 0.75-0.88 (d, 2H), 1.55-1.83 (m, 6H), 1.87-1.90 (m, 2H), 3.55 (q, 1H), 3.69 (q, 1H), 3.88 (t, 1H), 4.06 (t, 1H), 4.66 (s, 1H).

Step 4) 1-(2-hydroxyethyl)cyclopropanol

To a solution of 1-(2-(tetrahydro-2H-pyran-2-yloxy)ethyl)cyclopropanol (507 mg, 2.71 mmol) in 40 mL of methanol was added PPTS (68.1 mg, 0.271 mmol, Aldrich) in portions. After stirring at 40° C. overnight, the reaction was quenched with water (10 mL) and extracted with dichloromethane (20 mL×3). The combined organic phases were dried over $Na_2SO_4$ and concentrated in vacuo. The residue was purified by a silica gel column chromatography (PE: EtOAc=10:1) to give the desired compound as a pale yellow oil (150 mg, 54.3%).

$^1H$ NMR (400 MHz, $CDCl_3$): δ 0.55 (t, 2H), 0.85 (t, 2H), 1.85 (t, 2H), 4.02 (t, 2H).

Step 5) 2-(1-hydroxycyclopropyl)ethyl methanesulfonate

A mixture of 1-(2-hydroxyethyl)cyclopropanol (310 mg, 3.04 mmol) and triethylamine (614.1 mg, 6.08 mmol) in 10 mL of dichloromethane was stirred at −10° C. for 30 min. Methanesulfonyl chloride (348 mg, 3.04 mmol) was added via a syringe. After stirring at −10° C. for 1 hr, the reaction mixture was quenched with ice-water (2 mL) and extracted with dichloromethane (20 mL×4). The combined organic phases were dried over $Na_2SO_4$ and concentrated in vacuo to give yellow oil (used for the next step quickly).

Step 6) N-(3-fluoro-4-(7-(2-(1-hydroxycyclopropyl)ethoxy)quinolin-4-yloxy)phenyl)-1,5-dimethyl-3-oxo-2-phenyl-2,3-dihydro-1H-pyrazole-4-carboxamide To a mixture of N-(3-fluoro-4-(7-hydroxyquinolin-4-yloxy)phenyl)-1,5-dimethyl-3-oxo-2-phenyl-2,3-dihydro-1H-pyrazole-4-carboxamide (735.7 mg, 1.52 mmol) and 2-(1-hydroxycyclopropyl)ethyl methanesulfonate (3.04 mmol) in 8 mL of N,N-dimethylacetamide was added cesium carbonate (4.955 g, 15.2 mmol). After stirring at 40° C. for 1 day, the reaction was quenched with water (5 mL) and extracted with $CH_2Cl_2$ (20 mL×3). The combined organic phases were dried over $Na_2SO_4$ and concentrated in vacuo. The residue was chromatographed on a silica gel column ($CH_2Cl_2/CH_3OH$ (v/v)=45:1) to afford the title compound as a white solid (270 mg, 15.6%).

MS (ESI, pos. ion) m/z: 569.1 (M+1); LC-MS Rt: 3.948 min;

$^1H$ NMR (400 MHz, $CDCl_3$): δ 0.57 (d, J=8 Hz, 2H), 0.86 (d, J=8 Hz, 2H), 2.14 (t, 2H), 2.80 (s, 3H), 3.37 (s, 3H), 4.43 (t, 2H), 6.41 (d, J=4 Hz, 1H), 7.14-7.23 (m, 2H), 7.26-7.35 (m, 1H), 7.37-7.38 (m, 2H), 7.45-7.50 (m, 2H), 7.50-7.58 (m, 2H), 7.90-7.93 (dd, J=2.4 Hz, 1H), 8.27 (d, J=8 Hz, 1H), 8.58 (d, J=8 Hz, 1H), 10.89 (s, 1H).

Step 7) 1-(2-(4-(4-(1,5-dimethyl-3-oxo-2-phenyl-2,3-dihydro-1H-pyrazole-4-carboxamido)-2-fluorophenoxy)quinolin-7-yloxy)ethyl)cyclopropyl 2-(tert-butoxycarbonylamino)acetate To a mixture of N-(3-fluoro-4-(7-(2-(1-hydroxycyclopropyl)ethoxy)quinolin-4-yloxy)phenyl)-1,5-dimethyl-3-oxo-2-phenyl-2,3-dihydro-1H-pyrazole-4-carboxamide (218 mg, 0.384 mmol), N-Boc-glycine (133.4 mg, 0.768 mmol, Alfa), and DMAP (7.03 mg, 0.058 mmol, Aladdin) in 10 mL of dichloromethane was added DCC solid (323.4 mg, 1.54 mmol, Aldrich) slowly at 0° C. The reaction was then warmed up to rt and continued to stir at rt overnight. The reaction mixture was filtered and the solid was washed with dichloromethane (10 mL×2). The combined organic phases were washed with 20 mL of saturated $NaNCO_3$ solution followed by 20 mL of brine, dried over $Na_2SO_4$ and concentrated in vacuo. The residue was chromatographed on a silica gel column (PE: EA=1:6) to give the desired compound as a yellow solid (190 mg, 70%).

Step 8) 1-(2-(4-(4-(1,5-dimethyl-3-oxo-2-phenyl-2,3-dihydro-1H-pyrazole-4-carboxamido)-2-fluorophenoxy)quinolin-7-yloxy)ethyl)cyclopropyl 2-aminoacetate hydrochloride To a solution of 1-(2-(4-(4-(1,5-dimethyl-3-oxo-2-phenyl-2,3-dihydro-1H-pyrazole-4-carboxamido)-2-fluorophenoxy)quinolin-7-yloxy)ethyl)cyclopropyl 2-(tert-butoxycarbonylamino)acetate (190 mg, 0.262 mmol) in 8 mL of ethyl acetate was added a solution of HCl in EtOAc (0.93 mol/L, 5 mL) dropwise. The reaction mixture was stirred at rt for 30 minutes and then filtered. The solid was washed with ethyl acetate (20 mL×3) to afford the title compound as a white solid (54 mg, 30.3%).

MS (ESI, pos. ion) m/z: 626.0 (M+1); LC-MS Rt: 3.871 min;

$^1$H NMR (400 MHz, MeOD): δ 0.81-0.85 (t, J=13 Hz, 2H), 0.89-0.92 (t, J=12 Hz, 2H), 2.34 (t, J=6 Hz, 2H), 2.65 (s, 3H), 3.30 (s, 3H), 3.71 (s, 2H), 4.36 (t, J=6 Hz, 2H), 6.88-6.89 (d, J=6 Hz, 1H), 7.28-7.34 (m, 4H), 7.41 (s, 1H), 7.46-7.53 (m, 4H), 7.92-7.95 (d, J=12 Hz, 1H), 8.45-8.47 (d, J=9 Hz, 1H), 8.71-8.73 (d, J=7 Hz, 1H).

Example 71

1-(3-(4-(4-(2,3-dimethyl-5-oxo-1-phenyl-2,5-dihydro-1H-pyrazole-4-carboxamido)-2-fluorophenoxy)quinolin-7-yloxy)propyl)cyclopropyl 2-aminoacetate hydrochloride Step 1) 1-(3-hydroxypropyl)cyclopropanol To a mixture of dihydrofuran-2(3H)-one (2.0 g, 23 mmol) and $Ti(Oi\text{-}Pr)_4$ (1.32 g, 4.6 mmol, Aldrich) in 80 mL of dry THF at 15° C. under $N_2$ was added EtMgBr (60 mmol, 20 mL, 3M ether solution, Aldrich) dropwise via a syringe pump over 3 hrs, and the reaction temperature was always kept below 20° C. After stirring for additional 3 hrs, the reaction mixture was quenched with 60 mL of saturated $NH_4Cl$ aqueous solution, and was extracted with ethyl acetate (50 mL×3). The combined organic phases were dried over $Na_2SO_4$ and concentrated in vacuo. The orange oil residue was purified by a silica gel column chromatography (1:1 (v/v) EtOAc/n-hexane) to give the title compound as yellow oil (2.5 g, 93%).

Step 2) 3-(1-hydroxycyclopropyl)propyl methanesulfonate

A mixture of 1-(3-hydroxypropyl)cyclopropanol (140 mg, 1.2 mmol) and triethylamine (0.3 mL, 2.1 mmol) in 8 mL of dichloromethane was stirred at 0° C. for 10 min. Methanesulfonyl chloride (180 mg, 1.6 mmol) was then added to the mixture via a syringe. After stirring at 0° C. for 1 hr, the mixture was quenched with 2 mL of ice-water and extracted with dichloromethane (10 mL×3). The combined organic phases were dried over $Na_2SO_4$ and concentrated in vacuo to give 3-(1-hydroxycyclo-propyl)propyl methanesulfonate as yellow oil (used for the next step immediately).

Step 3) N-(3-fluoro-4-(7-(3-(1-hydroxycyclopropyl)propoxy)quinolin-4-yloxy)phenyl)-1,5-dimethyl-3-oxo-2-phenyl-2,3-dihydro-1H-pyrazole-4-carboxamide To a mixture of 3-(1-hydroxycyclopropyl)propyl methanesulfonate (240 mg, 1.2 mmol) and N-(3-fluoro-4-(7-hydroxyquinolin-4-yloxy)phenyl)-1,5-dimethyl-3-oxo-2-phenyl-2,3-dihydro-1H-pyrazole-4-carboxamide (300 mg, 0.62 mmol) in 5 mL of N,N-dimethylacetamide was added cesium carbonate (470 mg, 2.4 mmol). After stirring at rt for 12 hrs, then the mixture was warmed up to 40° C. and stirred for 6 hrs. The reaction mixture was diluted with 20 mL of water and extracted with ethyl acetate (40 mL×3). The combined organic phases were dried over $Na_2SO_4$ and concentrated in vacuo. The residue was purified by a silica gel column chromatography (5:1 (v/v) EtOAc/n-hexane) to afford the desired compound as a white solid (68 mg, 19%).

MS (ESI, pos. ion) m/z: 583.1 [M+1]; LC-MS Rt: 4.129 min.

$^1$H NMR (400 MHz, $CDCl_3$): δ 0.51 (m, 2H), 0.79 (m, 2H), 1.81 (t, J=8 Hz, 2H), 2.15 (m, 2H), 2.81 (s, 3H), 3.38 (s, 3H),

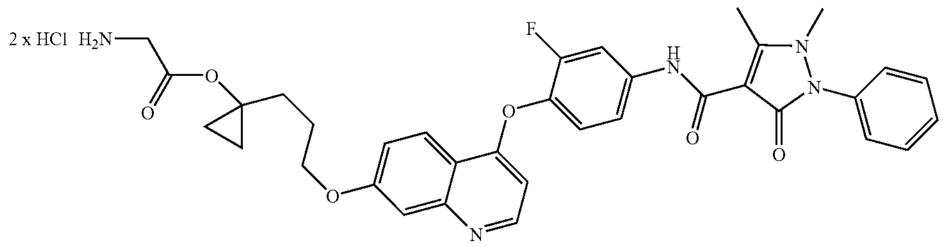

4.24 (t, J=8 Hz, 2H), 6.41 (d, J=4 Hz, 1H), 7.15-7.59 (m, 9), 7.91 (m, 1H), 8.27 (d, J=8 Hz, 1H), 8.58 (d, J=4 Hz, 1H), 10.87 (s, 1H).

Step 4) 1-(3-(4-(4-(2,3-dimethyl-5-oxo-1-phenyl-2,5-dihydro-1H-pyrazole-4-carbox-amido)-2-fluorophenoxy)quinolin-7-yloxy)propyl)cyclopropyl 2-(tert-butoxy-carbonylamino)acetate To a mixture of N-(3-fluoro-4-(7-(3-(1-hydroxycyclopropyl)propoxy)-quinolin-4-yl-oxy)phenyl)-1,5-dimethyl-3-oxo-2-phenyl-2,3-dihydro-1H-pyrazole-4-carboxamide (218 mg, 0.374 mmol), N-Boc-glycine (133.4 mg, 0.768 mmol, Alfa), and DMAP (7.03 mg, 0.058 mmol, Aladdin) in 10 mL of dichloromethane was added DCC solid (323.4 mg, 1.54 mmol, Aldrich) slowly at 0° C. The reaction was then warmed up to rt and continued to stir at rt overnight. The mixture was filtered and the solid was washed with $CH_2Cl_2$ (10 mL×2). The combined organic phases were washed with 15 mL of saturated $NaHCO_3$ solution followed by 15 mL of brine, dried over $Na_2SO_4$ and concentrated in vacuo. The residue was chromatographed on a silica gel column (PE: EtOAc=1:6) to give the desired compound as a yellow solid (160 mg, 60%).

MS (ESI, pos. ion) m/z: 740.2 (M+1); LC-MS Rt: 4.902 min.

Step 5) 1-(3-(4-(4-(2,3-dimethyl-5-oxo-1-phenyl-2,5-dihydro-1H-pyrazole-4-carboxamido)-2-fluorophenoxy)quinolin-7-yloxy)propyl)cyclopropyl 2-aminoacetate hydrochloride To the mixture of 1-(3-(4-(4-(2,3-dimethyl-5-oxo-1-phenyl-2,5-dihydro-1H-pyrazole-4-carboxamido)-2-fluorophenoxy)quinolin-7-yloxy)propyl)cyclopropyl 2-(tert-but-oxy-carbonylamino)acetate (160 mg, 0.216 mmol) in 8 mL of ethyl acetate was added a solution of HCl/EtOAc (0.93 mol/L, 5 mL) dropwise. The reaction mixture was stirred at rt for 30 minutes and then filtered. The solid was washed with ethyl acetate (10 mL×2) to afford the title compound as a white solid (55 mg, 37.9%).

MS (ESI, pos. ion) m/z: 640.1 (M+1); LC-MS Rt: 3.674 min;

$^1$H NMR (400 MHz, MeOD): δ 0.81-0.84 (t, J=8 Hz, 2H), 1.00-1.03 (t, J=8 Hz, 2H), 2.10-2.11 (d, J=2 Hz, 4H), 2.78 (s, 3H), 3.43 (s, 3H), 3.82 (s, 2H), 4.34-4.35 (d, J=2 Hz, 2H), 7.00-7.02 (dd, J=1 Hz, J=6 Hz, 1H), 7.44-7.48 (m, 4H), 7.52 (d, J=2 Hz, 1H), 7.58-7.66 (m, 4H), 8.03-8.07 (dd, J=2 Hz, J=12 Hz, 1H), 8.57-8.59 (d, J=10 Hz, 1H), 8.83-8.85 (d, J=6 Hz, 1H).

Example 72

1-((4-(4-(2,3-dimethyl-5-oxo-1-phenyl-2,5-dihydro-1H-pyrazole-4-carboxamido)-2-fluorophenoxy)quinolin-7-yloxy)methyl)cyclopropyl 2-aminoacetate hydrochloride

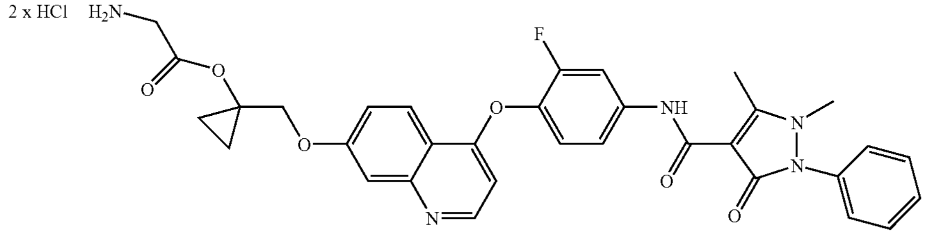

Step 1) ethyl 2-(tetrahydro-2H-pyran-2-yloxy)acetate

To a mixture of ethyl 2-hydroxyacetate (2 g, 20 mmol, Aldrich) and 3,4-dihydro-2H-pyran (3.2 g, 40 mmol, Alfa) in 40 mL of $CH_2Cl_2$ was added PPTS (500 mg, 2 mmol) slowly at rt. The mixture was stirred at rt for 4 hours, and then the mixture was washed with brine (20 mL×2), the combined organic phases were dried over $Na_2SO_4$ and concentrated in vacuo. The residue was purified by a silica gel column chromatography (PE: EtOAc=20:1) to give colorless oil (3.01 g, 81%).

$^1$H NMR (400 MHz, $CDCl_3$): δ 1.22-1.38 (m, 4H), 1.55-1.63 (m, 3H), 1.69-1.88 (m, 3H), 3.50-3.53 (m, 1H), 3.82-3.88 (m, 1H), 4.18-4.23 (m, 4H), 4.73-4.74 (t, J=4 Hz, 1H).

Step 2) 1-((tetrahydro-2H-pyran-2-yloxy)methyl)cyclopropanol

To a mixture of ethyl 2-(tetrahydro-2H-pyran-2-yloxy)acetate (1 g, 5.3 mmol) and $Ti(O\text{-}iPr)_4$ (1.06 mL, 3.5 mmol) in 18 mL THF was added EtMgBr (4.5 mL, 13.25 mmol, Aldrich) dropwise over 2 hrs under $N_2$. The reaction temperature was kept between 15 to 20° C. After stirring for 2 hrs, the reaction was quenched with 15 mL of saturated $NH_4Cl$ solution and extracted with EtOAc (20 mL×5). The combined organic phases were dried over $Na_2SO_4$ and concentrated in vacuo. The residue was purified by a silica gel column chromatography (PE: EtOAc=5:1) to afford the title compound as colorless oil (500 mg, 55%).

$^1$H NMR (400 MHz, $CDCl_3$): $^δ$ 0.55-0.85 (m, 4H), 1.55-1.65 (m, 4H), 1.74-1.87 (m, 2H), 3.50-3.55 (m, 2H), 3.79-3.82 (m, 1H), 3.93-3.98 (m, 2H), 4.64-4.66 (m, 1H).

Step 3) 1-((tetrahydro-2H-pyran-2-yloxy)methyl)cyclopropyl acetate

To a solution of 1-((tetrahydro-2H-pyran-2-yloxy)methyl) cyclopropanol (172 mg, 1 mmol) and acetic acid (120 mg, 2 mmol, Shantou Xilong chemical factory) in 2 mL of DCM was added DMAP (12 mg, 0.1 mmol, aladdin) at rt. After stirring for 30 min, DCC (840 mg, 4 mmol, Aldrich) was added at 0° C. The reaction was quenched with water after all of 1-((tetrahydro-2H-pyran-2-yloxy)methyl)cyclopropanol disappeared (monitored by TLC) (about 4 hours). The solid formed during the reaction was removed by filtration, and the filtrate was concentrated in vacuo. The residue was purified by a silica gel column chromatography (PE: EtOAc=20:1) to give the desired compound as yellow oil (130 mg, 60.7%).

$^1$H NMR (400 MHz, $CDCl_3$): δ 0.46 (m, 2H), 0.75-0.93 (m, 4H), 1.49-1.82 (m, 6H), 2.01 (s, 2H), 3.46-3.49 (t, J=5 Hz, 1H), 3.73-3.76 (d, J=12 Hz, 1H), 3.82 (m, 2H), 3.85-3.88 (d, J=12 Hz, 1H), 4.63-4.65 (t, J=3 Hz, 1H).

Step 4) 1-(hydroxymethyl)cyclopropyl acetate

To a mixture of 1-((tetrahydro-2H-pyran-2-yloxy)methyl) cyclopropyl acetate (149 mg, 0.696 mmol) in 10 mL of methanol was added PPTS (18 mg, 0.07 mmol, Aldrich) in portions. After stirring for 5 hrs at rt, the mixture was quenched with 10 mL of water and extracted with dichloromethane (20 mL×3). The combined organic phases were dried over $Na_2SO_4$ and concentrated in vacuo. The residue was purified by a silica gel column chromatography (PE: EtOAc=10:1) to give the title compound as pale yellow oil (46 mg, 35.5%).

$^1$H NMR (400 MHz, $CDCl_3$): δ 0.61-0.66 (m, 2H), 0.84-0.89 (m, 2H), 4.18 (s, 1H).

Step 5) (1-acetoxycyclopropyl)methyl methanesulfonate

A mixture of 1-(2-hydroxyethyl)cyclopropanol (86 mg, 0.843 mmol) and triethylamine (136 mg, 1.35 mmol) in 10 mL of dichloromethane was stirred at −10° C. for 30 min. Methanesulfonyl chloride (106 mg, 0.927 mmol) was then added via a syringe. After stirring at −10° C. for 1 hr, the reaction was quenched with 1 mL of ice-water and extracted with dichloromethane (20 mL×3). The combined organic phases were dried over sodium sulphate and concentrated in vacuo to afford the title compound as yellow oil (used for the next step immediately).

Step 6) 1-((4-(4-(1,5-dimethyl-3-oxo-2-phenyl-2,3-dihydro-1H-pyrazole-4-carboxamido)-2-fluorophenoxy)quinolin-7-yloxy)methyl)cyclopropyl acetate To a mixture of compound N-(3-fluoro-4-(7-hydroxyquinolin-4-yloxy)phenyl)-1,5-di-methyl-3-oxo-2-phenyl-2,3-dihydro-1H-pyrazole-4-carboxamide (342 mg, 0.708 mmol) and (1-acetoxycyclopropyl)methyl methanesulfonate (1.77 mmol) in 5 mL of DMA was added $Cs_2CO_3$ (2.8 g, 8.85 mmol). After stirring at 40° C. for 1 day, the reaction mixture was concentrated in vacuo and the residue was chromatographed on a silica gel column (50:1 (v/v) $CH_2Cl_2/CH_3OH$) to give the title compound as a white solid (110 mg, 26%).

MS (ESI, pos. ion) m/z: 569.1 (M+1); LC-MS Rt: 4.152 min.

Step 7) N-(3-fluoro-4-(7-((1-hydroxycyclopropyl)methoxy)quinolin-4-yloxy)phenyl)-1,5-dimethyl-3-oxo-2-phenyl-2,3-dihydro-1H-pyrazole-4-carboxamide To a solution of compounds 1-((4-(4-(1,5-dimethyl-3-oxo-2-phenyl-2,3-dihydro-1H-pyrazole-4-carboxamido)-2-fluorophenoxy)quinolin-7-yloxy)methyl)cyclopropyl acetate (110 mg, 0.18 mmol) in 8 mL of methanol was added KOH (100 mg, 1.78 mmol) slowly. After stirring at rt for 0.5 hr, the reaction mixture was filtered and the solid was washed with ethyl acetate (10 mL×2) to give the title compound as a white solid (100 mg, 29%).

MS (ESI, pos. ion) m/z: 555.1 (M+1); LC-MS Rt: 3.765 min.

$^1$H NMR (400 MHz, $CDCl_3$): δ 0.78-0.81 (t, J=5 Hz, 2H), 1.01-1.04 (t, J=5 Hz, 2H), 2.82 (s, 3H), 3.39 (s, 3H), 4.19 (s, 2H), 6.42-6.44 (d, J=5 Hz, 1H), 7.16-7.20 (t, J=8 Hz, 1H), 7.27-7.33 (m, 2H), 7.37-7.39 (d, J=9 Hz, 3H), 7.49-7.52 (t J=8 Hz, 1H), 7.56-7.60 (m, 2H), 7.91-7.95 (dd, J=2 Hz, J=12 Hz, 1H), 8.29-8.31 (d, J=9 Hz, 1H), 8.59-8.60 (d, J=5 Hz, 1H), 10.92 (s, 1H).

Step 8) 1-((4-(4-(1,5-dimethyl-3-oxo-2-phenyl-2,3-dihydro-1H-pyrazole-4-carboxamido)-2-fluorophenoxy)quinolin-7-yloxy)methyl)cyclopropyl 2-(tert-butoxycarbonylamino)acetate To a mixture of N-(3-fluoro-4-(7-((1-hydroxycyclopropyl) methoxy)-quinolin-4-yloxy)phenyl)-1,5-dimethyl-3-oxo-2-phenyl-2,3-dihydro-1H-pyrazole-4-carboxamide (100 mg, 0.18 mmol), N-Boc-glycine (63 mg, 0.36 mmol, Alfa), and DMAP (3 mg, 0.018 mmol, Aladdin) in 10 mL of dichloromethane was added DCC (189 mg, 0.9 mmol, Aldrich) slowly at 0° C. After stirring at rt overnight, the mixture was filtered and washed with dichloromethane (10 mL×2). The combined organic phases were dried over $Na_2SO_4$ and concentrated in vacuo. The residue was chromatographed on a silica gel column (PE: EtOAc=1:6) to give the title compound as a yellow solid (100 mg, 78%).

MS (ESI, pos. ion) m/z: 712.3 (M+1); LC-MS Rt: 4.762 min;

Step 9) 1-((4-(4-(1,5-dimethyl-3-oxo-2-phenyl-2,3-dihydro-1H-pyrazole-4-carboxamido)-2-fluorophenoxy)quinolin-7-yloxy)methyl)cyclopropyl 2-aminoacetate hydrochloride The compound 1-((4-(4-(1,5-dimethyl-3-oxo-2-phenyl-2,3-dihydro-1H-pyrazole-4-carboxamido)-2-fluorophenoxy) quinolin-7-yloxy)methyl)cyclopropyl 2-(tert-butoxycarbonylamino)acetate (80 mg, 0.112 mmol) was dissolved in ethyl acetate (8 mL). 2 mL of HCl in ethyl acetate (0.93 mol/L) was added dropwise and the reaction was stirred at rt for 30 minute. The solid was collected by filtration and washed with ethyl acetate (10 mL×2) to afford the title compound as a white solid (11 mg, 15%).

MS (ESI, pos. ion) m/z: 612.2 (M+1); LC-MS Rt: 3.639 min.

$^1$H NMR (400 MHz, MeOD): δ 1.19-1.23 (m, 4H), 2.77 (s, 3H), 3.43 (s, 3H), 3.43 (s, 3H), 3.88 (s, 2H), 4.63 (s, 2H), 7.01-7.02 (d, J=6 Hz, 1H), 7.42-7.48 (m, 4H), 7.51-7.52 (d,

J=2 Hz, 1H), 7.58-7.65 (m, 4H), 8.03-8.07 (dd, J=2 Hz, J=13 Hz, 1H), 8.57-8.60 (d, J=9 Hz, 1H), 8.85-8.86 (d, J=6 Hz, 1H), 10.96 (s, 1H).

Example 73

(R)-1-(4-(4-(6,7-dimethoxyquinolin-4-yloxy)-3-fluorophenylcarbamoyl)-5-methyl-3-oxo-2-phenyl-2,3-dihydropyrazol-1-yl)propan-2-yl 2-aminoacetate hydrochloride

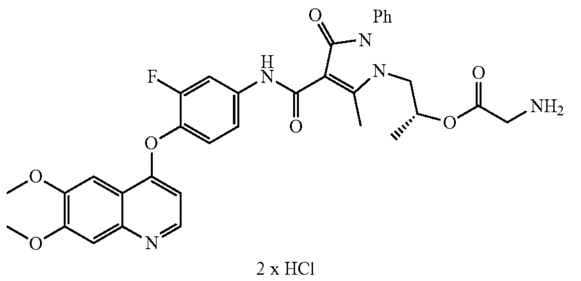

Step 1) 5-((3,4-dimethoxyphenylamino)methylene)-2,2-dimethyl-1,3-dioxane-4,6-dione A mixture of 3,4-dimethoxybenzenamine (10 g, 65 mmol) and $CH(OC_2H_5)_3$ (96.2 g, 650 mmol) in a 500 mL of round-bottom flask was stirred at room temperature for 30 minutes. 2,2-Dimethyl-1,3-dioxane-4,6-dione (9.4 g, 65 mmol) was then added and the reaction mixture was heated at 90° C. for 3.5 h. The reaction solution was cooled at −20° C. overnight. The solid was collected by filtration and washed with 2-methoxy-2-methyl propane (50 mL×3) to afford the title compound as a pale yellow powder (17.1 g, 85.5%).

MS (ESI, pos. ion) m/z: 637.2 (M×2+23); LC-MS Rt: 3.546 min.

$^1$H NMR (400 MHz, d$^6$-DMSO): δ 1.09 (d, J=6.4 Hz, 3H), 2.87 (s, 3H), 3.84 (dd, J=4.4 Hz, J=15.2 Hz, 1H), 3.96 (s, 3H), 4.19 (dd, J=6.8 Hz, J=15.6 Hz, 1H), 4.29 (m, 1H), 6.49 (d, J=5.2 Hz, 1H), 7.28-7.35 (m, 3H), 7.47-7.62 (m, 6H), 7.93 (d, J=13.6 Hz, 1H), 8.29 (d, J=9.2 Hz, 1H), 8.53 (d, J=5.2 Hz, 1H), 11.06 (s, 1H).

Step 2) 6,7-dimethoxyquinolin-4-ol 5-((3,4-Dimethoxyphenylamino)methylene)-2,2-dimethyl-1,3-dioxane-4,6-dione (16.1 g, 52 mmol) was added to a pre-heated 1000 mL round-bottom flask containing 1-phenoxy benzene (100 mL) at 230° C. The reaction was stirred for 5 min, and then cooled to 120° C. n-Hexane (100 mL) was added to the solution to allow the product to precipitate out from the reaction solution. The mixture was further stirred at rt overnight. The solid was collected and crystallized in a solution of EtOAc/n-hexane (50 mL, v/v=10/1) to afford the title compound as a brown solid (10.2 g, 95%).

Step 3) 4-(2-fluoro-4-nitrophenoxy)-6,7-dimethoxyquinoline

A solution of 6,7-dimethoxyquinolin-4-ol (50 g, 0.244 mol) and $Cs_2CO_3$ (159 g, 0.488 mol) in $CH_3CN$ (300 mL)/DMF (300 mL) was stirred at room temperature for 30 min. 1,2-Difluoro-4-nitrobenzene (42.7 g, 0.268 mol) was then added dropwise. After stirring at rt for 3.5 h, the reaction solution was concentrated in vacuo. Ice (500 mL) was added to the residual suspension and the mixture was stirred overnight for precipitation. The solid was collected by filtration and further purified by a silica gel column chromatography (EtOAc) to give the title compound as a pale yellow powder (43.1 g, 51.2%).

MS (ESI, pos. ion) m/z: 345.1 (M+1); LC-MS Rt: 3.394 min.

$^1$H NMR (400 MHz, $CDCl_3$): δ 4.04 (s, 3H), 4.07 (s, 3H), 6.56 (d, J=5.2 Hz, 1H), 7.35 (t, 1H), 7.45 (d, J=8.0 Hz, 1H), 8.14 (d, J=9.2 Hz, 1H), 8.20 (dd, J=2.4 Hz, J=9.6 Hz, 1H), 8.59 (d, J=4.8 Hz, 1H).

Step 4) 4-(6,7-dimethoxyquinolin-4-yloxy)-3-fluorobenzenamine

To a solution of 4-(2-fluoro-4-nitrophenoxy)-6,7-dimethoxyquinoline (16.0 g, 0.046 mol) and $NH_4Cl$ (6.0 g, 0.11 mol) in EtOH/$H_2O$ (150 mL, v/v=4:1) was added iron powder (12.4 g, 0.22 mol) at rt. The reaction mixture was heated to reflux for 2 h, then cooled down to rt. Celite (10 g) was then added and stirring for 30 min. The mixture was filtered and the solid was washed with MeOH (20 mL×3) and DCM (20 mL×3). The filtrate was washed with 30 mL of saturated $NaHCO_3$ aqueous. The aqueous phase was extracted with DCM (20 mL×3). The combined organic phases were washed with brine (20 mL×3), dried over $Na_2SO_4$, and concentrated in vacuo to give a yellow solid (0.9 g, 98%).

MS (ESI, pos. ion) m/z: 315.1 (M+1); LC-MS Rt: 2.919 min.

$^1$H NMR (400 MHz, $CDCl_3$): δ 4.05 (s, 3H), 4.07 (s, 3H), 6.41 (d, J=5.2 Hz, 1H), 6.51 (dd, J=2.4 Hz, J=8.8 Hz, 1H), 6.57 (dd, J=2.4 Hz, J=11.6 Hz, 1H), 7.04 (t, 1H), 7.42 (s, 1H), 7.60 (s, 1H), 8.48 (d, J=5.2 Hz, 1H).

Step 5) (R)—N-(4-(6,7-dimethoxyquinolin-4-yloxy)-3-fluorophenyl)-1-(2-hydroxypropyl)-5-methyl-3-oxo-2-phenyl-2,3-dihydro-1H-pyrazole-4-carboxamide To a solution of 4-(6,7-dimethoxyquinolin-4-yloxy)-3-fluorobenzenamine (5.0 g, 0.016 mol) and (R)-1-(2-hydroxypropyl)-5-methyl-3-oxo-2-phenyl-2,3-dihydro-1H-pyrazole-4-carboxylic acid (6.2 g, 0.022 mol) in $CH_2Cl_2$ (100 mL) at 0° C. was added TEA (5.5 g, 0.054 mol), followed by HATU (10.3 g, 0.027 mol) in portions. The reaction mixture was stirred at 0° C. for 2 h, warmed up to rt and continued to stir overnight. The reaction mixture was washed with water (30 mL×3). The organic phase was dried over $Na_2SO_4$ and concentrated in vacuo. The residue was crystallized in a mixture of EtOAc/n-hexane (50 mL, v/v=5:1) to give the title compound as a pale yellow solid (7.8 g, 85.2%).

MS (ESI, pos. ion) m/z: 573.3 (M+1); LC-MS Rt: 3.753 min;

$^1$H NMR (400 MHz, $CDCl_3$): δ 1.21 (d, J=5.4 Hz, 3H), 2.88 (s, 3H), 3.75 (d, J=3.2 Hz, 1H), 3.85 (m, 1H), 4.05 (s, 3H), 4.07 (s, 3H), 4.11 (t, 1H), 6.58 (d, J=5.6 Hz, 1H), 7.19 (t, 1H), 7.34 (m, 2H), 7.44 (m, 2H), 7.54 (m, 3H), 7.60 (s, 1H), 7.95 (dd, J=2.0 Hz, J=12.4 Hz, 1H), 8.49 (d, J=6.0 Hz, 1H), 10.91 (s, 1H).

Step 6) (R)-1-(4-(4-(6,7-dimethoxyquinolin-4-yloxy)-3-fluorophenylcarbamoyl)-5-methyl-3-oxo-2-phenyl-2,3-dihydropyrazol-1-yl)propan-2-yl-2-(tert-butoxycarbonylamino)acetate To a solution of (R)—N-(4-(6,7-dimethoxyquinolin-4-yloxy)-3-fluorophenyl)-1-(2-hydroxypropyl)-5-methyl-3-oxo-2-phenyl-2,3-dihydro-1H-pyrazole-4-carboxamide (2.0 g, 3.5 mmol), N-Boc-glycine (1.23 g, 7.0 mmol) and DMAP (0.86 g, 7.0 mmol) in $CH_2Cl_2$ (45 mL) at 0° C. was added EDC solid (2.02 g, 10.5 mmol) in portions. The reaction mixture was stirred at 0° C. for 2 h, then warmed up to rt and continued to stir overnight. The reaction mixture was diluted with $CH_2Cl_2$ (50 mL), and washed with 0.5 N HCl aqueous (20 mL), saturated $NaHCO_3$ (20 mL), and followed by brine (20 mL). The organic phase was dried over $Na_2SO_4$ and concentrated in vacuo. The residue was purified by a silica gel column chromatography (n-hexane/ethyl acetate at the ratio of 1:1 to 1:8) to give the title compound as a white powder (2.43 g, 95.2%).

MS (ESI, pos. ion) m/z: 730.3 (M+1); LC-MS Rt: 4.534 min;

$^1$H NMR (400 MHz, $CDCl_3$): δ 1.14 (d, J=6.4 Hz, 3H), 1.434 (s, 9H), 2.86 (s, 3H), 3.69 (dd, J=5.2 Hz, J=17.6 Hz, 1H), 3.84 (m, 2H), 4.02 (d, J=9.6 Hz, 1H), 4.05 (s, 3H), 4.07 (s, 3H), 4.11 (t, 1H), 5.02 (s, 1H), 6.43 (d, J=5.2 Hz, 1H), 7.18 (t, 1H), 7.30 (d, J=8.4 Hz, 1H), 7.38 (d, J=7.6 Hz, 2H), 7.42 (s, 1H), 7.49 (t, 1H), 7.58 (m, 3H), 7.92 (d, J=12.4 Hz, 1H), 8.49 (d, J=4.8 Hz, 1H), 10.82 (s, 1H).

Step 7) (R)-1-(4-(4-(6,7-dimethoxyquinolin-4-yloxy)-3-fluorophenylcarbamoyl)-5-methyl-3-oxo-2-phenyl-2,3-dihydropyrazol-1-yl)propan-2-yl 2-aminoacetate hydro-chloride To a solution of (R)-1-(4-(4-(6,7-dimethoxyquinolin-4-yloxy)-3-fluorophenylcarbamoyl)-5-methyl-3-oxo-2-phenyl-2,3-dihydropyrazol-1-yl)propan-2-yl-2-(tert-butoxycarbonyl amino)acetate (100 mg, 0.137 mmol) in EtOAc (15 mL) was added 3 mL of saturated HCl in EtOAc (3 mL). The reaction mixture was stirred at rt overnight. The solid formed was collected and was crystallized in MeOH/EtOAc (20 mL, v/v=1:5). The product was further washed with EtOAc (5 mL×3) and dried under vacuum overnight to afford the title compound as a white solid (88 mg, 83%).

MS (ESI, pos. ion) m/z: 630.3 (M+1); LC-MS Rt: 3.323 min;

$^1$H NMR (400 MHz, $CDCl_3$): δ 1.09 (d, J=6.4 Hz, 3H), 2.78 (s, 3H), 3.55 (dd, J=3.6 Hz, J=9.6 Hz, 1H), 3.82 (m, 2H), 3.97 (d, J=2.4 Hz, 1H), 4.04 (s, 3H), 4.05 (s, 3H), 4.35 (m, 1H), 4.89 (s, 1H), 6.98 (d, J=6.4 Hz, 1H), 7.44 (dd, J=1.2 Hz, J=7.2 Hz, 3H), 7.56 (t, 2H), 7.62 (m, 2H), 7.73 (s, 1H), 7.76 (s, 1H), 8.07 (dd, J=2.4 Hz, J=12.8 Hz, 1H), 8.63 (d, J=6.8 Hz, 1H), 10.95 (s, 1H).

Example 74

(S)—((R)-1-(4-(4-(6,7-dimethoxyquinolin-4-yloxy)-3-fluorophenylcarbamoyl)-5-methyl-3-oxo-2-phenyl-2,3-dihydropyrazol-1-yl)propan-2-yl)2-aminopropanoate hydrochloride

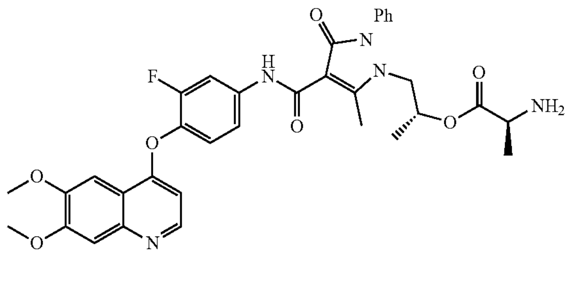

2 x HCl

Step 1) (S)—((R)-1-(4-(4-(6,7-dimethoxyquinolin-4-yloxy)-3-fluorophenylcarbamoyl)-5-methyl-3-oxo-2-phenyl-2,3-dihydropyrazol-1-yl)propan-2-yl)2-(benzyloxy-carbonylamino)propanoate The title compound was prepared according to the procedure described in Example of 73 Step 6 by using (R)—N-(4-(6,7-dimethoxyquinolin-4-yloxy)-3-fluorophenyl)-1-(2-hydroxypropyl)-5-methyl-3-oxo-2-phenyl-2,3-dihydro-1H-pyrazole-4-carboxamide (4.1 g, 7.2 mmol), (S)—N-Cbz-alanine (3.2 g, 14.4 mmol). The title compound was obtained as a white powder (4.2 g, 75.1%).

$^1$H NMR (400 MHz, $d^6$-DMSO): δ 1.14 (d, J=6.4 Hz, 3H), 1.39 (d, J=6.6 Hz, 3H), 2.86 (s, 3H), 3.84 (dd, J=5.2 Hz, J=17.6 Hz, 1H), 4.03 (s, 3H), 4.05 (s, 3H), 4.07 (d, J=9.6 Hz, 1H), 4.11 (t, 1H), 4.97 (s, 1H), 5.06 (s, 2H), 5.22 (d, J=7.2 Hz, 1H), 6.40 (dd, J=0.8 Hz, J=6.0 Hz, 1H), 7.16 (t, 1H), 7.22 (dd, J=2.8 Hz, J=12 Hz, 1H), 7.27 (t, 2H), 7.35 (m, 5H), 7.41 (m, 1H), 7.47 (m, 1H), 7.55 (m, 2H), 7.90 (dd, J=2.0 Hz, J=14.4 Hz, 1H), 8.28 (d, J=9.2 Hz, 1H), 8.66 (d, J=5.2 Hz, 1H), 10.81 (s, 1H).

Step 2) (S)—((R)-1-(4-(4-(6,7-dimethoxyquinolin-4-yloxy)-3-fluorophenylcarbamoyl)-5-methyl-3-oxo-2-phenyl-2,3-dihydropyrazol-1-yl)propan-2-yl)2-aminopropanoate To a solution of (S)—((R)-1-(4-(4-(6,7-dimethoxyquinolin-4-yloxy)-3-fluorophenyl-carbamoyl)-5-methyl-3-oxo-2-phenyl-2,3-dihydropyrazol-1-yl)propan-2-yl)2-(benzyloxy-carbonylamino)propanoate (200 mg, 0.257 mmol) in a mixture of EtOAc (15 mL) and MeOH (10 mL) was added catalytic amount of Pd/C (10%, ~55% w/w water content, 20 mg) under $N_2$ atmosphere. The suspension was degassed under vacuum and then purged with $H_2$. The reaction mixture was stirred at rt for 20 minutes under $H_2$ balloon. The mixture was filtered and the residue was washed with MeOH (5 mL×3). The filtrate used for the next step immediately.

Step 3) (S)—((R)-1-(4-(4-(6,7-dimethoxyquinolin-4-yloxy)-3-fluorophenylcarbamoyl)-5-methyl-3-oxo-2-phenyl-2,3-dihydropyrazol-1-yl)propan-2-yl)2-aminopropanoate hydrochloride The title compound was prepared according to the procedure described in Example 1 Step 3 by using (S)—((R)-1-(4-(4-(6,7-dimethoxyquinolin-4-yloxy)-3-fluorophenyl-carbamoyl)-5-methyl-3-oxo-2-phenyl-2,3-dihydropyrazol-1-yl)propan-2-yl)2-aminopropanoate (165.3 mg, 0.257 mmol) and a saturated HCl solution in EtOAc (5 mL). The title compound was obtained as a pale yellow solid (160 mg, 87%).

$^1$H NMR (400 MHz, d$^6$-DMSO): δ 1.11 (d, J=5.2 Hz, 3H), 1.35 (d, J=6.4 Hz, 3H), 2.84 (s, 3H), 3.82 (dd, J=6.4 Hz, J=14.4 Hz, 1H), 4.01 (s, 3H), 4.03 (s, 3H), 4.07 (d, J=8.8 Hz, 1H), 4.10 (t, 1H), 5.01 (s, 1H), 5.22 (d, J=3.6 Hz, 1H), 6.40 (dd, J=0.8 Hz, J=6.0 Hz, 1H), 7.16 (t, 1H), 7.22 (dd, J=2.8 Hz, J=12 Hz, 1H), 7.27 (t, 2H), 7.41 (m, 1H), 7.47 (m, 1H), 7.55 (m, 2H), 7.90 (dd, J=2.0 Hz, J=14.4 Hz, 1H), 8.28 (d, J=9.2 Hz, 1H), 8.66 (d, J=5.2 Hz, 1H), 10.85 (s, 1H).

Example 75

(R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-aminoacetate hydrochloride

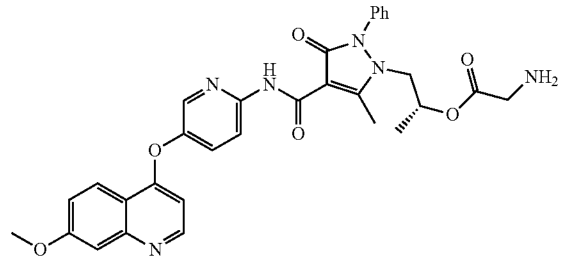

2 x HCl

Step 1) (R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl2-(tert-butoxycarbonylamino)-Acetate The title compound was prepared according to the procedure described in Example of 73 Step 6 by using (R)-1-(2-hydroxypropyl)-N-(6-(7-methoxyquinolin-4-yloxy)pyridin-3-yl)-5-methyl-3-oxo-2-phenyl-2,3-dihydro-1H-pyrazole-4-carboxamide (4.2 g, 7.9 mmol), N-Boc-glycine (2.77 g, 15.8 mmol, Shanghai Hanhong Chemical CO., LTD.). The title compound was obtained as a pale yellow solid (4.32 g, 80.2%).

$^1$H NMR (400 MHz, $CDCl_3$): δ 1.14 (d, J=6.4 Hz, 3H), 1.43 (s, 9H), 3.85 (s, 3H), 3.67 (dd, J=4.8 Hz, J=18.4 Hz, 1H), 3.81 (dd, J=4.0 Hz, J=15.6 Hz, 1H), 3.89 (dd, J=6.8 Hz, J=18.8 Hz, 1H), 3.98 (s, 3H), 4.04 (dd, J=8.8 Hz, J=24.4 Hz, 1H), 5.01 (m, 1H), 6.43 (d, J=5.2 Hz, 1H), 7.23 (dd, J=2.4 Hz, J=8.8 Hz, 1H), 7.37 (dd, J=1.2 Hz, J=7.2 Hz, 2H), 7.42-7.48 (t, 2H), 7.49-7.58 (t, 3H), 8.24 (dd, J=2.4 Hz, J=5.2 Hz, 2H), 8.37 (d, J=8.8 Hz, 1H), 8.60 (d, J=5.2 Hz, 1H), 11.19 (s, 1H).

Step 2) (R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl 2-aminoacetate hydrochloride The title compound was prepared according to the procedure described in Example 1 Step 3 by using (R)-1-(4-(5-(7-methoxyquinolin-4-yloxy)pyridin-2-ylcarbamoyl)-5-methyl-3-oxo-2-phenyl-2,3-dihydropyrazol-1-yl)propan-2-yl2-(tert-butoxycarbonyl amino)acetate (100 mg, 0.146 mmol) and a saturated HCl solution in EtOAc (3 mL). The title compound was crystallized in MeOH/EtOAc (20 mL, v/v=1:5) to afford the title compound as a white solid (84.2 mg, 76%).

$^1$H NMR (400 MHz, d$^6$-DMSO): δ 1.09 (d, J=6.0 Hz, 3H), 2.80 (s, 3H), 3.79 (dd, J=5.2 Hz, J=17.6 Hz, 1H), 4.00 (s, 2H), 4.04 (s, 3H), 4.30 (dd, J=9.2 Hz, J=16.4 Hz, 1H), 4.89 (s, 1H), 7.01 (d, J=6.8 Hz, 1H), 7.44 (d, J=7.6 Hz, 2H), 7.55 (t, 2H), 7.63 (t, 3H), 7.74 (s, 1H), 7.97 (d, J=8.4 Hz, 1H), 8.43-8.52 (m, 2H), 8.99 (d, J=6.4 Hz, 1H), 11.28 (s, 1H).

Example 76

1-(N-(4-(7-(3-(7-hydroxy-5-azaspiro[2.4]heptane-5-yl)propoxy)-6-methoxyquinolin-4-yloxy)-3-fluorophenyl)-N-(4-fluorophenyl)cyclopropane-1,1-dicarboxamide)-2-aminoacetate hydrochloride

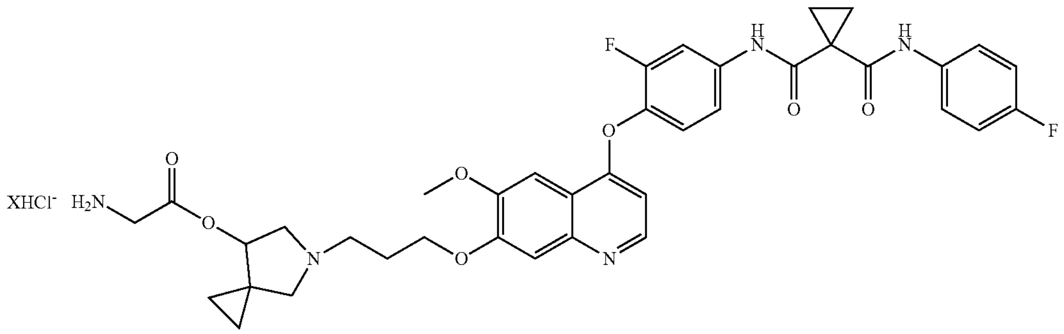

Step 1) ethyl 1-acetylcyclopropanecarboxylate

To a solution of ethyl 3-oxobutanoate (26 g, 200 mmol) in acetone (500 mL) was added potassium carbonate (82.8 g, 600 mmol) followed by 1,2-dibromoethane (45.12 g, 240 mmol). The reaction was refluxed for 24 hrs, the reaction mixture was then filtered. The filtrate was concentrated in vacuo, and the residue was purified by a silica gel column chromatography (1:50(v/v) EtOAc/n-hexane) to afford the title compound as colorless oil (18.7 g, 60%).

MS (ESI, pos. ion) m/z: 157 (M+1);

$^1$H NMR (400 MHz, $CDCl_3$): δ 1.25-1.29 (t, J=7.2 Hz, 3H), 1.45 (s, 4H), 2.45 (s, 3H), 4.18-4.20 (q, 2H).

Step 2) ethyl 1-(2-bromoacetyl)cyclopropanecarboxylate

To a 100 mL of round-bottomed flask was added ethyl 1-acetylcyclo-propanecarboxylate (15.6 g, 100 mmol) and NBS solid (21.36 g, 120 mmol), followed by p-toluene sulfonic acid (1.9 g, 10 mmol). After stirring at rt for 8 hrs, the reaction mixture was extracted with diethyl ether (200 mL) and washed with 80 mL of water. The organic phase was then dried over anhydrous $Na_2SO_4$ and concentrated in vacuo. The residue was purified by a silica gel column chromatography (1:30(v/v)EtOAc/n-hexane) to give the title compound as colorless oil (16.68 g, 71%).

MS (ESI, pos. ion) m/z: 235, 237 (M+1);

$^1$H NMR (400 MHz, $CDCl_3$): δ 1.27 (t, J=7.2 Hz, 3H), 1.59-1.64 (m, 4H), 4.19-4.24 (q, $J_1$=14.4 Hz, $J_2$=7.2 Hz, 2H), 4.49 (s, 2H).

Step 3) 5-((R)-α-methylbenzyl)-4,7-dioxo-5-aza-spiro[2.4]heptane

To a solution of ethyl 1-(2-bromoacetyl)cyclopropanecarboxylate (4.7 g, 20 mmol) in THF (60 mL) was added (R)-α-methylbenzylamine (2.9 g, 24 mmol) and $Et_3N$ (4.04 g, 40 mmol). After stirring at rt for 3 days, the reaction mixture was concentrated in vacuo, and the residue was extracted with EtOAc (50 mL×2) and washed with water (30 mL). The combined organic phases were dried over anhydrous $Na_2SO_4$, filtered and the filtrate was concentrated in vacuo. The residue was purified by a silica gel column chromatography (EtOAc) to afford the title compound as a yellow solid (3.66 g, 80%).

MS (ESI, pos. ion) m/z: 230 (M+1);

$^1$H NMR (400 MHz, $CDCl_3$): δ 1.58-1.60 (m, 4H), 1.62-1.63 (d, J=5.6 Hz, 3H), 3.49-3.53 (d, J=17.6 Hz, 1H), 3.83-3.88 (d, J=17.6 Hz, 1H), 5.80-5.82 (q, 1H), 7.26-7.39 (m, 5H).

Step 4) 5-((R)-α-methylbenzyl)-7-hydroxy-5-aza-spiro[2.4]heptane

To a suspension of $LiAlH_4$ (0.995 g, 26.2 mmol) in THF (40 mL) was added a solution of 5-((R)-α-methylbenzyl)-4,7-dioxo-5-azaspiro[2.4]heptane (3.0 g, 13.1 mmol) in THF (10 mL) at 0° C. The reaction mixture was stirred at 0° C. for 2 hrs, then warmed up to 50° C. and continued to stir for 6 hrs. The reaction mixture was then cooled to 0° C. and EtOAc (10 mL) and $H_2O$ (10 mL) were added. The suspension was filtered and the filtrate was concentrated in vacuo. The residue was purified by a silica gel column chromatography (1:3 (v/v) 2-butanol/n-hexane) to afford the title compound as colorless oil (2.4 g, 85%).

MS (ESI, pos. ion) m/z: 218 (M+1).

Step 5) 7-hydroxy-5-azaspiro[2.4]heptane

To a solution of 5-((R)-α-methylbenzyl)-7-hydroxy-5-azaspiro[2.4]heptane (2.4 g, 11.1 mmol) in ethanol (30 mL) was added the catalytic amount of Pd/C. The suspension was then stirred under $H_2$ for 3 hrs. The suspension was filtered and the filtrate was concentrated in vacuo to afford the desired compound as light orange oil (1.23 g, 98%). The crude product was used for the next step without further purification.

MS (ESI, pos. ion) m/z: 114 (M+1).

Step 6) t-Butyl 4-(7-(benzyloxy)-6-methoxyquinolin-4-yloxy)-3-fluorophenylcarbamate To a suspension of NaH (184 mg, 7.68 mmol) in THF (20 mL) was added 4-(7-(benzyloxy)-6-methoxyquinolin-4-yloxy)-3-fluorobenzenamine (1 g, 2.56 mmol). After stirring at rt for 10 min, $(Boc)_2O$ (1.14 mg, 5.12 mol) was added to the suspension. The reaction was continued to stir at rt for 36 h. The reaction was quenched with water (2 mL). The solvent was removed in vacuo, and the residue was partitioned between $CH_2Cl_2$ (20 mL) and water (10 mL). The organic layer was separated, dried over $Na_2SO_4$ and concentrated in vacuo. The residue was purified by a silica gel column chromatography (EtOAC:Hexane=1:5) to afford the title compound as light yellow foam (800 mg, 64%).

MS (ESI, pos. ion) m/z: 491.2 (M+1); LC-MS Rt: 3.475 min;

$^1$H-NMR (400 MHz, $CDCl_3$): δ 1.541 (s, 9H), 4.066 (s, 3H), 5.330 (s, 2H), 6.370-6.383 (d, J=5.2 Hz, 1H), 7.076-7.097 (d, J=8.4 Hz, 1H), 7.148-7.191 (t, J=8.4 Hz, 1H), 7.270 (s, 1H), 7.323-7.359 (t, J=7.2 Hz, 1H), 7.375-7.412 (t, J=7.2 Hz, 1H), 7.455 (s, 1H), 7.508-7.527 (d, J=7.6 Hz, 2H), 7.549-7.582 (d, J=13.2 Hz, 1H), 7.601 (s, 1H), 8.448-8.461 (d, J=5.2 Hz, 1H).

Step 7) tert-Butyl 3-fluoro-4-(7-hydroxy-6-methoxyquinolin-4-yloxy)phenylcarbamate To a solution of tert-butyl 4-(7-(benzyloxy)-6-methoxyquinolin-4-yloxy)-3-fluorophenylcarbamate (800 mg, 1.632 mmol) in ethanol (50 mL) was added a catalytic amount of Pd/C. The suspension was stirred at rt under $H_2$ for 3 h. The reaction mixture was filtered, and the filtrate was concentrated in vacuo to give the title compound as a light green solid (650 mg, 99%).

MS (ESI, pos. ion) m/z: 401.2 (M+1); LC-MS Rt: 3.097 min;

$^1$H-NMR (400 MHz, d-DMSO): δ1.499 (s, 9H), 3.954 (s, 3H), 6.328-6.341 (d, J=5.2 Hz, 1H), 7.285 (s, 1H), 7.321-7.334 (d, J=5.2 Hz, 1H), 7.348-7.391 (t, J=8.4 Hz, 1H), 7.506 (s, 1H), 7.631-7.665 (d, J=13.6 Hz, 1H), 8.391-8.404 (d, J=5.2 Hz, 1H), 9.763 (s, 1H), 10.175 (s, 1H).

Step 8) tert-Butyl 3-fluoro-4-(7-(3-hydroxypropoxy)-6-methoxyquinolin-4-yloxy)phenylcarbamate To a solution of tert-butyl 3-fluoro-4-(7-hydroxy-6-methoxyquinolin-4-yloxy)phenylcarbamate (400 mg, 1 mmol) in DMF (4 mL) was added $K_2CO_3$ (276 mg, 2 mmol) and 3-bromopropan-1-ol (154 mg, 1.1 mmol). The reaction was stirred at rt overnight. The solvent was removed, and the residue was partitioned between water (10 mL) and $CH_2Cl_2$ (20 mL). The organic layer was separated, dried over $Na_2SO_4$ and concentrated in vacuo. The residue was purified by a silica gel column chromatography (EtOAC to 10% methanol in EtOAC) to give the title compound as a light yellow solid (300 mg, 65%).

MS (ESI, pos. ion) m/z: 459.2 (M+1); LC-MS Rt: 3.021 min;

$^1$H-NMR (400 MHz, $CDCl_3$): δ 1.531 (s, 9H), 2.159-2.215 (m, 2H), 3.925-3.953 (t, J=5.6 Hz, $J_2$=5.2 Hz, 2H), 3.999 (s, 3H), 4.360-4.389 (t, $J_1$=5.6 Hz, $J_2$=6.0 Hz, 2H), 6.363-6.377 (d, J=5.6 Hz, 1H), 6.961 (s, 1H), 7.066-7.080 (d, J=5.6 Hz, 1H), 7.144-7.187 (t, J=4.8 Hz, 1H), 7.395 (s, 1H), 7.528 (s, 1H), 7.555-7.586 (d, J=12.4 Hz, 1H), 8.438-8.451 (d, J=5.2 Hz, 1H).

Step 9) 3-(4-(4-(tert-Butoxycarbonyl)-2-fluorophenoxy)-6-methoxyquinolin-7-yloxy)propyl methanesulfonate To a solution of tert-butyl 3-fluoro-4-(7-(3-hydroxypropoxy)-6-methoxyquinolin-4-yloxy)phenylcarbamate and $Et_3N$ in $CH_2Cl_2$ was added dropwise a solution of MsCl in $CH_2Cl_2$ at 0° C. The reaction was then stirred at 0° C. for 1 h. The solution was washed with water, and the organic layer was dried over $Na_2SO_4$ and concentrated in vacuo to give the title compound as light yellow oil (351 mg). The compound was used in the next step without further purification.

MS (ESI, pos. ion) m/z: 537.2 (M+1); LC-MS Rt: 3.285 min;

Step 10) tert-Butyl 3-fluoro-4-(7-N-(4-(7-(3-(7-hydroxy-5-azaspiro[2.4]heptane-5-yl)propoxy)-6-methoxyquinolin-4-yloxy))phenylcarbamate To a solution of 3-(4-(4-(tert-butoxycarbonyl)-2-fluorophenoxy)-6-methoxyquinolin-7-yloxy)propyl methanesulfonate (351 mg, 0.655 mmol) in DMA (4 mL) was added 7-hydroxy-5-azaspiro[2.4]heptane (110 mg, 0.982 mmol) and $Cs_2CO_3$ (975 mg, 3 mmol). The reaction was heated at 40° C. for 24 h. The solvent was then removed in vacuo, and the residue was partitioned between $CHCl_3$ (30 mL) and water (15 mL). The organic layer was separated, dried over $Na_2SO_4$ and concentrated in vacuo. The residue was purification by a silica gel column chromatography (EtOAC to 20% methanol in EtOAC) to give the title compound as a light yellow solid (180 mg, 50%).

MS (ESI, pos. ion) m/z: 554.3 (M+1); LC-MS Rt: 2.782 min;

$^1$H-NMR (400 MHz, $CDCl_3$): δ 0.661-0.748 (m, 2H), 0.781-0.830 (m, 1H), 1.040-1.089 (m, 1H), 1.542 (s, 9H), 2.267-2.300 (m, 2H), 2.726-2.751 (d, J=10 Hz, 1H), 3.023-3.063 (m, 2H), 3.075-3.131 (dd, $J_1$=14.8 Hz, $J_2$=7.6 Hz, 1H), 3.282-3.298 (d, J=6.4 Hz, 1H), 3.306-3.323 (d, J=6.8 Hz, 1H), 3.852-3.863 (d, J=4.4 Hz, 1H), 4.028 (s, 3H), 4.282-4.348 (m, 2H), 6.374-6.388 (d, J=5.6 Hz, 1H), 6.948 (s, 1H), 7.096-7.118 (d, J=8.8 Hz, 1H), 7.152-7.192 (t, J=8.4 Hz, 1H), 7.534 (s, 1H), 7.565-7.601 (d, J=14.4 Hz, 2H), 8.437-8.450 (d, J=5.2 Hz, 1H).

Step 11) 3-Fluoro-4-(7-N-(4-(7-(3-(7-hydroxy-5-azaspiro[2.4]heptane-5-yl)propoxy)-6-methoxyquinolin-4-yloxy))benzenamine To a suspension of tert-butyl 3-fluoro-4-(7-N-(4-(7-(3-(7-hydroxy-5-azaspiro[2.4]heptane-5-yl)propoxy)-6-methoxyquinolin-4-yloxy))phenylcarbamate (100 mg, 0.18 mmol) in EtOAc (1 mL) was added HCl/EtOAc (3 mol/L, 1 mL). The suspension was then stirred at rt for 3 h. The solution was concentrated in vacuo to give the title compound as a white solid (110 mg, 100% (as HCl salt)).

MS (ESI, pos. ion) m/z: 454.2 (M+1); LC-MS Rt: 2.341 min;

Step 12) N-(4-(7-(3-(7-hydroxy-5-azaspiro[2.4]heptane-5-yl)propoxy)-6-methoxyquinolin-4-yloxy)-3-fluorophenyl)-N-(4-fluorophenyl)cyclopropane-1,1-dicarboxamide To a solution of 3-Fluoro-4-(7-N-(4-(7-(3-(7-hydroxy-5-azaspiro[2.4]heptane-5-yl)propoxy)-6-methoxyquinolin-4-yloxy))benzenamine (52 mg, 0.115 mmol) and 1-(4-fluorophenylcarbamoyl)cyclopropanecarboxylic acid (27 mg, 0.12 mmol) in DCM (2 mL) was added HOAt (3.2 mg, 0.023 mmol) and HATU (33 mg, 0.17 mmol) at rt. The reaction was stirred at rt for 2 hours. The reaction was then heated to 30° C. and continued to stir for 2 hours. The mixture was washed with $H_2O$ (25 mL), and the organic layer was dried over anhydrous $Na_2SO_4$ and concentrated in vacuo. The residue was purified by a silica gel column chromatography to afford the title compound as a yellow solid (38 mg, 50%).

MS (ESI, pos. ion) m/z: 659 (M+1);

$^1$H NMR (400 MHz, $CDCl_3$): δ 0.58-0.66 (m, 2H), 0.74-0.78 (m, 1H), 0.95-1.00 (m, 1H), 1.62-1.65 (q, $J_1$=7.6 Hz, $J_2$=8.4 Hz, $J_3$=4.4 Hz, $J_4$=5.2 Hz, 2H), 1.79-1.82 (q, $J_1$=7.2 Hz, $J_2$=8.4 Hz, $J_3$=4.4 Hz, $J_4$=5.6 Hz, 2H), 2.05-2.16 (m, 2H), 2.39-2.42 (d, J=8.8 Hz, 1H), 2.68-2.77 (m, 2H), 2.80-2.83 (dd, $J_1$=$J_2$=10 Hz, $J_3$=$J_4$=4.8 Hz, 1H), 2.96-2.98 (d, J=8.8 Hz, 1H), 3.03-3.05 (d, J=10 Hz, 1H), 3.74-3.75 (d, J=3.6 Hz, 1H), 4.04 (s, 3H), 4.30-4.31 (m, 2H), 6.38-6.39 (d, J=5.6 Hz, 1H), 7.05-7.08 (d, J=6.4 Hz, 2H), 7.19-7.23 (t, $J_1$=$J_2$=8.4 Hz, 1H), 7.27-7.29 (d, J=9.6 Hz, 1H), 7.41-7.47 (q, $J_1$=$J_2$=6.8 Hz, $J_3$=$J_4$=4.8 Hz, 1H), 7.56 (s, 1H), 7.69 (s, 1H), 7.75-7.78 (dd, $J_1$=$J_2$=12 Hz, $J_3$=$J_4$=2.4 Hz, 1H), 8.38 (s, 1H), 8.44-8.46 (d, J=5.6 Hz, 1H).

Step 13) 1-(N-(4-(7-(3-(7-hydroxy-5-azaspiro[2.4]heptane-5-yl)propoxy)-6-methoxyquinolin-4-yloxy)-3-fluorophenyl)-N-(4-fluorophenyl)cyclopropane-1,1-dicarboxamide)-2-(tert-butoxycarbonylamino) acetate To a solution of N-(4-(7-(3-(7-hydroxy-5-azaspiro[2.4]heptane-5-yl)propoxy)-6-methoxyquinolin-4-yloxy)-3-fluorophenyl)-N-(4-fluorophenyl)cyclopropane-1,1-dicarboxamide (100 mg, 0.152 mmol), Boc-Glycine (40 mg, 0.228 mmo, Shanghai Haiqu Chemical Ltd) and DMAP (10 mg, 0.076 mmol, Shanghai Haiqu Chemical Ltd) in dried DCM (2 mL) was added EDCI (43.6 mg, 0.228 mmol, Haiqu Chemical Ltd). The reaction was then stirred at rt for 2 h. The solution was diluted with $CH_2Cl_2$ (15 mL) and washed with water (10 mL). The organic layer was dried and concentrated. The residual was purified by silica column to afford the title compound as a white solid (50 mg, 40%).

MS (ESI, pos. ion) m/z: 816.4 (M+1); LC-MS Rt: 3.334 min;

$^1$H NMR (400 MHz, $CDCl_3$): δ 0.68 (m, 2H), 0.87 (m, 2H), 1.44 (s, 9H), 1.63 (m, 2H), 1.80 (m, 2H), 2.16 (m, 2H), 2.53 (d, J=3.0 Hz, 1H), 2.78 (m, 2H), 2.93 (d, J=2.8 Hz, 2H), 3.18 (s, 1H), 3.92 (d, J=5.6 Hz, 2H), 4.02 (s, 3H), 4.26 (m, 2H), 4.93 (d, J=3.6 Hz, 1H), 6.38 (d, J=5.2 Hz, 1H), 7.06 (m, 2H), 7.21 (t, J=8.8 Hz, 1H), 7.45 (m, 3H), 7.55 (s, 1H), 7.74-7.78 (dd, $J_1$=2.4 Hz, $J_2$=2.4 Hz, 1H), 8.33 (s, 1H), 8.46 (d, J=5.6 Hz, 1H), 10.04 (s, 1H).

Step 14) 1-(N-(4-(7-(3-(7-hydroxy-5-azaspiro[2.4]heptane-5-yl)propoxy)-6-methoxyquinolin-4-yloxy)-3-fluorophenyl)-N-(4-fluorophenyl)cyclopropane-1,1-dicarboxamide)-2-aminoacetate hydrochloride To a solution of 1-(N-(4-(7-(3-(7-hydroxy-5-azaspiro[2.4]heptane-5-yl)propoxy)-6-methoxyquinolin-4-yloxy)-3-fluorophenyl)-N-(4-fluorophenyl)cyclopropane-1,1-dicarboxamide)-2-(tert-butoxycarbonylamino)acetate (50 mg, 0.06 mmol) in EtOAc (0.5 mL) was added saturated HCl in EOAc (0.5 mL). The reaction was stirred at rt for 3 h. The solvent was removed under reduced pressure to give the title compound as a white solid (30 mg, 64%).

MS (ESI, pos. ion) m/z: 716.3 (M+1); LC-MS Rt: 2.720 min;

$^1$H NMR (400 MHz, $CD_3OD$): δ 1.03 (m, 2H), 1.15 (m, 2H), 1.60 (t, J=1.6 Hz, 2H), 1.67 (s, 2H), 1.99 (s, 1H), 2.47 (m, 2H), 3.69-3.76 (m, 4H), 3.86 (m, 1H), 3.99 (s, 2H), 4.11 (s, 3H), 4.50 (s, 2H), 5.15 (d, J=12 Hz, 1H), 6.99 (d, J=6.8 Hz, 1H), 7.08 (m, 2H), 7.46-7.58 (m, 5H), 7.88 (s, 1H), 7.95 (d, J=12.8 Hz, 1H), 8.73 (d, J=6.8 Hz, 1H).

Example 77

1-(N-(4-(7-(3-(7-hydroxy-5-azaspiro[2.4]heptane-5-yl)propoxy)quinolin-4-yloxy)-3-fluorophenyl)-N-(4-fluorophenyl)cyclopropane-1,1-dicarboxamide)-2-aminoacetate hydrochloride

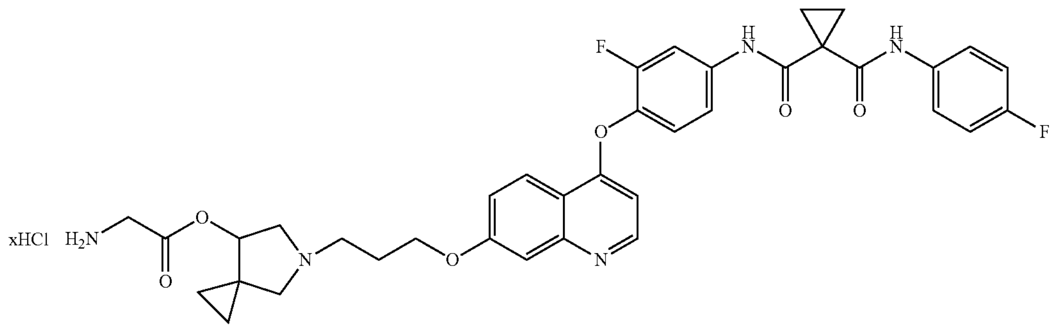

Step 1) Diethyl cyclopropane-1,1-dicarboxylate

To a solution of diethyl malonate (3.2 g, 20 mmol) and anhydrous potassium carbonate powder (6.9 g, 50 mmol) in DMF (50.0 mL) was added 1,2-dibromoethane (4.136 g, 22 mmol). After stirring for 2 hrs, catalytic amount of TBAI (0.738 g, 2.0 mmol) was added and the mixture was continued to stir at room temperature for 8 hrs. The reaction mixture was filtered and the solid was washed with diethyl ether 3 times. The filtrate was diluted with water (200 mL) and extracted with diethyl ether (75 mL×4). The combined organic phases were washed with 70 mL of brine, dried over $Na_2SO_4$ and concentrated in vacuo. The residue was chromatographed with a short alumina column (1:10 (v/v) EtOAc/n-hexane) to afford the desired compound as yellow oil (3.3 g, 88.7%).

$^1$H NMR (400 MHz, $CDCl_3$): δ 1.27 (m, J=6.8 Hz, 6H), 1.42 (m, 4H), 4.18 (m, 4H).

Step 2) 1-(Ethoxycarbonyl)cyclopropanecarboxylic acid

To a solution of diethyl cyclopropane-1,1-dicarboxylate (4.77 g, 25.6 mmol) in ethanol (40 mL) was added KOH (1.43 g, 25.6 mmol) in $H_2O$ (8 mL), and the reaction mixture was stirred at room temperature overnight. The ethanol was removed under reduced pressure. The residue was neutralized with HCl (6 mL, 5 mol/L), then extracted with EtOAc (100 mL×3). The combined organic phases were dried over $Na_2SO_4$, filtered and the filtrate was concentrated in vacuo to give the title compound as a white solid (3.58 g, 88.4%).

$^1$H NMR (400 MHz, $CDCl_3$): δ 1.27 (t, J=6.7 Hz, 3H), 1.83 (m, 2H), 1.86 (m, 2H), 4.25 (m, 2H).

Step 3) Ethyl 1-(4-fluorophenylcarbamoyl)cyclopropanecarboxylate

To a mixture of 1-(ethoxycarbonyl)cyclopropanecarboxylic acid (12.9 g, 81.6 mmol), 4-fluorobenzenamine (9.06 g, 81.6 mmol, Alfa-Aesar) and HOAt (2.22 g, 16.3 mmol, Shanghai Medped Co. Ltd.) in DCM (80 mL) was added EDCI (18.76 g, 97.9 mmol, Shanghai Medped Co. Ltd.) in portions at rt. The reaction was warmed up to 45° C. and stirred for 3 h. The mixture was extracted with water (150 mL×5), followed by brine (100 mL). The organic phase was dried over anhydrous $Na_2SO_4$ and concentrated in vacuo. The residue was recrystallized in n-hexane to give the title compound as a pale yellow solid (12.83 g, 63%).

MS (ESI, pos. ion) m/z: 252.0 (M+1);

$^1$H NMR (400 MHz, $CDCl_3$): δ1.28-1.31 (q, 3H), 1.61-1.62 (d, 2H), 1.66-1.69 (q, 2H), 1.80-1.83 (m, 2H), 7.00-7.05 (m, 2H), 7.54-7.57 (m, 2H), 10.91 (s, 1H).

Step 4) 1-(4-Fluorophenylcarbamoyl)cyclopropanecarboxylic acid

To a mixture of ethyl 1-((4-fluorophenyl)carbamoyl)cyclopropane-carboxylate (8.9 g, 35.4 mmol) in EtOH/THF (50/50 mL, Guangdong Guanghua Chem. Co. Ltd.) was added KOH (3.98 g, 70.8 mmol, Guangdong Guanghua Chem. Co. Ltd.) aqueous solution dropwise via a syringe. The reaction was stirred at RT overnight under $N_2$. The mixture was concentrated in vacuo. The residue was then acidified to pH 2 with 5 N HCl and extracted with EtOAc (150 mL×4), the combined organic phases were dried over anhydrous $Na_2SO_4$ and concentrated in vacuo. The residue was recrystallized in EtOAc/n-hexane (1:40 v/v) to give the title compound as a white solid (7.66 g, 97%).

MS (ESI, neg. ion) m/z: 221.9 (M−1);

$^1$H NMR (400 MHz, d6-DMSO): δ1.41 (s, 4H), 7.13-7.18 (m, 2H), 7.61-7.66 (m, 2H), 10.59 (s, 1H), 11.09 (bs, 1H).

Step 5) N-(4-(7-(Benzyloxy)quinolin-4-yloxy)-3-fluorophenyl)-N-(4-fluorophenyl)cyclopropane-1,1-dicarboxamide To a solution of 4-(7-(benzyloxy)quinolin-4-yloxy)-3-fluorobenzenamine) (3.6 g, 10 mmol) and 1-(4-fluorophenylcarbamoyl)cyclopropanecarboxylic acid (2.678 g, 12 mmol) in DCM (50 mL) was added TEA (1 g, 10 mmol) and HATU (6.84 g, 18 mmol) at rt. The reaction was then heated to 40° C. and stirred overnight. The mixture was washed with $H_2O$ (25 mL), and the organic layer was dried over anhydrous $Na_2SO_4$ and concentrated in vacuo. The residue was purified by a silica gel column chromatography (1:1 EtOAc/petroleum ether) to afford the title compound as a yellow solid (5.5 g, 97%).

MS (ESI, pos. ion) m/z: 566.2 (M+1); LC-MS Rt: 3.485 min;

$^1$H NMR (400 MHz, $CDCl_3$): δ 1.62 (q, $J_1$=5.2 Hz, $J_2$=3.2 Hz, 2H), 1.76 (q, $J_1$=4.4 Hz, $J_2$=3.2 Hz, 2H), 5.21 (s, 2H), 6.38 (q, $J_1$=0.8 Hz, $J_2$=4.8 Hz, 1H), 7.04 (m, 2H), 7.07-7.74 (m, 13H), 7.74-7.78 (m, 1H), 8.28 (d, J=9.2 Hz, 1H), 8.56 (d, J=5.2 Hz, 1H), 8.64 (s, 1H), 10.13 (s, 1H).

Step 6) N-(3-Fluoro-4-(7-hydroxyquinolin-4-yloxy) phenyl)-N-(4-fluorophenyl)cyclopropane-1,1-dicarboxamide To a solution of N-(4-(7-(benzyloxy)quinolin-4-yloxy)-3-fluorophenyl)-N-(4-fluorophenyl)cyclopropane-1,1-dicarboxamide (5.5 g, 9.73 mmol) in MeOH (500 mL) was added a catalytic amount of Pd/C (10%). The reaction mixture was stirred at rt under $H_2$ atmosphere overnight. The mixture was filtered through a celite pad, and the filtrate was concentrated in vacuo to afford the title compound as a yellow solid (4.6 g, 93%).

MS (ESI, pos. ion) m/z: 476.2 (M+1); LC-MS Rt: 3.234 min;

$^1$H NMR (400 MHz, d6-DMSO): δ 1.49 (m, 4H), 6.84 (d, J=6.8 Hz, 1H), 7.16 (t, J=8.8 Hz, 2H), 7.49-7.66 (m, 6H), 7.99 (d, J=13.2 Hz, 1H), 8.46 (d, J=9.2 Hz, 1H), 8.88 (d, J=6.4 Hz, 1H), 9.99 (s, 1H), 10.52 (s, 1H), 11.80 (s, 1H).

Step 7) 3-(7-hydroxy-5-azaspiro[2.4]heptane-5-yl)propanol

To a solution of 7-hydroxy-5-azaspiro[2.4]heptane (1.23 g, 11.0 mmol) in THF (40 mL) was added 3-bromopropanol (2.3 g, 16.65 mmol) and $Et_3N$ (2.24 g, 22.2 mmol). The reaction mixture was stirred at rt for 12 hrs and then concentrated in vacuo. The residue was purified by a silica gel column chromatography (100:50:2(v/v/v)EtOAc/$CH_3OH$/$Et_3N$) to afford the desired compound as orange oil (1.14 g, 60%).

MS (ESI, pos. ion) m/z: 172 (M+1); LC-MS Rt: 0.178 min;

$^1$H NMR (400 MHz, $CDCl_3$): δ 0.59 (m, 1H), 0.62 (m, 1H), 0.70-0.72 (m, 1H), 0.87-0.92 (m, 1H), 1.68-1.74 (m, 2H), 2.39-2.41 (d, J=9.2 Hz, 1H), 2.70-2.74 (m, 2H), 2.84-2.87 (m, 2H), 2.88-2.92 (dd, $J_1$=10.4 Hz, $J_2$=4.8 Hz, 1H), 3.73-3.75 (m, 1H), 3.77-3.80 (t, J=5.2 Hz, 2H).

Step 8) 3-(7-hydroxy-5-azaspiro[2.4]heptane-5-yl)propyl methanesulfonate

To a solution of 3-(7-hydroxy-5-azaspiro[2.4]heptane-5-yl)propanol (1.14 g, 6.67 mmol) and $Et_3N$ (1.35 g, 13.34 mmol) in $CH_2Cl_2$ (20 mL) was added methanesulfonyl chloride (1.15 g, 10 mmol) dropwise at 0° C. The reaction was then stirred at 0° C. for 3 hrs. The reaction mixture was washed with cold water (10 mL) and the organic layer was dried over anhydrous $Na_2SO_4$, filtered and concentrated in vacuo to afford the title compound as orange oil. The crude product was used for the next step without further purification.

Step 9) N-(4-(7-(3-(7-hydroxy-5-azaspiro[2.4]heptane-5-yl)propoxy)-quinolin-4-yloxy)-3-fluorophenyl)-N-(4-fluorophenyl)cyclopropane-1,1-dicarboxamide To a solution of N-(3-fluoro-4-(7-hydroxy-quinolin-4-yloxy)phenyl)-N-(4-fluorophenyl)cyclopropane-1,1-dicarboxamide (266 mg, 0.56 mmol) in DMA (3 mL) was added 3-(7-hydroxy-5-azaspiro[2.4]heptane-5-yl)propylmethanesulfonate (283 mg, 1.14 mmol) and $Cs_2CO_3$ (556 mg, 1.71 mmol). The reaction was then stirred at rt for 2 days. The solvent was then removed and the residue was partioned between saturated $NaHCO_3$ aqueous solution (15 mL) and $CHCl_3$ (30 mL). The organic layer was separated, dried over anhydrous $Na_2SO_4$, filtered. The filtrate was concentrated in vacuo. The residue was purified by a silica gel column chromatography (100:15:1(v/v/v) EtOAc/$CH_3OH$/$Et_3N$) to afford the title compound as a white solid (290 mg, 82%).

MS (ESI, pos. ion) m/z: 629.0 (M+1); LC-MS Rt: 2.768 min;

$^1$H-NMR (400 MHz, $CDCl_3$): δ 0.553-0.685 (m, 2H), 0.712-0.795 (m, 1H), 0.922-0.985 (m, 1H), 1.613-1.645 (q, $J_1$=8 Hz, $J_2$=2.7 Hz, 2H), 1.787-1.818 (q, $J_1$=8 Hz, $J_2$=4.8 Hz, 2H), 2.2027-2.095 (m, 2H), 2.366-2.388 (d, J=8.8 Hz, 1H), 2.657-2.731 (m, 2H), 2.786-2.823 (dd, $J_1$=10 Hz, $J_2$=4.8 Hz, 1H), 2.883-2.905 (d, J=8.8 Hz, 1H), 2.948-2.977 (dd, $J_1$=10 Hz, $J_2$=1.6 Hz, 1H), 3.727-3.739 (d, J=8.8 Hz, 1H), 4.117-4.183 (m, 2H), 6.365-6.378 (d, J=8.8 Hz, 1H), 7.038-7.090 (m, 2H), 7.188-7.282 (m, 3H), 7.433-7.475 (m, 2H), 7.508-7.514 (d, J=2.4 Hz, 1H), 7.740-7.776 (dd, $J_1$=12 Hz, $J_2$=2.4 Hz, 1H), 8.240-8.263 (d, J=9.2 Hz, 1H), 8.551-8.575 (d, J=9.6 Hz, 1H), 9.977 (m, 1H).

Step 10) 1-(N-(4-(7-(3-(7-hydroxy-5-azaspiro[2.4]heptane-5-yl)propoxy)quinolin-4-yloxy)-3-fluorophenyl)-N-(4-fluorophenyl)cyclopropane-1,1-dicarboxamide)-2-(tert-butoxycarbonylamino)acetate To a solution of N-(4-(7-(3-(7-hydroxy-5-azaspiro[2.4]heptane-5-yl)propoxy)quinolin-4-yloxy)-3-fluorophenyl)-N-(4-fluorophenyl)cyclopropane-1,1-dicarboxamide (50 mg, 0.079 mmol), Boc-Glycine (21 mg, 0.119 mmol) and DMAP (2 mg, 0.016 mmol) in $CH_2Cl_2$ (1 mL) was added EDCI (24 mg, 0.12 mmol). The reaction was then stirred at rt for 2 h. The solution was diluted with $CH_2Cl_2$ (15 mL) and washed with water (10 mL). The organic layer was dried and concentrated. The residual was purified by silica column to afford the title compound as a white foam solid (50 mg, 80%).

MS (ESI, pos. ion) m/z: 786.4 (M+1); LC-MS Rt: 3.442 min;

$^1$H-NMR (400 MHz, $CDCl_3$): δ 0.632-0.646 (m, 2H), 0.675-0.703 (m, 2H), 1.437 (s, 9H), 1.611-1.642 (q, $J_1$=7.6 Hz, $J_2$=4.8 Hz, 2H), 1.771-1.802 (q, $J_1$=8 Hz, $J_2$=4 Hz, 2H), 2.091 (m, 2H), 2.457-2.479 (d, J=8.8 Hz, 1H), 2.709-2.747 (t, J=7.6 Hz, 2H), 2.889-2.912 (d, J=9.2 Hz, 2H), 3.095-3.136 (dd, $J_1$=6.4 Hz, $J_2$=5.2 Hz, 2H)3.910-3.924 (d, J=5.6 Hz, 2H), 4.136-4.194 (t, J=6 Hz, 2H), 4.934-4.943 (d, J=3.6 Hz, 1H), 6.356-6.371 (d, J=6 Hz, 1H), 7.209-7.072 (t, J=8.4 Hz, 2H), 7.196-7.225 (dd, $J_1$=9.2 Hz, $J_2$=2.4 Hz, 2H), 7.258-7.279 (d, J=8.4 Hz, 1H), 7.383-7.389 (d, J=2.4 Hz, 1H), 7.445-7.467

(dd, $J_1$=8.8 Hz, $J_2$=2 Hz, 2H), 7.731-7.767 (dd, $J_1$=12 Hz, $J_2$=2.4 Hz, 1H), 8.231-8.254 (d, J=9.2 Hz, 1H), 8.556-8.569 (d, J=5.2 Hz, 1H), 10.055 (s, 1H).

Step 11) 1-(N-(4-(7-(3-(7-hydroxy-5-azaspiro[2.4] heptane-5-yl)propoxy)quinolin-4-yloxy)-3-fluorophenyl)-N-(4-fluorophenyl)cyclopropane-1,1-dicarboxamide)-2-aminoacetate hydrochloride To a solution of 1-(N-(4-(7-(3-(7-hydroxy-5-azaspiro[2.4] heptane-5-yl)propoxy)quinolin-4-yloxy)-3-fluorophenyl)-N-(4-fluorophenyl)cyclopropane-1,1-dicarboxamide)-2-(tert-butoxycarbonylamino)acetate (50 mg, 0.064 mmol) in EtOAc (0.5 mL) was added saturated HCl in EOAc (0.5 mL). The reaction was stirred at rt for 3 h. The solvent was removed under reduced pressure to give the title compound as a white solid (50 mg).

MS (ESI, pos. ion) m/z: 686.2 (M+1); LC-MS Rt: 2.712 min;

$^1$H-NMR (400 MHz, $CDCl_3$): δ 0.995-1.050 (m, 2H), 1.143-1.195 (m, 2H), 1.600 (s, 3H), 1.663 (s, 2H), 1.991-2.050 (m, 2H), 2.453-2.470 (d, J=6.8 Hz, 2H), 2.488-2.505 (dd, $J_1$=4.4 Hz, $J_2$=4 Hz, 1H), 3.598-3.633 (t, J=6.8 Hz, 2H), 3.971-3.998 (m, 2H), 4.468 (s, 2H), 5.1-5.19 (dd, 1H), 6.994-7.011 (d, J=6.8 Hz, 1H), 7.046-7.098 (m, 2H), 7.482-7.514 (m, 1H), 7.545-7.579 (m, 2H), 7.610-7.663 (m, 2H), 7.975-8.012 (t, J=12.4 Hz, 1H), 8.580-8.608 (dd, $J_1$=9.2 Hz, $J_2$=2 Hz, 1H), 8.848-8.881 (t, J=6.8 Hz, 1H).

Example 78

1-((4-(4-(1-(carbamoyl)cyclopropanecarboxamido)-2-fluorophenoxy)-6-methoxyquinolin-7-yloxy)methyl)cyclopropyl 2-aminoacetate $^1$H NMR (400 MHz, $CDCl_3$): δ 0.94-1.01 (m, 2H), 1.04-1.12 (m, 2H), 1.50-1.63 (m, 4H), 1.71 (m, 1H), 1.82 (m, 1H), 3.44 (t, J=4.8 Hz, 1H), 3.80 (t, J=8.8 Hz, 1H), 3.92 (d, J=11.6 Hz, 1H), 4.02 (d, J=12 Hz, 1H), 4.69 (s, 1H), 7.43 (t, J=7.2 Hz, 2H), 7.55 (t, J=7.2 Hz, 1H), 8.03 (d, J=8 Hz, 2H).

Step 2) 1-(hydroxymethyl)cyclopropyl benzoate

To a mixture of 1-((tetrahydro-2H-pyran-2-yloxy)methyl) cyclopropyl benzoate (2 g, 7.2 mmol) in 30 mL of MeOH was added PPTS (2.7 g, 10.8 mmol, Aldrich) at rt. The reaction mixture was stirred at rt overnight, then concentrated and purified by a silica gel column chromatography (4:1 (v/v) petroleum ether/EtOAc) to afford the title compound as colorless oil (1.2 g, 87%).

MS (ESI, pos. ion) m/z: 215.1 (M+Na); LC-MS Rt: 2.949 min;

$^1$H NMR (400 MHz, $CDCl_3$): δ 1.05 (m, 2H), 1.12 (m, 2H), 3.92 (s, 2H), 7.45 (m, 2H), 7.60 (m, 1H), 8.01 (t, J=1.6 Hz, 2H).

Step 3) 1-((methylsulfonyloxy)methyl)cyclopropyl benzoate

To a mixture of 1-(hydroxymethyl)cyclopropyl benzoate (500 mg, 2.6 mmol) and TEA (394 mg, 3.9 mmol, Shantou Xilong chemical factory) in 50 mL of dry $CH_2Cl_2$, was added MsCl (357 mg, 3.12 mmol, Shanghai Haiqu chemical Ltd.) dropwise via a syringe at rt. After stirring for 2 hrs at rt, the mixture was diluted with icewater and extracted with $CH_2Cl_2$ (30 mL×2). The combined organic phases were dried over $Na_2SO_4$ and concentrated in vacuo to give the title compound as pale yellow solid (590 mg, 84%).

MS (ESI, pos. ion) m/z: 293.1 (M+Na); LC-MS Rt: 3.295 min;

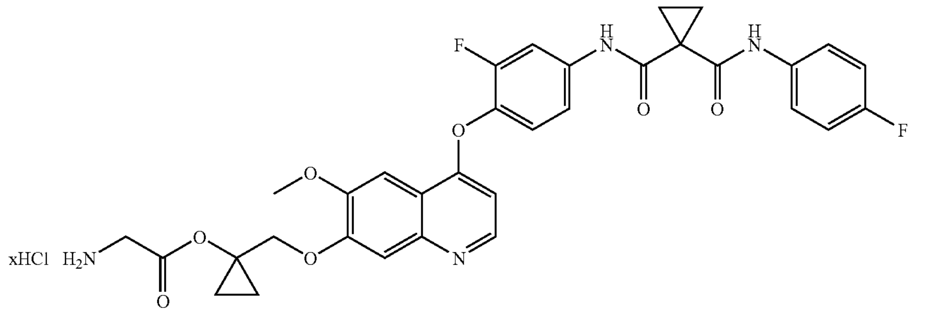

Step 1) 1-((tetrahydro-2H-pyran-2-yloxy)methyl)cyclopropyl benzoate

To a mixture of 1-((tetrahydro-2H-pyran-2-yloxy)methyl) cyclopropanol (1.6 g, 9.3 mmol) and benzoic acid (1.25 g, 11.16 mmol, Shanghai Haiqu chemical Ltd.) in 50 mL of $CH_2Cl_2$ was added DMAP (227 mg, 1.86 mmol, Shanghai Haiqu chemical Ltd.) and EDCI (2.73 g, 14.25 mmol, Shanghai Haiqu chemical Ltd.) at rt. The reaction mixture was stirred at rt overnight, then concentrated and purified by a silica gel column chromatography (20:1 (v/v) petroleum ether/EtOAc)) to afford the title compound as colorless oil (1.8 g, 70%).

MS (ESI, pos. ion) m/z: 299.2 (M+Na); LC-MS Rt: 3.659 min;

$^1$H NMR (400 MHz, $CDCl_3$): δ 1.14 (s, 2H), 1.22 (s, 2H), 3.04 (s, 3H), 4.6 (s, 2H), 7.45 (t, J=7.6 Hz, 2H), 7.58 (d, J=7.2 Hz, 1H), 8.02 (d, J=7.6 Hz, 2H).

Step 4) 1-((4-(4-(1-(carbamoyl)cyclopropanecarboxamido)-2-fluorophenoxy)-6-methoxyquinolin-7-yloxy)methyl)cyclopropyl benzoate To a mixture of 1-((methylsulfonyloxy)methyl)cyclopropyl benzoate (801 mg, 2.97 mmol) and N-(3-fluoro-4-(7-hydroxy-6-methoxy quinolin-4-yloxy)phenyl)-N-(4-fluorophenyl)cyclopropane-1,1-dicarboxamide (1 g, 1.98 mmol) in DMA (5 mL) were added $Cs_2CO_3$ (1.93 g, 5.94 mmol, Aladdin). The reaction was heated at 45° C. overnight. The solvent was then removed in vacuo, and the residual was diluted with $CHCl_3$ (30 mL). The organic layer was dried over $Na_2SO_4$ and concentrated in vacuo. The residual was purified by a silica gel column chromatography (EtOAc) to afford the title compound as a light yellow solid (800 mg, 60%).

MS (ESI, pos. ion) m/z: 680.2 (M+1); LC-MS Rt: 3.852 min;

Step 5) N-(3-fluoro-4-(7-((1-hydroxycyclopropyl)methoxy)-6-methoxyquinolin-4-yloxy)phenyl)-N-(4-fluorophenyl)cyclopropane-1,1-dicarboxamide To a solution of 1-((4-(4-(1-(carbamoyl)cyclopropanecarboxamido)-2-fluorophenoxy)-6-methoxyquinolin-7-yloxy)methyl)cyclopropyl benzoate (800 mg, 1.178 mmol) in $CH_3OH$ (10 mL) was added aqueous NaOH (94 mg, 2.356 mmol) solution (5 mL). The reaction was stirred at rt overnight. The suspension was concentrated, and the residual was purified by a silica gel column chromatography (EtOAc to 100:1 (v/v) EtOAc/$CH_3OH$) to give the title product as a white solid (520 mg, 77%).

MS (ESI, pos. ion) m/z: 576.2 (M+1); LC-MS Rt: 3.167 min;

$^1$H NMR (400 MHz, $CDCl_3$): δ 0.767 (m, 2H), 1.008 (m, 2H), 1.637 (m, 2H), 1.807 (m, 2H), 4.040 (s, 3H), 4.202 (s, 2H), 6.397-6.409 (d, J=4.8 Hz, 1H), 7.047-7.088 (d, J=4.8 Hz, 2H), 7.222-7.243 (d, J=4.8 Hz, 1H), 7.410 (s, 1H), 7.447-7.478 (t, J=6 Hz, 2H), 7.580 (s, 1H), 7.761-7.791 (d, J=12 Hz, 1H), 8.427 (s, 1H), 8.474-8.487 (d, J=5.2 Hz, 1H), 10.119 (s, 1H).

Step 6) 1-((4-(4-(1-(carbamoyl)cyclopropanecarboxamido)-2-fluorophenoxy)-6-methoxy quinolin-7-yloxy)methyl)cyclopropyl 2-(tert-butoxycarbonyl) acetate To a solution of N-(3-fluoro-4-(7-((1-hydroxycyclopropyl)methoxy)-6-methoxyquinolin-4-yloxy)phenyl)-N-(4-fluorophenyl)cyclopropane-1,1-dicarboxamide (150 mg, 0.26 mmol), N-Boc-glycine (68 mg, 0.39 mmol) and DMAP (16 mg, 0.13 mmol) in $CH_2Cl_2$ (2 mL) was added EDCI (100 mg, 0.52 mmol). The reaction was stirred at rt for 2 h. The solution was diluted with $CH_2Cl_2$ (15 mL) and washed with water (10 mL). The organic layer was dried over $Na_2SO_4$ and concentrated in vacuo. The residual was purified by a silica gel column chromatography to afford the title compound as a white foam solid (150 mg, 78.5%).

MS (ESI, pos. ion) m/z: 733.2 (M+1); LC-MS Rt: 3.479 min;

$^1$H NMR (400 MHz, $CDCl_3$): δ 1.103-1.134 (m, 4H), 1.454 (s, 9H), 1.625-1.656 (q, $J_1$=7.2 Hz, $J_2$=8 Hz, $J_3$=4.4 Hz, $J_4$=5.2 Hz, 2H), 1.797-1.829 (q, $J_1$=7.2 Hz, $J_2$=8.8 Hz, $J_3$=4.4 Hz, $J_4$=5.6 Hz, 2H), 3.899-3.912 (d, J=5.2 Hz, 2H), 4.043 (s, 3H), 4.473 (s, 2H), 6.404-6.418 (d, J=5.6 Hz, 1H), 7.055-7.098 (t, J=8.8 Hz, 2H), 7.205-7.248 (t, J=8.8 Hz, 1H), 7.283-7.306 (d, J=9.2 Hz, 1H), 7.394 (s, 1H), 7.467-7.489 (dd, $J_1$=10.8 Hz, $J_2$=8 Hz, $J_3$=4.4 Hz, $J_4$=6 Hz, 2H), 7.585 (s, 1H), 7.757-7.793 (dd, $J_1$=12 Hz, $J_2$=2.4 Hz, 1H), 8.378 (s, 1H), 8.472-8.485 (d, J=5.2 Hz, 1H), 10.031 (s, 1H).

Step 7) 1-((4-(4-(1-(carbamoyl)cyclopropanecarboxamido)-2-fluorophenoxy)-6-methoxyquinolin-7-yloxy)methyl)cyclopropyl 2-aminoacetate To a solution of 1-((4-(4-(1-(carbamoyl)cyclopropanecarboxamido)-2-fluorophenoxy)-6-methoxyquinolin-7-yloxy)methyl)cyclopropyl 2-(tert-butoxycarbonyl)acetate (150 mg, 0.20 mmol) in EtOAc (1 mL) was added HCl/EOAc (3 mmol/L, 1 mL). The reaction was stirred at rt for 3 h. The solvent was removed under reduced pressure to give the title compound as a white solid (170 mg).

MS (ESI, pos. ion) m/z: 634.2 (M+1); LC-MS Rt: 2.831 min;

$^1$H NMR (400 MHz, d-DMSO): δ 1.156-1.183 (m, 4H), 1.474-1.540 (m, 4H), 3.809 (s, 2H), 4.072 (s, 3H), 4.571 (s, 2H), 6.914-6.930 (d, J=6.4 Hz, 1H), 7.132-7.176 (t, J=8.8 Hz, 2H), 7.531-7.575 (t, J=8.8 Hz, 1H), 7.623-7.673 (m, 3H), 7.776-7.794 (d, J=7.2 Hz, 2H), 7.984-8.018 (d, J=13.6 Hz, 1H), 8.807-8.823 (d, J=6 Hz, 1H), 10.047 (s, 1H), 10.573 (s, 1H).

Example 79

1-(2-(4-(2-fluoro-4-(1-(phenylcarbamoyl)cyclopropanecarboxamido)phenoxy)quinolin-7-yloxy)ethyl)cyclopropyl 2-aminoacetate hydrochloride

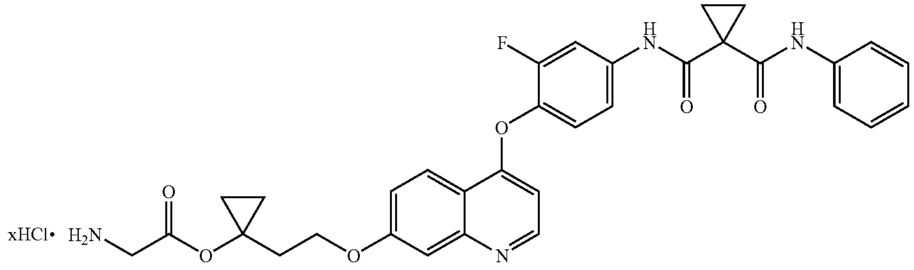

Step 1) benzyl 3-hydroxypropanoate

3-Hydroxypropanoic acid solution (12 g, 40 mmol, 30% in $H_2O$ solution, TCI, TOKYOKASEI) and KOH (2.24 g, 40 mmol, Shantou Xilong chemical factory) was stirred at rt for 30 min, the mixture was concentrated in vacuo to give a white solid. The solid was suspended in 50 mL of DMF was added BnBr (4.75 mL, 40 mmol, Aldrich) via a syringe at rt. After stirring at 80° C. for 5 h, the reaction mixture concentrated in vacuo. The residue was purified by a silica gel column chromatography (10:1 (v/v) petroleum ether/EtOAc) to give the title compound as colorless oil (3.35 g, 46%).

MS (ESI, pos. ion) m/z: 203.1 (M+Na); LC-MS Rt: 2.743 min;

$^1$H NMR (400 MHz, $CDCl_3$): δ 2.61 (d, J=4.4 Hz, 2H), 3.86 (s, J=4.8 Hz, 2H), 5.14 (s, 2H), 7.35 (s, 5H).

Step 2) benzyl 3-(tetrahydro-2H-pyran-2-yloxy)propanoate

To a mixture of benzyl 3-hydroxypropanoate (3.35 g, 18.6 mmol) and DHP (3.12 g, 37.2 mmol, Alfa) in dichloromethane (100 mL) was added PPTS (5.6 g, 22.3 mmol, Aldrich) in portions. The reaction mixture was stirred at rt overnight, and was quenched with 50 mL of $H_2O$. The organic layer was dried over $Na_2SO_4$ and concentrated in vacuo. The residue was purified by a silica gel column chromatography (10:1 (v/v) petroleum ether/EtOAc) to give the title compound as colorless oil (4.25 g, 86%).

MS (ESI, pos. ion) m/z: 287.2 (M+Na); LC-MS Rt: 3.915 min;

$^1$H NMR (400 MHz, $CDCl_3$): δ 1.49-1.76 (m, 6H), 2.68 (t, J=6.4 Hz, 2H), 3.49 (t, J=4.4 Hz, 1H), 3.72 (m, 1H), 3.82 (t, J=8.8 Hz, 1H), 4.03 (m, 1H), 4.63 (s, 1H), 5.17 (s, 2H), 7.35 (d, J=10.4 Hz, 5H).

Step 3) 1-(2-(tetrahydro-2H-pyran-2-yloxy)ethyl) cyclopropanol

To a mixture of benzyl 3-(tetrahydro-2H-pyran-2-yloxy) propanoate (4.2 g, 15.9 mmol) in 60 mL of THF was added $Ti(Oi-Pr)_4$ (2.4 mL, 07.95 mmol, d=0.955 g/L, Aldrich) via a syringe under nitrogen at rt. After stirring at 18° C. for 30 min, EtMgBr (13.25 mL, 3.975 mmol, 3M ether solution, Aldrich) was added via a syringe pump over 3 hrs. The reaction was quenched with 50 mL of water. The mixture was filtered through a celite pad and the filtrate was extracted with ethyl acetate (100 mL×3). The combined organic phases were dried over $Na_2SO_4$ and concentrated in vacuo. The residue was purified by a silica gel column chromatography (10:1 (v/v) petroleum ether/EtOAc) to afford the title compound as colorless oil (2.56 g, 86.5%).

MS (ESI, pos. ion) m/z: 209.2 (M+Na); LC-MS Rt: 2.644 min;

$^1$H NMR (400 MHz, $CDCl_3$): δ 0.49 (m, 2H), 0.80 (m, 2H), 1.55-1.83 (m, 6H), 1.87-1.90 (m, 2H), 3.57 (m, 1H), 3.72 (m, 1H), 3.90 (m, 1H), 4.09 (m, 1H), 4.68 (q, 1H).

Step 4) 1-(2-(tetrahydro-2H-pyran-2-yloxy)ethyl) cyclopropyl benzoate

To a mixture of 1-(2-(tetrahydro-2H-pyran-2-yloxy)ethyl) cyclopropanol (730 mg, 4.05 mmol) and benzoic acid (590 mg, 4.86 mmol) in 30 mL of $CH_2Cl_2$ was added DMAP (98.8 mg, 0.81 mmol, Shanghai Haiqu chemical Ltd.) and EDCI (1.16 g, 6.08 mmol, Shanghai Haiqu chemical Ltd.) at rt. The reaction mixture was stirred at rt overnight, then concentrated and purified by a silica gel column chromatography (20:1 (v/v) petroleum ether/EtOAc)) to afford the title compound as colorless oil (690 mg, 60%).

MS (ESI, pos. ion) m/z: 313.2 (M+Na); LC-MS Rt: 3.801 min;

$^1$H NMR (400 MHz, $CDCl_3$): δ 0.88 (m, 2H), 1.02 (m, 2H), 1.48-1.83 (m, 7H), 2.16-2.30 (m, 2H), 3.52 (m, 1H), 3.61 (m, 1H), 3.90 (m, 1H), 3.99 (m, 1H), 4.62 (t, J=3.2 Hz, 1H), 7.45 (m, 2H), 7.56 (m, 1H), 8.01 (m, 2H).

Step 5) 1-(2-hydroxyethyl)cyclopropyl benzoate

To a mixture of 1-(2-(tetrahydro-2H-pyran-2-yloxy)ethyl) cyclopropyl benzoate (690 mg, 2.38 mmol) in 20 mL of MeOH was added PPTS (896 mg, 3.57 mmol, Aldrich) at rt. The reaction mixture was stirred at rt overnight, then concentrated and purified by a silica gel column chromatography (4:1 (v/v) petroleum ether/EtOAc) to the title compound as light yellow oil (320 mg, 65%).

MS (ESI, pos. ion) m/z: 229.2 (M+Na); LC-MS Rt: 2.997 min;

$^1$H NMR (400 MHz, $CDCl_3$): δ 0.92 (m, 2H), 1.08 (m, 2H), 2.10 (t, J=6.0 Hz, 2H), 2.78 (s, 1H), 3.79 (s, 2H), 7.46 (t, J=8.0 Hz, 2H), 7.58 (t, J=7.2 Hz, 1H), 8.02 (t, J=7.2 Hz, 2H).

Step 6) 2-(1-(benzoyloxy)cyclopropyl)ethyl methanesulfonate

To a mixture of 1-(2-hydroxyethyl)cyclopropyl benzoate (320 mg, 1.55 mmol) and TEA (235 mg, 2.33 mmol, Shantou Xilong chemical factory) in 20 mL of dry $CH_2Cl_2$, was added MsCl (213 mg, 1.86 mmol, Shanghai Haiqu chemical Ltd.) dropwise via a syringe at rt. After stirring for 2 hrs at rt, the mixture was diluted with icewater and extracted with $CH_2Cl_2$ (30 mL). The organic phase was dried over $Na_2SO_4$ and concentrated in vacuo to give the title compound as a pale yellow solid (400 mg, 90%).

MS (ESI, pos. ion) m/z: 307.1 (M+Na); LC-MS Rt: 3.348 min.

Step 7) 1-(2-(4-(2-fluoro-4-(1-(phenylcarbamoyl) cyclopropanecarboxamido)phenoxy)quinolin-7-yloxy)ethyl)cyclopropyl benzoate To a mixture of N-(3-fluoro-4-(7-hydroxyquinolin-4-yloxy)phenyl)-N-phenylcyclo-propane-1,1-dicarboxamide (91 mg, 0.2 mmol) and 2-(1-(benzoyloxy)cyclopropyl)ethyl methanesulfonate (113.6 mg, 0.4 mmol) in DMF (3 mL) were added $Cs_2CO_3$ (195 mg, 0.6 mmol, Aladdin). The reaction was stirred at 50° C. overnight. The solvent was then removed in vacuo, and the residue was extracted with $CHCl_3$ (30 mL). The organic layer was dried over $Na_2SO_4$ and concentrated in vacuo. The residue was purified by a silica gel column chromatography (EtOAc) to afford the title compound as a light yellow solid (75 mg, 58%).

MS (ESI, pos. ion) m/z: 646.2 (M+1); LC-MS Rt: 3.686 min;

$^1$H NMR (400 MHz, $CDCl_3$): δ 0.93 (t, J=7.2 Hz, 2H), 1.08 (t, J=6.0 Hz, 2H), 1.62 (m, 2H), 1.81 (m, 2H), 2.48 (t, J=6.4 Hz, 2H), 4.35 (t, J=6.4 Hz, 2H), 6.36 (d, J=5.2 Hz, 1H), 7.07 (m, 1H), 7.19 (t, J=9.2 Hz, 2H), 7.35-7.55 (m, 8H), 7.75 (m, 1H), 8.0 (d, J=7.6 Hz, 3H), 8.20 (d, J=9.2 Hz, 1H), 8.56 (d, J=5.2 Hz, 1H), 10.14 (s, 1H).

Step 8) N-(3-fluoro-4-(7-(2-(1-hydroxycyclopropyl) ethoxy)quinolin-4-yloxy)phenyl)-N-phenylcyclopropane-1,1-dicarboxamide To a solution of 1-(2-(4-(2-fluoro-4-(1-(phenylcarbamoyl) cyclopropane-carboxamido)phenoxy)quinolin-7-yloxy) ethyl)cyclopropyl benzoate (75 mg, 0.116 mmol) in $CH_3OH$ (5 mL) was added aqueous LiOH (8.35 mg, 0.348 mmol) solution (1 mL). The reaction was stirred at rt overnight. The suspension was then concentrated in vacuo, and the residue was purified by silica gel column (EtOAc to 100:1 (v/v) EtOAc/$CH_3OH$) to give the title compound as a white solid (40 mg, 64%).

MS (ESI, pos. ion) m/z: 542.2 (M+1); LC-MS Rt: 3.225 min;

$^1$H NMR (400 MHz, $CD_3OD$): δ 0.63 (t, J=5.6 Hz, 2H), 0.78 (t, J=5.6 Hz, 2H), 1.67 (s, 4H), 2.15 (t, J=6.8 Hz, 2H), 4.44 (t, J=6.8 Hz, 2H), 6.51 (d, J=5.6 Hz, 1H), 7.16 (t, J=7.2

Hz, 1H), 7.32-7.47 (m, 6H), 7.58 (d, J=8.0 Hz, 2H), 7.85 (m, 1H), 8.32 (d, J=9.2 Hz, 1H), 8.56 (d, J=5.2 Hz, 1H).

Step 9) 1-(2-(4-(2-fluoro-4-(1-(phenylcarbamoyl)cyclopropanecarboxamido)phenoxy)quinolin-7-yloxy)ethyl)cyclopropyl 2-(tert-butoxycarbonylamino)acetate To a solution of N-(3-fluoro-4-(7-(2-(1-hydroxycyclopropyl)ethoxy)-quinolin-4-yloxy)phenyl)-N-phenylcyclopropane-1,1-dicarboxamide (27 mg, 0.05 mmol), 2-(tert-butoxy carbonylamino)acetic acid (13 mg, 0.075 mmo, Shanghai Haiqu chemical Ltd) and DMAP (3 mg, 0.025 mmol, Shanghai Haiqu chemical Ltd) in dried DCM (3 mL) was added EDCI (15 mg, 0.075 mmol, Shanghai Haiqu chemical Ltd), the mixture was stirred at rt overnight. The reaction mixture was washed with $H_2O$, and the organic layer was dried with $Na_2SO_4$ and concentrated. The residue was purified by flash chromagraphy on silica gel to give the product as a white solid (30 mg, 85%).

MS (ESI, pos. ion) m/z: 699.2 (M+1); LC-MS Rt: 3.656 min;

$^1$H NMR (400 MHz, $CDCl_3$): δ 0.88 (m, 2H), 0.98 (m, 2H), 1.62 (m, 2H), 1.81 (m, 2H), 2.48 (t, J=6.4 Hz, 2H), 4.35 (t, J=6.4 Hz, 2H), 6.36 (d, J=5.2 Hz, 1H), 7.07 (m, 1H), 7.19 (t, J=9.2 Hz, 2H), 7.35-7.55 (m, 8H), 7.75 (m, 1H), 8.0 (d, J=7.6 Hz, 3H), 8.20 (d, J=9.2 Hz, 1H), 8.56 (d, J=5.2 Hz, 1H), 10.14 (s, 1H).

Step 10) 1-(2-(4-(2-fluoro-4-(1-(phenylcarbamoyl)cyclopropanecarboxamido)phenoxy)quinolin-7-yloxy)ethyl)cyclopropyl 2-aminoacetate hydrochloride To a solution of 1-(2-(4-(2-fluoro-4-(1-(phenylcarbamoyl)cyclopropane-carboxamido)phenoxy)quinolin-7-yloxy)ethyl)cyclopropyl 2-(tert-butoxycarbonylamino)acetate (23 mg, 0.03 mmol) in EtOAc (1 mL) was added HCl (2 mol/L in EtOAc, 1 mL). The mixture was stirred at rt for 2 h, and then concentrated in vacuo to give the title compound as a white solid (15 mg, 83%).

MS (ESI, pos. ion) m/z: 599.2 (M+1); LC-MS Rt: 2.956 min;

$^1$H NMR (400 MHz, $CD_3OD$): δ 0.99 (t, J=5.6 Hz, 2H), 1.08 (t, J=5.6 Hz, 2H), 1.62 (m, 2H), 1.69 (s, 4H), 2.50 (t, J=6.4 Hz, 2H), 3.86 (s, 2H), 4.53 (t, J=6.4 Hz, 2H), 7.02 (dd, $J_1$=0.8 Hz, $J_2$=6.4 Hz, 1H), 7.16 (m, 1H), 7.34-7.38 (m, 2H), 7.48-7.67 (m, 6H), 7.96-7.99 (dd, $J_1$=2.4 Hz, $J_2$=12.8 Hz, 1H), 8.61 (d, J=9.2 Hz, 1H), 8.88 (d, J=6.8 Hz, 1H).

Stability of the Compounds in Aqueous Solution, in Whole Blood and in Liver Microsomes Example A General HPLC Analysis Method An Agilent 1200 HPLC equipped with G1311A Quat pumps, a G1322A degasser, a G1316A TCC (Temperature Control of Column, maintained at 35° C.), a G1315 DAD detector and a G1329A autosampler was used in the analysis. An Agilent Zorbax Eclipse Plus XDB-C18, 4.6×150 mm, 5 μM column was used for the analysis. 5 μL of the samples were injected. The HPLC peaks were recorded via UV wavelength at 210 nm.

Analysis condition A: The mobile phase was acetonitrile (A) and 0.03 M $KH_2PO_4$ solution (B) (pH=6.5, adjusted with 1.0 M aq KOH). The flow rate was 1.0 mL/min. The gradient condition was 30% A: 70% B to 70% A: 30% B in 25 min, then the mobile phase was returned to 70% A:30% B in 5 min and maintained for 5 min. Analysis condition B: The mobile phase was acetonitrile (A) and 0.03 M $KH_2PO_4$ solution B (pH=4.0, adjusted with 10% AQ $H_3PO_4$). The flow rate was 2.0 mL/min. The gradient condition was shown in Table 3:

TABLE 3

| Time (min) | A (MeCN) | B (buffer, pH = 4.0) |
|---|---|---|
| 0-2 | 10 | 90 |
| 2-13 | 10-42 | 90-58 |
| 13-18 | 42 | 58 |
| 18-25 | 42-65 | 58-35 |
| 25-35 | 65 | 35 |

Example B

General LC/MS/MS Analysis Method

An Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100×4.6 mm I.D., 5 μM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70:30, v/v). The flow rate was 0.6 mL/min. Column was maintained at ambient temperature. 20 μL of the samples were injected.

Example C

Methods for Determination of Stability in Aqueous Solution

The stability of compounds was evaluated in one or more in vitro aqueous systems. Experimental conditions used for the in vitro studies are summarized in Table 4. Aliquots (20 μL) were removed from the stock solution at different time points. Samples were analyzed by HPLC methods as described herein. Samples with high concentrations were diluted to 0.1 mg/mL before HPLC sample injection.

Data Analysis

The values of the AUC (area under curve) were used to quantify the compound in solution. % Remaining of compound is calculated compared to the initial quantity at time zero. Half-life is then calculated based on first-order reaction kinetics.

The compounds disclosed herein were generally stable in $H_2O$ and 0.9% NaCl aq solution at 4° C. and 25° C. at pH<4 for 24 hours (decomposition<1.0%).

TABLE 4

| | |
|---|---|
| Sample Solution: | (1) $H_2O$; (2) 0.9% NaCl aq solution; (3) Aqueous Solution with Adjusted pH Values (adjusted with 1.0 M of HCl or $NaHPO_4$ aq solution); (4) 20% aq. $H_2O_2$ |
| Sample Concentration (mg/mL): | (1) 0.1; (2) 0.5; (3) 1.0; (4) 2.5; (5) 5.0; (6) 10.0; (7) 20.0; (8) 50.0; (9) 100.0 |

TABLE 4-continued

| | |
|---|---|
| Temperature: | (1) 4° C.; (2) 25° C.; (3) 25° C. under light (4500 LX); (4) 40° C.; (5) 60° C. |
| Time Point: | (1) 4 h; (2) 8 h; (3) 1 day; (4) 2 day; (5) 3 day; (6) 5 day; (7) 10 day |
| PH Value: | (1) 2; (2) 3; (3) 4; (4) 5; (5) 6; (6) 7; (7) 8 |

Example D

Methods for Determination of Stability in Human Whole Blood

Samples with low (1 μg/mL) and high (10 μg/ml) concentration (stock samples) were prepared by dissolving the compound into fresh human blood. Samples were incubated at 37° C. and aliquots were taken at 0 min, 10 min, 30 min, 1 hour and 3 hours (duplicated samples, 50 μL each). MeOH (100 μL) was added to the aliquots immediately and centrifuged at 11,000 rpm for 10 min. The upper solution layer was separated. Quenched blood samples were stored at −80° C. until analyzed by LC/MS/MS.

Data Analysis

% Remaining of compound is calculated compared to the initial quantity at time zero. Half-life is then calculated based on first-order reaction kinetics (k is decomposition rate constant, $t_{1/2}$=0.693/k).

Some of the compounds disclosed herein exhibited $t_{1/2}$ ranging from 7 to 30 hours.

Example E

Methods for Determination of Stability in Human Liver Microsomes

Human liver microsomes incubations were conducted in duplicate in polypropylene tubes. The typical incubation mixtures consisted of human liver microsomes (0.5 mg protein/mL), compounds of interest (5 μM) and NADPH (1.0 mM) in a total volume of 200 μL potassium phosphate buffer (PBS, 100 mM, pH7.4). Compounds were dissolved in DMSO and diluted with PBS such that the final concentration of DMSO was 0.05%. The enzymatic reactions were commenced with the addition of protein after a 3-min preincubation and incubated in a water bath open to the air at 37° C. Reactions were terminated at various time points (0, 5, 10, 15, 30, 60 min) by adding equal volume of ice-cold acetonitrile. The samples were stored at −80° C. until LC/MS/MS assays.

The concentrations of compounds in the incubation mixtures of human liver microsomes were determined by a LC/MS/MS method. The ranges of the linearity in the concentration range were determined for each tested compounds.

A parallel incubation was performed using denatured microsomes as the negative control, and reactions were terminated at various time points (0, 15, 60 min) after incubation at 37° C.

Dextromethorphan (70 μM) was selected as the positive control, and reactions were terminated at various time points (0, 5, 10, 15, 30, 60 min) after incubation at 37° C. Both positive and negative control samples were included in each assay to ensure the integrity of the microsomal incubation system.

Data Analysis

The concentrations of compounds in human liver microsome incubations were plotted as a percentage of the relevant zero time point control for each reaction. The in vivo $CL_{int}$ were extrapolated (ref: Naritomi Y, Terashita S, Kimura S, Suzuki A, Kagayama A, Sugiyama Y. Prediction of human hepatic clearance from in vivo animal experiments and in vitro metabolic studies with liver microsomes from animals and humans. *Drug Metabolism and Disposition* 2001, 29: 1316-1324.)

The compounds disclosed herein generally exhibited high clearance values ($CL_{int}$>12 mL/min/kg).

Example F

Evaluation of Pharmacokinetics after Oral Dosing of the Compounds in Mice, Rats, Dogs and Monkeys Compounds were assessed in pharmacokinetic studies in mice, rats, dogs or monkeys. The compounds were administered as a water solution or 2% HPMC+1% Tween-80 in water solution. For the intravenous administration, the animals were given at 1 mg/kg dose. For the oral (p.o.) dosing, mice and rats were given 5 mg/kg dose and dogs and monkeys were given 10 mg/kg dose. The blood samples (0.3 mL) were drawn at 0.25, 0.5, 1.0, 2.0, 3.0, 4.0, 6.0, 8.0, 12 and 24 h time points and centrifuged at 3,000 rpm for 10 min. The plasma solutions were collected, stored at −20° C. until analyzed by LC/MS/MS as described above.

The alcohols (the metabolites) were generally the major compounds found in animal's plasma. Parent compounds (amino esters) generally demonstrated low systemic exposure when administrated orally.

Biological Activity

The following representative assays were performed in assessing the biological activities of compounds disclosed herein. They are given to illustrate the invention in a non-limiting fashion.

Example G c-Met Inhibition Assays

In a pilot study, the compounds disclosed herein were screened for their c-Met inhibitory activity. The CycLex Research Product CycLex Met Kinase Assay/Inhibitor Screening Kit, is a single-site, semi-quantitative immunoassay for kinase activity of recombinant catalytic domain of Met and is used for screening the compounds disclosed herein. Plates are pre-coated with a "Tyrosine kinase-substrate-1", which can be easily phosphorylated by recombinant catalytic domain of Met. The detector antibody is PY-39, an antibody that specifically detects the phosphotyrosine residue on "Tyrosine kinase-substrate-1".

To perform the test, the recombinant catalytic domain of Met was diluted in Kinase Buffer, pipetted into the wells and allowed to phosphorylate "Tyrosine kinase-substrate-1" on the wells in the presence of $Mg^{2+}$, $Mn^{2+}$ and ATP. The amount of phosphorylated "Tyrosine kinase-substrate-1" was measured by binding it with a horseradish peroxidase conjugate of PY-39, a anti-phosphotyrosine monoclonal antibody, which then catalyzed the conversion of the chromogenic substrate tetra-methylbenzidine (TMB) from a colorless solution to a blue solution (or yellow after the addition of stopping reagent). The color was quantified by spectrophotometry and reflected the relative amount of Met kinase activity in the sample.

Summary of Procedre

Add 100 μL of reaction mixture to the wells

Incubate for 60 min at 30° C.

Wash the wells

Add 100 μL of HRP conjugated anti-phosphotyrosine antibody

Incubate for 60 min at roon temp.

Wash the wells Add 100 μL of Substrate Reagent

Add 100 μL of Stop Solution

Measure absorbance at 450 nm

All samples and standards were assayed in triplicate. The compounds studied in kinase inhibition assays were alcohols (the metabolites) from the parent amino ester compounds, in addition to the amino esters disclosed herein. The metabolite alcohols generally showed IC50 values of 1 μM or below for inhibition of c-Met, with some compounds inhibiting c-Met with an IC50 below 100 nM.

Example H

Kinase Inhibition Assays

Human C-Met Kinase Assay

Human c-Met is incubated with 8 mM MOPS pH 7.0, 0.2 mM EDTA, 250 μM KKKSPGEYVNIEFG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

Human KDR Kinase Assay

Human KDR is incubated with 8 mM MOPS pH 7.0, 0.2 mM EDTA, 0.33 mg/mL myelin basic protein, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

The above kinase assays and others can be carried out at Millipore's KinaseProfiler Service, Billerica, Mass., US.

The alcohols (the metabolites) from the amino ester compounds disclosed herein generally showed IC50 values for inhibition of c-Met and KDR of 2 μM or below, with some alcohols inhibiting c-Met and KDR with an IC50 below 100 nM.

Example I

Human Xenograft Tumor Models

Human U87MG Glioblastoma Xenograft Tumor Model

In a pilot study, the efficacy of compounds disclosed herein was evaluated in a standard murine model of tumorigenesis. Human tumor cells were generated with human glioblastoma cells (U87MG cells, ATCC) and were grown as subcutaneous tumors in 6-7 week old female nude mice (BALB/cA nu/nu, Shanghai SLAC Laboratory Animal, Co.) (n=10 for vehicle group, n=8 for each dosing group). When tumors reached a volume of 100-200 mm$^3$, animals were randomly divided into vehicle control (2% HPMC+1% Tween-80 in water) and compound groups. Subsequent administration of compound by oral gavage (10-100 mpk/dose, dissolved in purified water or 2% HPMC+1% Tween-80 in water) begins anywhere from day 0 to day 15 post tumor cell challenge and generally continues with once a day for the duration of the experiment.

Human MKN45 Gastric Adenocarcinoma Xenograft Tumor Model

Xenografts were also generated with human gastric tumor cells (MKN45 cells, ATCC) and were grown as subcutaneous tumors in 6-7 week old female nude mice (BALB/cA nu/nu, Shanghai SLAC Laboratory Animal, Co.) (n=10 for vehicle group, n=8 for each dosing group). When tumors reached a volume of 60-150 mm$^3$, animals were randomly divided into vehicle control (2% HPMC+1% Tween-80 in water) and compound groups. Subsequent administration of compound by oral gavage (10-60 mpk/dose, dissolved in purified water or 2% HPMC+1% Tween-80 in water) begins anywhere from day 0 to day 15 post tumor cell challenge and generally continues with once a day for the duration of the experiment.

Tumor Growth Inhibition (TGI) Analysis

Progression of tumor growth is assessed by tumor volumes and recorded as a function of time. The long (L) and short (W) axes of the subcutaneous tumors were measured with calipers twice weekly, and the tumor volume (TV) calculated as (L×W$^2$)/2). TGI was calculated from the difference between the median tumor volumes of vehicle-treated and drug-treated mice, expressed as a percentage of the median tumor volume of the vehicle-treated control group, by the following relation:

$$\%\ TGI = \left(\frac{\text{Median Tumor } Volume_{control} - \text{Median Tumor } Volume_{drug\text{-}treated}}{\text{Median Tumor } Volume_{control}}\right) \times 100$$

Initial statistical analysis is done by repeated measures analysis of variance (RMANOVA). Followed by Scheffe psot hoc testing for multiple comparisons. Vehicle alone (2%

HPMC+1% Tween-80, or the like) is the negative control. Compounds disclosed herein were generally active at or less than 100 mpk.

Example 53 was administrated orally (p.o.) at doses of 10, 30 and 100 mg/kg once a day (QD), for 21 consecutive days. All doses produced statistically significant, dose-dependent inhibition of growth of U87MG tumors grown subcutaneously in athymic nude mice. On the last day of treatment (Day 21), the 10, 30 and 100 mg/kg doses decreased mean tumor volume by 47%, 76%, and 99% (TGI), respectively, compared to the mean tumor volume of the vehicle-treated group.

Example 72 was administrated orally (p.o.) at doses of 10, 30 and 60 mg/kg once a day (QD), for 18 consecutive days. All doses produced statistically significant, dose-dependent inhibition of growth of MKN45 tumors grown subcutaneously in athymic nude mice. On the last day of treatment (Day 18), the 10, 30 and 60 mg/kg (dosed from days 0-10 and days 13-18) doses decreased mean tumor volume by 29%, 62%, and 87% (TGI), respectively, compared to the mean tumor volume of the vehicle-treated group.

Finally, it should be noted that there are alternative ways of implementing the present invention. Accordingly, the present embodiments are to be considered as illustrative and not restrictive and the invention is not be limited to the details given herein, but may be modified within the scope and equivalents of the appended claims. All publications and patents cited herein are incorporated by reference.

What is claimed is:

1. A compound of the Formula (I):

Formula (I)

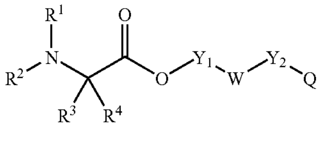

or a recemic mixture, a diastereoisomer, an enantiomer, a geometric isomer, a tautomer, an N-oxide, or a pharmaceutically acceptable salt thereof, wherein:

each of $R^1$, $R^2$, $R^3$ and $R^4$ is independently H, —C(=O)$R^{11}$, —C(=O)O$R^{11}$, —C(=O)—N$R^{11}R^{11a}$, $R^{11}R^{11a}$N—$O_2$S—, $R^{11}O_2$S—, $R^{11a}R^{11}$N-alkyl, $R^{11}$O-alkyl, aliphatic, haloaliphatic, arylaliphatic, heterocyclyl aliphatic, cycloalkyl aliphatic, aryl, heteroaryl, heterocyclyl, or carbocyclyl, with the proviso that $R^1$ and $R^2$, together with the nitrogen atom they are attached to, optionally form a substituted or unsubstituted 3-8 membered heterocyclic ring; and $R^3$ and $R^4$, together with the carbon atom they are attached to, optionally form a substituted or unsubstituted 3-8 membered carbocyclic or heterocyclic ring;

each of $Y_1$ and $Y_2$ is independently a divalent group derived from aliphatic-C(=O)—, aliphatic-C(=O)O—, aliphatic-C(=O)N$R^{11}$—, —$R^{11}$N—$O_2$S-aliphatic, —$O_2$S—, —$R^{11}$N-aliphatic, —S(=O)-aliphatic, or —$R^{11}$N—C(=O)-aliphatic; or fused bicyclylalkylene, fused hetero-bicyclyl alkylene, spiro bicyclylalkylene, spiro heterobicyclyl alkylene, arylalkylene, heteroarylalkylene, alkylene; haloalkylene, heterocyclylene, carbocyclylene, heterocyclylalkylene, carbocyclylalkylene, fused bicyclylene, fused heterobicyclylene, spiro bicyclylene, spiro heterobicyclylene, arylene, or heteroarylene;

W is O, N—$R^{11}$ or $(CR^{12}R^{12a})$m; m is 0, 1, 2 or 3;

Q is:

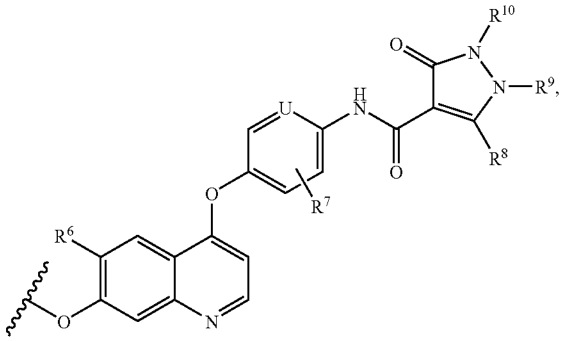

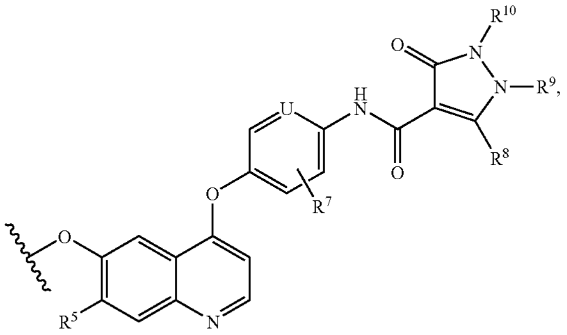

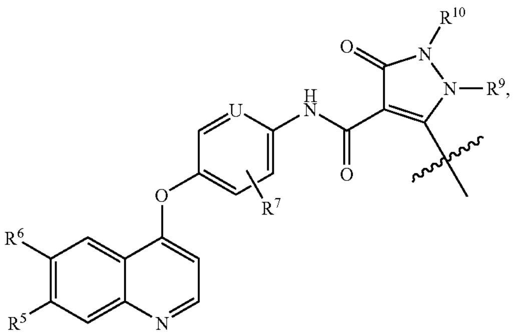

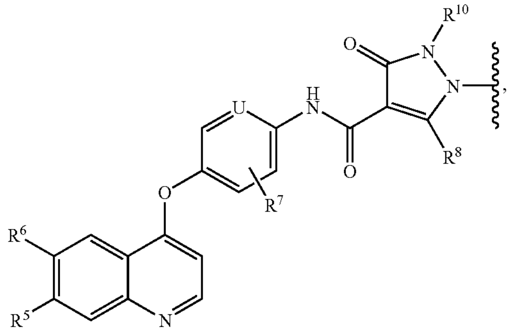

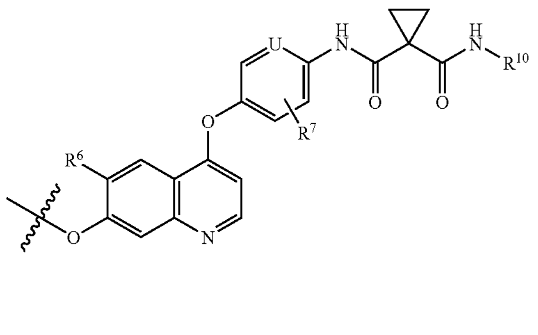

or

-continued

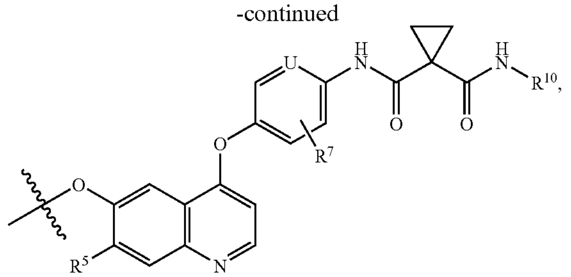

wherein U is $CR^{12}$ or N;

each of $R^5$, $R^6$ is independently H, F, Cl, Br, I, —CN, hydroxyl, $R^{11a}R^{11}N$—, —C(=O)—$R^{11}$, —C(=O)—$OR^{11}$, —C(=O)$NR^{11}R^{11a}$, —OC(=O)$NR^{11}R^{11a}$, —OC(=O)$OR^{11}$, —$NR^{11}$C—(=O)$NR^{11}R^{11a}$, —$NR^{11}$C(=O)$OR^{11a}$, —$NR^{11}$C(=O)—$R^{11a}$, $R^{11}R^{11a}N$—$O_2S$—, $R^{11}O_2S$—, $R^{11}O_2S$—$R^{11a}N$—, $R^{11a}R^{11}N$-alkyl, $R^{11}$(S=O)-alkyl, $R^{11}R^{11a}N$—(C=O)-alkyl, $R^{11a}R^{11}N$-alkoxy, $R^{11}$(S=O)-alkoxy, $R^{11}R^{11a}N$—(C=O)-alkoxy, aliphatic, alkoxy, hydroxy-alkoxy, amino-alkoxy, hydroxy-substituted aminoalkoxy, haloalkoxy, amino-substituthed haloalkoxy, alkylamino haloalkoxy, hydroxy-substituted haloalkoxy, alkylaminoalkoxy, alkoxy-alkoxy, arylalkoxy, heterocyclylalkoxy, carbocyclylalkoxy, heterocyclyl(hydroxy-alkoxy), carbocyclyl(hydroxyalkoxy), aryl(hydroxyalkoxy), aryloxyalkoxy, aryloxy, heterocyclyloxyalkoxy, carbocyclyloxyalkoxy, heterocyclyloxy, cycloalkyloxy, (heterocyclo)hydroxyalkoxy, azidoalkoxy, fused bicyclyl, fused heterobicyclyl, fused bicyclyl aliphatic, fused heterobicyclyl aliphatic, fused bicycloxy, fused heterobicycloxy, fused bicycloxoalkoxy, fused heterobicycloxoalkoxy, fused bicyclyl aminoalkoxy, fused hetero-bicyclyl aminoalkoxy, spiro bicyclyl, spiro heterobicyclyl, spiro bicyclyl aliphatic, spiro heterobicyclyl aliphatic, spiro bicycloxy, spiro heterobicycloxy, spiro bicycloxo-alkoxy, spiro heterobicycloxoalkoxy, spiro bicyclylaminoalkoxy, spiro heterobicyclyl-aminoalkoxy, aryl, heteroaryl, arylaliphatic or heteroarylaliphatic;

$R^7$ is one or more substituents independently selected at each occurrence from H, F, Cl, Br, I, —CN, hydroxyl, $R^{11a}R^{11}N$—, aliphatic, alkoxy, haloalkyl, hetero-cyclyl, heterocyclylalkyl, cycloalkyl, cycloalkylalkyl, cycloalkylalkoxy, and heterocyclylalkoxy;

each of $R^8$, $R^9$ and $R^{10}$ is independently H, —C(=O)$R^{11}$, —C(=O)$OR^{11}$, —C(=O)—$NR^{11}R^{11a}$, $R^{11}R^{11a}N$—$O_2S$—, $R^{11}O_2S$—, $R^{11a}R^{11}N$-alkyl, $R^{11}$(S=O)-alkyl, $R^{11}R^{11a}N$(C=O)-alkyl, aliphatic, hydroxyalkyl, hydroxy-substituted aminoalkyl, haloalkyl, amino-substituthed haloalkyl, alkylamino haloalkyl, hydroxy-substituted haloalkyl, alkoxyalkyl, arylalkyl, heterocyclylalkyl, carbocyclylalkyl, heterocyclyl-hydroxyalkyl, carbocyclyl-hydroxyalkyl, aryl-hydroxyalkyl, aryloxyalkyl, heterocyclyloxyalkyl, carbocyclyloxy-alkyl, heterocyclylyl, cycloalkylyl, (heterocyclo)hydroxy-alkyl, azidoalkyl, fused bicyclyl, fused heterobicyclyl, fused bicyclyl aliphatic, fused heterobicyclyl aliphatic, fused bicycloxoalkyl, fused heterobicycloxoalkyl, fused bicyclyl aminoalkyl, fused heterobicyclyl aminoalkyl, spiro bicyclyl, spiro heterobicyclyl, spiro bicyclyl aliphatic, spiro heterobicyclyl aliphatic, spiro bicycloxoalkyl, spiro hetero-bicycloxoalkyl, spiro bicyclylaminoalkyl, spiro heterobicyclylaminoalkyl, aryl, heteroaryl, arylaliphatic or heteroarylaliphatic;

each of $R^{11}$ and $R^{11a}$ is independently H, aliphatic, haloaliphatic, hydroxy-aliphatic, aminoaliphatic, alkoxyaliphatic, alkylaminoaliphatic, alkylthio-aliphatic, aryl-aliphatic, heterocyclylaliphatic, cycloalkylaliphatic, aryl, heteroaryl, heterocyclyl, or carbocyclyl, with th eproviso that where $R^{11}$ and $R^{11a}$ are bonded to the same nitrogen atom, $R^{11}$ and $R^{11a}$, together with the nitrogen atom they are attached to, optionally form a substituted or unsubstituted 3-8 membered ring, comprising a spiro ring or a bicyclic ring; and each of $R^{12}$ and $R^{12a}$ is independently H, F, Cl, Br, I, —CN, hydroxyl, —$NR^{11a}R^{11}$, —OC(=O)$R^{11}$, —C(=O)$R^{11}$, —C(=O)$OR^{11}$, —C(=O)$NR^{11}R^{11a}$, —OC(=O)$NR^{11}R^{11a}$, —OC(=O)$OR^{11}$, —$NR^{11}$C(=O)$NR^{11}R^{11a}$, —$NR^{11}$C(=O)$OR^{11a}$, —$NR^{11}$—C(=O)—$R^{11a}$, $R^{11}R^{11a}N$—$O_2S$—, $R^{11}O_2S$—, $R^{11}O_2S$—N($R^{11a}$)—, alkoxy, cycloalkoxy, heterocycloalkoxy, aliphatic, haloaliphatic, hydroxyaliphatic, aminoaliphatic, alkoxyaliphatic, alkylaminoaliphatic, alkylthioaliphatic, arylaliphatic, heterocyclyl-aliphatic, cycloalkylaliphatic, aryl, heteroaryl, heterocyclyl, or carbocyclyl, with the proviso that where $R^{12}$ and $R^{12a}$ are bonded to the same carbon atom, $R^{12}$ and $R^{12a}$, together with the carbon atom they are attached to, optionally form a substituted or unsubstituted 3-8 membered carbocyclic or heterocyclic ring.

2. The compound according to claim 1, wherein the pharmaceutically acceptable salt is a salt with hydrochloric acid, hydrobromic acid, sulfuric acid, nitric acid, phosphoric acid, acetic acid, maleic acid, succinic acid, mandelic acid, fumaric acid, malonic acid, malic acid, 2-hydroxypropanic acid, pyruvic acid, oxalic acid, glycolic acid, salicylic acid, glucuronic acid, galacturonic acid, citric acid, tartaric acid, aspartic acid, glutamic acid, benzoic acid, cinnamic acid, p-toluenesulfonic acid, benzenesulfonic acid, mthanesulfonic acid, ethanesulfonic acid, trifluoromthanesulfonic acid, or a combination thereof.

3. The compound according to claim 1, wherein the α-amino acetyl group defined by $R^1$, $R^2$, $R^3$ and $R^4$ of Formula (I) is derived from a naturally occurring and commercially available α-amino acid or an optically isomer thereof.

4. The compound according to claim 3, wherein the natural and commercially available α-amino acid is isoleucine, leucine, lysine, methionine, phenylalanine, threonine, tryptophan, valine, alanine, asparagine, aspartate, glutamate, glutamine, proline, serine, para-tyrosine, arginine, histidine, cysteine, glycine, sarcosine, N,N-dimethyl glycine, homoserine, norvaline, norleucine, ornithine, homocysteine, homophenylalanine, phenylglycine, ortho-tyrosine, meta-tyrosine or hydroxyproline.

5. The compound according to claim 4, wherein the natural α-amino acid is isoleucine, leucine, lysine, methionine, phenylalanine, threonine, tryptophan, valine, alanine, asparagine, aspartate, glutamate, glutamine, proline, serine, tyrosine, arginine, or histidine, each of which has a S-configuration at the α-position.

6. The compound according to claim 4, wherein the natural and commercially available α-amino acid is the cysteine having a R-configuration at its α-position.

7. The compound according to claim 4, wherein the natural and commercially available α-amino acid is glycine, sarcosine or N,N-dimethyl glycine, each of which is a non-chiral compound.

8. The compound according to claim 1, wherein each of $Y_1$ and $Y_2$ is independently a divalent group derived from $C_{1-6}$aliphatic-C(=O)—, $C_{1-6}$aliphatic-C(=O)O—, $C_{1-6}$aliphatic-C(=O)$NR^{11}$—, —$R^{11}N$—$O_2SC_{1-6}$aliphatic, —$O_2S$—

$C_{1-6}$aliphatic, —$R^{11}NC_{1-6}$aliphatic, —S(═O)$C_{1-6}$ aliphatic, or —$R^{11}$N—C(═O)—$C_{1-6}$aliphatic; or fused $C_{6-10}$bicyclyl $C_{1-6}$alkylene, fused $C_{5-9}$ hetero-bicyclyl $C_{1-6}$ alkylene, spiro $C_{7-11}$bicyclyl $C_{1-6}$ alkylene, spiro $C_{6-10}$heterobicyclyl $C_{1-6}$ alkylene, $C_{1-6}$haloalkylene, $C_{2-8}$heterocyclylene, $C_{3-8}$carbocyclylene, $C_{2-8}$heterocyclyl $C_{1-6}$ alkylene, $C_{3-8}$carbocyclyl $C_{1-6}$alkylene, fused $C_{6-10}$bicyclylene, fused $C_{5-9}$heterobicyclyl-ene, spiro $C_{7-11}$bicyclylene, or spiro $C_{6-10}$heterobicyclylene;

W is O, N—$R^{11}$ or $(CR^{12}R^{12a})$m; m is 0, 1 or 2;

Q is:

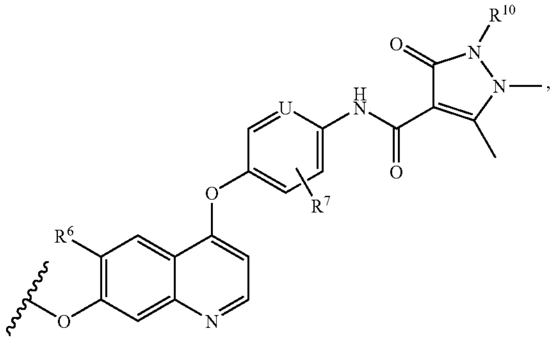

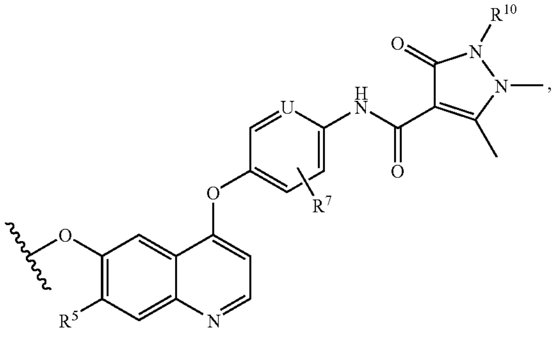

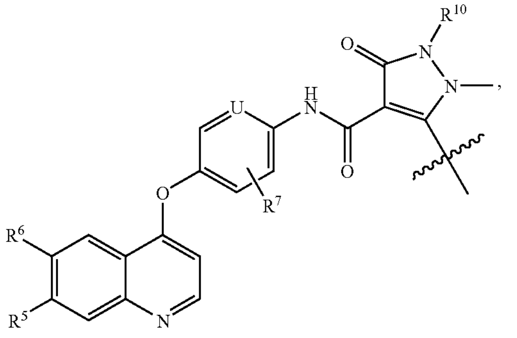

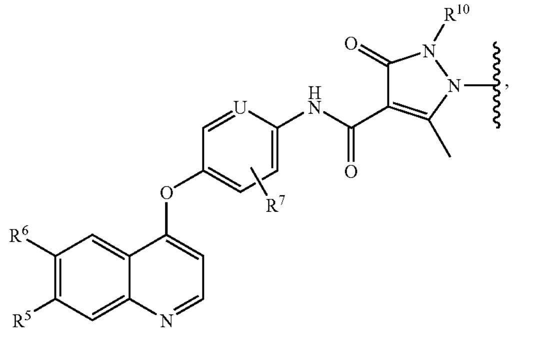

-continued

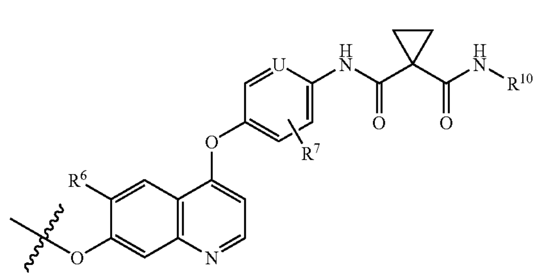

or

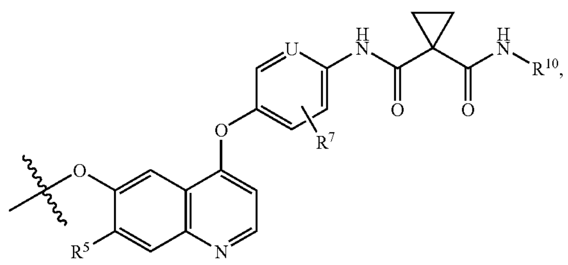

wherein U is CH or N;

Each of $R^5$ and $R^6$ is independently H or methoxy;

$R^7$ is H or F;

$R^{10}$ is phenyl or fluorophenyl;

Each of $R^{11}$ and $R^{11a}$ is independently H, $C_{1-3}$alkyl, $C_{1-3}$haloalkyl, $C_{1-3}$ hydroxy-alkyl, $C_{1-3}$aminoalkyl, $C_{1-3}$alkoxy $C_{1-3}$alkyl, $C_{1-3}$ alkylamino $C_{1-3}$alkyl, $C_{6-10}$aryl $C_{1-3}$alkyl, $C_{5-9}$heterocyclyl $C_{1-3}$alkyl, $C_{3-6}$cycloalkyl $C_{1-3}$alkyl, $C_{6-10}$aryl, $C_{5-9}$heteroaryl, $C_{2-5}$ hetero-cyclyl, or $C_{3-6}$carbocyclyl, with the proviso that where $R^{11}$ and $R^{11a}$ are bonded to the same nitrogen atom, $R^{11}$ and $R^{11a}$ together with the nitrogen atom they are attached to, optionally form a substituted or unsubstituted 3-8 membered ring, comprising a spiro ring or a fused bicyclic ring; and Each of $R^{12}$ and $R^{12a}$ is independently H, F, Cl, Br, I, hydroxyl, —$NR^{11a}R^{11}$, —OC(═O)$R^{11}$, —C(═O)$R^{11}$, —C(═O)$OR^{11}$, —C(═O)$NR^{11}R^{11a}$, —OC(═O)$NR^{11}R^{11a}$, —OC(═O)$OR^{11}$, —$NR^{11}$C(═O)$NR^{11}R^{11a}$, —$NR^{11}$C(═O)$OR^{11a}$, —$NR^{11}$C(═O)—$R^{11a}$, $R^{11}R^{11a}$N—$O_2$S—, $R^{11}O_2$S—, $R^{11}R^{11a}O_2$SN—, —CN, hydroxyl, $C_{1-6}$alkoxy, $C_{3-6}$cycloalkoxy, $C_{2-5}$ hetero-cyclo $C_{1-6}$alkoxy, $C_{1-6}$aliphatic, $C_{1-6}$haloaliphatic, hydroxy $C_{1-6}$aliphatic, amino $C_{1-6}$ aliphatic, $C_{1-6}$alkoxy $C_{1-6}$aliphatic, $C_{1-6}$alkylamino $C_{1-6}$aliphatic, $C_{1-6}$alkylthio $C_{1-6}$aliphatic, $C_{6-10}$aryl $C_{1-6}$aliphatic, $C_{1-9}$ heteroaryl $C_{1-6}$aliphatic, $C_{2-5}$heterocyclyl $C_{1-6}$ aliphatic, $C_{3-6}$cycloalkyl $C_{1-6}$aliphatic, $C_{6-10}$aryl, $C_{1-9}$heteroaryl, $C_{2-5}$heterocyclyl, or $C_{3-6}$ carbocyclyl, with the proviso that where $R^{12}$ and $R^{12a}$ are bonded to the same carbon atom, $R^{12}$ and $R^{12a}$, together with the carbon atom they are attached to, optionally form a substituted or unsubstituted 3-8 membered carbocyclic or heterocyclic ring.

9. The compound according to claim 1, wherein Q is:
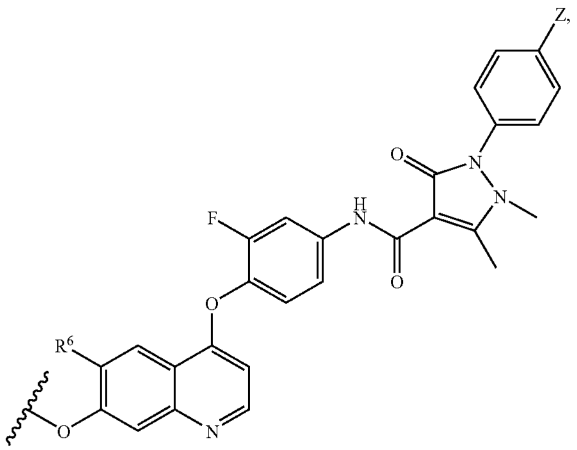
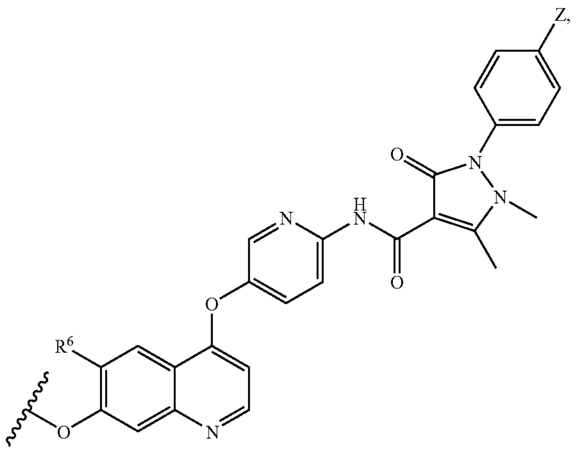
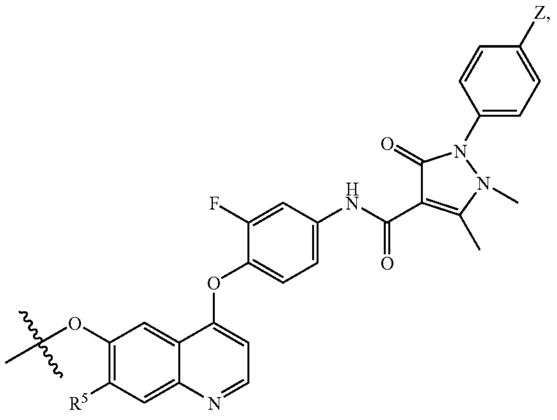
-continued
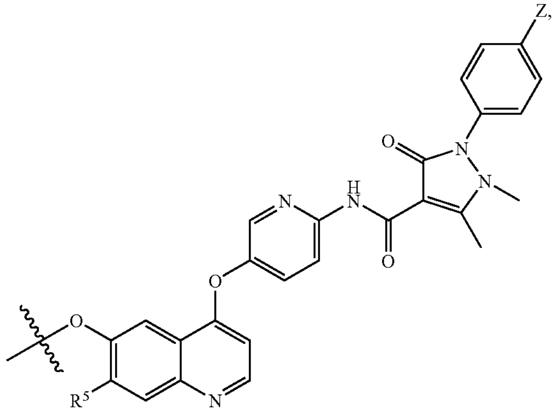
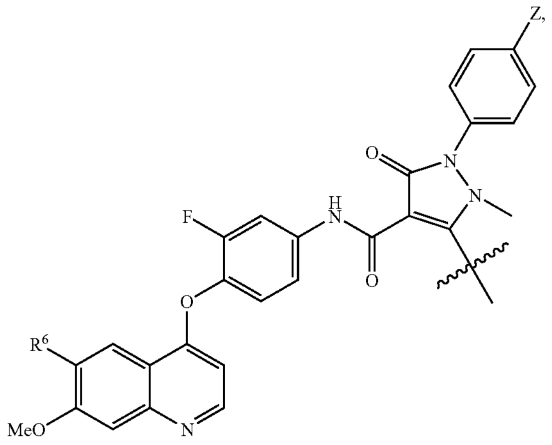
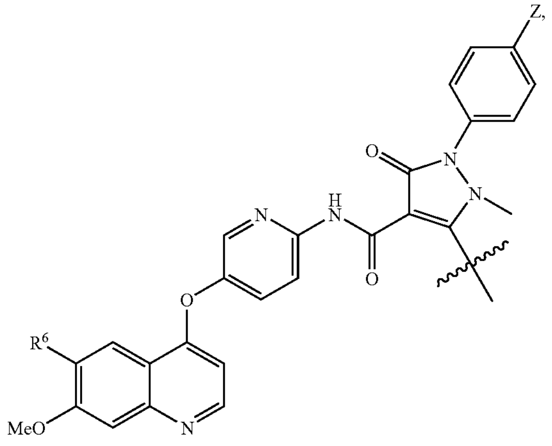

-continued
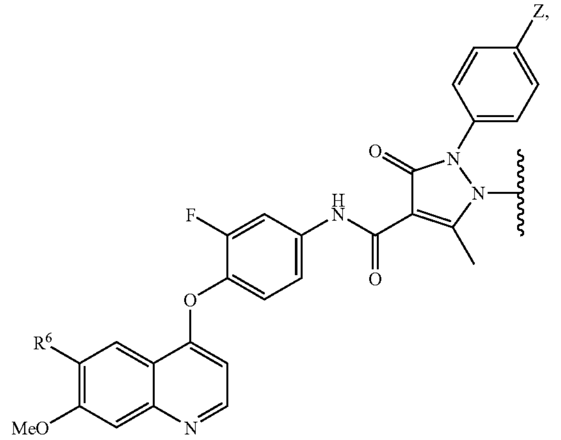
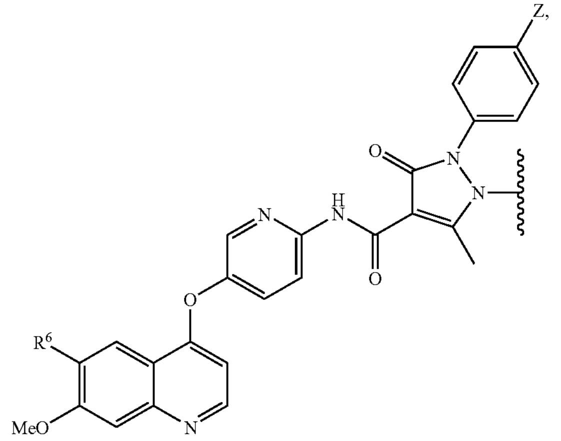
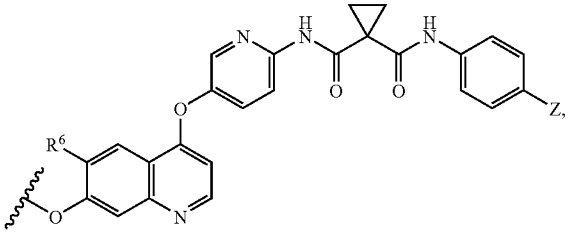
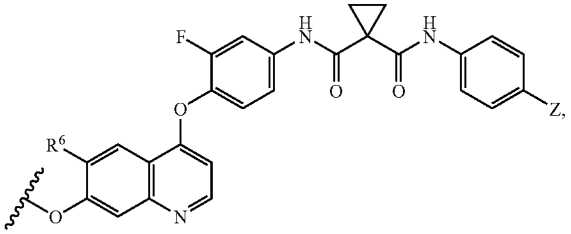
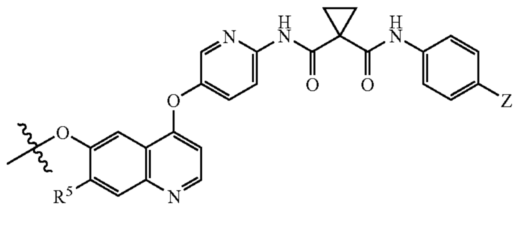
or
-continued
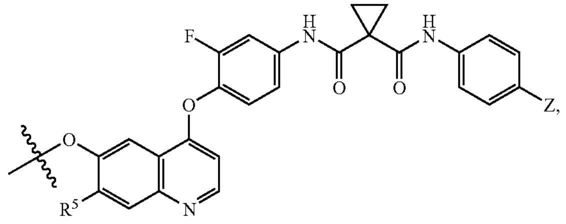
wherein each of $R^5$ and $R^6$ is independently H or OMe; Z is H or F.
10. The compound according to claim 1, wherein the substructure defined by $Y_1$, $Y_2$, W and Q is:
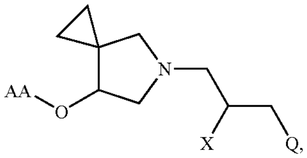
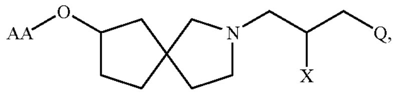
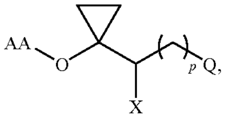
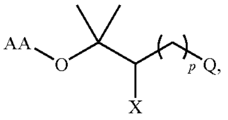
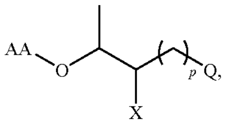
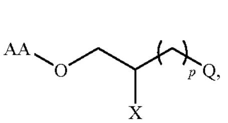
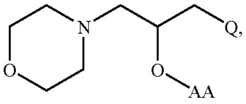
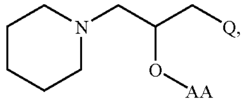
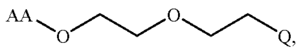
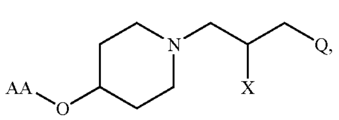
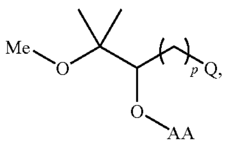
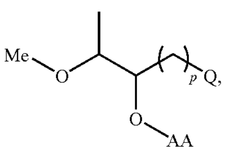
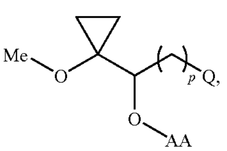
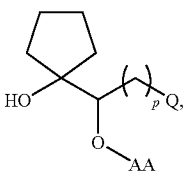
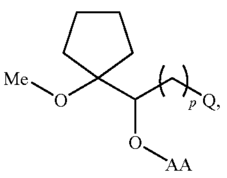
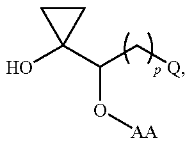
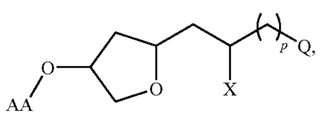

-continued
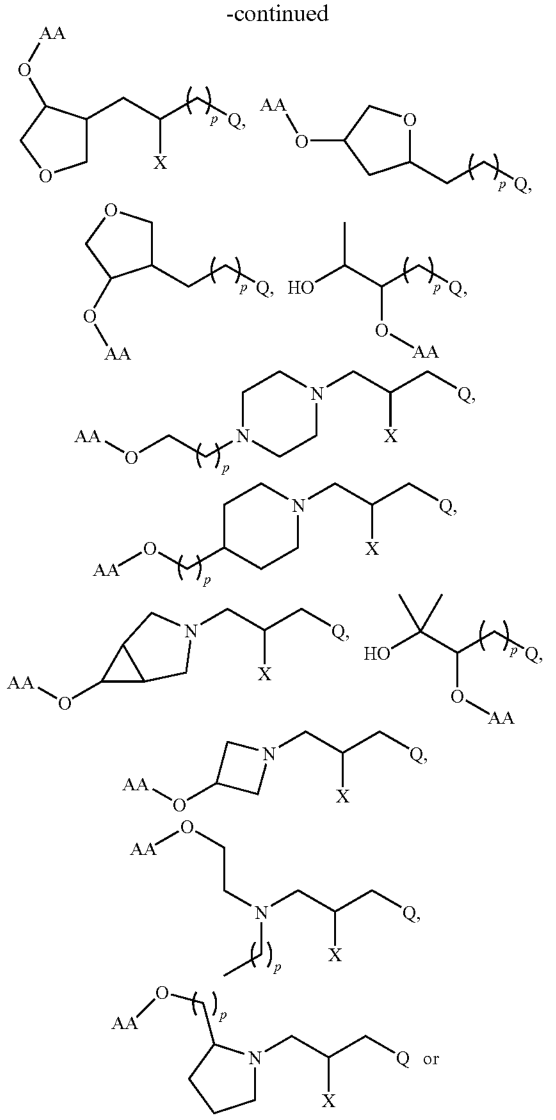
or
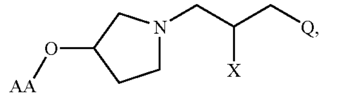
wherein AA is an amino acetyl moiety defined by $R^1$, $R^2$, $R^3$ and $R^4$; X is H or OH; p is 0, 1, 2 or 3.
11. The compound of claim 1 having one of the following structures:
(1)
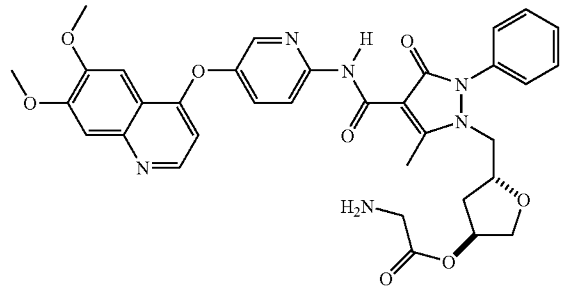
-continued
(2)
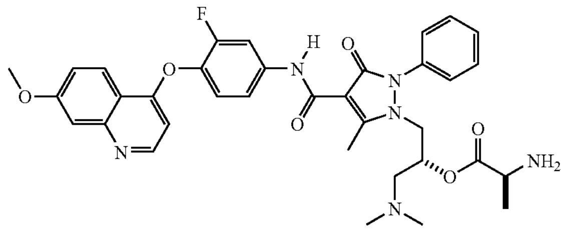
(3)
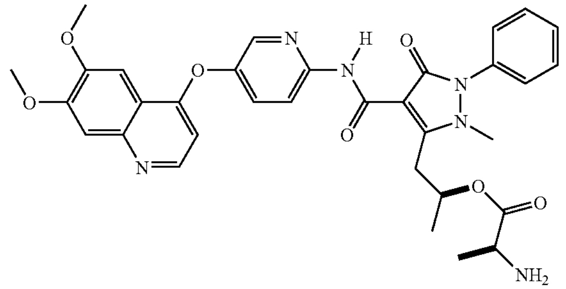
(4)
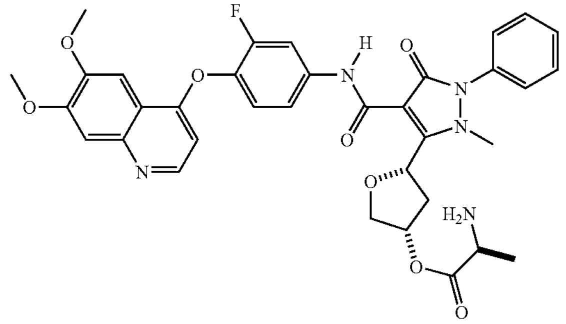
(5)
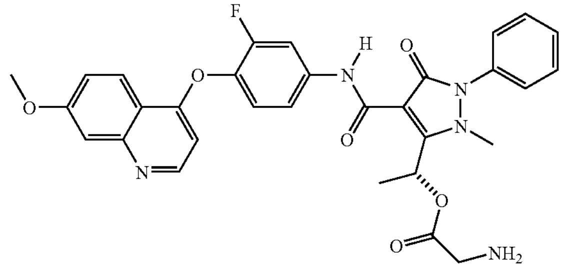
(6)
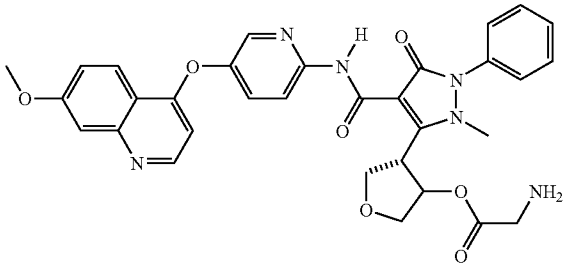

-continued
(7)
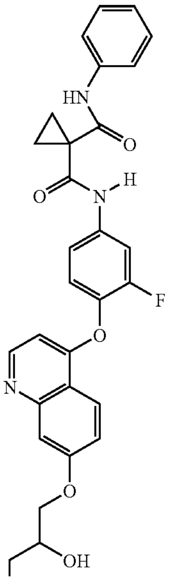
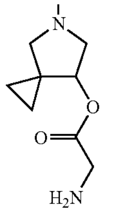
(8)
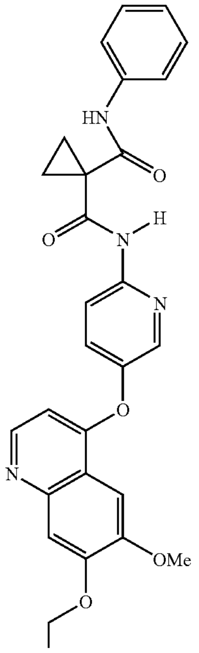
-continued
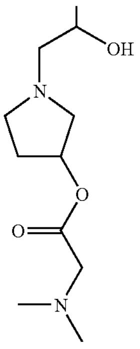
(9)
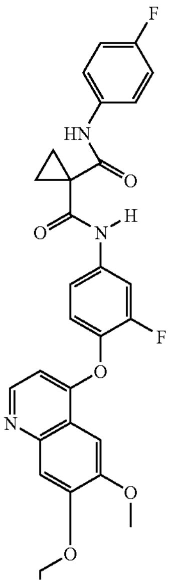
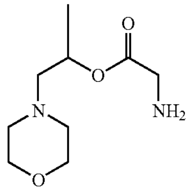

-continued
(10)
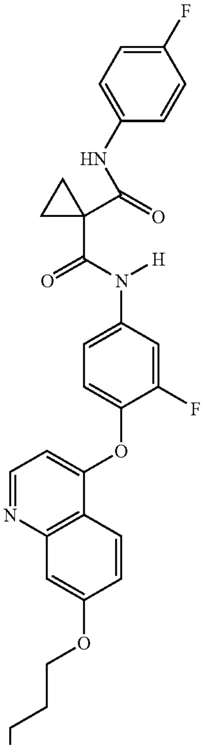
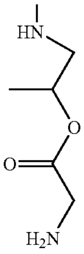
(11)
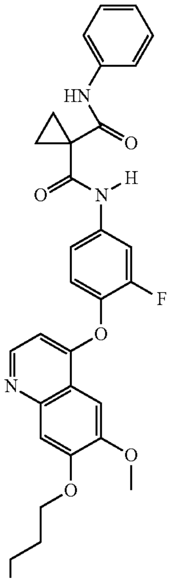
-continued
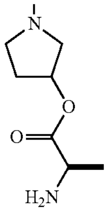
(12)
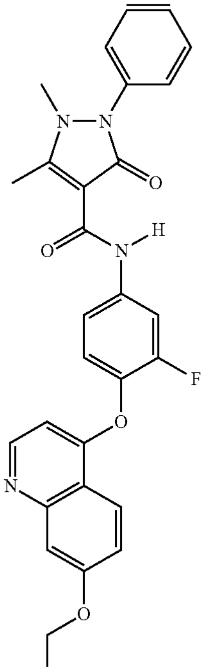
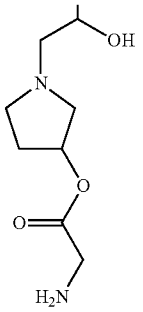

-continued
(13)
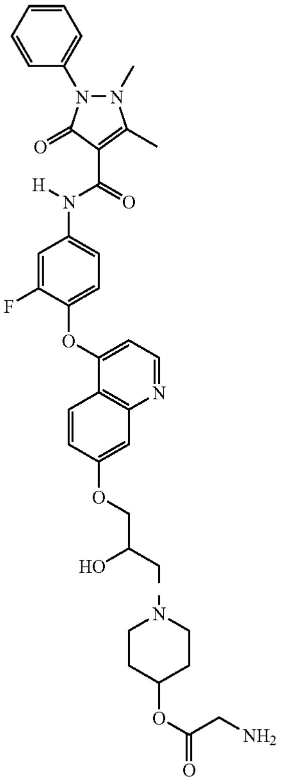
(14)
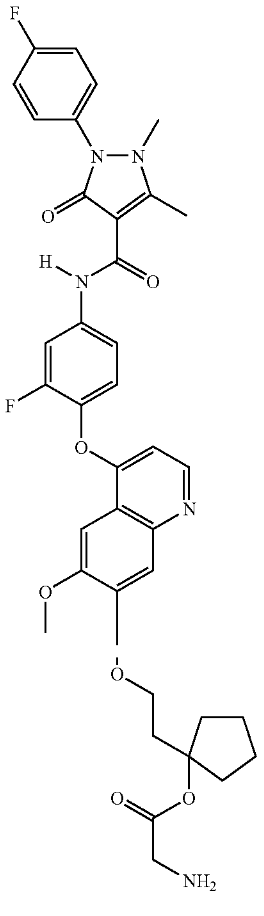
-continued
(15)
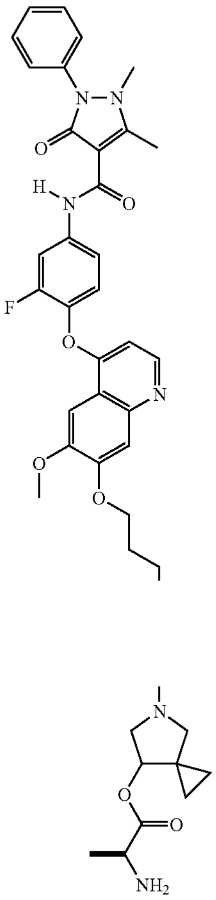
(16)
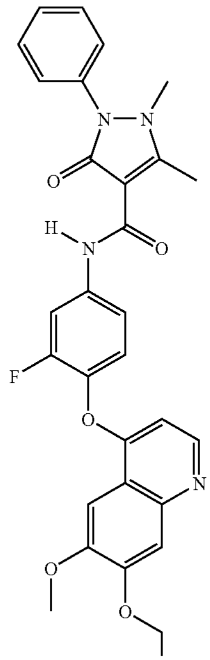

-continued
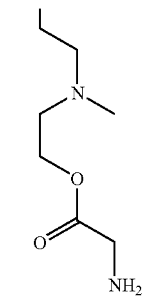
(17)
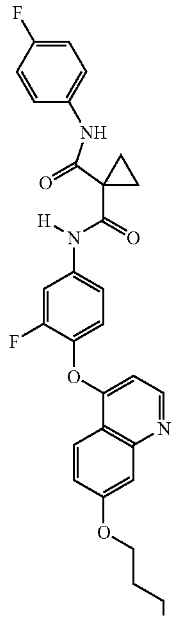
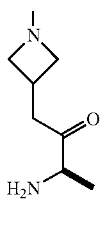
-continued
(18)
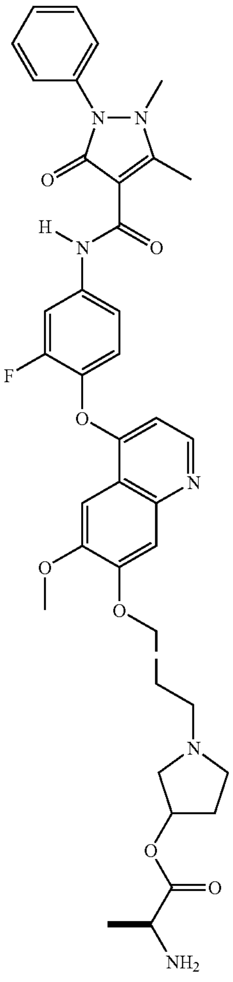
(19)
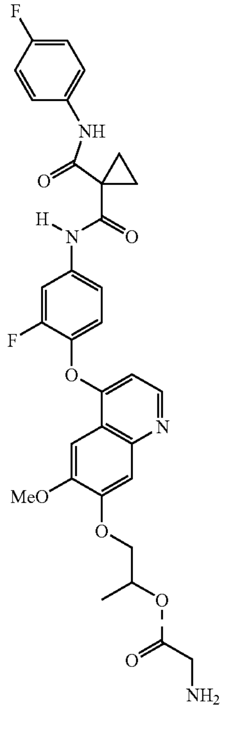

-continued
(20)
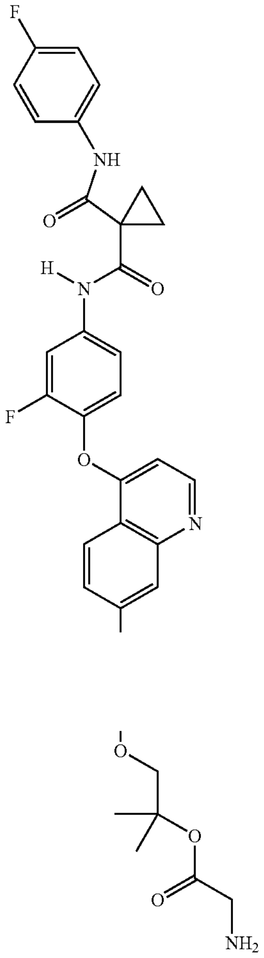
(21)
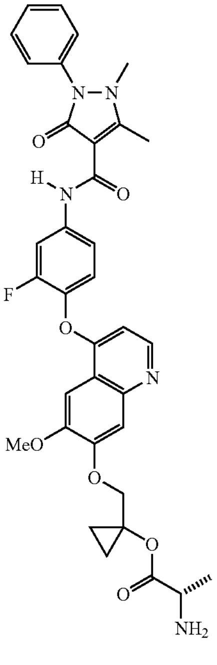
-continued
(22)
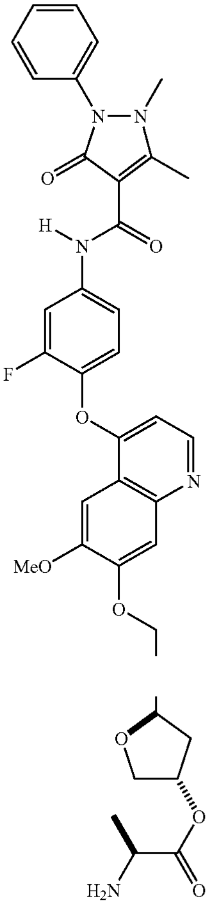
(23)
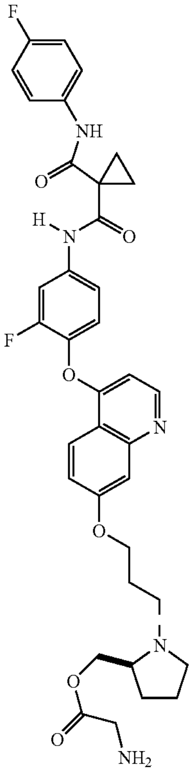

-continued
(24)
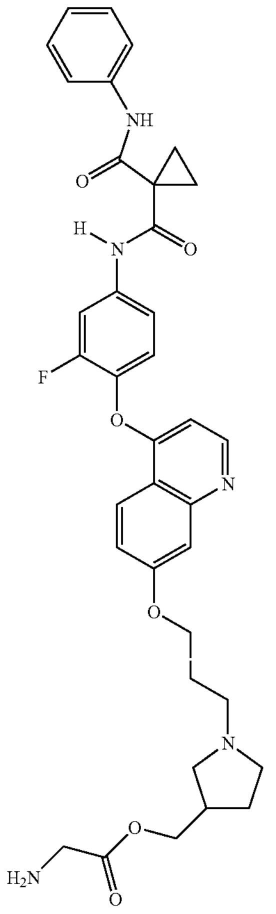
-continued
(25)
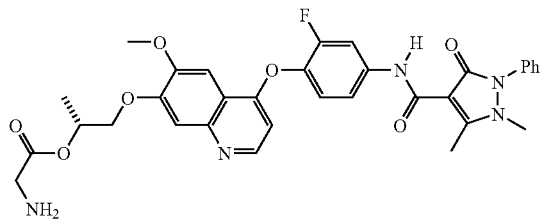
and
(26)
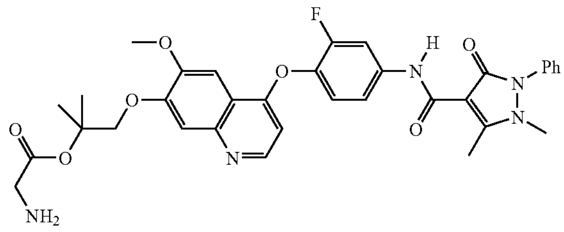
or a pharmacetical acceptable salt thereof.
12. A compound according to claim 1, wherein the compound has one of the following structures:
(Example 1)
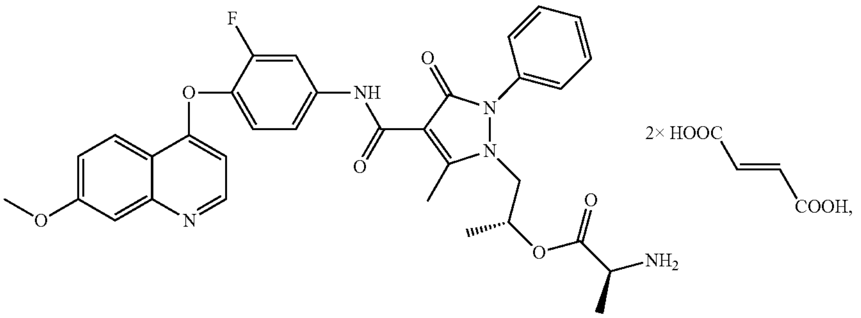
(Example 2)
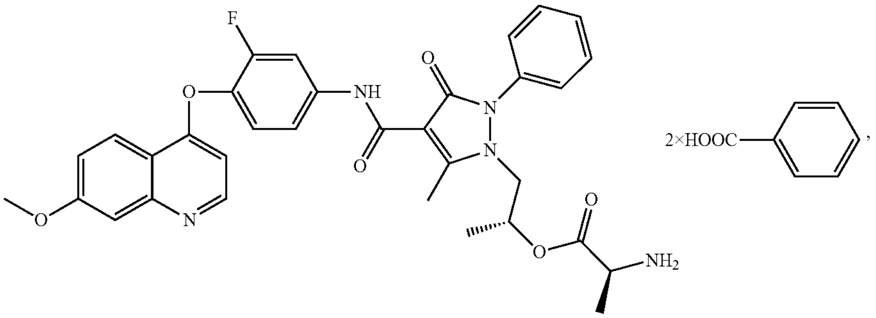

-continued
(Example 3)
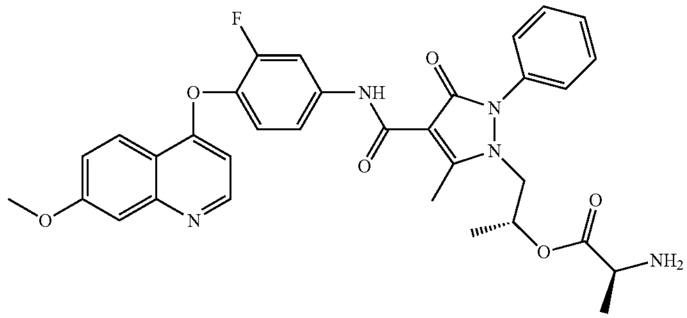
2 × $CH_3SO_3H$,
(Example 4)
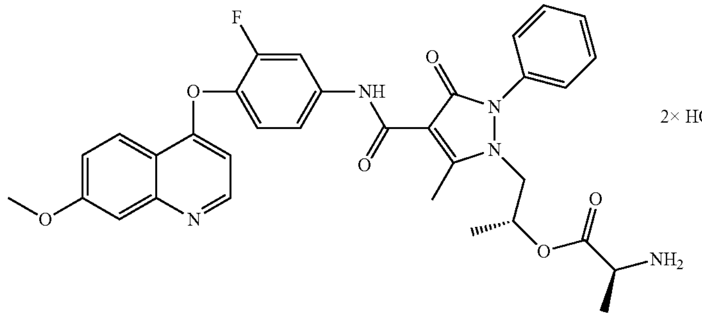
2× 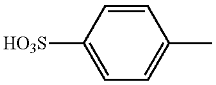 ,
(Example 5)
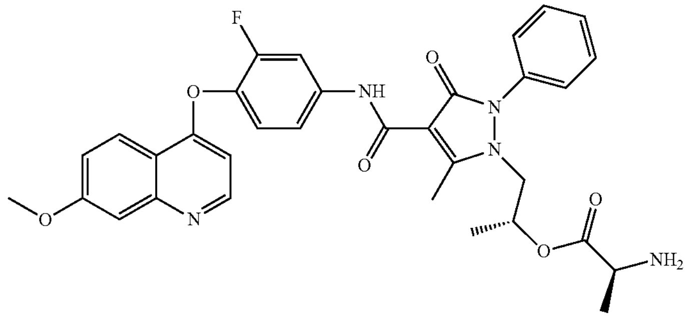
HOOC—$CH_2OOH$,
(Example 6)
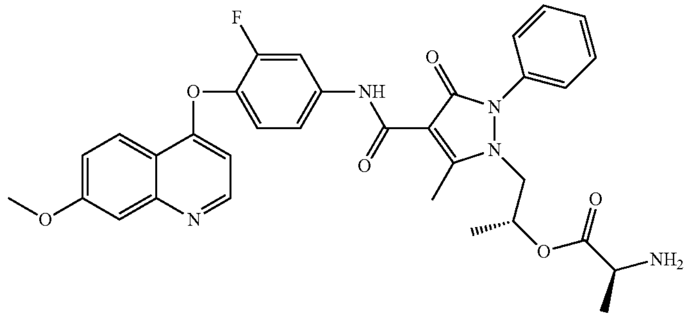
2.5 × 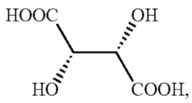
(Example 7)
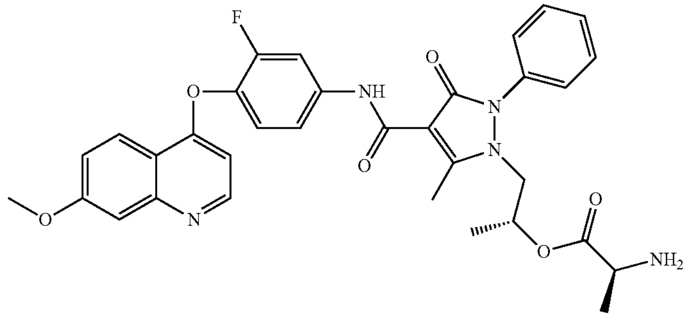
2 × HCl, -continued
(Example 8)
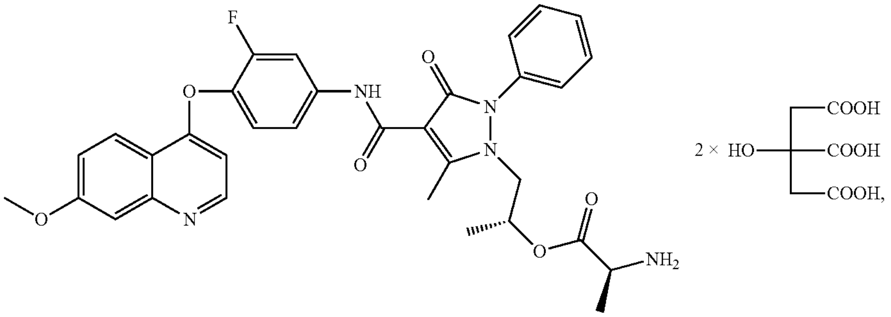
(Example 9)
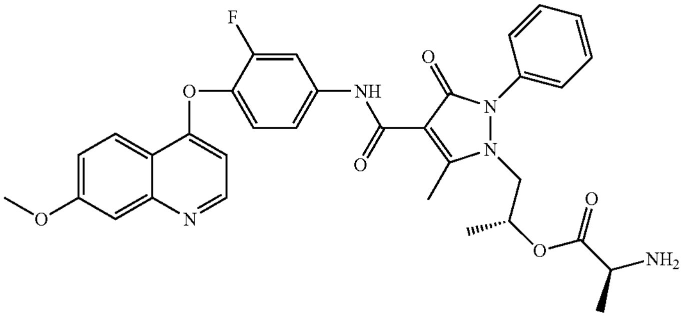
$H_2SO_4$,
(Example 10)
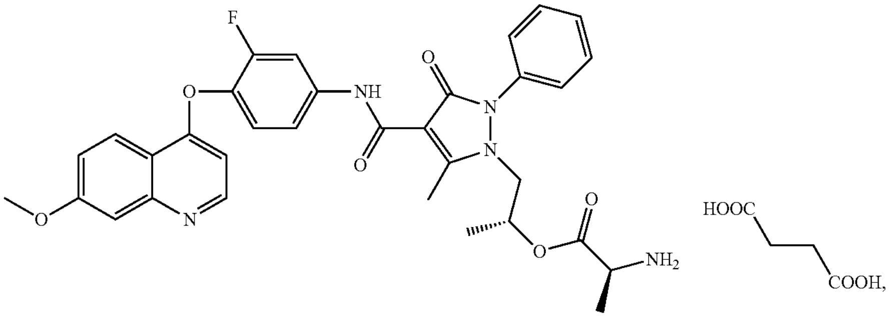
(Example 11)
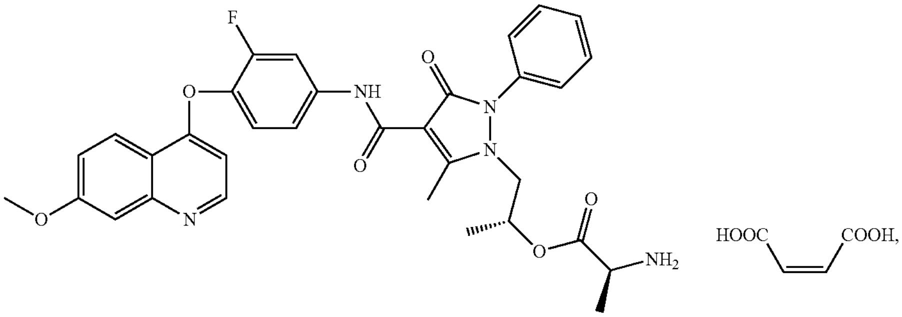
(Example 12)
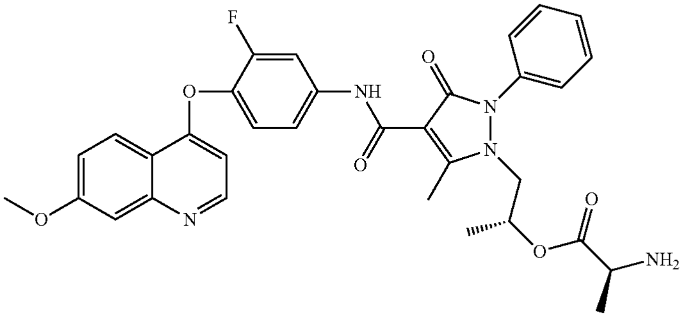
$H_3PO_4$, -continued
(Example 13)
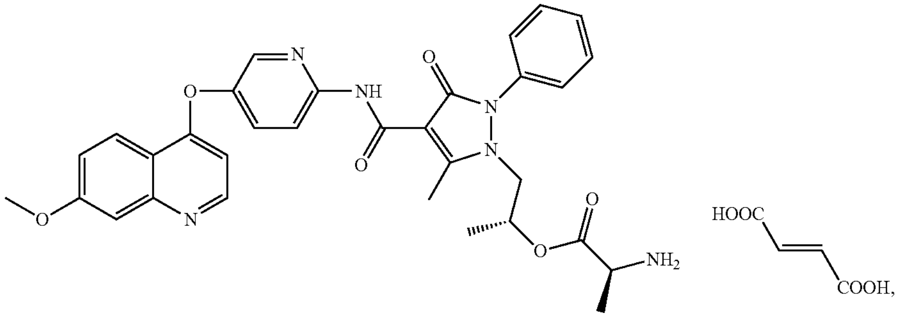
(Example 14)
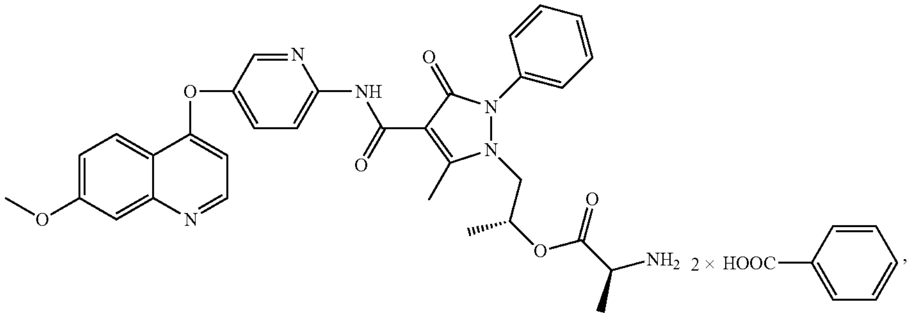
(Example 15)
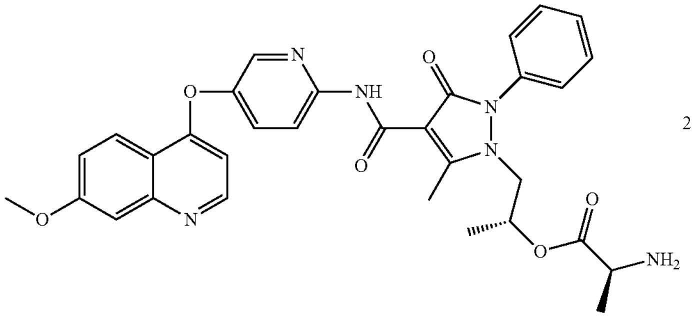
2 × $CH_3SO_3H$,
(Example 16)
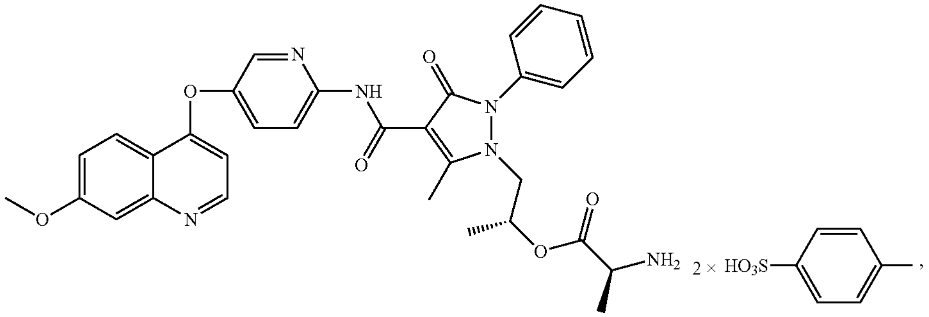
(Example 17)
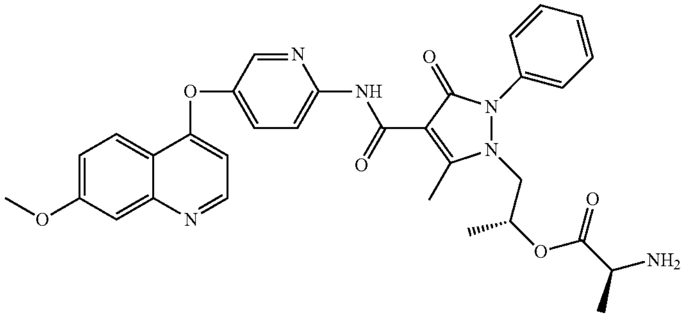
HOOC—COOH, -continued
(Example 18)
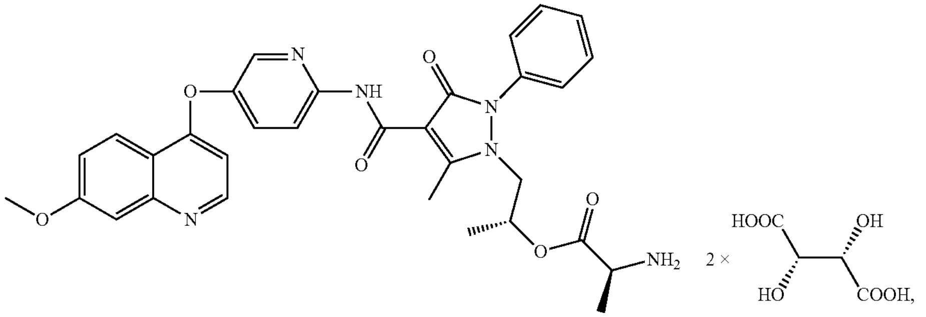
(Example 19)
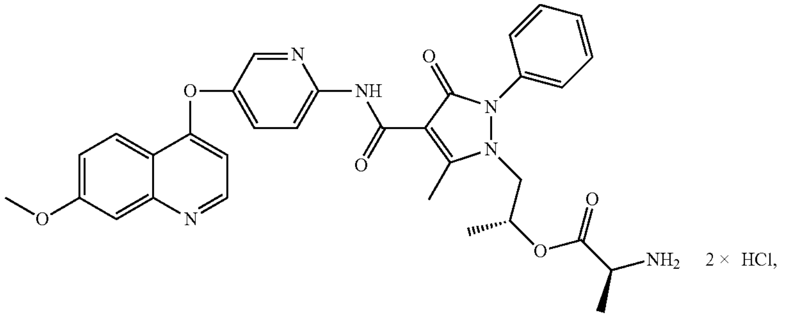
(Example 20)
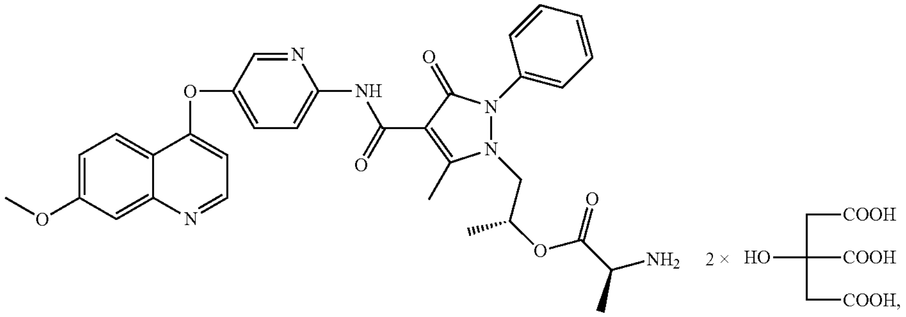
(Example 21)
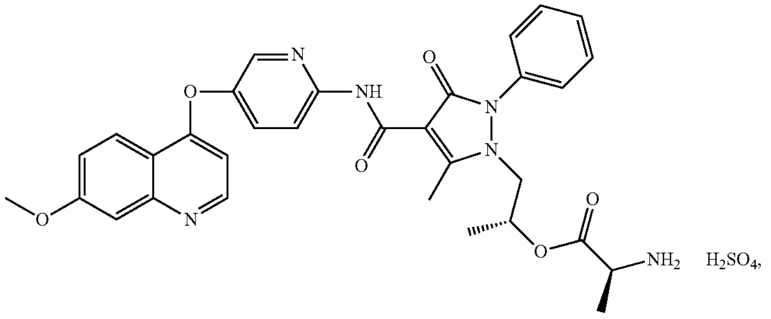
(Example 22)
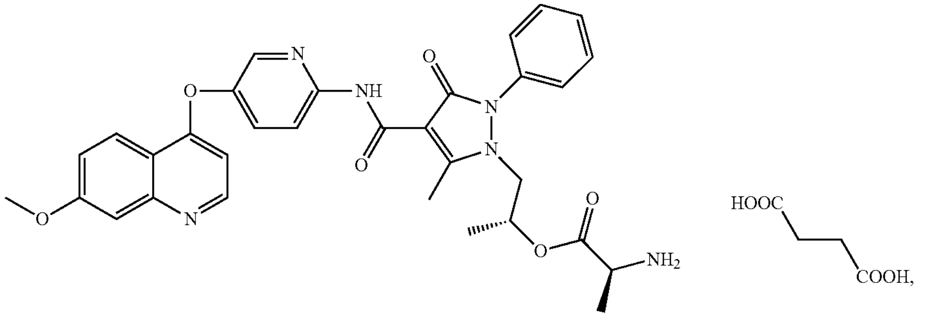

-continued
(Example 23)
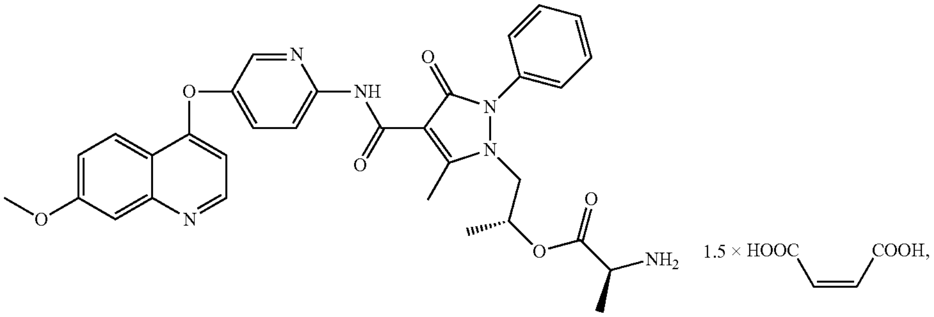
(Example 24)
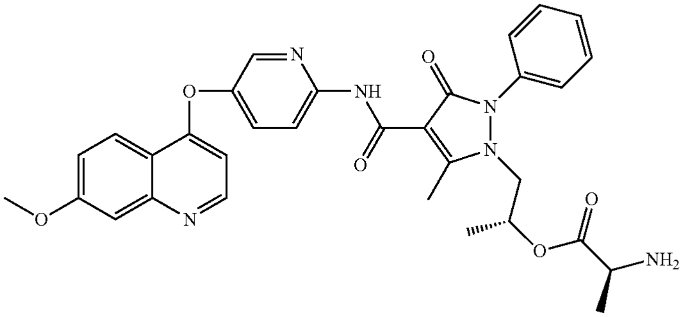
$H_3PO_4$,
(Example 25)
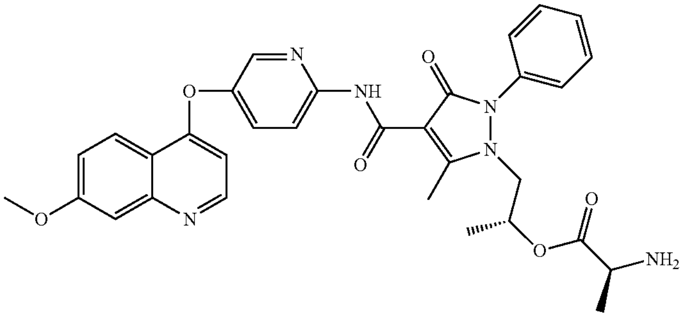
2 × $CH_3COOH$,
(Example 26)
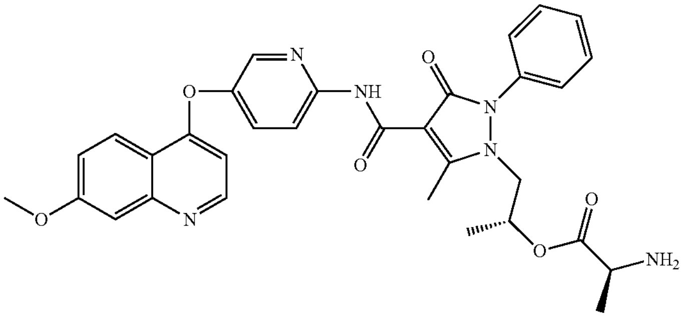
2 × $C_2H_5SO_3H$,
(Example 27)
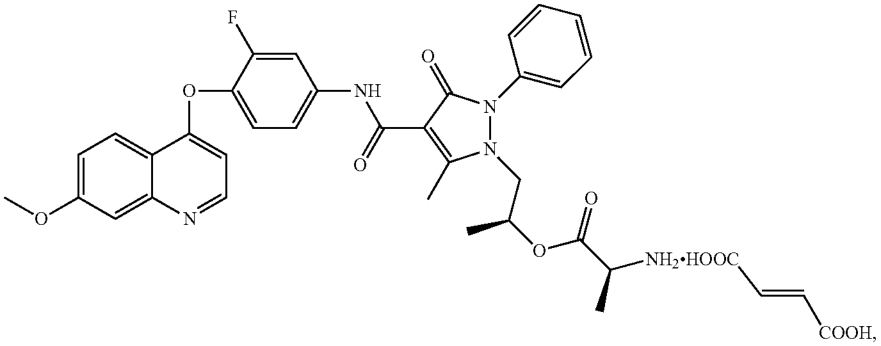

-continued
(Example 28)
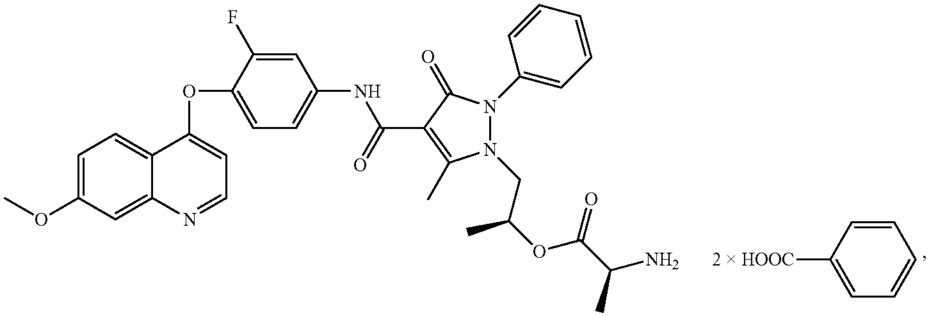
(Example 29)
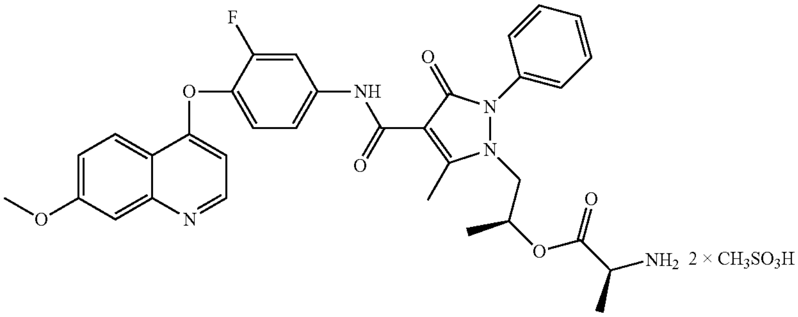
2 × $CH_3SO_3H$
(Example 30)
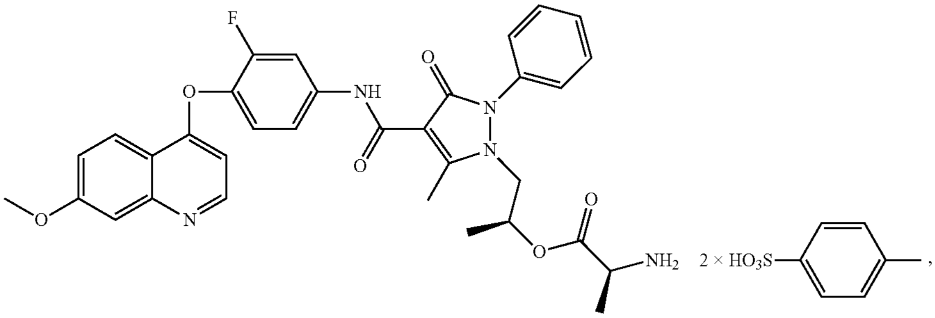
(Example 31)
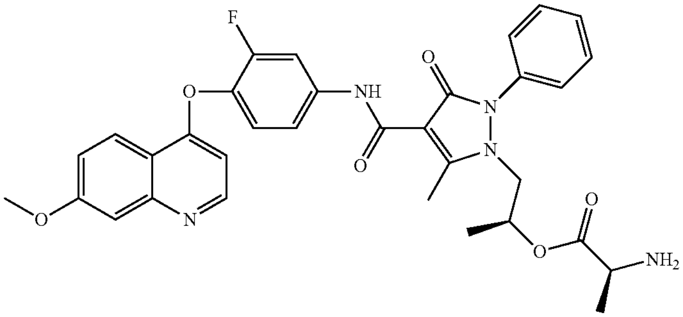
$H_2SO_4$,
(Example 32)
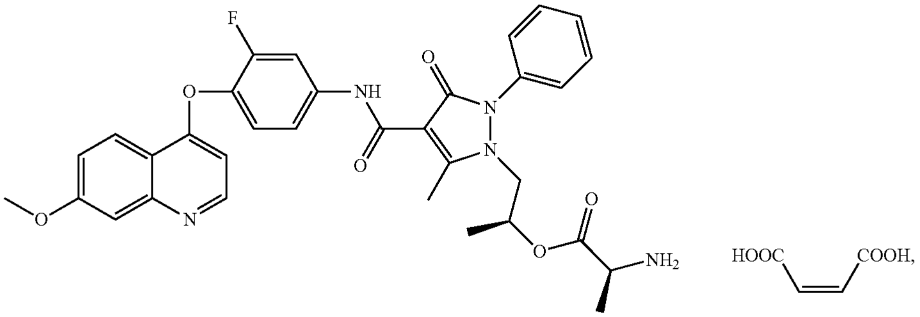

-continued
(Example 33)
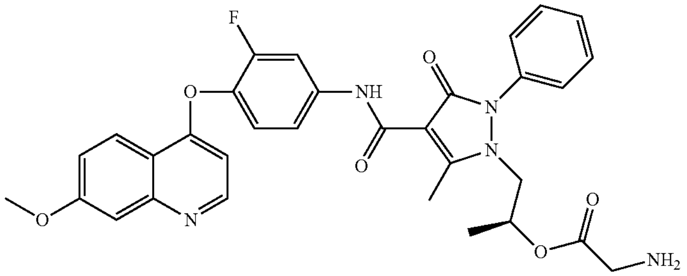
2 × HCl,
(Example 34)
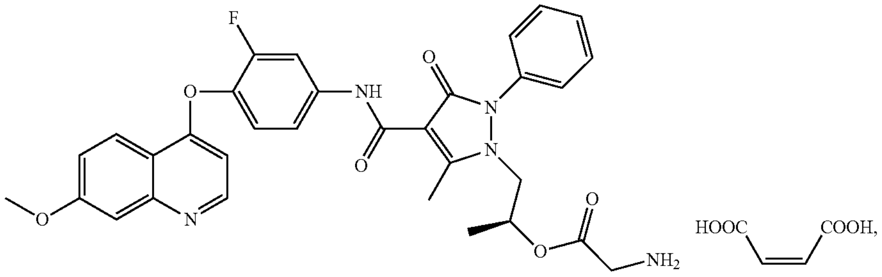
(Example 35)
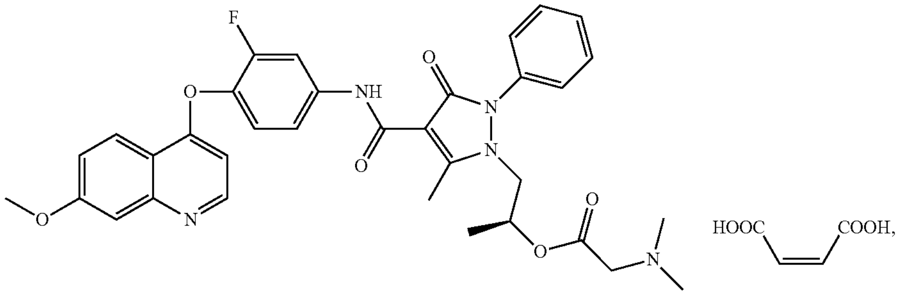
(Example 36)
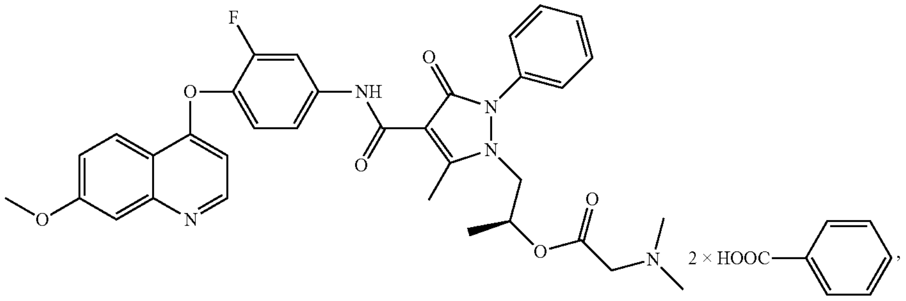
(Example 37)
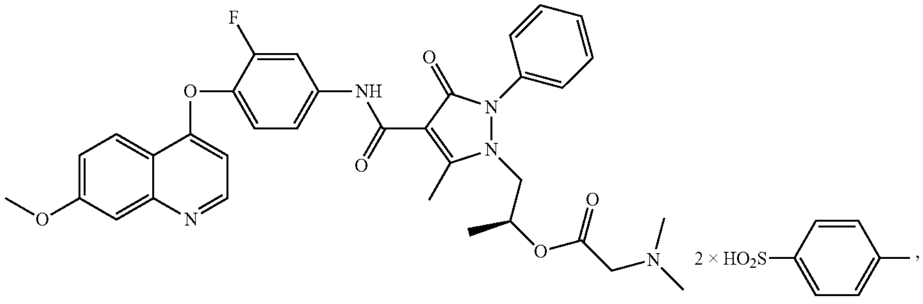

-continued
(Example 38)
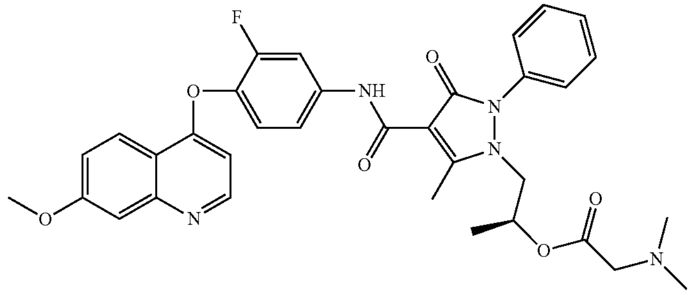
2 × $CH_3SO_3H$
(Example 39)
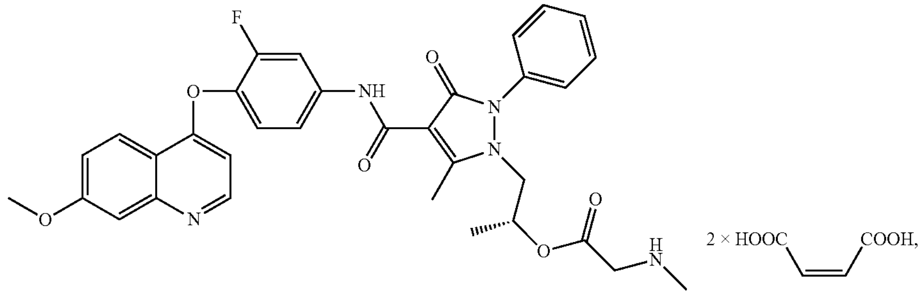
(Example 40)
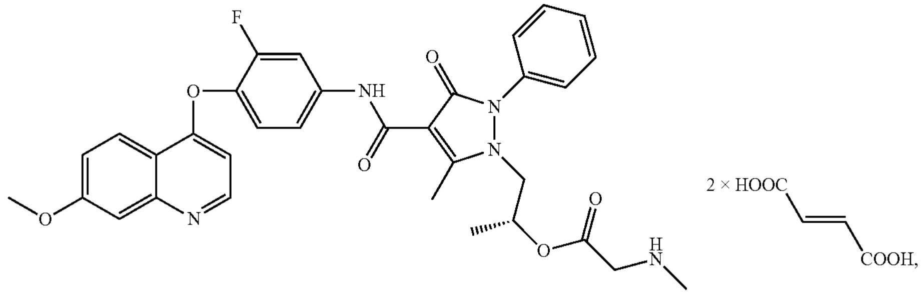
(Example 41)
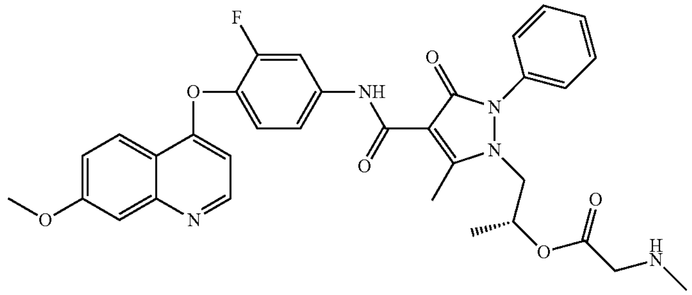
2 × HCl,
(Example 42)
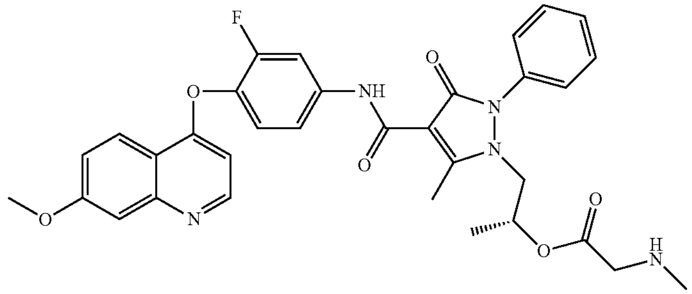
$H_2SO_4$, -continued
(Example 43)
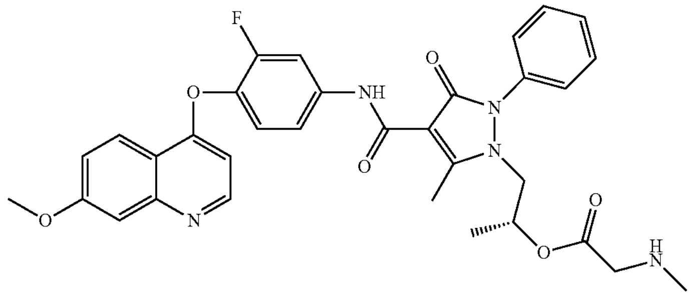
$H_3PO_4$,
(Example 44)
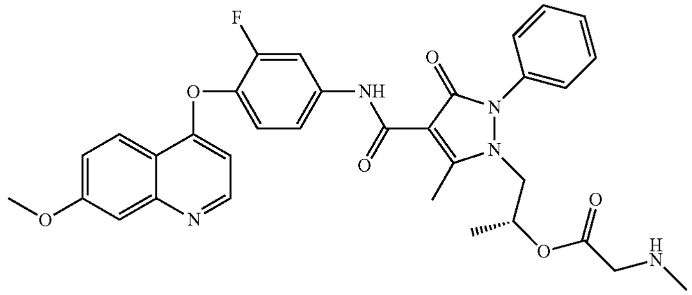
$2 \times CH_3SO_3H$,
(Example 45)
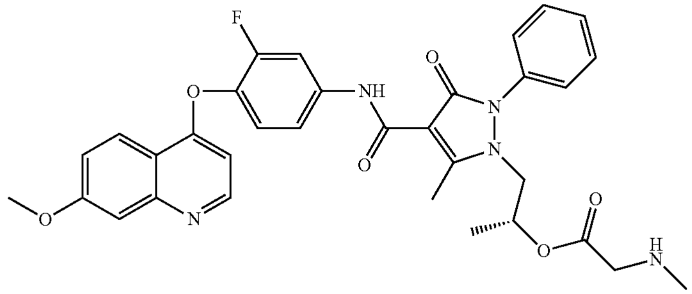
$2 \times C_2H_5SO_3H$,
(Example 46)
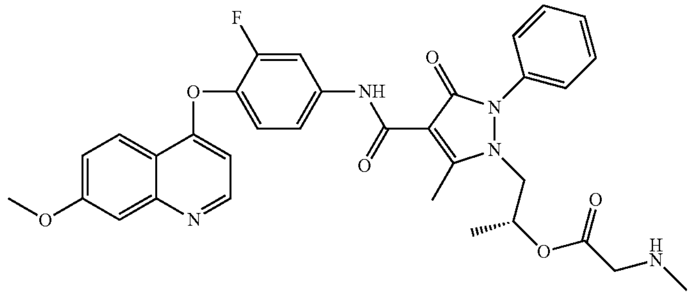
2 ×
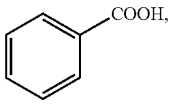
(Example 47)
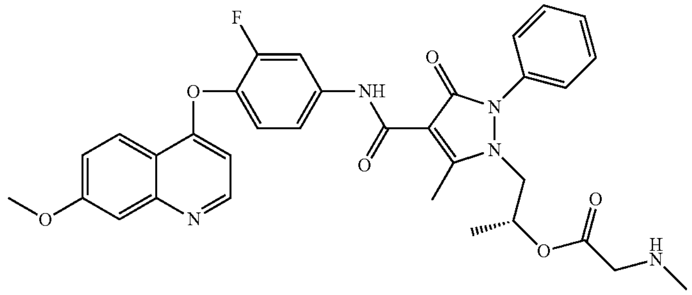
2 ×
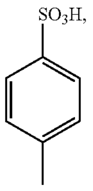

-continued
(Example 48)
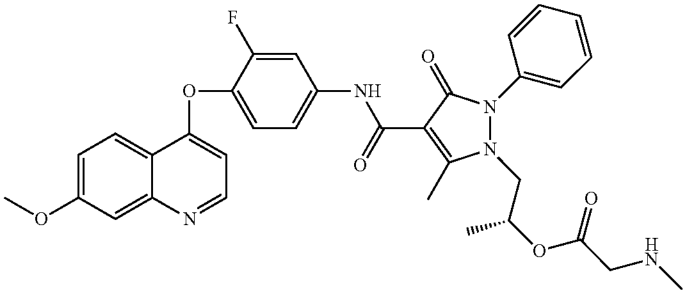
2 × $CH_3COOH$,
(Example 49)
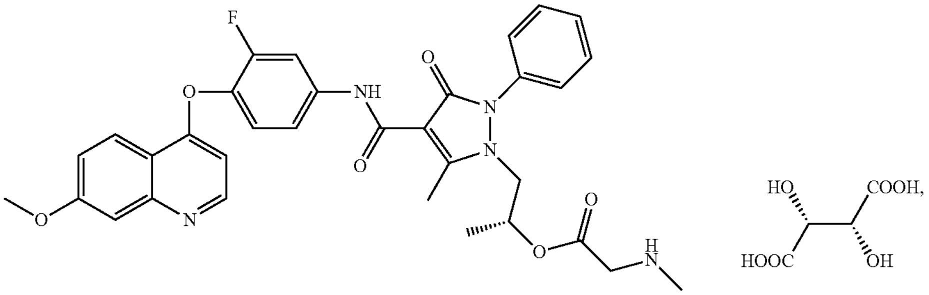
(Example 50)
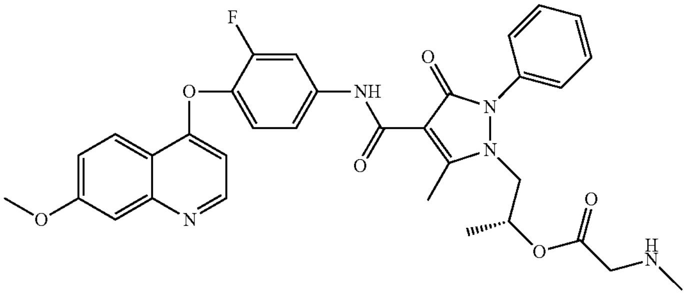
HOOC—COOH,
(Example 51)
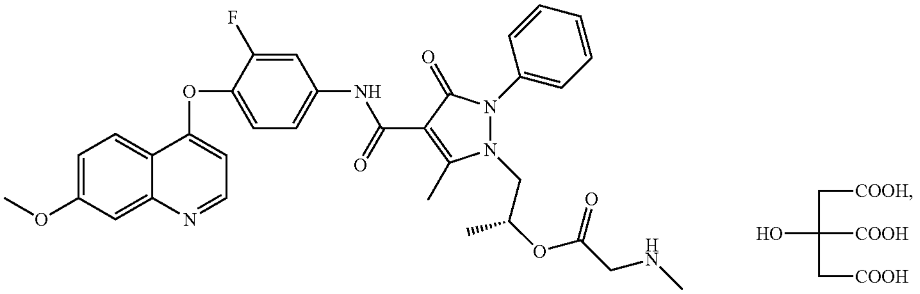
(Example 52)
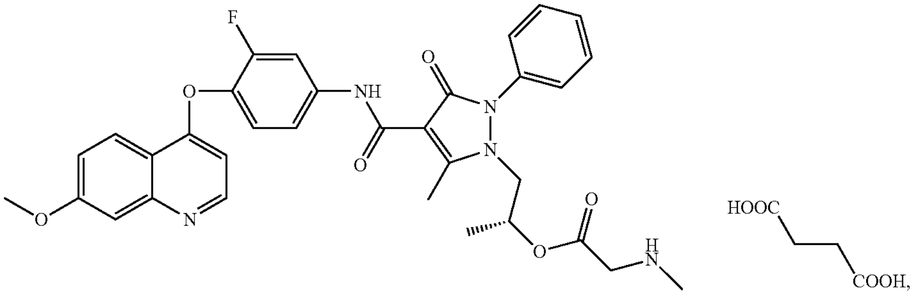

-continued
(Example 53)
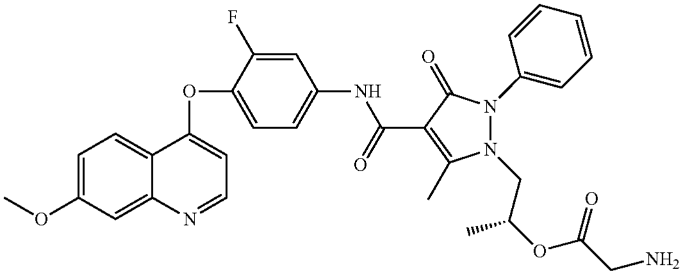
$2 \times HCl$,
(Example 54)
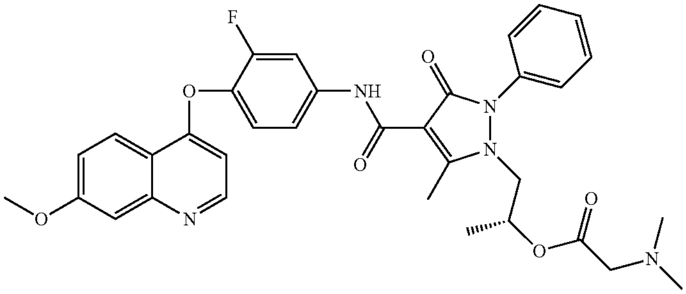
$2 \times HCl$,
(Example 55)
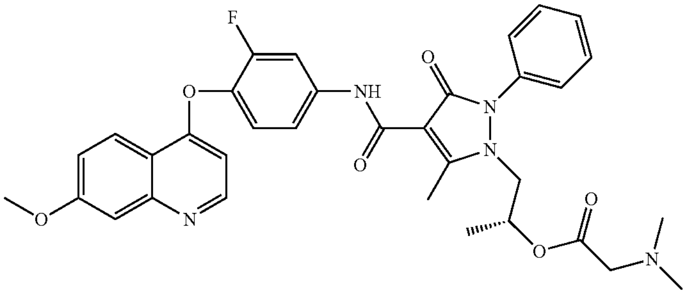
$H_2SO_4$,
(Example 56)
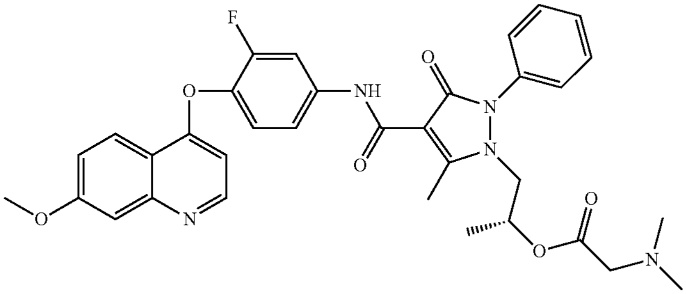
2 ×
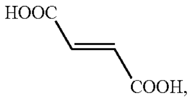
(Example 57)
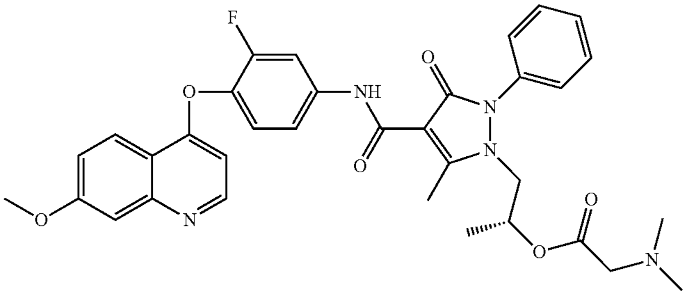
$2 \times CH_3COOH$, -continued
(Example 58)
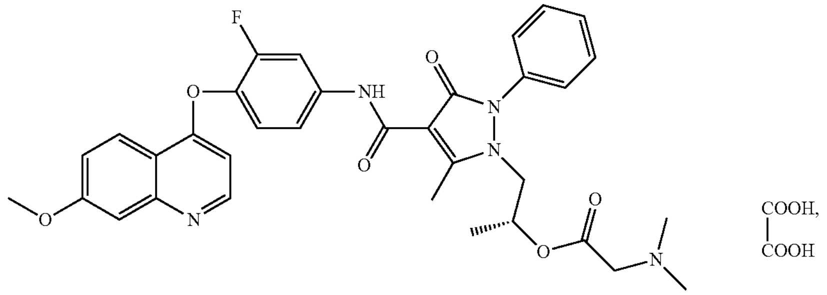
(Example 59)
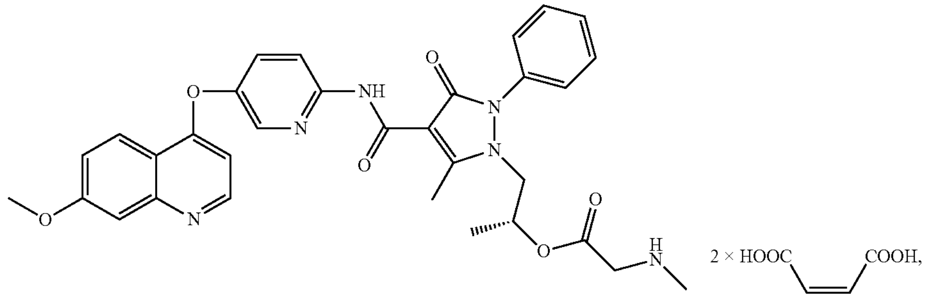
(Example 60)
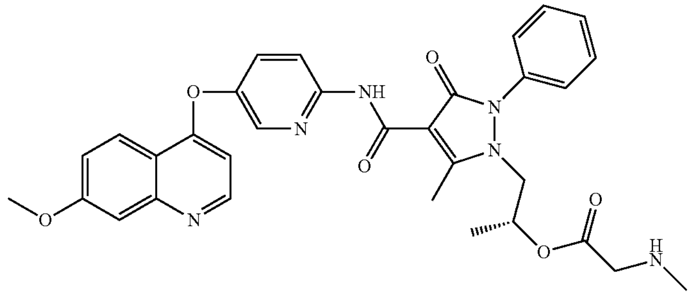
2 × HCl,
(Example 61)
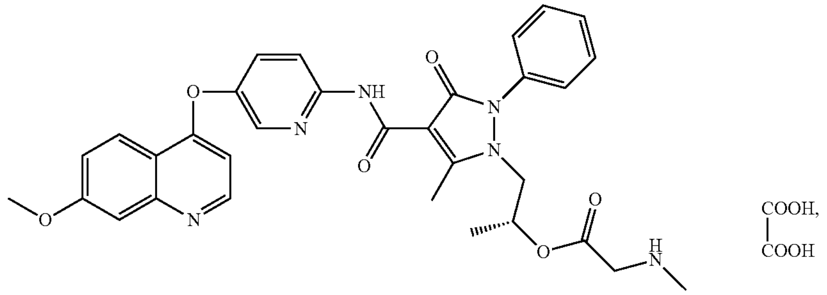
(Example 62)
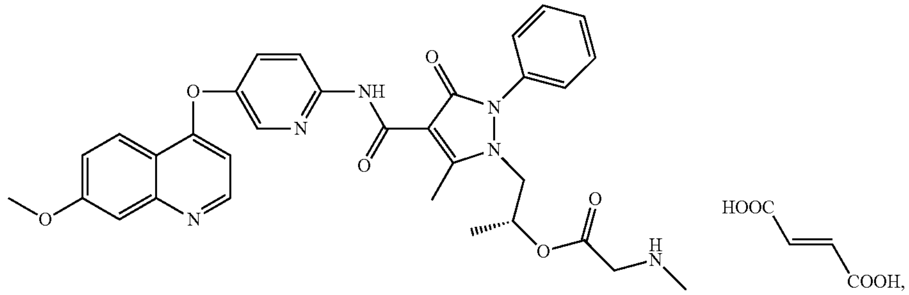

-continued
(Example 63)
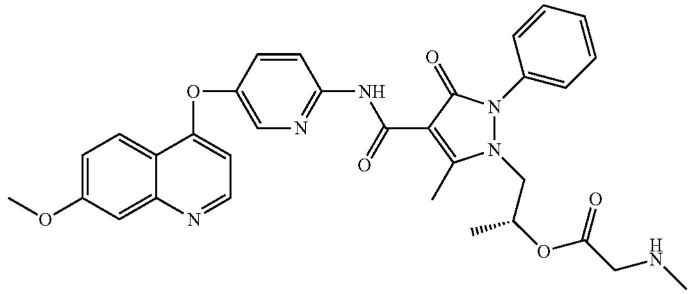
2 × $CH_3COOH$,
(Example 64)
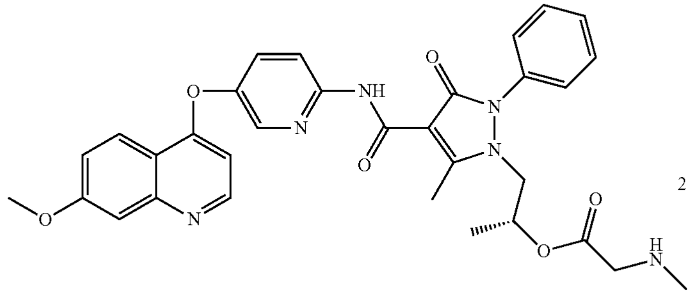
2 × 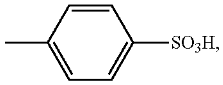
(Example 65)
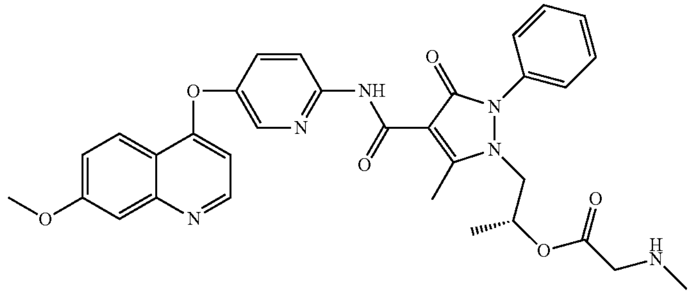
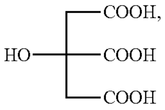
(Example 66)
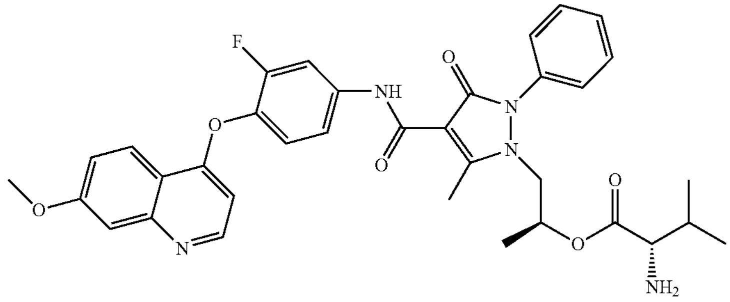
2 × HCl,
(Example 67)
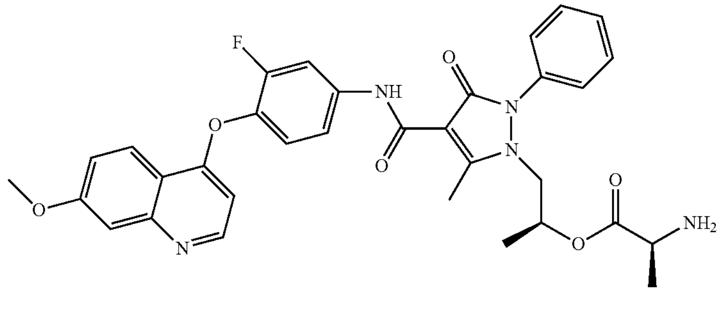
2 × HCl, -continued
(Example 68)
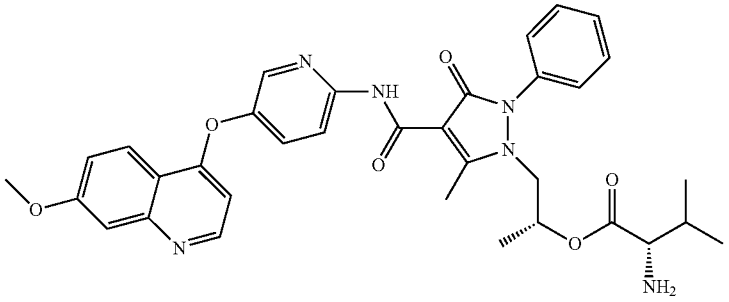
2 × HCl,
(Example 69)
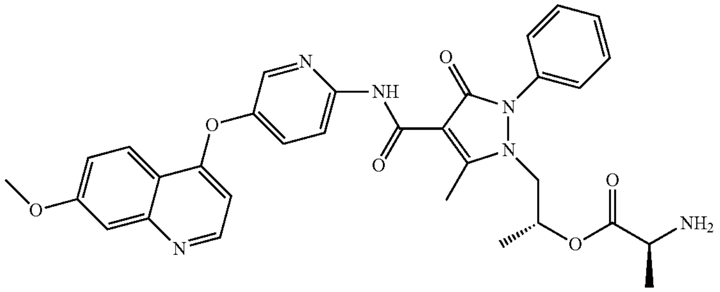
2 × HCl,
(Example 70)
2 × HCl
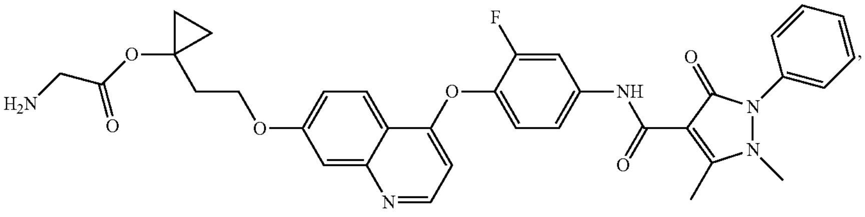
,
(Example 71)
2 × HCl
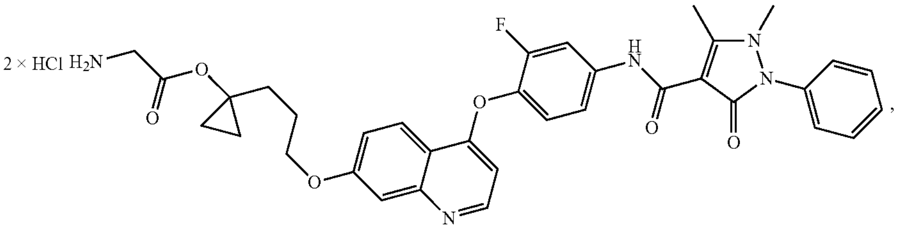
,
(Example 72)
2 × HCl
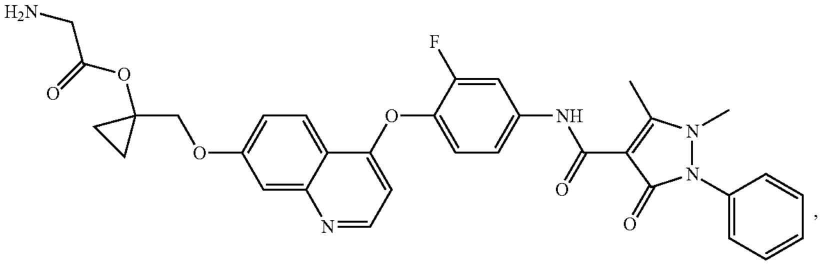
, -continued
(Example 73)
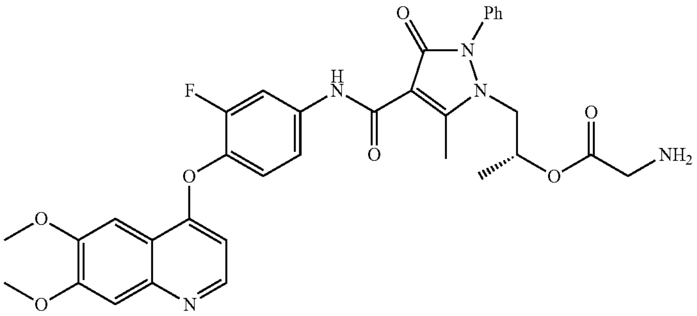
2 × HCl,
(Example 74)
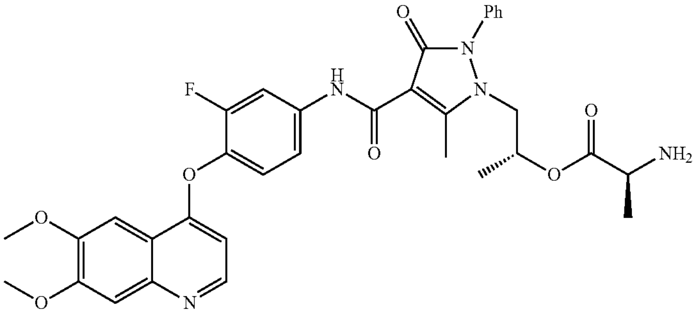
2 × HCl,
(Example 75)
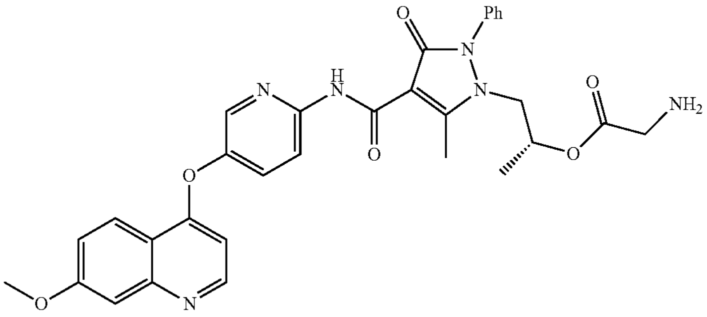
2 × HCl,
(Example 76)
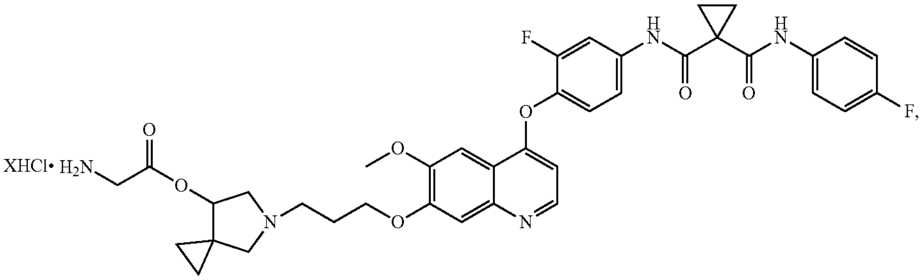
(Example 77)
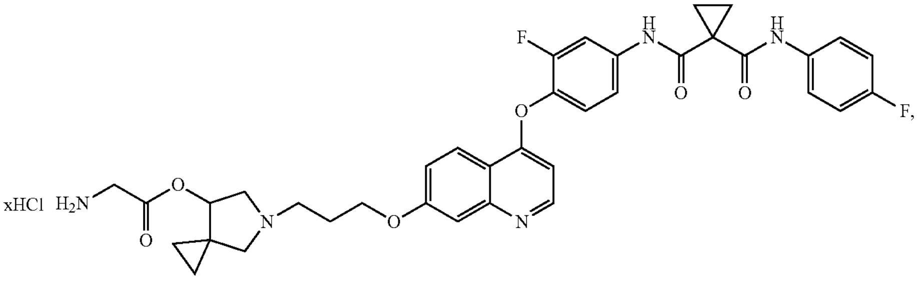

-continued (Example 78)

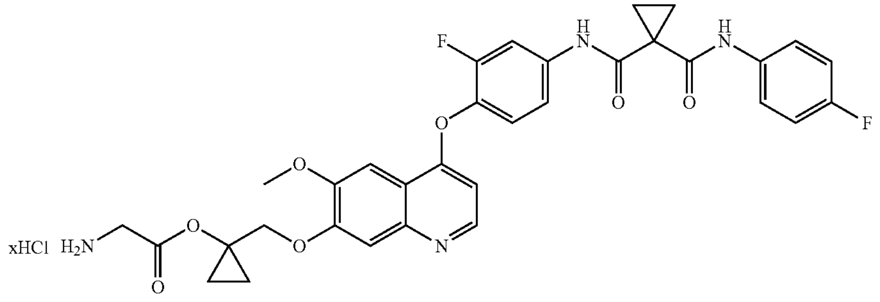

and (Example 79)

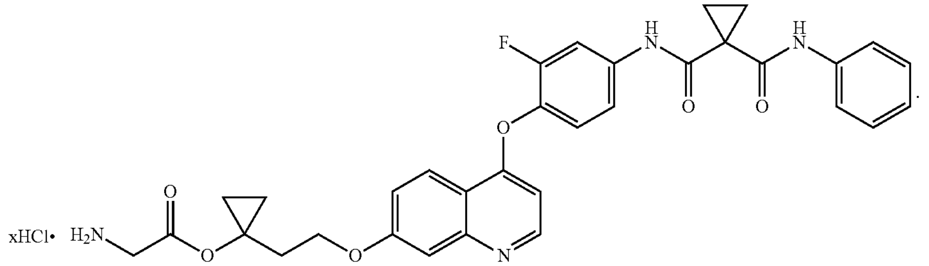

13. A pharmaceutical composition comprising a compound according to claim 1 and a pharmaceutically acceptable carrier, excipient, diluent, adjuvant, vehicle or a combination thereof.

14. The pharmaceutical composition according to claim 13 further comprising a therapeutic agent selected from a chemotherapeutic agent, an anti-proliferative agent, an agent for treating atherosclerosis, an agent for treating lung fibrosis, or a combination thereof.

15. The pharmaceutical composition according to claim 14, wherein the additional therapeutic agent is adriamycin, rapamycin, temsirolimus, everolimus, ixabepilone, gemcitabin, cyclophosphamide, dexamethasone, etoposide, fluorouracil, imatinib mesylate, dasatinib, nilotinib, erlotinib, lapatinib, iressa, sorafenib, sunitinib, an interferon, carboplatin, topotecan, taxol, vinblastine, vincristine, temozolomide, tositumomab (Bexxar), trabedectin, Avastin (bevacizumab), Herceptin (trastuzumab), Erbitux (cetuximab), Vectibix (panitumumab), or a combination thereof.

16. A method of managing, treating or lessening the severity of a proliferative disorder in a patient comprising administering to the patient the compound of claim 1.

17. A method of managing, treating or lessening the severity of a proliferative disorder in a patient comprising administering to the patient the pharmaceutical composition of claim 13.

18. The method according to claim 16, wherein the proliferative disorder is metastatic cancer, colon cancer, gastric adenocarcinoma, bladder cancer, breast cancer, kidney cancer, liver cancer, lung cancer, thyroid cancer, cancer of the head and neck, prostate cancer, pancreatic cancer, cancer of the CNS, glioblastoma, a myeloproliferative disorder, atherosclerosis or lung fibrosis.

19. The method according to claim 17, wherein the proliferative disorder is metastatic cancer, colon cancer, gastric adenocarcinoma, bladder cancer, breast cancer, kidney cancer, liver cancer, lung cancer, thyroid cancer, cancer of the head and neck, prostate cancer, pancreatic cancer, cancer of the CNS, glioblastoma, a myeloproliferative disorder, atherosclerosis or lung fibrosis.

20. A method of inhibiting or modulating protein kinase activity in a biological sample comprising contacting a biological sample with the compound according to claim 1.

21. A method of inhibiting or modulating protein kinase activity in a biological sample comprising contacting a biological sample with the pharmaceutical composition according to claim 13.

22. The method of claim 20, wherein the protein kinases are receptor tyrosine kinases.

23. The method of claim 22, wherein the receptor tyrosine kinases are KDR and/or c-Met.

24. The method of claim 21, wherein the protein kinases are receptor tyrosine kinases.

25. The method of claim 24, wherein the receptor tyrosine kinases are KDR and/or c-Met.

* * * * *